(12) United States Patent
Klaerner et al.

(10) Patent No.: US 10,934,380 B1
(45) Date of Patent: Mar. 2, 2021

(54) CROSSLINKED POLY(ALLYLAMINE) POLYMER PHARMACEUTICAL COMPOSITIONS

(71) Applicant: Tricida, Inc., South San Francisco, CA (US)

(72) Inventors: Gerrit Klaerner, Hillsborough, CA (US); Eric F. Connor, Los Gatos, CA (US); Randi K. Gbur, Brisbane, CA (US); Matthew J. Kade, Berkeley, CA (US); Paul H. Kierstead, Oakland, CA (US); Kalpesh N. Biyani, Dublin, CA (US); Son H. Nguyen, Milpitas, CA (US); Scott M. Tabakman, Palo Alto, CA (US)

(73) Assignee: TRICIDA, INC., South San Francisco, CA (US)

( * ) Notice: Subject to any disclaimer, the term of this patent is extended or adjusted under 35 U.S.C. 154(b) by 0 days.

(21) Appl. No.: 16/138,932

(22) Filed: Sep. 21, 2018

Related U.S. Application Data

(60) Provisional application No. 62/562,554, filed on Sep. 25, 2017.

(51) Int. Cl.
*C08F 226/02* (2006.01)
*A61K 31/785* (2006.01)
*C08G 73/02* (2006.01)

(52) U.S. Cl.
CPC .......... *C08F 226/02* (2013.01); *A61K 31/785* (2013.01); *C08G 73/024* (2013.01)

(58) Field of Classification Search
CPC .............................. C08F 226/02; A61K 31/785
See application file for complete search history.

(56) References Cited

U.S. PATENT DOCUMENTS

| | | | |
|---|---|---|---|
| 5,496,545 A | 3/1996 | Holmes-Farley et al. | |
| 5,667,775 A | 9/1997 | Holmes-Farley et al. | |
| 5,753,706 A | 5/1998 | Hsu | |
| 6,726,905 B1 | 4/2004 | Mandeveille, III et al. | |
| 7,459,502 B2 | 12/2008 | Connor et al. | |
| 7,767,229 B1 | 8/2010 | Milne et al. | |
| 8,349,305 B2 | 1/2013 | Chang et al. | |
| 8,394,416 B2 | 3/2013 | Bianchi et al. | |
| 8,986,669 B2 | 3/2015 | Huval et al. | |
| 9,205,107 B2 | 12/2015 | Klaerner et al. | |
| 9,925,214 B2 | 3/2018 | Klaerner et al. | |
| 9,993,500 B2 | 6/2018 | Klaerner et al. | |
| 10,363,268 B2 | 7/2019 | Klaerner et al. | |
| 10,369,169 B1 | 8/2019 | Klaerner et al. | |
| 10,391,118 B2 | 8/2019 | Klaerner et al. | |
| 2004/0059065 A1 | 3/2004 | Goto et al. | |
| 2005/0220890 A1 | 10/2005 | Charmot et al. | |
| 2010/0189679 A1 | 7/2010 | Inoue et al. | |
| 2017/0095441 A1 | 4/2017 | Kwok et al. | |
| 2018/0021370 A1 | 1/2018 | Klaerner et al. | |

FOREIGN PATENT DOCUMENTS

| | | | |
|---|---|---|---|
| EP | 1931689 | 2/2015 | |
| WO | 9940990 | 8/1999 | |
| WO | 2007022435 | 2/2007 | |
| WO | 2014197725 | 12/2014 | |
| WO | WO-2014197725 A1 * | 12/2014 | .......... A61K 31/785 |
| WO | 2016094685 A1 | 6/2016 | |
| WO | WO-2016094685 A1 * | 6/2016 | .......... A61K 31/785 |
| WO | 2017193024 | 11/2017 | |
| WO | 2017193050 | 11/2017 | |
| WO | 2017193064 | 11/2017 | |
| WO | 2019090176 | 5/2019 | |
| WO | 2019090177 | 5/2019 | |
| WO | 2019236124 | 12/2019 | |
| WO | 2019236636 | 12/2019 | |
| WO | 2019236639 | 12/2019 | |

OTHER PUBLICATIONS

Akizawa, et al., Long-Term Treatment of Hyperphosphatemia With Bixalomer in Japanese Hemodialysis Patients, Therapeutic Apheresis and Dialysis, 2013, 17(6): 612-619.

Akizawa et al., Randomized Controlled Trial of Bixalomer Versus Sevelamer Hydrochloride in Hemodialysis Patients With Hyperphosphatemia, Therapeutic Aphreresis and Dialysis, 2014, 18(2):122-131.

Akizawa et al., Bixalomer in Hyperphosphatemic Patients With Chronic Kidney Disease Not on Dialysis: Phase 3 Randomized Trial, Therapeutic Apheresis and Dialysis, 2016, 10 pages.

Akizawa et al., Long-Term Safety and Efficacy of Bixalomer in Hyperphosphatemic Patients With Chronic Kidney Disease Not on Dialysis, Therapeutic Apheresis and Dialysis, 2017, 7pgs.

Bushinsky et al., Randomized, Controlled Trial of TRC101 to Increase Serum Bicarbonate in Patients with CKD, Clin J Am Soc Nephrol, 2018, 10pgs.

Inoue et al., Highly selective and low-swelling phosphate-binding polymer for hyperphosphatema theraphy, Chem. Letters, 2012, 41, 932-933.

Wesson et al., Veverimer versus placebo in patients with metabolic acidosis associated with chronic kidney disease: a multicentre, randomised, double-blind, controlled, phase 3 trial, The Lancet, 11 pgs. Mar. 8, 2019.

Remuzzi G.., Role of Endothelin in the Development of Glomerulosclerosis, Kidney and Blodd Ress Res., 19: 182-183 1996.

Ruiz-Ortega et al., Involvement of angiotensin II and endothelin in matrix protein production and renal sclerosis, Jour. Hypertension, 12: S51-S58 1994.

(Continued)

*Primary Examiner* — Ling Siu Choi
*Assistant Examiner* — David L Miller
(74) *Attorney, Agent, or Firm* — Bryan Cave Leighton Paisner LLP

(57) ABSTRACT

Pharmaceutical compositions for and methods of treating an animal, including a human, and methods of preparing such compositions. The pharmaceutical compositions contain crosslinked amine polymers and may be used, for example, to treat diseases or other metabolic conditions in which removal of a target species from the gastrointestinal tract would provide physiological benefits.

10 Claims, No Drawings

(56) References Cited

OTHER PUBLICATIONS

Seccia et al., Role of angiotensin II, endothelin-1 and L-type calcium channel in the development of glomerular, tubulointerstitial and perivascular fibrosis, Journal of Hypertension, 26:2022-2029 2008.
Shah et al., Serum Bicarbonate Levels and the Progression of Kidney Disease: A Cohort Study, Am J Kidney Dis 54:270-277 2009.
Stein et al., Role of an improvement in acid-base status and nutrition in CAPD patients, Kidney International, 52: 1089-1095 1997.
Szeto et al., Oral Sodium Bicarbonate for the Treatment of Metabolic Acidosis in Peritoneal Dialysis Patients: A Randomized Placebo-Control Trial, J Am Soc Nephrol 14: 2119-2126 2003.
Tangri et al., A Predictive Model for Progression of Chronic Kidney Disease to Kidney Failure, JAMA, 305(15): 1553-1559 2011.
Wesson D. E., Endogenous Endothelins Mediate Increased Acidification in Remnant Kidneys, J Am Soc Nephrol 12: 1826-1835 2001.
Wesson et al., Angiotensin II receptors mediate increased distal nephron acidification caused by acid retention, Kidney International, 82: 1184-1194 2012.
Wesson et al., Angiotensin II-mediated GFR decline in subtotal nephrectomy is due to acid retention associated with reduced GFR, Nephrol Dial Transplant, 30: 762-770 2015.
European Patent Office, Extended Search Report for EP App. 17793497.3, 11 pages dated Mar. 17, 2020.
Anonymous, Tricida Announces Positive Topline Phase 1/2 Clinical Trial Results for TRC101 in 135 Subjects with Chronic Kidney Disease and Metabolic Acidosis, Business Wire, 2 pages Jan. 9, 2017.
Abramowitz et al., Effects of Oral Sodium Bicarbonate in Patients with CKD, Clin J Am Soc Nephrol, 8: 714-720 2013.
Abramowitz, M.K., Acid-Base Balance and Physical Function, Clin J Am Soc Nephrol, 9: 2030-2032 2014.
Abramowitz, M.K., Metabolic Acidosis and Cardiovascular Disease Risk in CKD, Clin J Am Soc Nephrol, 13, 2 pgs. 2018.
Aronson et al., Effects of pH on Potassium: New Explanations for Old Observations, J Am Soc Nephrol, 22: 1981-1989 2011.
Ballasi et al., Correction of metabolic acidosis improves insulin resistance in chronic kidney disease, BMC Nephrology, 17: 158-167 2016.
Williams et al., Failure of Dietary Protein and Phosphate Restriction to Retard the Rate of Progression of Chronic Renal Failure: A Prospective, Randomized, Controlled Trial, 81(294): 837-855 1991.
Wesson et al., Long-term safety and efficacy of veverimer in patients with metabolic acidosis in chronic kidney disease: a multicentre, randomised, blinded, placebo-controlled, 40-week extension, Lancet, 11 pgs. 2019.
Biggar et al., Sevelamer carbonate for the treatment of hyperphosphatemia in patients with kidney failure (CKD III-V), Expert Opin. Pharmacother, 11(16): 2739-2750 2010.
Bushinsky, D. A., Tolerance to Sodium in Patients With CKD-Induced Metabolic Acidosis: Does the Accompanying Anion Matter?, 73(6): 858-865 2019.
Chen et al., Is an Increased Serum Bicarbonate Concentration during Hemodialysis Associated with an Increased Risk of Death?, Semin. Dial., 27(3): 259-262 2014.
Chen et al., Advances in management of chronic metabolic acidosis in chronic kidney disease, Pharm. Thera., 28: 8 pgs 2019.
Dawson-Hughes et al., Impact of supplementation with bicarbonate on lower-extremity muscle performance in older men and women, Osteoporos Int., 21(7): 1171-1179 2010.
De Iorio et al., Very Low-Protein Diet (VLPD) Reduces Metabolic Acidosis in Subjects with Chronic Kidney Disease: The "Nutritional Light Signal" of the Renal Acid Load, Nutrients, 9: 69-82 2017.
De Iorio et al., Treatment of metabolic acidosis with sodium bicarbonate delays progression of chronic kidney disease: the UBI Study, Journal of Nephrology, 32: 989-1001 2019.

Disthabanchong et al., Oral Sodium Bicarbonate Improves Thyroid Function in Predialysis Chronic Kidney Disease, Am J Nephrol., 32: 549-556 2010.
Dobre et al., Serum bicarbonate and cardiovascular events in hypertensive adults: results from the Systolic Blood Pressure Intervention Trial, Nephrol Dial Transplant, 1-8 2019.
Dobre et al., Current Status of Bicarbonate in CKD, J Am Soc Nephrol., 26(3): 515-523 2015.
Dobre et al., Persistent High Serum Bicarbonate and the Risk of Heart Failure in Patients With Chronic Kidney Disease (CKD): A Report From the Chronic Renal Insufficiency Cohort (CRIC) Study, J Am Heart Assoc., 17 pgs. 2015.
Domrongkitchaipron et al., Bone histology and bone mineral density after correction of acidosis in distal renal tubular acidosis, Kidney International., 62: 2160-2166 2002.
Dubey et al., Correction of metabolic acidosis improves muscle mass and renal function in chronic kidney disease stages 3 and 4: a randomized controlled trial, Nephrol Dial Transplant, 9 pgs 2018.
Gennari et al., Effect of Dietary Protein Intake on Serum Total CO2 Concentration in Chronic Kidney Disease: Modification of Diet in Renal Disease Study Findings, Clin J Am Soc Nephrol., 1: 52-57 2006.
Gonzalez et al., Sevelamer carbonate increases serum bicarbonate in pediatric dialysis patients, Pediatr Nephrol., 25: 373-375 2010.
Greene et al., Role of Aldosterone in the Remnant Kidney Model in the Rat, J. Clin. Invest., 98(4): 1063-1068 1996.
Halperin et al., Ammonium Excretion in Chronic Metabolic Acidosis: Benefits and Risks, American Journal of Kidney Diseases, 14(4): 267-271 1989.
Harris et al., Mechanism of Hyperkalemia-Induced Metabolic Acidosis, J Am Soc Nephrol, 29: 1411-1425 2018.
Jeong et al., Effect of Bicarbonate Supplementation on Renal Function and Nutritional Indices in Predialysis Advanced Chronic Kidney Disease, Electrolyte Blood Press, 12: 80-87 2014.
Ketteler et al., Efficacy and Tolerability of Sevelamer Carbonate in Hyperphosphatemic Patients Who Have Chronic Kidney Disease and Are Not on Dialysis, Clin J Am Soc Nephrol, 3: 1125-1130 2008.
Kittiskulnam et al., Impact of Serum Bicarbonate Levels on Muscle Mass and Kidney Function in Pre-Dialysis Chronic Kidney Disease Patients, Am J Nephrol., 11 pgs 2019.
Kraut et al., Metabolic acidosis: pathophysiology, diagnosis and management, Nature Reviews Nephrology, 6: 274-285 2010.
Mathur et al., Effects of Correction of Metabolic Acidosis on Blood Urea and Bone Metabolism in Patients with Mild to Moderate Chronic Kidney Disease: A Prospective Randomized Single Blind Controlled Trial, Renal Failure, 28: 1-5, 2006.
Melamed et al., Effects of Sodium Bicarbonate in CKD Stages 3 and 4: A Randomized, Placebo-Controlled, Multicenter Clinical Trial, Am J Kidney Dis., 10pgs 2019.
Mircescu et al., Effects of a Supplemented Hypoproteic Diet in Chronic Kidney Disease, Journal of Renal Nutrition, 17(3): 179-188 2007.
Nath et al., Increased Ammoniagenesis as a Determinant of Progressive Renal Injury, Am. Jour. Kid. Dis. 17(6): 654-657 1991.
Nathan et al., The effect of intensive treatment of diabetes on the development and progression of long-term complications in insulin-dependent diabetes mellitus, New Eng. Jour. Med., 329(14): 977-986 1993.
Navaneethan et al., Effects of Treatment of Metabolic Acidosis in CKD A Systematic Review and Meta-Analysis, CJASN, 14: 10 pgs 2019.
Perry et al., Sevelamer Carbonate: A Review in Hyperphosphataemia in Adults with Chronic Kidney Disease, Drugs, 74: 771-792 2014.
Phisitkul et al., Amelioration of metabolic acidosis in patients with low GFR reduced kidney endothelin production and kidney injury, and better preserved GFR, Kidney International, 77: 617-623 2010.
Pisani et al., 6-tips diet: a simplified dietary approach in patients with chronic renal disease. A clinical randomized trial, Clin Exp Nephrol, 10 pgs 2015.
Mount, D. B., Potassium balance in acid-base disorders, retrieved from www.uptodate.com/contents/potassium-balance-in-acid-base-

(56) References Cited

OTHER PUBLICATIONS disorders?search=hyperkalemia%20and%20metabolic%20acidosis&source=search_result&selectedTitle=1~150&usage_type=default&display_rank, 5 pgs 2018.

Raphael et al., Higher serum bicarbonate levels within the normal range are associated with better survival and renal outcomes in African Americans. Kidney International, 79: 356-362 2011.

Raphael et al., Bicarbonate Concentration, Acid-Base Status, and Mortality in the Health, Aging, and Body Composition Study, Clin J Am Soc Nephrol, 11: 9 pgs 2016.

Raphael et al., Urine Ammonium Predicts Clinical Outcomes in Hypertensive Kidney Disease, J Am Soc Nephrol 28: 2483-2490 2017.

Wolf et al., The Renin-Angiotensin System and Progression of Renal Disease: From Hemodynamics to Cell Biology, Nephron Physiol. 93: 3-13 2003.

Raphael K. L, Metabolic Acidosis in CKD: Core Curriculum 2019, AJKD, 13 pgs. 2019.

De Brito-Ashurst et al., Acidosis: progression of chronic kidney disease and quality of life, Pediatr Nephrol, 30: 873-879 2015.

Dobre et al., Serum Bicarbonate Concentration and cognitive Function in Hypertensive Adults, Clin J Am Soc Nephrol., 13(4): 596-603 2018.

Fan et al., A randomized, crossover design study of sevelamer carbonate powder and sevelamer hydrochloride tablets in chronic kidney disease patients on haemodialysis, European Renal Associations European, 5 pgs. 2011.

Raphael et al., A Randomized Trial Comparing the Safety, Adherence, and Pharmacodynamics Profiles of Two Doses of Sodium Bicarbonate in CKD: the BASE Pilot Trial, JASN 31: 14 pgs. 2020.

\* cited by examiner

CROSSLINKED POLY(ALLYLAMINE) POLYMER PHARMACEUTICAL COMPOSITIONS

The present disclosure relates to a crosslinked poly(allylamine) substrate-binding polymers that may be used as a nonabsorbed pharmaceutical for a therapeutic application. More specifically, it relates to pharmaceutical compositions comprising such polymers, and to a process for the preparation of such polymers.

Colesevalem is a nonabsorbed crosslinked poly(allylamine) polymer that is used therapeutically as a bile acid sequestrant. As described, for example, in U.S. Pat. No. 5,607,669, colesevalem may be prepared by forming poly(allylamine) from allylamine, crosslinking the poly(allylamine) with epichlorohydrin, modifying the crosslinked composition with bromodecane and (6-bromohexyl) trimethylammonium bromide, and replacing the bromide ions with chloride ions when the material is washed. The resulting material contains repeat units corresponding to the following structures:

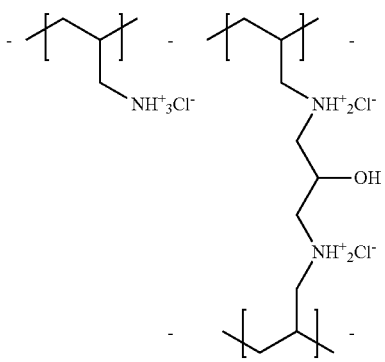

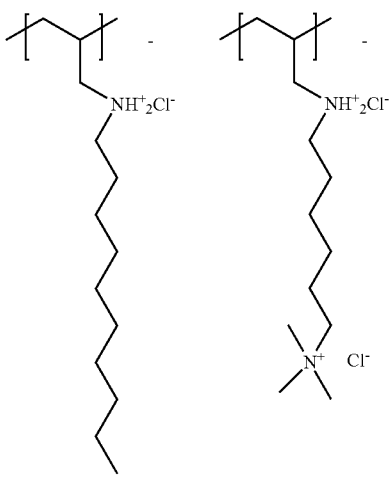

Sevelamer is a phosphate-binding, nonabsorbed crosslinked poly(allyl)amine polymer (corresponding to Formula (III)) that is used therapeutically to treat hyperphosphatemia,

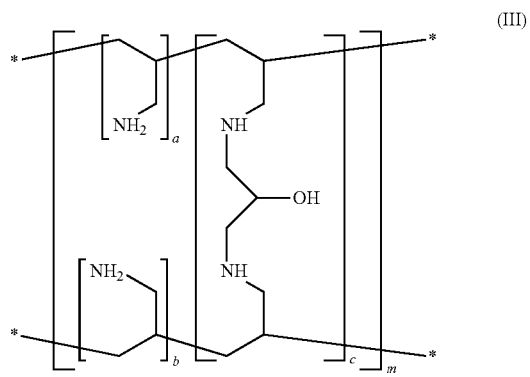

Sevelamer may be prepared by forming poly(allylamine), neutralizing the poly(allylamine) and crosslinking the neutralized poly(allylamine) with epichlorohydrin as described, for example, in U.S. Pat. No. 4,255,431.

According to Bianchi et al. (U.S. Pat. No. 8,394,416B2), crosslinking a poly(allylamine) with epichlorohydrin or other suitable difunctional molecules may lead to a poor compositional homogeneity of the final crosslinked polymer. Bianchi et al. further report that this is particularly true if the difunctional crosslinking molecule is not soluble in the aqueous solvent that is the solvent of choice for the polymerization of allylamine, and if the two functional groups have of the molecule have different reactivity (U.S. Pat. No. 8,394,416B2 at column 3, lines 54-62). To overcome these recited disadvantages, Bianchi et al. propose a one-step process for preparing crosslinked poly(allylamine) polymers in which allylamine is reacted with a crosslinking agent corresponding to Formula (2) or a salt thereof in the presence of an acid, radical initiator and a solvent.

Formula 2

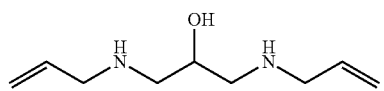

In U.S. Patent Publication No. 2010/0189679, Inoue et al. disclose crosslinked poly(allylamine) polymers having both relatively high phosphate absorption capacity and a swelling ratio in the range of 2-5 for the treatment of hyperphosphatemia. The crosslinked poly(allylamine) polymer is obtained by polymerization of allylammonium dihydrogen phosphate with an addition salt of N,N'-diallyl-1,3-diaminopropane in an amount of 5 to 25 mol % with respect to the amount of the allylammonium dihydrogen phosphate.

In U.S. Pat. No. 9,205,107, Klaerner et al. disclose crosslinked poly(allylamine) polymers that may be used to treat metabolic conditions in which removal of protons and/or chloride ions from the gastrointestinal tract would provide physiological benefits such as increasing serum bicarbonate concentrations. A range of crosslinked amine polymers are disclosed therein, including crosslinked poly(allylamine) polymers prepared by simultaneous polymerization of allylamine and crosslinking the polymer with a diallylamine.

Although the preparation of poly(allylamine) polymers from allylamine and a diallylamine crosslinker as described by Bianchi et al., Inoue et al. and Klaerner et al. provide certain advantages over crosslinking a linear poly(allylamine) with epichlorohydrin, the resulting crosslinked amine polymers may have undesirable process-related impurities or degradation products such as allylamine or derivatives thereof. In some instances, incomplete incorporation of diallylamine or multiallylamine crosslinkers can lead to unsaturated substituents covalently attached to the polymer backbone that can cause stability limiting generation of allylamine and related impurities during the work up including drying of the poly(allylamine) or upon storage. Such mechanisms of generating allylamine impurities include but are not limited to oxygen, temperature, water, acid and base mediated removal of the unsaturated substituents resulting in allylamine or related impurities.

One approach to improve the purity profile and stability profile of a polymer comprising a monoallylamine and a multiallylamine is to improve the polymerization efficiency (i.e., improve conversion of the allyl groups). In general, methods to improve polymerization efficiency are those that favor chain propagation over propagation-limiting processes, such as chain transfer, chain termination, and radical coupling. During the radical polymerization step, these methods include, but are not limited to:

a) increasing the concentration of monomer and multifunctional crosslinker in the monomer droplet solution,
b) increasing the relative concentration of a multiallylamine crosslinker by adding a monoallylamine in a semi-batch or continuous process over the course of the reaction,
c) reducing the reaction temperature to favor propagation, or
d) increasing the initiator concentration or amount.

Any one, or combination, of these or other methods could improve crosslinking efficiency as measured by residual polymer backbone attached (i.e., pendent) allyl groups in $^{13}$C NMR and reduced allylamine formation in the final polymer. Specifically, by minimizing the number of unreacted allyl groups from the multiallylamine crosslinker, the purity profile and stability profile of the resulting polymer can be improved.

Among the various aspects of the present disclosure, therefore, may be noted a process for the preparation of compositions having therapeutic applications. The process comprises (a) in a first step, forming a poly(allylamine) polymer in the form of beads in a concurrent polymerization and crosslinking reaction mixture comprising a monoallylamine, a multiallylamine, a radical polymerization initiator, a surfactant, an acid, water and an organic solvent system wherein less than 2.5% of the total number of carbon atoms comprised by the crosslinked poly(allylamine) polymer are sp$^2$ allyl carbons, and
(b) in a second step, further crosslinking the poly(allylamine) polymer in a reaction mixture comprising a crosslinking agent, a swelling agent for the poly(allylamine) polymer, and a dispersing solvent system to form a crosslinked poly(allylamine) polymer having a swelling ratio of less than 2.

A further aspect of the present disclosure is a crosslinked poly(allylamine) polymer in bead form comprising the residues of a monoallylamine or a salt thereof and a multiallylamine or a salt thereof wherein sp$^2$ allyl carbons pendent to the crosslinked poly(allylamine) polymer backbone constitute less than 2.5% of the total number of carbon atoms comprised by the crosslinked poly(allylamine) polymer and the crosslinked poly(allylamine) polymer has a swelling ratio of less than 2.

A further aspect of the present disclosure is a pharmaceutical composition comprising a crosslinked poly(allylamine) polymer described herein.

A further aspect of the present disclosure is a composition for treating an acid base disorder comprising a crosslinked poly(allylamine) polymer described herein.

A further aspect of the present disclosure is a crosslinked poly(allylamine) polymer as described herein in a sealed container.

A further aspect of the present disclosure is a pharmaceutical product comprising a crosslinked poly(allylamine) polymer of as described herein in a sealed container comprising a moisture barrier.

A further aspect of the present disclosure is a pharmaceutical product comprising a crosslinked poly(allylamine) polymer as described herein in a sealed container comprising an oxygen barrier.

A further aspect of the present disclosure is a pharmaceutical product comprising a crosslinked poly(allylamine) polymer as described herein in a sealed container comprising a moisture barrier and an oxygen barrier.

A further aspect of the present disclosure is a pharmaceutical product comprising a crosslinked poly(allylamine) polymer as described herein in a sealed sachet.

A further aspect of the present disclosure is a pharmaceutical product comprising a crosslinked poly(allylamine) polymer as described herein in a sealed container comprising a polymer, metal, glass or ceramic material.

A further aspect of the present disclosure is a pharmaceutical product comprising a sealed container containing a crosslinked poly(allylamine) polymer as described herein and an inert atmosphere.

A further aspect of the present disclosure is a pharmaceutical product comprising a sealed container and a crosslinked poly(allylamine) polymer as described herein within the sealed container, the sealed container comprising a multi-layer laminate of an inner contact layer, an outer layer; and a barrier layer disposed between the contact layer and outer layer.

A further aspect of the present disclosure is a pharmaceutical product comprising a sealed container and a crosslinked poly(allylamine) polymer as described herein within the sealed container, the sealed container comprising a multi-layer laminate of an inner contact layer, an outer layer; and an oxygen-barrier layer disposed between the contact layer and outer layer.

A further aspect of the present disclosure is a pharmaceutical product comprising a sealed container and a crosslinked poly(allylamine) polymer as described herein within the sealed container, the sealed container comprising a multi-layer laminate of an inner contact layer, an outer layer; and a moisture-barrier layer disposed between the contact layer and outer layer.

A further aspect of the present disclosure is a pharmaceutical product comprising a sealed container and a crosslinked poly(allylamine) polymer as described herein within the sealed container, the sealed container comprising a multi-layer laminate of an inner contact layer, an outer layer; and an oxygen-barrier layer and a moisture-barrier layer disposed between the contact layer and outer layer.

A further aspect of the present disclosure is a pharmaceutical product comprising a sealed container and a crosslinked poly(allylamine) polymer as described herein within the sealed container, the sealed container comprising a multi-layer laminate of an inner contact layer, an outer layer; and an oxygen-scavenging layer disposed between the contact layer and the outer layer.

A further aspect of the present disclosure is a method of treating an acid/base disorder in an animal by oral administration of a pharmaceutical composition comprising a crosslinked poly(allylamine) as described herein.

A further aspect of the present disclosure is a method of treating an individual afflicted with an acid-base disorder characterized by a baseline serum bicarbonate value of less than 22 mEq/l, the method comprising oral administration of a daily dose of a pharmaceutical composition comprising a crosslinked poly(allylamine) as described herein having the capacity to bind at least 5 mEq of a target species as it transits the digestive system to achieve a clinically significant increase in the serum bicarbonate value of at least 1 mEq/l from baseline within a treatment period not greater than 1 month, the target species being selected from the group consisting of protons, strong acids, and conjugate bases of strong acids.

Other aspects and features will be in part apparent and in part pointed out hereinafter.

Abbreviations and Definitions

The following definitions and methods are provided to better define the present invention and to guide those of ordinary skill in the art in the practice of the present invention. Unless otherwise noted, terms are to be understood according to conventional usage by those of ordinary skill in the relevant art. The term "absorption capacity" as used herein in connection with a polymer and a swelling agent (or in the case of a mixture of swelling agents, the mixture of swelling agents) is the amount of the swelling agent (or such mixture) absorbed during a period of at least 16 hours at room temperature by a given amount of a dry polymer (e.g., in the form of a dry bead) immersed in an excess amount of the swelling agent (or such mixture).

The abbreviations appearing in the following table shall have the indicated meaning:

| Abbreviation | Meaning |
| --- | --- |
| AA | Allylamine ($CH_2CHCH_2NH_2$) |
| AA at release | The amount of allylamine upon first isolating the polymer at the point of completion of manufacture |
| AA Stability | The amount (ppm) of allylamine formed per day in either the "In-Air Stability Assay (Stability Assay 1)", the "Heated Stability Assay (Stability assay 2)", or the "Stability assessment when packaged in a MylarFoil sachet assay (Stability Assay 3)" |
| AME | Allylmethylether ($CH_2CHCH_2OCH_3$) |
| AME at release | The amount of allylmethylether upon first isolating the polymer at the point of completion of manufacture |
| AOH | Allylalcohol ($CH_2CHCH_2OH$) |
| AOH at release | The amount of allylalcohol upon first isolating the polymer at the point of completion of manufacture |
| DCE | 1,2-dichloroethane ($ClCH_2CH_2Cl$) |
| DCE at release | The amount 1,2-dichloroethane upon first isolating the polymer at the point of completion of manufacture |
| DCP | 1,3-dichloropropane ($ClCH_2CH_2CH_2Cl$) |

The term "acrylamide" denotes a moiety having the structural formula $H_2C\!=\!CH\!-\!C(O)NR\!-\!*$, where * denotes the point of attachment of the moiety to the remainder of the molecule and R is hydrogen, hydrocarbyl, or substituted hydrocarbyl.

The term "acrylic" denotes a moiety having the structural formula $H_2C\!=\!CH\!-\!C(O)O\!-\!*$, where * denotes the point of attachment of the moiety to the remainder of the molecule.

The term "alicyclic", "alicyclo" or "alicyclyl" means a saturated monocyclic group of 3 to 8 carbon atoms and includes cyclopentyl, cyclohexyl, cycloheptyl, and the like.

The term "adult" refers to an individual over 18 years of age.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n-butyl, isobutyl, sec-butyl, tert-butyl, pentyl, iso-amyl, hexyl and the like, and alkenyl moieties of comparable chain length.

The term "alkanol" denotes an alkyl moiety that has been substituted with at least one hydroxyl group. In some embodiments, alkanol groups are "lower alkanol" groups comprising one to six carbon atoms, one of which is attached to an oxygen atom. In other embodiments, lower alkanol groups comprise one to three carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about four carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkyl group" as used, either alone or within other terms such as "haloalkyl group," "am inoalkyl group" and "alkylamino group", encompasses saturated linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkylamino group" refers to amino groups directly attached to the remainder of the molecule via the nitrogen atom of the amino group and wherein the nitrogen atom of the alkylamino group is substituted by one or two alkyl groups. In some embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino, pentamethyleneamine and the like.

The term "allyl" as used herein denotes a moiety having the structural formula $H_2C\!=\!CH\!-\!CH_2\!-\!$, where * denotes the point of attachment of the moiety to the remainder of the molecule. In some embodiments, the point of attachment * is to a heteroatom in the remainder of the molecule, such as nitrogen.

The term "allyl equivalents" as used herein means the total number of moles of allyl groups comprised by a monoallylamine monomer and a multiallylamine crosslinker, in combination, present in a reaction mixture.

The term "allylamine" denotes a moiety having the structural formula $H_2C=CH-CH_2N(X_8)(X_9)$, wherein $X_8$ and $X_9$ are independently hydrogen, hydrocarbyl, or substituted hydrocarbyl, or $X_8$ and $X_9$ taken together form a substituted or unsubstituted alicyclic, aryl, or heterocyclic moiety, each as defined in connection with such term, typically having from 3 to 8 atoms in the ring.

The term "amine" or "amino" as used alone or as part of another group, represents a group of formula $-N(X_8)(X_9)$, wherein $X_8$ and $X_9$ are independently hydrogen, hydrocarbyl, or substituted hydrocarbyl, heteroaryl, or heterocyclo, or $X_8$ and $X_9$ taken together form a substituted or unsubstituted alicyclic, aryl, or heterocyclic moiety, each as defined in connection with such term, typically having from 3 to 8 atoms in the ring.

The term "amine-reactive functional groups" encompasses functional groups that are susceptible to reaction with an amine moiety. For example, a halogen, such as chloride, may act as an amine-reactive functional group in an $S_N2$ reaction.

The term "aminoalkyl group" encompasses linear or branched alkyl groups having one to about ten carbon atoms, any one of which may be substituted with one or more amino groups, directly attached to the remainder of the molecule via an atom other than a nitrogen atom of the amine group(s). In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 5 to 10 carbon atoms, typically 5 to 7 carbon atoms, and more typically 5 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The phrase "at release" shall mean in the as-manufactured state at the point of completion of manufacture.

A "batch process" as used herein denotes a process in which the reactants are fed into a reactor, the reaction is carried out, and the reaction product is removed from the reactor at the conclusion of the reaction.

The term "bead" is used to describe a crosslinked polymer that is substantially spherical in shape.

The term "bicarbonate equivalent" is used to describe an organic acid or anion that yields bicarbonate when metabolized. Citrate and succinate are exemplary bicarbonate equivalents.

The term "binds" as used herein in connection with a polymer and one or more ions, that is, a cation (e.g. proton-binding" polymer) and an anion, is an "ion-binding" polymer and/or when it associates with the ion, generally though not necessarily in a non-covalent manner, with sufficient association strength that at least a portion of the ion remains bound under the in vitro or in vivo conditions in which the polymer is used for sufficient time to effect a removal of the ion from solution or from the body.

In certain embodiments, the term "clinically significant increase" as used herein in connection with a treatment refers to a treatment that improves or provides a worthwhile change in an individual from a dysfunctional state back to a relatively normal functioning state, or moves the measurement of that state in the direction of normal functioning, or at least a marked improvement to untreated. A number of methods can be used to calculate clinical significance. A non-exhaustive list of methods for calculating clinical significance includes: Jacobson-Truax, Gulliksen-Lord-Novick, Edwards-Nunnally, Hageman-Arrindell, and Hierarchical Linear Modeling (HLM).

A "continuous process" as used herein denotes a process in which one or more reactants are continuously fed into a reactor and a reaction product emerges as a continuous stream of product.

The term "crosslinker" as used, either alone or within other terms, encompasses hydrocarbyl or substituted hydrocarbyl, linear or branched molecules capable of reacting with any of the described monomers, or the infinite polymer network, as described in Formula 1, more than one time. The reactive group in the crosslinker can include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, α,β-unsaturated carbonyls, ketones, aldehydes, pentafluoroaryl groups, vinyl, allyl, acrylate, methacrylate, acrylamide, methacrylamide, styrenic, acrylonitriles and combinations thereof. In one exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

The term "diallylamine" denotes an amino moiety having two allyl groups.

The terms "dry bead" and "dry polymer" refer to beads or polymers that contain no more than 5% by weight of a non-polymer swelling agent or solvent. Often the swelling agent/solvent is water remaining at the end of a purification. This is generally removed by lyophilization or oven drying before storage or further crosslinking of a preformed poly (allylamine) polymer. The amount of swelling agent/solvent can be measured by heating (e.g., heating to 100-200° C.) and measuring the resulting change in weight. This is referred to a "loss on drying" or "LOD."

The term "ethereal" denotes a moiety having an oxygen bound to two separate carbon atoms as depicted the structural formula $*-H_xC-O-CH_x-*$, where * denotes the point of attachment to the remainder of the moiety and x independently equals 0, 1, 2, or 3.

The term "gel" is used to describe a crosslinked polymer that has an irregular shape.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "heteroaliphatic" describes a chain of 1 to 25 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., —CH(OH)—CH(NH$_2$)— where the carbon atom is a member of a chain of atoms) or it may be one of the chain atoms (e.g., —ROR— or —RNHR— where each R is aliphatic). Heteroaliphatic encompasses heteroalkyl and heterocyclo but does not encompass heteroaryl.

The term "heteroalkyl" describes a fully saturated heteroaliphatic moiety.

The term "heteroaryl" means a monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. "Heteroarylene" means a divalent heteroaryl radical.

The term "heteroatom" means an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The term "heterocyclo," "heterocyclic," or heterocyclyl means a saturated or unsaturated group of 4 to 8 ring atoms in which one or two ring atoms are heteroatom such as N, O, B, P and S(O)$_n$, where n is an integer from 0 to 2, the remaining ring atoms being carbon. Additionally, one or two ring carbon atoms in the heterocyclyl ring can optionally be replaced by a —C(O)— group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

"Initiator" is a term used to describe a reagent that initiates a polymerization.

The term "molecular weight per nitrogen" or "MW/N" represents the calculated molecular weight in the polymer per nitrogen atom. It represents the average molecular weight to present one amine function within the crosslinked polymer. It is calculated by dividing the mass of a polymer sample by the moles of nitrogen present in the sample. "MW/N" is the inverse of theoretical capacity, and the calculations are based upon the feed ratio, assuming full reaction of crosslinker and monomer. The lower the molecular weight per nitrogen the higher the theoretical capacity of the crosslinked polymer.

The term "monoallylamine" denotes an amino moiety having one allyl group.

The term "multiallylamine" denotes an amino moiety having two or more allyl groups and includes, for example, diallylamines, triallylamines, etc.

The term "nonabsorbable" as used herein takes its normal meaning in the art. Therefore, if something is nonabsorbable it is not absorbed during its passage through the human GI tract. This could be measured by any appropriate means. One option known to the skilled person would be to examine faeces to see if the nonabsorbable material is recovered after passing through the GI tract. As a practical matter, the amount of a nonabsorbable material recovered in this scenario will never be 100% of the material administered. For example, about 90-99% of the material might be recovered from the faeces. Another option known to the skilled person would be to look for the presence of the material in the lymph, blood, interstitial fluid, secretions from various organs (e.g., pancreas, liver, gut, etc.) or in the body of organs (e.g., liver, kidney, lungs, etc.) as oral administration of a nonabsorbable material would not result in an increase in the amount of that material in these matrices and tissues. Nonabsorbable compositions may be particulate compositions that are essentially insoluble in the human GI tract and have a particle size that is large enough to avoid passive or active absorption through the human GI tract. As an example, nonabsorbable compositions is meant to imply that the substance does not enter the lymph, blood, interstitial fluids or organs through the main entry points of the human GI tract, namely by paracellular entry between gut epithelial cells, by endocytic uptake through gut epithelial cells, or through entry via M cells comprising the gut epithelial antigen sampling and immune surveillance system (Jung, 2000), either through active or passive transport processes. There is a known size limit for a particulate to be absorbed in the human GI tract (Jung et al., European Journal of Pharmaceutics and Biopharmaceutics 50 (2000) 147-160; Jani et al., Internation. Journal of Pharmaceutics, 84 (1992) 245-252; and Jani et al., J. Pharm. Pharmacol. 1989, 41:809-812), so the skilled person would know that materials that, when in the GI tract, have a size of at least 1 micrometers would be nonabsorbable.

"Optional" or "optionally" means that the subsequently described event or circumstance may but need not occur, and that the description includes instances where the event or circumstance occurs and instances in which it does not. For example, "heterocyclyl group optionally substituted with an alkyl group" means that the alkyl may but need not be present, and the description includes embodiments in which the heterocyclyl group is substituted with an alkyl group and embodiments in which the heterocyclyl group is not substituted with alkyl.

The term "partially incorporated multiallylamine residue" as used herein denotes the residue of a multiallylamine that (i) has been incorporated into a poly(allylamine) polymer and (ii) possesses at least one pendant allyl group (i.e., at least one allyl group that did not participate in a reaction to become a chain atom of and is merely "dangling" from the poly(allylamine) polymer backbone chain). For example, a partially incorporated diallylamine residue is the residue of a diallylamine in which one of the two allyl groups of the incorporated diallylamine is a pendant allyl group of the polymer chain.

"Particle size" is measured by wet laser diffraction using Mie theory. Particles are dispersed in an appropriate solvent, such as water or methanol, and added to the sample chamber to achieve red channel obscuration of 10-20%. Sonication may be performed, and a dispersing agent, such as a surfactant (e.g. Tween-80), may be added in order to disrupt weak particle-particle interactions. The refractive index setting of the particles used for size distribution calculation is selected to minimize artifacts in the results and the R parameter value, determined by the laser diffraction software. The D(0.1), D(0.5), and D(0.9) values characterizing the particle size distribution by volume-basis are recorded.

"Pharmaceutically acceptable" as used in connection with a carrier, diluent or excipient means a carrier, diluent or an excipient, respectively, that is useful in preparing a pharmaceutical composition that is generally safe, non-toxic and neither biologically nor otherwise undesirable for veterinary use and/or human pharmaceutical use.

The term "post polymerization crosslinking" is a term that describes a reaction to an already formed bead or gel, where more crosslinking is introduced to the already formed bead or gel to create a bead or gel that has an increased amount of crosslinking.

The term "post polymerization modification" is a term that describes a modification to an already formed bead or gel, where a reaction or a treatment introduces an additional functionality. This functionality can be linked either covalently or non-covalently to the already formed bead.

The term "semi-batch process" as used herein denotes refers to a variation of a batch process in which one or more reactants is added intermittently or continuously to the reactor.

"Simulated Gastric Fluid" or "SGF" Assay describes a test to determine total chloride binding capacity for a test polymer using a defined buffer that simulates the contents of gastric fluid as follows: Simulated gastric fluid (SGF) consists of 35 mM NaCl, 63 mM HCl, pH 1.2. To perform the assay, the free-amine polymer being tested is prepared at a concentration of 2.5 mg/ml (25 mg dry mass) in 10 mL of SGF buffer. The mixture is incubated at 37° C. overnight for ~12-16 hours with agitation on a rotisserie mixer. Unless another time period is otherwise stated, SGF binding data or binding capacities recited herein are determined in a time period of this duration. After incubation and mixing, the tubes containing the polymer are centrifuged for 2 minutes at 500-1000×g to pellet the test samples. Approximately 750 microliters of supernatant are removed and filtered using an appropriate filter, for example a 0.45 micrometer pore-size syringe filter or an 800 microliter, 1 micrometer pore-size, 96-well, glass filter plate that has been fitted over a 96-well 2 mL collection plate. With the latter arrangement multiple samples tested in SGF buffer can be prepared for analysis, including a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter may be used in lieu of the filter plate, to retrieve ~2-4 mL of filtrate into a 15 mL container. After filtration, the respective filtrates are diluted 4× with water and the chloride content of the filtrate is measured via ion chromatography (IC). The IC method (e.g. Dionex ICS-2100, Thermo Scientific) consists of an AS11 column and a 15 mM KOH mobile phase, an injection volume of 5 microliters, with a run time of 3 minutes, a washing/rinse volume of 1000 microliters, and flow rate of 1.25 mL/min. To determine the chloride bound to the polymer, the following calculation is completed:

$$\frac{(Cl \text{ start} - Cl \text{ eq}) \times 4}{2.5}.$$

Binding capacity expressed as mmol chloride/g polymer: where Cl start corresponds to the starting concentration of chloride in the SGF buffer, Cl eq corresponds to the equilibrium value of chloride in the diluted measured filtrates after exposure to the test polymer, 4 is the dilution factor and 2.5 is the polymer concentration in mg/mi.

"Simulated Small Intestine Inorganic Buffer" or "SIB" is a test to determine the chloride and phosphate binding capacity of free amine test polymers in a selective specific interfering buffer assay (SIB). The chloride and phosphate binding capacity of free amine test polymers was determined using the selective specific interfering buffer assay (SIB) as follows: The buffer used for the SIB assay comprises 36 mM NaCl, 20 mM $NaH_2PO_4$, 50 mM 2-(N-morpholino)ethanesulfonic acid (MES) buffered to pH 5.5. The SIB buffer contains concentrations of chloride, phosphate and pH that are present in the human duodenum and upper gastrointestinal tract (Stevens T, Conwell D L, Zuccaro G, Van Lente F, Khandwala F, Purich E, et al. Electrolyte composition of endoscopically collected duodenal drainage fluid after synthetic porcine secretin stimulation in healthy subjects. Gastrointestinal endoscopy. 2004; 60(3):351-5, Fordtran J, Locklear T. Ionic constituents and osmolality of gastric and small-intestinal fluids after eating. Digest Dis Sci. 1966; 11(7):503-21) and is an effective measure of the selectivity of chloride binding compared to phosphate binding by a polymer. To perform the assay, the free amine polymer being tested is prepared at a concentration of 2.5 mg/ml (25 mg dry mass) in 10 mL of SIB buffer. The mixture is incubated at 37° C. for 1 hour with agitation on an orbital shaker at 200 to 300 rotations per minute. Unless another time period is otherwise stated, SIB binding data or binding capacities recited herein are determined in a time period of this duration. After incubation and mixing, the tubes containing the polymer are centrifuged for 2 minutes at 1000×g to pellet the test samples. 750 microliter of supernatant is removed and filtered using an 800 microliter, 1 micrometer pore-size, 96-well, glass filter plate that has been fitted over a 96-well 2 mL collection plate; with this arrangement multiple samples tested in SIB buffer can be prepared for analysis, including the standard controls of free amine sevelamer, free amine bixalomer and a control tube containing blank buffer that is processed through all of the assay steps. With the samples arrayed in the filter plate and the collection plate fitted on the bottom, the unit is centrifuged at 1000×g for 1 minute to filter the samples. In cases of small sample sets, a syringe filter (0.45 micrometer) may be used in lieu of the filter plate, to retrieve ~2-4 mL of filtrate into a 15 mL vial. After filtration into the collection plate, the respective filtrates are diluted before measuring for chloride or phosphate content. For the measurement of chloride and phosphate, the filtrates under analysis are diluted 4× with water. The chloride and phosphate content of the filtrate is measured via ion chromatography (IC). The IC method (e.g. Dionex ICS-2100, Thermo Scientific) consists of an AS24A column, a 45 mM KOH mobile phase, an injection volume of 5 microliters, with a run time of about 10 minutes, a washing/rinse volume of 1000 microliter, and flow rate of 0.3 mL/min. To determine the chloride bound to the polymer, the following calculation is completed:

$$\text{Binding capacity expressed as mmol chloride/g polymer} = \frac{Cl_{start} - Cl_{final} \times 4}{2.5}$$

where $Cl_{start}$ corresponds to the starting concentration of chloride in the SIB buffer, $Cl_{final}$ corresponds to the final value of chloride in the measured diluted filtrates after exposure to the test polymer, 4 is the dilution factor and 2.5 is the polymer concentration in mg/ml. To determine the phosphate bound to the polymer, the following calculation is completed:

$$\text{Binding capacity expressed as mmol phosphate/g polymer} = \frac{P_{start} - P_{final} \times 4}{2.5}$$

where $P_{start}$ corresponds to the starting concentration of phosphate in the SIB buffer, $P_{final}$ corresponds to the final value of phosphate in the measured diluted filtrates after exposure to the test polymer, 4 is the dilution factor and 2.5 is the polymer concentration in mg/ml.

The term "$sp^2$ allyl carbon" as used herein denotes each of the two $sp^2$ hybridized carbon atoms comprised by an allyl moiety.

The term "substituted hydrocarbyl," "substituted alkyl," "substituted alkenyl," "substituted aryl," "substituted heterocyclo," or "substituted heteroaryl" as used herein denotes hydrocarbyl, alkyl, alkenyl, aryl, heterocyclo, or heteroaryl moieties which are substituted with at least one atom other than carbon and hydrogen, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, keto, acyl, acyloxy, nitro, amino, amido, nitro, cyano, thiol, ketals, acetals, esters and ethers.

"Swelling Ratio" or simply "Swelling" describes the amount of water absorbed by a given amount of polymer divided by the weight of the polymer aliquot. The Swelling Ratio is expressed as: swelling=(g swollen polymer−g dry polymer)/g dry polymer. The method used to determine the Swelling Ratio for any given polymer comprised the following:

a. 50-100 mg of dry (less than 5 weight % water content) polymer is placed into an 11 mL sealable test tube (with screw cap) of known weight (weight of tube=Weight A).

b. Deionized water (10 mL) is added to the tube containing the polymer. The tube is sealed and tumbled for 16 hours (overnight) at room temperature. After incubation, the tube is centrifuged at 3000×g for 3 minutes and the supernatant is carefully removed by vacuum suction. For polymers that form a very loose sediment, another step of centrifugation is performed.

c. After step (b), the weight of swollen polymer plus tube (Weight B) is recorded.

d. Freeze at −40° C. for 30 minutes. Lyophilize for 48 h. Weigh dried polymer and test tube (recorded as Weight C).

e. Calculate g water absorbed per g of polymer, defined as: [(Weight B−Weight A)−(Weight C−Weight A)]/(Weight C−Weight A).

A "target ion" is an ion to which the polymer binds, and usually refers to the major ions bound by the polymer, or the ions whose binding to the polymer is thought to produce the therapeutic effect of the polymer (e.g. proton and chloride binding which leads to net removal of HCl).

The term "theoretical capacity" represents the calculated, expected binding of hydrochloric acid in an "SGF" assay, expressed in mmol/g. The theoretical capacity is based on the assumption that 100% of the amines from the monomer(s) and crosslinker(s) are incorporated in the crosslinked polymer based on their respective feed ratios. Theoretical capacity is thus equal to the concentration of amine functionalities in the polymer (mmol/g). The theoretical capacity assumes that each amine is available to bind the respective anions and cations and is not adjusted for the type of amine formed (e.g. it does not subtract capacity of quaternary amines that are not available to bind proton).

"Therapeutically effective amount" means the amount of a proton-binding crosslinked amine polymer that, when administered to a patient for treating a disease, is sufficient to effect such treatment for the disease. The amount constituting a "therapeutically effective amount" will vary depending on the polymer, the severity of the disease and the age, weight, etc., of the mammal to be treated.

"Treating" or "treatment" of a disease includes (i) inhibiting the disease, i.e., arresting or reducing the development of the disease or its clinical symptoms; or (ii) relieving the disease, i.e., causing regression of the disease or its clinical symptoms. Inhibiting the disease, for example, would include prophylaxis.

The term "triallylamine" denotes an amino moiety having three allyl groups.

The term "vinyl" denotes a moiety having the structural formula $R_xH_yC=CH-*$, where * denotes the point of attachment of the moiety to the remainder of the molecule, and wherein X and Y are independently 0, 1 or 2, such that X+Y=2, and R is hydrocarbyl or substituted hydrocarbyl. In some embodiments, the point of attachment * is to a heteroatom in the remainder of the molecule, such as nitrogen.

The term "water equivalents" means the number of moles of water.

The term "weight percent crosslinker" represents the calculated percentage, by mass, of a polymer sample that is derived from the crosslinker. Weight percent crosslinker is calculated using the feed ratio of the polymerization, and assumes full conversion of the monomer and crosslinker(s). The mass attributed to the crosslinker is equal to the expected increase of molecular weight in the infinite polymer network after reaction (e.g. 1,3-dichloropropane is 113 amu, but only 42 amu are added to a polymer network after crosslinking with DCP because the chlorine atoms, as leaving groups, are not incorporated into the polymer network).

Protocol for Other Assays and Determinations Referenced Herein

Cation IC Extraction Procedure: To a tightly closing vial with capacity between 15 and 50 mL, poly(allylamine) polymer (~1.0 g) is added 10 mL of 1.2 M HCl. The vial is shaken at room temperature for at least 24 hours. The supernatant is filtered through a 0.45 micrometer syringe filter followed by a neutralization column before being analyzed by ion chromatography (IC). The IC (e.g. Dionex ICS-5000, Thermo Scientific) method consists of a CG19 guard column and CS19 analytical column, a methane sulfonic acid (MSA) eluent generator, an injection volume of 25 microliters, with a run time of about 40 minutes and flow rate of 0.3 mL/min. The MSA concentration is 2 mM for 10 minutes, followed by a ramp to 70 mM MSA from 10 to 28 minutes, a hold at 70 mM MSA for 3 minutes, and re-equilibration at 2 mM MSA for 9 minutes. This procedure is used to measure allylamine content of 0.25 ppm or higher. If samples contain less than 0.25 ppm then the extraction supernatant are analyzed by LCMS as described in the following procedure.

To a tightly closing vial with capacity between 15 and 50 mL, polyallylamine polymer (~1.0 g) is added 10 mL of 1.2 M HCl. The vial is shaken at 200 RPM at room temperature for at least 24 hours. The supernatant is filtered through a 0.45 micrometer syringe filter. The sample is diluted two-fold with internal standard (IS), consisting of 10 micrograms/mL diethylamine in 0.1% heptaflurobutyric acid (HFBA) in water. The HPLC method (e.g. Agilent 1260 HPLC) consists of a Acclaim 120 C18 2.1×50 mm column with 5 micrometer particle size, an injection volume of 5 microliters, mobile phase consisting of A) 0.1% HFBA in water and B) 0.1% HFBA in acetonitrile, with a gradient of 0% B for 3 minutes, ramp to 100% B from 3-3.5 minutes, hold at 100% B from 3.5-6 minutes, and equilibration at 0% B until 10 minutes, with a flow rate of 0.4 mL/min. The mass spectrometer (MS) method (e.g. API 4000 triple quadrupole tandem MS) with electrospray ionization with source temperature approximately 500° C. and voltage of 5000 V. in positive ion, multiple reaction monitoring mode with allylamine Q1 and Q3 masses approximately 58.7 and 58.1 amu, respectively and IS Q1 and Q3 masses approximately 74.7 and 73.1 amu. Gas source pressure, collision energy, declustering potential, entrance potential and exit potential are optimized for the instrumentation employed.

Determination of Crosslinker Incorporation by $^{13}C$ NMR: The quantitative $^{13}C$ solid state magic angle spinning (MAS) NMR measurement is performed on a Bruker AVANCE III 800 MHz (18.8 T) standard bore spectrometer, operating at 800.25 MHz and 201.24 MHz for $^{1}H$ and $^{13}C$, respectively, with a 4 mm zirconia rotor system at a spinning frequency of 16 kHz. A single pulse experiment is performed with a 30 degree excitation pulse of 1.2 μs using an 8 s relaxation delay, which is optimized for quantitative analysis, an 8.6 ms acquisition time, and an acumination of about 20,000 scans. 100 kHz proton decoupling was applied during $^{13}C$ data acquisition. The chemical shift is referenced to the TMS standard. Integration of the allyl carbon peaks between 110-150 ppm and alkyl carbon peaks between 0-80 ppm is used to quantitate the percent $sp^2$ allyl carbons of the poly(allylamine) polymer using the following formula:

$$\% \ sp2 \ \text{allyl carbons} = \frac{\text{peak integration (110-150 ppm)}}{\text{peak integration (0-80 ppm)} + \text{peak integration (110-150 ppm)}} \times 100$$

When introducing elements of the present invention or the preferred embodiments(s) thereof, the articles "a", "an", "the" and "said" are intended to mean that there are one or more of the elements. The terms "comprising", "including" and "having" are intended to be inclusive and not exclusive (i.e., there may be other elements in addition to the recited elements).

GC-FID Extraction Procedure: To a tightly closing vial with capacity between 10 and 20 mL, containing poly (allylamine) polymer (~0.1 g) is added 5 mL of acetonitrile. To a second tightly closing vial with capacity between 10 and 20 mL, containing polyallylamine polymer (~1.5 g) is added 5 mL of methanol. The vials are closed and shaken at room temperature at 200 RPM for 24 hours. The supernatant is filtered through a 0.45 micrometer syringe filter before being analyzed by gas chromatography with flame ionization detection (GC-FID). The GC (e.g. Agilent 6890) method consists of an approximately 4 meter DB-1 column, 0.32 mm inner diameter coupled in series with a 30 meter DB-wax column, 0.32 mm inner diameter, with constant helium flow of 2.5 mL/min. Injection of 2 microliters is performed into an inlet at 200 C, with a split ratio of 1:10. The oven gradient program consists of a 5 minute hold at 40 C, followed by a 10 C/min ramp to 180 C, followed by a 20 C/min ramp to 240 C and a hold of 3 minutes. FID acquisition is performed at a temperature of 300 C.

Heated Stability Assay (Stability Assay 2): Into two separate tightly closing vials with capacity between 15 and 50 mL, is massed poly(allylamine) polymer (1.0 g each). The sample from one vial is extracted directly to determine the starting allylamine content according to the Cation IC Extraction Procedure. The remaining sample is sealed tightly, and then put into a convection oven set to 60° C. After 72 hours, the samples are removed from the oven, cooled to 4° C., and then extracted in the same way described by Cation IC Extraction Procedure.

Impurity Analysis at Release Assay: Into three separate tightly closing vials with capacity between 15 and 50 mL, is massed dried poly(allylamine) polymer (1.0 g in the first vial, 1.5 g in the second vial, and 0.1 g into the third vial). The sample from one vial containing 1.0 g poly(allylamine) polymer is extracted to determine the starting allylamine content according to the Cation IC Extraction Procedure. The remaining two samples are extracted to determine the starting allyl methyl ether, and allyl alcohol content according to the GC-FID extraction procedure.

In-Air Stability Assay (Stability Assay 1): To a 35 mL HDPE bottle is added 4.5 g of poly(allylamine) polymer. The bottle is closed, and then stored in a 60% humidity controlled chamber held at 25° C. for 7 days. The bottle is removed from the chamber and the polymer sample extracted to determine allylamine content according to the Cation IC Extraction Procedure.

Stability assessment when packaged in a MylarFoil sachet assay (Stability Assay 3): To a 3-side sealed approximately 2.5"×3" sachet composed of a laminate containing a metal foil layer, is added about 3 g of poly(allylamine) polymer and then the sachet is heat sealed. Multiple sachets of poly(allylamine) polymer are prepared and then placed into individual test chambers that were controlled at 25° C. and 60% relative humidity, and 40° C. and 75% relative humidity for up to 6 months. At the desired time, sachets are removed from each test chamber and the polymer samples are extracted to determine allylamine content according to the Cation IC Extraction Procedure.

EMBODIMENTS

In accordance with one aspect of the present disclosure, the crosslinked poly(allylamine) polymers disclosed herein may be used therapeutically. In one embodiment, the crosslinked poly(allylamine) polymer may be used to bind clinically significant amounts of a target species from the gastrointestinal tract of an animal including, for example, humans, upon administration of a therapeutically effective amount (i.e., an effective dose) of the crosslinked poly(allylamine) polymer to achieve a therapeutic or prophylactic benefit. For example, in one embodiment the crosslinked poly(allylamine) polymer may be used to bind clinically significant amounts of bile acids as described in U.S. Pat. No. 5,607,669 (Mandeville et al.). In another embodiment, the crosslinked poly(allylamine) polymer may be used to bind clinically significant amounts of phosphate as described in U.S. Pat. No. 8,394,416B2 (Bianchi et al.) or U.S. Patent Publication No. 2010/0189679 (Inoue et al.). In another embodiment, the crosslinked poly(allylamine) polymer may be used to bind clinically significant amounts of (i) protons, (ii) the conjugate base(s) of one or more strong acids, and/or (iii) one or more strong acids (e.g., HCl and/or $H_2SO_4$).

In accordance with one aspect of the present disclosure, a crosslinked poly(allylamine) polymer may be formed in steps: a (first) concurrent polymerization and crosslinking step (sometimes referred to as the "first crosslinking step" or, more simply, the "first step") and, optionally, a (second) post-polymerization crosslinking step (sometimes referred to as the "second crosslinking step" or, more simply, the "second step"). In the first step, the crosslinking is preferably capacity-sparing, i.e., free amine sparing, crosslinking from carbon to carbon. In the second step, the crosslinking is amine-consuming and is directed towards tuning for selectivity for the target species. Based on the desired high capacity, the C—N ratio is preferably optimized to maximize amine functionalities for target species binding, while still maintaining a spherical polymer particle of controlled particle size to ensure non absorption and acceptable mouth feel that is stable under GI conditions. It should be noted that the terms "first" and "second" are merely used to designate relative order as between these two steps, and that other steps may be contemplated as part of the process, either before, after, or between the "first step" and the "second step."

In the first step, a monoallylamine monomer and a multiallylamine crosslinker are concurrently polymerized and crosslinked in a heterogeneous reaction mixture comprising the monoallylamine monomer, the multiallylamine crosslinker, a radical initiator, water and an organic solvent to form a polymer network that is crosslinked through a carbon backbone. Advantageously, each crosslinking reaction in this step forms a carbon-carbon bond (as opposed to substitution reactions in which a carbon-heteroatom bond is formed during crosslinking), and the amine functionalities of the monoallylamine monomer and the multiallylamine crosslinker do not undergo crosslinking reactions and are preserved in the final polymer (i.e., primary amines of the monoallylamine monomer and the multiallylamine crosslinker remain primary, secondary amines remain secondary, and tertiary amines remain tertiary). The resulting poly(allylamine) polymer may then be further crosslinked in a second step with a crosslinking agent possessing amine-reactive moieties.

As previously noted, unincorporated monoallylamine (i.e., monoallylamine that is not covalently incorporated into the polymer) and partially incorporated multiallylamine residues can be a source of allylamine impurities (i.e., allylamine and derivatives thereof such as allylalkylethers and allylalcohols) in the poly(allylamine) product. In accordance with one embodiment of the present disclosure, process parameters may be controlled to limit the amount of allyl impurities (i) released by the crosslinked poly(allylamine) polymer in the as-manufactured state (i.e., upon completion of the second step, also sometimes referred to herein as "at-release")), and/or (ii) released by the crosslinked poly(allylamine) polymer as a function of storage and time.

In general, it is preferred that the crosslinked poly(allylamine) polymer contain less than 20 ppm allylamine in the as-manufactured state. For example, in one embodiment the crosslinked poly(allylamine) polymer contains less than 15 ppm allylamine in the as-manufactured state. By way of further example, in one such embodiment the crosslinked poly(allylamine) polymer contains less than 12.5 ppm allylamine in the as-manufactured state. By way of further example, in one such embodiment the crosslinked poly(allylamine) polymer contains less than 10 ppm allylamine in the as-manufactured state. By way of further example, in one such embodiment the crosslinked poly(allylamine) polymer contains less than 7.5 ppm allylamine in the as-manufactured state. By way of further example, in one such embodiment the crosslinked poly(allylamine) polymer contains less than 5 ppm allylamine in the as-manufactured state. By way of further example, in one such embodiment the crosslinked poly(allylamine) polymer contains less than 4 ppm allylamine in the as-manufactured state. By way of further example, in one such embodiment the crosslinked poly(allylamine) polymer contains less than 3 ppm allylamine in the as-manufactured state. By way of further example, in one such embodiment the crosslinked poly(allylamine) polymer contains less than 2 ppm allylamine in the as-manufactured state. By way of further example, in one such embodiment the crosslinked poly(allylamine) polymer contains less than 1 ppm allylamine in the as-manufactured state. By way of further example, in one such embodiment the crosslinked poly(allylamine) polymer contains less than 500 ppb allylamine in the as-manufactured state. By way of further example, in one such embodiment the crosslinked poly(allylamine) polymer contains less than 100 ppb allylamine in the as-manufactured state. By way of further example, in one such embodiment the crosslinked poly(allylamine) polymer contains less than 50 ppb allylamine in the as-manufactured state. By way of further example, in one such embodiment the crosslinked poly(allylamine) polymer contains less than 1 ppb allylamine in the as-manufactured state. By way of further example, in one such embodiment the amount of allylamine, if any, in the crosslinked poly(allylamine) polymer is less than the detection limit for allylamine in the as-manufactured state. In each such exemplary embodiment recited in this paragraph, the allylamine content may be determined by the Impurity Analysis at Release Assay followed by the Cation IC Extraction Procedure.

In one embodiment, the crosslinked poly(allylamine) polymer has a stability profile such that upon storage in a sealed enclosure for 3 months at 25° C. after manufacture the crosslinked poly(allylamine) polymer contains less than 20 ppm allylamine. For example, in one embodiment the crosslinked poly(allylamine) polymer contains less than 15 ppm allylamine upon storage in a sealed enclosure for 3 months at 25° C. after manufacture. By way of further example, in one such embodiment the crosslinked poly(allylamine) polymer contains less than 12.5 ppm allylamine upon storage in a sealed enclosure for 3 months at 25° C. after manufacture. By way of further example, in one such embodiment the crosslinked poly(allylamine) polymer contains less than 10 ppm allylamine upon storage in a sealed enclosure for 3 months at 25° C. after manufacture. By way of further example, in one such embodiment the crosslinked poly(allylamine) polymer contains less than 7.5 ppm allylamine upon storage in a sealed enclosure for 3 months at 25° C. after manufacture. By way of further example, in one such embodiment the crosslinked poly(allylamine) polymer contains less than 5 ppm allylamine upon storage in a sealed enclosure for 3 months at 25° C. after manufacture. By way of further example, in one such embodiment the crosslinked poly(allylamine) polymer contains less than 4 ppm allylamine upon storage in a sealed enclosure for 3 months at 25° C. after manufacture. By way of further example, in one such embodiment the crosslinked poly(allylamine) polymer contains less than 3 ppm allylamine upon storage in a sealed enclosure for 3 months at 25° C. after manufacture. By way of further example, in one such embodiment the crosslinked poly(allylamine) polymer contains less than 2 ppm allylamine upon storage in a sealed enclosure for 3 months at 25° C. after manufacture. By way of further example, in one such embodiment the crosslinked poly(allylamine) polymer contains less than 1 ppm allylamine upon storage in a sealed enclosure for 3 months at 25° C. after manufacture. By way of further example, in one such embodiment the crosslinked poly(allylamine) polymer contains less than 500 ppb allylamine upon storage in a sealed enclosure for 3 months at 25° C. after manufacture. By way of further example, in one such embodiment the crosslinked poly(allylamine) polymer contains less than 100 ppb allylamine upon storage in a sealed enclosure for 3 months at 25° C. after manufacture. By way of further example, in one such embodiment the crosslinked poly(allylamine) polymer contains less than 50 ppb allylamine upon storage in a sealed enclosure for 3 months at 25° C. after manufacture. By way of further example, in one such embodiment the crosslinked poly(allylamine) polymer contains less than 1 ppb allylamine upon storage in a sealed enclosure for 3 months at 25° C. after manufacture. By way of further example, in one such embodiment the amount of allylamine, if any, in the crosslinked poly(allylamine) polymer is less than the detection limit for allylamine upon storage in a sealed enclosure for 3 months at 25° C. after manufacture. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 6 months at 25° C. after manufacture the crosslinked poly(allylamine) polymer contains less than 20 ppm allylamine. For example, in one embodiment the crosslinked poly(allylamine) polymer contains less than 15 ppm allylamine upon storage in a sealed enclosure for 6 months at 25° C. after manufacture. By way of further example, in one such embodiment the crosslinked poly(allylamine) polymer contains less than 12.5 ppm allylamine upon storage in a sealed enclosure for 6 months at 25° C. after manufacture. By way of further example, in one such embodiment the crosslinked poly(allylamine) polymer contains less than 10 ppm allylamine upon storage in a sealed enclosure for 6 months at 25° C. after manufacture. By way of further example, in one such embodiment the crosslinked poly(allylamine) polymer contains less than 7.5 ppm allylamine upon storage in a sealed enclosure for 6 months at 25° C. after manufacture. By way of further example, in one such embodiment the crosslinked poly(allylamine) polymer contains less than 5 ppm allylamine upon storage in a sealed enclosure for 6 months at 25° C. after manufacture. By way of further example, in one such embodiment the crosslinked poly(allylamine) polymer contains less than 4 ppm allylamine upon storage in a sealed enclosure for 6 months at 25° C. after manufacture. By way of further example, in one such embodiment the crosslinked poly(allylamine) polymer contains less than 3 ppm allylamine upon storage in a sealed enclosure for 6 months at 25° C. after manufacture. By way of further example, in one such embodiment the crosslinked poly(allylamine) polymer contains less than 2 ppm allylamine upon storage in a sealed enclosure for 6 months at 25° C. after manufacture. By way of further example, in one such embodiment the crosslinked poly(allylamine) polymer contains less than 1 ppm allylamine upon storage in a sealed enclosure for 6 months at 25° C. after manufacture. By way of further example, in one such embodiment the crosslinked poly(allylamine) polymer contains less than 500 ppb allylamine upon storage in a sealed enclosure for 6 months at 25° C. after manufacture. By way of further example, in one such embodiment the crosslinked poly(allylamine) polymer contains less than 100 ppb allylamine upon storage in a sealed enclosure for 6 months at 25° C. after manufacture. By way of further example, in one such embodiment the crosslinked poly(allylamine) polymer contains less than 50 ppb allylamine upon storage in a sealed enclosure for 6 months at 25° C. after manufacture. By way of further example, in one such embodiment the crosslinked poly(allylamine) polymer contains less than 1 ppb allylamine upon storage in a sealed enclosure for 6 months at 25° C. after manufacture. By way of further example, in one such embodiment the amount of allylamine, if any, in the crosslinked poly(allylamine) polymer is less than the detection limit for allylamine upon storage in a sealed enclosure for 6 months at 25° C. after manufacture. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 9 months at 25° C. after manufacture the crosslinked poly(allylamine) polymer contains less than 20 ppm allylamine. For example, in one embodiment the crosslinked poly(allylamine) polymer contains less than 15 ppm allylamine upon storage in a sealed enclosure for 9 months at 25° C. after manufacture. By way of further example, in one such embodiment the crosslinked poly(allylamine) polymer contains less than 12.5 ppm allylamine upon storage in a sealed enclosure for 9 months at 25° C. after manufacture. By way of further example, in one such embodiment the crosslinked poly(allylamine) polymer contains less than 10 ppm allylamine upon storage in a sealed enclosure for 9 months at 25° C. after manufacture. By way of further example, in one such embodiment the crosslinked poly(allylamine) polymer contains less than 7.5 ppm allylamine upon storage in a sealed enclosure for 9 months at 25° C. after manufacture. By way of further example, in one such embodiment the crosslinked poly(allylamine) polymer contains less than 5 ppm allylamine upon storage in a sealed enclosure for 9 months at 25° C. after manufacture. By way of further example, in one such embodiment the crosslinked poly(allylamine) polymer contains less than 4 ppm allylamine upon storage in a sealed enclosure for 9 months at 25° C. after manufacture. By way of further example, in one such embodiment the crosslinked poly(allylamine) polymer contains less than 3 ppm allylamine upon storage in a sealed enclosure for 9 months at 25° C. after manufacture. By way of further example, in one such embodiment the crosslinked poly(allylamine) polymer contains less than 2 ppm allylamine upon storage in a sealed enclosure for 9 months at 25° C. after manufacture. By way of further example, in one such embodiment the crosslinked poly(allylamine) polymer contains less than 1 ppm allylamine upon storage in a sealed enclosure for 9 months at 25° C. after manufacture. By way of further example, in one such embodiment the crosslinked poly(allylamine) polymer contains less than 500 ppb allylamine upon storage in a sealed enclosure for 9 months at 25° C. after manufacture. By way of further example, in one such embodiment the crosslinked poly(allylamine) polymer contains less than 100 ppb allylamine upon storage in a sealed enclosure for 9 months at 25° C. after manufacture. By way of further example, in one such embodiment the crosslinked poly(allylamine) polymer contains less than 50 ppb allylamine upon storage in a sealed enclosure for 9 months at 25° C. after manufacture. By way of further example, in one such embodiment the crosslinked poly(allylamine) polymer contains less than 1 ppb allylamine upon storage in a sealed enclosure for 9 months at 25° C. after manufacture. By way of further example, in one such embodiment the amount of allylamine, if any, in the crosslinked poly(allylamine) polymer is less than the detection limit for allylamine upon storage in a sealed enclosure for 9 months at 25° C. after manufacture. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 12 months at 25° C. after manufacture the crosslinked poly(allylamine) polymer contains less than 20 ppm allylamine. For example, in one embodiment the crosslinked poly(allylamine) polymer contains less than 15 ppm allylamine upon storage in a sealed enclosure for 12 months at 25° C. after manufacture. By way of further example, in one such embodiment the crosslinked poly(allylamine) polymer contains less than 12.5 ppm allylamine upon storage in a sealed enclosure for 12 months at 25° C. after manufacture. By way of further example, in one such embodiment the poly(allylamine) polymer contains less than 10 ppm allylamine upon storage in a sealed enclosure for 12 months at 25° C. after manufacture. By way of further example, in one such embodiment the poly(allylamine) polymer contains less than 7.5 ppm allylamine upon storage in a sealed enclosure for 12 months at 25° C. after manufacture. By way of further example, in one such embodiment the crosslinked poly(allylamine) polymer contains less than 5 ppm allylamine upon storage in a sealed enclosure for 12 months at 25° C. after manufacture. By way of further example, in one such embodiment the crosslinked poly(allylamine) polymer contains less than 4 ppm allylamine upon storage in a sealed enclosure for 12 months at 25° C. after manufacture. By way of further example, in one such embodiment the crosslinked poly(allylamine) polymer contains less than 3 ppm allylamine upon storage in a sealed enclosure for 12 months at 25° C. after manufacture. By way of further example, in one such embodiment the crosslinked poly(allylamine) polymer contains less than 2 ppm allylamine upon storage in a sealed enclosure for 12 months at 25° C. after manufacture. By way of further example, in one such embodiment the crosslinked poly(allylamine) polymer contains less than 1 ppm allylamine upon storage in a sealed enclosure for 12 months at 25° C. after manufacture. By way of further example, in one such embodiment the crosslinked poly(allylamine) polymer contains less than 500 ppb allylamine upon storage in a sealed enclosure for 12 months at 25° C. after manufacture. By way of further example, in one such embodiment the crosslinked poly(allylamine) polymer contains less than 100 ppb allylamine upon storage in a sealed enclosure for 12 months at 25° C. after manufacture. By way of further example, in one such embodiment the crosslinked poly(allylamine) polymer contains less than 50 ppb allylamine upon storage in a sealed enclosure for 12 months at 25° C. after manufacture. By way of further example, in one such embodiment the crosslinked poly(allylamine) polymer contains less than 1 ppb allylamine upon storage in a sealed enclosure for 12 months at 25° C. after manufacture. By way of further example, in one such embodiment the amount of allylamine, if any, in the crosslinked poly(allylamine) polymer is less than the detection limit for allylamine upon storage in a sealed enclosure for 12 months at 25° C. after manufacture. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 3 months at 25° C. the allylamine content of the crosslinked poly(allylamine) polymer increases less than 20 ppm allylamine. For example, in one embodiment the crosslinked poly(allylamine) polymer has a stability profile such that upon storage in a sealed enclosure for 3 months at 25° C. the allylamine content of the crosslinked poly(allylamine) polymer increases less than 15 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 12.5 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 10 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 7.5 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 5 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 4 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 3 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 2 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 1 ppm. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 500 ppb. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 100 ppb. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 50 ppb. By way of further example, in one such embodiment the crosslinked poly(allylamine) polymer has a stability profile such that upon storage in a sealed enclosure for 3 months at 25° C. the allylamine content of the crosslinked poly(allylamine) polymer increases less than 1 ppb. By way of further example, in one such embodiment the crosslinked poly(allylamine) polymer has a stability profile such that upon storage in a sealed enclosure for 3 months at 25° C. there is no detectible increase in the allylamine content of the poly(allylamine) polymer. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 6 months at 25° C. the allylamine content of the crosslinked poly(allylamine) polymer increases less than 20 ppm allylamine. For example, in one embodiment the crosslinked poly(allylamine) polymer has a stability profile such that upon storage in a sealed enclosure for 6 months at 25° C. the allylamine content of the crosslinked poly(allylamine) polymer increases less than 15 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 12.5 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 10 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 7.5 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 5 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 4 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 3 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 2 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 1 ppm. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 500 ppb. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 100 ppb. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 50 ppb. By way of further example, in one such embodiment the crosslinked poly(allylamine) polymer has a stability profile such that upon storage in a sealed enclosure for 6 months at 25° C. the allylamine content of the crosslinked poly(allylamine) polymer increases less than 1 ppb. By way of further example, in one such embodiment the crosslinked poly(allylamine) polymer has a stability profile such that upon storage in a sealed enclosure for 6 months at 25° C. there is no detectible increase in the allylamine content of the poly(allylamine) polymer. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 9 months at 25° C. the allylamine content of the crosslinked poly(allylamine) polymer increases less than 20 ppm allylamine. For example, in one embodiment the crosslinked poly(allylamine) polymer has a stability profile such that upon storage in a sealed enclosure for 9 months at 25° C. the allylamine content of the crosslinked poly(allylamine) polymer increases less than 15 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 12.5 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 10 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 7.5 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 5 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 4 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 3 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 2 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 1 ppm. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 500 ppb. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 100 ppb. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 50 ppb. By way of further example, in one such embodiment the crosslinked poly(allylamine) polymer has a stability profile such that upon storage in a sealed enclosure for 9 months at 25° C. the allylamine content of the crosslinked poly(allylamine) polymer increases less than 1 ppb. By way of further example, in one such embodiment the crosslinked poly(allylamine) polymer has a stability profile such that upon storage in a sealed enclosure for 9 months at 25° C. there is no detectable increase in the allylamine content of the poly(allylamine) polymer. In each such exemplary embodiment recited in this paragraph, the allylamine content may be determined by the Cation IC Extraction Procedure.

In one embodiment, the crosslinked poly(allylamine) polymer has a stability profile such that upon storage in a sealed enclosure for 12 months at 25° C. the allylamine content of the crosslinked poly(allylamine) polymer increases less than 20 ppm allylamine. For example, in one embodiment the crosslinked poly(allylamine) polymer has a stability profile such that upon storage in a sealed enclosure for 12 months at 25° C. the allylamine content of the crosslinked poly(allylamine) polymer increases less than 15 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 12.5 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 10 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 7.5 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 5 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 4 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 3 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 2 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 1 ppm. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 500 ppb. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 100 ppb. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 50 ppb. By way of further example, in one such embodiment the crosslinked poly(allylamine) polymer has a stability profile such that upon storage in a sealed enclosure for 12 months at 25° C. the allylamine content of the crosslinked poly(allylamine) polymer increases less than 1 ppb. By way of further example, in one such embodiment the crosslinked poly(allylamine) polymer has a stability profile such that upon storage in a sealed enclosure for 12 months at 25° C. there is no detectable increase in the allylamine content of the poly(allylamine) polymer. In each such exemplary embodiment recited in this paragraph, the allylamine content may be determined by the Cation IC Extraction Procedure.

In some embodiments, the crosslinked poly(allylamine) comprises the residue of a monoallylamine corresponding to Formula 1 or a salt thereof:

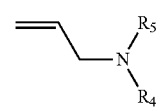

Formula 1 wherein $R_4$ and $R_5$ are independently hydrogen, hydrocarbyl, or substituted hydrocarbyl. In one embodiment, for example, $R_4$ and $R_5$ are independently hydrogen, saturated hydrocarbon, unsaturated aliphatic, aryl, heteroaryl, unsaturated heteroaliphatic, heterocyclic, or heteroalkyl. By way of further example, in one such embodiment $R_4$ and $R_5$ are independently hydrogen, aliphatic, heteroaliphatic, aryl, or heteroaryl. By way of further example, in one such embodiment $R_4$ and $R_5$ are independently hydrogen, alkyl, alkenyl, vinyl, aryl, aminoalkyl, alkanol, haloalkyl, hydroxyalkyl, ethereal, heteroaryl or heterocyclic. By way of further example, in one such embodiment $R_4$ and $R_5$ are independently hydrogen, alkyl, aminoalkyl, alkanol, aryl, haloalkyl, hydroxyalkyl, ethereal, or heterocyclic. By way of further example, in one such embodiment $R_4$ and $R_5$ (in combination with the nitrogen atom to which they are attached) together constitute part of a ring structure, so that the monomer as described by Formula 1 is a nitrogen-containing heterocycle (e.g., piperidine). By way of further example, in one embodiment $R_4$ and $R_5$ are independently hydrogen, aliphatic or heteroaliphatic. By way of further example, in one embodiment $R_4$ and $R_5$ are independently hydrogen, or aminoalkyl. By way of further example, in one embodiment $R_4$ and $R_5$ are hydrogen. In each of the foregoing embodiments recited in this paragraph, the residue may be the residue of a salt of the monoallylamine of Formula 1, e.g., the residue of a hydrochloric acid salt, sulfuric acid salt, phosphoric acid salt, hydrobromic acid salt or a combination thereof.

In some embodiments, the crosslinked poly(allylamine) polymer comprises the residue of a multiallylamine corresponding to Formula 3 or a salt thereof:

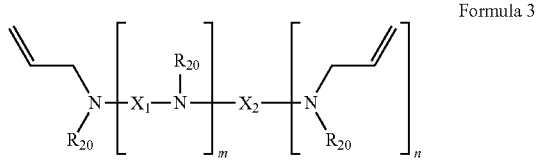

Formula 3 wherein each $R_{20}$ is hydrogen, hydrocarbyl or substituted hydrocarbyl, each $X_1$ is independently hydrocarbyl or substituted hydrocarbyl, $X_2$ is hydrocarbyl or substituted hydrocarbyl, m is a non-negative integer and n is at least 1. For example, in one such embodiment, each $R_{20}$ is independently hydrogen, aliphatic, aryl, heteroaliphatic, or heteroaryl. By way of further example, in one such embodiment each $R_{20}$ is independently hydrogen, aliphatic, or heteroaliphatic. By way of further example, in one such embodiment each $R_{20}$ is independently hydrogen, alkyl, allyl, vinyl, or aminoalkyl. By way of further example, in one such embodiment each $R_{20}$ is independently hydrogen, alkyl, allyl, vinyl, —$(CH_2)_d NH_2$, or —$(CH_2)_d N[(CH_2)_e NH_2)]_2$ where d and e are independently 2-4. In each of the foregoing exemplary embodiments of this paragraph, n may have a value selected from the group consisting of 1-20, 1-15, 1-10, 1-5, 1-2, and 1. In each of the foregoing exemplary embodiments of this paragraph, m may have a value selected from the group consisting of 0-5, 0-4, 0-3, 0-2, and 0-1. By way of further example, in one such embodiment, n is 2-4. In each of the foregoing embodiments recited in this paragraph, the residue may be the residue of a salt of the multiallylamine of Formula 3, e.g., the residue of a hydrochloric acid salt, sulfuric acid salt, phosphoric acid salt, hydrobromic acid salt or a combination thereof.

In certain embodiments, the crosslinked poly(allylamine) polymer comprises the residue of a multiallylamine corresponding to Formula 3A or a salt thereof:

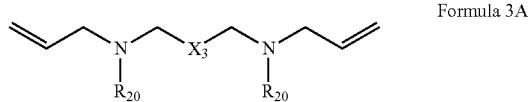

Formula 3A wherein each $R_{20}$ is hydrogen, hydrocarbyl or substituted hydrocarbyl, $X_3$ is —$CH(R_{70})$— or —$CH_2N(R_{70})CH_2$—, and $R_{70}$ is hydrogen, hydroxyl, or aminoalkyl. For example, in one such embodiment, each $R_{20}$ is independently hydrogen, aliphatic, aryl, heteroaliphatic, or heteroaryl. By way of further example, in one such embodiment each $R_{20}$ is independently hydrogen, aliphatic, or heteroaliphatic. By way of further example, in one such embodiment each $R_{20}$ is independently hydrogen, alkyl, allyl, vinyl, or aminoalkyl. By way of further example, in one such embodiment each $R_{20}$ is independently hydrogen, alkyl, allyl, vinyl, —$(CH_2)_d NH_2$, or —$(CH_2)_d N[(CH_2)_e NH_2)]_2$ where d and e are independently 2-4. By way of further example, in one such embodiment $X_3$ is —$CH(R_{70})$—. By way of further example, in one such embodiment $X_3$ is —$CH(R_{70})$— and $R_{70}$ is hydrogen or hydroxy. By way of further example, in one such embodiment $X_3$ is —$CH(R_{70})$— and $R_{70}$ is hydrogen. By way of further example, in one such embodiment $X_3$ is —$CH_2N(R_{70})CH_2$—. By way of further example, in one such embodiment $X_3$ is —$CH_2N(R_{70})CH_2$— and $R_{70}$ is hydrogen or aminoalkyl. By way of further example, in one such embodiment $X_3$ is —$CH_2N(R_{70})CH_2$— and $R_{70}$ is aminoalkyl. By way of further example, in one such embodiment $X_3$ is —$CH_2N(R_{70})CH_2$— and $R_{70}$ is hydrogen. By way of further example, in one such embodiment, n is 2-4. In each of the foregoing embodiments recited in this paragraph, the residue may be the residue of a salt of the multiallylamine of Formula 3A, e.g., the residue of a hydrochloric acid salt, sulfuric acid salt, phosphoric acid salt, hydrobromic acid salt or a combination thereof.

To facilitate the concurrent polymerization and crosslinking reaction, the monoallylamine and the multiallylamine are preferably protonated in the reaction mixture. In one embodiment, therefore, the monoallylamine and/or the multiallylamine are introduced to the reaction mixture as their respective acid salts (e.g., hydrochloric acid, phosphoric acid, sulfuric acid or hydrobromic acid salt form). Alternatively, the monoallylamine and/or the multiallylamine may be introduced to the reaction mixture in their free amine form(s) and acid can be separately added to the reaction mixture. In either embodiment, the reaction mixture comprises sufficient acid to maintain the monoallylamine and the multiallylamine in the aqueous phase. Typically, the reaction mixture will contain at least 0.5 equivalents of acid per allylamine equivalent in the reaction mixture (independent of whether the acid was introduced as the acid salt of the monoallylamine and/or the multiallylamine or whether it was separately added to the reaction mixture). In certain embodiments, the reaction mixture will contain at least 0.75 equivalents of acid per allylamine equivalent in the reaction mixture. In certain embodiments, the reaction mixture will contain at least 1 equivalent of acid per allylamine equivalent in the reaction mixture.

Exemplary monoallylamines (2-Propen-1-ylamine, 1-(Allylamino)-2-aminoethane, and 1[N-Allyl(2-aminoethyl)amino]-2-aminoethane) and exemplary multiallylamine crosslinkers (1,4-Bis(allylamino)butane, 1,2-Bis(allylamino)ethane, 2-(Allylamino)-1-[2-(allylamino)ethylamino]ethane, 1,3-Bis(allylamino)propane, 1,3-Bis(allylamino)-2-propanol and N,N,N-triallylamine) for the synthesis of poly(allylamine) polymers described herein include those listed in Table C. As illustrated, 2-Propen-1-ylamine, 1-(Allylamino)-2-aminoethane, 1-[N-Allyl(2-aminoethyl)amino]-2-aminoethane) and exemplary multiallylamine crosslinkers (1,4-Bis(allylamino)butane, 1,2-Bis (allylamino)ethane, 2-(Allylamino)-1-[2-(allylamino)ethylamino]ethane, 1,3-Bis(allylamino)propane, and 1,3-Bis (allylamino)-2-propanol are in the HCl salt form and N,N,N-triallylamine is illustrated in the free base form. As previously noted, each of these monoallylamines and multiallylamines may be introduced to the reaction mixture in a salt form (e.g., as a hydrochloric acid salt, sulfuric acid salt, phosphoric acid salt, hydrobromic acid salt or a combination thereof), in the free base form, or a combination thereof.

allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl

TABLE C

| Abbreviation | Common name | IUPAC name | Structure | MW (g/mol) |
|---|---|---|---|---|
| DABDA1 | Diallylbutyldiamine | 1,4-Bis(allylamino)butane | | 241.2 |
| DAEDA1 | Diallylethyldiamine | 1,2-Bis(allylamino)ethane | | 213.15 |
| DAEDA2 | Diallyldiethylenetriamine | 2-(Allylamino)-1-[2-(allylamino)ethyl-amino]ethane | | 292.67 |
| DAPDA | Diallylpropyldiamine | 1,3-Bis(allylamino)propane | | 227.17 |
| POHDA | Diallylamineisopropanol | 1,3-Bis(allylamino)-2-propanol | | 243.17 |
| AAH | Allylamine | 2-Propen-1-ylamine | | 93.5 |
| AEAAH | Aminoethylallylamine | 1-(Allylamino)-2-aminoethane | | 173.08 |
| BAEAAH | Bis(2-aminoethyl)allylamine | 1-[N-Allyl(2-aminoethyl)amino]-2-aminoethane | | 252.61 |
| TAA | Triallylamine | N,N,N-triallylamine | | 137.22 |

In certain embodiments, the concurrent polymerization and crosslinking reaction may include one or more other monomers, oligomers or other polymerizable groups in addition to the monoallylamine and the multiallylamine. Such copolymer architectures can include, but are not limited to, block or block-like polymers, graft copolymers, and random copolymers. Non-limiting examples of other comonomers which may be used alone or in combination with the monoallylamine and the multiallylamine in the concurrent polymerization and crosslinking reaction include: styrene, allylamine hydrochloride, substituted monomers and combinations thereof. Functionalized versions of these monomers may also be used. Additional specific monomers or comonomers that may be used in this invention include, but are not limited to, 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacryl amide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinyltether, butadiene, isoprene, chloroprene, ethylene, vinyl acetate, and combinations thereof.

The concurrent polymerization and crosslinking step reaction mixture comprises a radical polymerization initiator in addition to the monoallylamine monomer and the multiallylamine crosslinker. The initiator may be selected from any of a wide range of initiators, including cationic and radical polymerization initiators. Exemplary polymerization initiators for the concurrent polymerization and crosslinking step reaction include peroxy and azo free-radical initiators, such as azodiisobutyronitrile, azodiisovaleronitrile, dimethylazodiisobutyrate, 2,2'azo bis(isobutyronitrile), 2,2'-azobis(N,N'-dimethyl-eneisobutyramidine)dihydrochloride, 2,2'-azobis(2-methylpropionamidine)dihydrochloride, 2,2'-azobis(2-amidinopropane)dihydrochloride, 2,2'-azobis(N,N'-dimethyleneisobutyramidine), 1,1'-azo bis(I-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, dimethyl bis(butylperoxy)hexane.

Experience to-date has shown that the amount of initiator relative to the amount of monoallylamine and multiallylamine in the reaction mixture has an influence on the characteristics of the resulting polymer. For example, the amount of partially incorporated multiallylamine tends to increase as the ratio of the number of allyl equivalents to the number of initiator equivalents in the reaction mixture increases. Typically, therefore, the ratio of the number of allyl equivalents possessed by the monoallylamine and multiallylamine, in combination, to the number of initiator equivalents introduced to the reaction mixture will be in the range of about 6:1 to about 70:1, respectively. For example, in one such embodiment, the ratio of the number of allyl equivalents possessed by the monoallylamine and multiallylamine, in combination, to the number of initiator equivalents introduced to the reaction mixture will be about 7:1 to about 60:1, respectively. By way of further example, in one such embodiment, the ratio of the number of allyl equivalents possessed by the monoallylamine and multiallylamine, in combination, to the number of initiator equivalents introduced to the reaction mixture will be about 8:1 to about 50:1, respectively. By way of further example, in one such embodiment, the ratio of the number of allyl equivalents possessed by the monoallylamine and multiallylamine, in combination, to the number of initiator equivalents introduced to the reaction mixture will be about 10:1 to about 45:1, respectively. By way of further example, in one such embodiment, the ratio of the number of allyl equivalents possessed by the monoallylamine and multiallylamine, in combination, to the number of initiator equivalents introduced to the reaction mixture will be about 15:1 to about 40:1, respectively. By way of further example, in one such embodiment, the ratio of the number of allyl equivalents possessed by the monoallylamine and multiallylamine, in combination, to the number of initiator equivalents introduced to the reaction mixture will be about 17.5:1 to about 35:1, respectively. By way of further example, in one such embodiment, the ratio of the number of allyl equivalents possessed by the monoallylamine and multiallylamine, in combination, to the number of initiator equivalents introduced to the reaction mixture will be about 20:1 to about 30:1, respectively. By way of further example, in one such embodiment, the ratio of the number of allyl equivalents possessed by the monoallylamine and multiallylamine, in combination, to the number of initiator equivalents introduced to the reaction mixture will be about 22.5:1 to about 30:1, respectively. By way of further example, in one such embodiment, the ratio of the number of allyl equivalents possessed by the monoallylamine and multiallylamine, in combination, to the number of initiator equivalents introduced to the reaction mixture will be about 25:1 to about 27.5:1, respectively.

Experience to-date has also shown that the combined amount of monoallylamine and multiallylamine relative to the amount of water in the reaction mixture has an influence on the characteristics of the resulting polymer. Typically, therefore, the weight ratio of the combined amount of monoallylamine and multiallylamine to the amount of water in the reaction mixture will be in the range of about 0.01 to about 3, respectively. For example, in one embodiment the weight ratio of the combined amount of monoallylamine and multiallylamine to the amount of water in the reaction mixture will be in the range of about 0.05 to about 2.75, respectively. By way of further example, in one such embodiment the weight ratio of the combined amount of monoallylamine and multiallylamine to the amount of water in the reaction mixture will be in the range of about 0.07 to about 2.5, respectively. By way of further example, in one such embodiment the weight ratio of the combined amount of monoallylamine and multiallylamine to the amount of water in the reaction mixture will be in the range of about 0.1 to about 2.25, respectively. By way of further example, in one such embodiment the weight ratio of the combined amount of monoallylamine and multiallylamine to the amount of water in the reaction mixture will be in the range of about 0.15 to about 2, respectively. By way of further example, in one such embodiment the weight ratio of the combined amount of monoallylamine and multiallylamine to the amount of water in the reaction mixture will be in the range of about 0.2 to about 1.75, respectively. By way of further example, in one such embodiment the weight ratio of the combined amount of monoallylamine and multiallylamine to the amount of water in the reaction mixture will be in the range of about 0.25 to about 1.5, respectively. By way of further example, in one such embodiment the weight ratio of the combined amount of monoallylamine and multiallylamine to the amount of water in the reaction mixture will be in the range of about 0.25 to about 1.25, respectively. By way of further example, in one such embodiment the weight ratio of the combined amount of monoallylamine and multiallylamine to the amount of water in the reaction mixture will be in the range of about 0.3 to about 1, respectively. By way of further example, in one such embodiment the weight ratio of the combined amount of monoallylamine and multiallylamine to the amount of water in the reaction mixture will be in the range of about 0.35 to about 0.75, respectively. By way of further example, in one such embodiment the weight ratio of the combined amount of monoallylamine and multiallylamine to the amount of water in the reaction mixture will be in the range of about 0.4 to about 0.5, respectively. In each of these exemplary embodiments in this paragraph, it is assumed that the monoallylamine and multiallylamine species are in their respective free amine forms for purposes of the weight ratio calculation.

Experience to-date has further shown that the ratio of the number of allyl equivalents to the number of water equivalents in the reaction mixture has an influence on the characteristics of the resulting polymer. Typically, therefore, the ratio of the number of allyl equivalents possessed by the monoallylamine and multiallylamine, in combination, to the number of water equivalents introduced to the reaction mixture will be in the range of about 0.01:1 to about 1:1, respectively. For example, in one such embodiment, the ratio of the number of allyl equivalents possessed by the monoallylamine and multiallylamine, in combination, to the number of water equivalents introduced to the reaction mixture will be about 0.015:1 to about 0.75:1, respectively. By way of further example, in one such embodiment, the ratio of the number of allyl equivalents possessed by the monoallylamine and multiallylamine, in combination, to the number of water initiator equivalents introduced to the reaction mixture will be about 0.02:1 to about 0.5:1, respectively. By way of further example, in one such embodiment, the ratio of the number of allyl equivalents possessed by the monoallylamine and multiallylamine, in combination, to the number of water initiator equivalents introduced to the reaction mixture will be about 0.03:1 to about 0.4:1, respectively. By way of further example, in one such embodiment, the ratio of the number of allyl equivalents possessed by the monoallylamine and multiallylamine, in combination, to the number of water initiator equivalents introduced to the reaction mixture will be about 0.04:1 to about 0.3:1, respectively. By way of further example, in one such embodiment, the ratio of the number of allyl equivalents possessed by the monoallylamine and multiallylamine, in combination, to the number of water initiator equivalents introduced to the reaction mixture will be about 0.05:1 to about 0.25:1, respectively. By way of further example, in one such embodiment, the ratio of the number of allyl equivalents possessed by the monoallylamine and multiallylamine, in combination, to the number of water initiator equivalents introduced to the reaction mixture will be about 0.06:1 to about 0.2:1, respectively. By way of further example, in one such embodiment, the ratio of the number of allyl equivalents possessed by the monoallylamine and multiallylamine, in combination, to the number of water initiator equivalents introduced to the reaction mixture will be about 0.07:1 to about 0.175:1, respectively. By way of further example, in one such embodiment, the ratio of the number of allyl equivalents possessed by the monoallylamine and multiallylamine, in combination, to the number of water initiator equivalents introduced to the reaction mixture will be about 0.08:1 to about 0.15:1, respectively.

To produce polymeric beads rather than a gel, the reaction mixture for the concurrent polymerization and crosslinking step is preferably a heterogeneous reaction mixture comprising a surfactant, water and an organic solvent system (in addition to the monoallylamine, multiallylamine, acid and initiator). Advantageously, heterogeneous polymerization processes produce polymer particles in the form of substantially spherical beads, whose diameter may be controlled in the 3 to 1000 micrometer range, preferably in the 10 to 500 micrometer range, and, in some embodiments, in the 40-180 micrometer range.

In general, the surfactant comprised by the reaction mixture for the concurrent polymerization and crosslinking step may be ionic or non-ionic. Exemplary surfactants include sorbitan monolaurate, sorbitan monooleate, sorbitan monostearate, sorbitan monopalmitate, ethylene glycol monostearate, glyceryl monostearate, polyethylene glycol monostearate, polyethylene glycol hydrogenated castor oil, polyoxyethylene sorbitan monolaurate, polyoxyethylene sorbitan monooleate, polyethylene glycol and diisooctyl sulfosuccinate, branched dodecylbenzenesulfonic acid, linear dodecylbenzenesulfonic acid, sodium branched alkylbenzenesulfonate, sodium branched dodecylbenzenesulfonate, sodium alpha olefin sulfonate, sodium linear alkylbenzenesulfonate, isopropylamine branched alkylbenzenesulfonate, sodium lauryl sulfate.

The organic solvent system comprised by the concurrent polymerization and crosslinking step reaction mixture may be any of a wide range of water-immiscible organic solvents that may be used to disperse an aqueous phase. Exemplary organic solvent systems may comprise hexane, cyclohexane, heptane, octane, decane, petroleum ether, liquid paraffin, chlorobenzene, toluene, xylenes, ethyl acetate, propyl acetate and isopropyl acetate, or a combination of two or more thereof.

The concurrent polymerization and crosslinking step reaction mixture contain any of a wide range of acids. For example, in one embodiment the concurrent polymerization and crosslinking step reaction mixture contains a mineral acid or an organic acid. Exemplary mineral acids include hydrochloric acid, sulfuric acid and phosphoric acid. Exemplary organic acids include formic acid, acetic acid, and citric acid. In one embodiment, the concurrent polymerization and crosslinking reaction step reaction mixture comprises an acid selected from the group consisting of hydrochloric acid, phosphoric acid, sulfuric acid, acetic acid, methylphosphoric acid, formic acid, citric acid, and combinations thereof. In general, the concurrent polymerization and crosslinking reaction step reaction mixture comprises at least 0.4 equivalents of acid per allyl amine equivalent. For example, in one embodiment the concurrent polymerization and crosslinking reaction step reaction mixture comprises at least 0.6 equivalents of acid per allyl amine equivalent. By way of further example, in one such embodiment the concurrent polymerization and crosslinking reaction step reaction mixture comprises at least 0.8 equivalents of acid per allyl amine equivalent. By way of further example, in one such embodiment the concurrent polymerization and crosslinking reaction step reaction mixture comprises at least 0.9 equivalents of acid per allyl amine equivalent. By way of further example, in one such embodiment the concurrent polymerization and crosslinking reaction step reaction mixture comprises at least 0.95 equivalents of acid per allyl amine equivalent. By way of further example, in one such embodiment the concurrent polymerization and crosslinking reaction step reaction mixture comprises at least 1.0 equivalents of acid per allyl amine equivalent. By way of further example, in one such embodiment the concurrent polymerization and crosslinking reaction step reaction mixture comprises at least 1 equivalent of acid per allyl amine equivalent. In each of the foregoing embodiments, the acid may be introduced to the concurrent polymerization and crosslinking reaction step reaction mixture independent of the addition of the monoallylamine and multiallylamine to the first step reaction mixture. Alternatively, in each of the foregoing embodiments, the acid may be introduced to the concurrent polymerization and crosslinking reaction step reaction mixture may be introduced to the first step reaction mixture as a component of the acid salt of the monoallylamine, the multiallylamine or both the monoallylamine and the multiallylamine.

The concurrent polymerization and crosslinking reaction step may be carried out at a temperature in the range of about 25° C. to about 85° C. Typically, the concurrent polymerization and crosslinking reaction step will be carried out at a temperature in the range of about 30° C. to about 80° C. In some embodiments, the concurrent polymerization and crosslinking reaction step will be carried out at a temperature in the range of about 35° C. to about 70° C. In some embodiments, the concurrent polymerization and crosslinking reaction step will be carried out at a temperature in the range of about 40° C. to about 70° C. In some embodiments, the concurrent polymerization and crosslinking reaction step will be carried out at a temperature in the range of about 45° C. to about 70° C. In general, the temperature may be held relatively constant over the course of the reaction or it may be ramped in a continuous or step-wise manner.

The concurrent polymerization and crosslinking reaction step may be carried out for a reaction time of at least about 2 hours. Typically, the concurrent polymerization and crosslinking reaction step will be carried out for a reaction time of at least about 5 hours. In some embodiments, the concurrent polymerization and crosslinking reaction step will be carried out for a reaction time of at least about 10 hours. In some embodiments, the concurrent polymerization and crosslinking reaction step will be carried out for a reaction time of at least about 15 hours. In some embodiments, the concurrent polymerization and crosslinking reaction step will be carried out for a reaction time of at least about 20 hours. In some embodiments, the concurrent polymerization and crosslinking reaction step will be carried out for a reaction time of at least about 25 hours. In some embodiments, the concurrent polymerization and crosslinking reaction step will be carried out for a reaction time of at least about 30 hours. In some embodiments, the concurrent polymerization and crosslinking reaction step will be carried out for a reaction time of at least about 35 hours. In some embodiments, the concurrent polymerization and crosslinking reaction step will be carried out for a reaction time of at least about 40 hours. Typically, however, the concurrent polymerization and crosslinking reaction step will be carried out for a reaction time of no more than about 50 hours.

In general, the concurrent polymerization and crosslinking reaction step may include, a lone polymerization reaction, stepwise addition of individual starting materials via a series of reactions, the stepwise addition of blocks of monomers, or combinations thereof. The reaction may be carried out as a batch, semi-batch or continuous process.

In one embodiment, the concurrent polymerization and crosslinking step yields preformed poly(allylamine) polymer beads having a target species binding capacity, and a target Swelling Ratio. For example, in one such embodiment the beads have a chloride binding capacity of at least 10 mmol/g in Simulated Gastric Fluid ("SGF") and a Swelling Ratio in the range of 1 to 10. In one embodiment, the preformed poly(allylamine) polymer beads are characterized by Swelling Ratio of about 2 and 10, more typically about 2 to about 8, and in some embodiments about 2 to 3, about 3 to 4 or about 4 to about 6.

Additionally, if the preformed poly(allylamine) polymer beads resulting from the first polymerization step are protonated, this may reduce the amount of nitrogen-nitrogen crosslinking in the second crosslinking step. Accordingly, in certain embodiments the preformed poly(allylamine) polymer is at least partially deprotonated by treatment with a base, preferably a strong base such as a hydroxide base. For example, in one embodiment the base may be NaOH, KOH, $NH_4OH$, $NaHCO_3$, $Na_2CO_3$, $K_2CO_3$, LiOH, $Li_2CO_3$, CsOH or other metal hydroxides. If the charges are removed from the preformed crosslinked amine polymer bead by deprotonation, the bead will tend to collapse and the crosslinking agent used in the second crosslinking step may not be able to access binding sites on the polymer unless the bead is prevented from collapsing. One means of preventing the crosslinked polymer bead from collapsing is the use of a swelling agent such as water to swell the bead, thereby allowing the second-step crosslinker to access binding sites.

As previously noted, multiallylamine monomers that are only partially incorporated into poly(allylamine) polymer in the first step will introduce pendant allyl groups (i.e., at least one allyl group that did not participate in a reaction to become a chain atom of and is merely "dangling" from the poly(allylamine) polymer backbone chain) to the poly(allylamine) polymer. As such, a determination of the number of $sp^2$ allyl carbons pendent to the crosslinked poly(allylamine) polymer backbone remaining in the poly(allylamine) polymer upon completion of the concurrent polymerization and crosslinking step (i.e., the first step) may be used to determine the amount of partially-incorporated multiallylamine. In general, it is preferred that the number of $sp^2$ allyl carbons constitute a low percentage of total carbon atoms in the poly(allylamine) polymer. For example, in one embodiment, $sp^2$ allyl carbons pendent to the poly(allylamine) polymer backbone constitute less than 2.5% of the total number of carbon atoms in the polymer. By way of further example, in one embodiment $sp^2$ allyl carbons pendent to the poly(allylamine) polymer backbone constitute less than 2.25% of the total number of carbon atoms in the polymer. By way of further example, in one embodiment $sp^2$ allyl carbons pendent to the poly(allylamine) polymer backbone constitute less than 2% of the total number of carbon atoms in the polymer. By way of further example, in one embodiment $sp^2$ allyl carbons pendent to the poly(allylamine) polymer backbone constitute less than 1.9% of the total number of carbon atoms in the polymer. By way of further example, in one embodiment $sp^2$ allyl carbons pendent to the poly(allylamine) polymer backbone constitute less than 1.8% of the total number of carbon atoms in the polymer. By way of further example, in one embodiment $sp^2$ allyl carbons pendent to the poly(allylamine) polymer backbone constitute less than 1.7% of the total number of carbon atoms in the polymer. By way of further example, in one embodiment $sp^2$ allyl carbons pendent to the poly(allylamine) polymer backbone constitute less than 1.6% of the total number of carbon atoms in the polymer. By way of further example, in one embodiment $sp^2$ allyl carbons pendent to the poly(allylamine) polymer backbone constitute less than 1.5% of the total number of carbon atoms in the polymer. By way of further example, in one embodiment $sp^2$ allyl carbons pendent to the poly(allylamine) polymer backbone constitute less than 1.4% of the total number of carbon atoms in the polymer. By way of further example, in one embodiment $sp^2$ allyl carbons pendent to the poly(allylamine) polymer backbone constitute less than 1.3% of the total number of carbon atoms in the polymer. By way of further example, in one embodiment $sp^2$ allyl carbons pendent to the poly(allylamine) polymer backbone constitute less than 1.2% of the total number of carbon atoms in the polymer. By way of further example, in one embodiment $sp^2$ allyl carbons pendent to the poly(allylamine) polymer backbone constitute less than 1.1% of the total number of carbon atoms in the polymer. By way of further example, in one embodiment $sp^2$ allyl carbons pendent to the poly(allylamine) polymer backbone constitute less than 1% of the total number of carbon atoms in the polymer. By way of further example, in one embodiment $sp^2$ allyl carbons pendent to the poly(allylamine) polymer backbone constitute less than 0.9% of the total number of carbon atoms in the polymer. By way of further example, in one embodiment $sp^2$ allyl carbons pendent to the poly(allylamine) polymer backbone constitute less than 0.8% of the total number of carbon atoms in the polymer. By way of further example, in one embodiment $sp^2$ allyl carbons pendent to the poly(allylamine) polymer backbone constitute less than 0.75% of the total number of carbon atoms in the polymer. By way of further example, in one embodiment $sp^2$ allyl carbons pendent to the poly(allylamine) polymer backbone constitute less than 0.7% of the total number of carbon atoms in the polymer. By way of further example, in one embodiment $sp^2$ allyl carbons pendent to the poly(allylamine) polymer backbone constitute less than 0.6% of the total number of carbon atoms in the polymer. By way of further example, in one embodiment $sp^2$ allyl carbons pendent to the poly(allylamine) polymer backbone constitute less than 0.5% of the total number of carbon atoms in the polymer. By way of further example, in one embodiment $sp^2$ allyl carbons pendent to the poly(allylamine) polymer backbone constitute less than 0.4% of the total number of carbon atoms in the polymer. By way of further example, in one embodiment $sp^2$ allyl carbons pendent to the poly(allylamine) polymer backbone constitute less than 0.3% of the total number of carbon atoms in the polymer. By way of further example, in one embodiment $sp^2$ allyl carbons pendent to the poly(allylamine) polymer backbone constitute less than 0.25% of the total number of carbon atoms in the polymer. By way of further example, in one embodiment $sp^2$ allyl carbons pendent to the poly(allylamine) polymer backbone constitute less than 0.2% of the total number of carbon atoms in the polymer. By way of further example, in one embodiment $sp^2$ allyl carbons pendent to the poly(allylamine) polymer backbone constitute less than 0.1% of the total number of carbon atoms in the polymer. By way of further example, in one embodiment $sp^2$ allyl carbons pendent to the poly(allylamine) polymer backbone constitute less than 0.05% of the total number of carbon atoms in the polymer. By way of further example, in one embodiment $sp^2$ allyl carbons pendent to the poly(allylamine) polymer backbone are not detectible in the polymer beads. In each of the foregoing exemplary embodiments, the percentage of $sp^2$ allyl carbons pendent to the poly(allylamine) polymer backbone in the beads may be determined by quantitative $^{13}C$ solid state magic angle spinning (MAS) NMR measurement on a Bruker AVANCE III 800 MHz (18.8 T) standard bore spectrometer, operating at 800.25 MHz and 201.24 MHz for $^1H$ and $^{13}C$, respectively, with a 4 mm zirconia rotor system at a spinning frequency of 16 kHz as more fully described elsewhere herein.

In the second crosslinking step, the preformed poly(allylamine) polymer is crosslinked with a crosslinker containing amine reactive moieties to form a post-polymerization crosslinked polymer. In one such embodiment, the crosslinker is a compound containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. Exemplary crosslinking agents that may be used in such post-polymerization crosslinking reactions further include, but are not limited to, one or more multifunctional crosslinking agents such as: dihaloalkanes, haloalkyloxiranes, alkyloxirane sulfonates, di(haloalkyl)amines, tri(haloalkyl)amines, diepoxides, triepoxides, tetraepoxides, bis(halomethyl)benzenes, tri(halomethyl)benzenes, tetra(halomethyl)benzenes, epihalohydrins such as epichlorohydrin and epibromohydrin poly (epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy)diphenylmethane, bisphenol F diglycidyl ether, 1,4-bis(2',3'epoxypropyl)perfluoro-n-butane, 2,6-di (oxiran-2-ylmethyl)-1,2,3,5,6,7-hexahydropyrrolo[3,4-f] isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris [[3-(epoxypropoxy)propyl]dimethylsilyloxy]-1,3,5,7,9,11, 14-heptacyclopentyltricyclo[7,3,3,15,11]heptasiloxane, 4,4'methylenebis(N, N-diglycidylaniline), bis(halomethyl) benzene, bis(halomethyl)biphenyl and bis(halomethyl) naphthalene, toluene diisocyanate, acrylol chloride, methyl acrylate, ethylene bisacrylamide, pyromethallic dianhydride, succinyl dichloride, dimethylsuccinate, 3-chloro-1-(3-chloropropylamino-2-propanol, 1,2-bis(3-chloropropylamino) ethane, Bis(3-chloropropyl)amine, 1,3-Dichloro-2-propanol, 1,3-Dichloropropane, 1-chloro-2,3-epoxypropane, and tris[(2-oxiranyl)methyl]amine.

In general, it is preferred that the number of $sp^2$ allyl carbons constitute a low percentage of total carbon atoms in the post-polymerization crosslinked polymer. For example, in one embodiment, $sp^2$ allyl carbons pendent to the post-polymerization crosslinked polymer backbone constitute less than 2.5% of the total number of carbon atoms in the polymer. By way of further example, in one embodiment $sp^2$ allyl carbons pendent to the post-polymerization crosslinked polymer backbone constitute less than 2.25% of the total number of carbon atoms in the polymer. By way of further example, in one embodiment $sp^2$ allyl carbons pendent to the post-polymerization crosslinked polymer backbone constitute less than 2% of the total number of carbon atoms in the polymer. By way of further example, in one embodiment $sp^2$ allyl carbons pendent to the post-polymerization crosslinked polymer backbone constitute less than 1.9% of the total number of carbon atoms in the polymer. By way of further example, in one embodiment $sp^2$ allyl carbons pendent to the post-polymerization crosslinked polymer backbone constitute less than 1.8% of the total number of carbon atoms in the polymer. By way of further example, in one embodiment $sp^2$ allyl carbons pendent to the post-polymerization crosslinked polymer backbone constitute less than 1.7% of the total number of carbon atoms in the polymer. By way of further example, in one embodiment $sp^2$ allyl carbons pendent to the post-polymerization crosslinked polymer backbone constitute less than 1.6% of the total number of carbon atoms in the polymer. By way of further example, in one embodiment $sp^2$ allyl carbons pendent to the post-polymerization crosslinked polymer backbone constitute less than 1.5% of the total number of carbon atoms in the polymer. By way of further example, in one embodiment $sp^2$ allyl carbons pendent to the post-polymerization crosslinked polymer backbone constitute less than 1.4% of the total number of carbon atoms in the polymer. By way of further example, in one embodiment $sp^2$ allyl carbons pendent to the post-polymerization crosslinked polymer backbone constitute less than 1.3% of the total number of carbon atoms in the polymer. By way of further example, in one embodiment $sp^2$ allyl carbons pendent to the post-polymerization crosslinked polymer backbone constitute less than 1.25% of the total number of carbon atoms in the polymer. By way of further example, in one embodiment $sp^2$ allyl carbons pendent to the post-polymerization crosslinked polymer backbone constitute less than 1.2% of the total number of carbon atoms in the polymer. By way of further example, in one embodiment $sp^2$ allyl carbons pendent to the post-polymerization crosslinked polymer backbone constitute less than 1.1% of the total number of carbon atoms in the polymer. By way of further example, in one embodiment $sp^2$ allyl carbons pendent to the post-polymerization crosslinked polymer backbone constitute less than 1% of the total number of carbon atoms in the polymer. By way of further example, in one embodiment $sp^2$ allyl carbons pendent to the post-polymerization crosslinked polymer backbone constitute less than 0.9% of the total number of carbon atoms in the polymer. By way of further example, in one embodiment $sp^2$ allyl carbons pendent to the post-polymerization crosslinked polymer backbone constitute less than 0.8% of the total number of carbon atoms in the polymer. By way of further example, in one embodiment $sp^2$ allyl carbons pendent to the post-polymerization crosslinked polymer backbone constitute less than 0.75% of the total number of carbon atoms in the polymer. By way of further example, in one embodiment $sp^2$ allyl carbons pendent to the post-polymerization crosslinked polymer backbone constitute less than 0.7% of the total number of carbon atoms in the polymer. By way of further example, in one embodiment $sp^2$ allyl carbons pendent to the post-polymerization crosslinked polymer backbone constitute less than 0.6% of the total number of carbon atoms in the polymer. By way of further example, in one embodiment $sp^2$ allyl carbons pendent to the post-polymerization crosslinked polymer backbone constitute less than 0.5% of the total number of carbon atoms in the polymer. By way of further example, in one embodiment $sp^2$ allyl carbons pendent to the post-polymerization crosslinked polymer backbone constitute less than 0.4% of the total number of carbon atoms in the polymer. By way of further example, in one embodiment $sp^2$ allyl carbons pendent to the post-polymerization crosslinked polymer backbone constitute less than 0.3% of the total number of carbon atoms in the polymer. By way of further example, in one embodiment $sp^2$ allyl carbons pendent to the post-polymerization crosslinked polymer backbone constitute less than 0.25% of the total number of carbon atoms in the polymer. By way of further example, in one embodiment $sp^2$ allyl carbons pendent to the post-polymerization crosslinked polymer backbone constitute less than 0.2% of the total number of carbon atoms in the polymer. By way of further example, in one embodiment $sp^2$ allyl carbons pendent to the post-polymerization crosslinked polymer backbone constitute less than 0.1% of the total number of carbon atoms in the polymer. By way of further example, in one embodiment $sp^2$ allyl carbons pendent to the post-polymerization crosslinked polymer backbone constitute less than 0.05% of the total number of carbon atoms in the polymer. By way of further example, in one embodiment $sp^2$ allyl carbons pendent to the post-polymerization crosslinked polymer backbone are not detectible in the polymer beads. In each of the foregoing exemplary embodiments, the percentage of $sp^2$ allyl carbons pendent to the post-polymerization crosslinked polymer backbone in the beads may be determined by quantitative $^{13}C$ solid state magic angle spinning (MAS) NMR measurement on a Bruker AVANCE III 800 MHz (18.8 T) standard bore spectrometer, operating at 800.25 MHz and 201.24 MHz for $^1H$ and $^{13}C$, respectively, with a 4 mm zirconia rotor system at a spinning frequency of 16 kHz as more fully described elsewhere herein.

In those embodiments in which the ratio of sp3 carbon to sp2 carbon in the crosslinker used in the second crosslinking step exceeds the ratio of sp3 carbon to sp2 carbon in the preformed poly(allylamine) polymer, the resulting post-polymerization crosslinked polymer will have a ratio of sp3 carbon to sp2 carbon that is greater than the ratio of sp3 carbon to sp2 carbon in the preformed poly(allylamine) polymer. Thus, for example, in those embodiments in which the crosslinker used in the second crosslinking step contains sp3 carbon but no sp2 carbon, the second crosslinking reaction will increase the amount of sp3 carbon in the post-polymerization crosslinked polymer while the amount of sp2 carbon will remain unchanged relative to the preformed poly(allylamine) polymer. In certain embodiments, for example, in which the crosslinker contains sp3 carbon but no sp2 carbon (e.g., a dihaloalkane) and the preformed poly(allylamine) polymer is significantly crosslinked in the second crosslinking step, the incremental increase of sp3 carbon can be sufficient to degrade the signal to noise ratio for sp2 carbon, thereby decreasing measurement sensitivity. In certain embodiments, therefore, rather than directly measuring the amounts of sp2 carbon and sp3 carbon in the resulting post polymerization crosslinked polymer by NMR, it may be advantageous to measure the amount of sp2 carbon in the preformed poly(allylamine) polymer, determining how much sp3 carbon (and sp2 carbon, if any) was added to the polymer during the second crosslinking step, and then calculating the relative proportion of sp2 and sp3 carbon in the resulting post-polymerization crosslinked polymer. Examples are given in Tables 10 and 11 in which the percent of sp2 carbon were experimentally determined for both poly(allylamine) polymers and corresponding crosslinked poly(allylamine) polymers. For those in which sp2 carbon could be quantified in the crosslinked poly(allylamine) polymer, the average ratio of the percent of sp2 carbon in crosslinked poly(allylamine) polymers to the corresponding poly(allylamine) polymer was about 0.9. This factor was applied where applicable throughout Table 11 part 2 in order to calculate the percent of sp2 carbon comprising certain examples of crosslinked poly(allylamine) polymers in Table 11.

In one embodiment, the crosslinker for the step 2 crosslinking reaction is selected from a crosslinker appearing in Table B.

comprised by the dispersing solvent system to preformed poly(allylamine) polymer in the reaction mixture is at least 2:1 (milliliters of solvent:grams of preformed poly(allylamine) polymer). By way of further example, in one such embodiment the ratio of solvent comprised by the dispersing solvent system to preformed poly(allylamine) polymer in the reaction mixture is at least 3:1 (milliliters of solvent:grams of preformed poly(allylamine) polymer). By way of further example, in one such embodiment the ratio of solvent comprised by the dispersing solvent system to preformed poly(allylamine) polymer in the reaction mixture is at least 4:1 (milliliters of solvent:grams of preformed poly(allylamine) polymer). By way of further example, in one such embodiment the ratio of solvent comprised by the dispersing solvent system to preformed poly(allylamine) polymer in the reaction mixture is at least 5:1 (milliliters of solvent:grams of preformed poly(allylamine) polymer). By way of further example, in one such embodiment the ratio of solvent comprised by the dispersing solvent system to preformed poly(allylamine) polymer in the reaction mixture is at least 7.5:1 (milliliters of solvent:grams of preformed poly(allylamine) polymer). By way of further example, in one such

TABLE B

| Abbreviation | Common name | IUPAC name | | MW (g/mol) |
|---|---|---|---|---|
| BCPA | Bis(3-chloropropyl)amine | Bis(3-chloropropyl)amine | 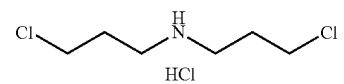 HCl | 206.54 |
| DC2OH | 1,3-dichloroisopropanol | 1,3-Dichloro-2-propanol | 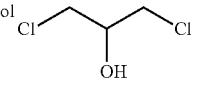 | 128.98 |
| DCE | dichloroethane | 1,2-dichloroethane | 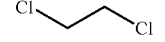 | 98.96 |
| DCP | Dichloropropane | 1,3-Dichloropropane | 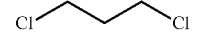 | 112.98 |
| ECH | Epichlorohydrin | 1-chloro-2,3-epoxypropane | 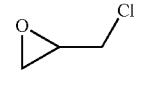 | 92.52 |
| TGA | Triglycidyl amine | Tris[(2-oxiranyl)methyl]amine | 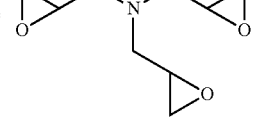 | 185.22 |
| BCPOH | Bis(3-chloropropyl)amine-OH | 3-Chloro-1-(3-chloropropylamino)-2-propanol | 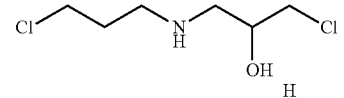 | 186.08 |
| BCPEDA | Bis(chloropropyl)ethylenediamine | 1,2-Bis(3-chloropropylamin)-ethane | 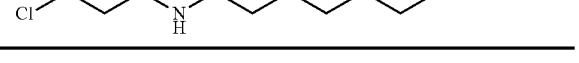 | 213.15 |

In one embodiment, the preformed poly(allylamine) polymer formed in the concurrent polymerization and crosslinking reaction is further crosslinked in a second crosslinking step in a reaction mixture comprising a crosslinking agent, a swelling agent for the preformed poly(allylamine) polymer, and a dispersing solvent system. The dispersing solvent system comprises a sufficient amount of solvent to disperse the preformed crosslinked poly(allylamine) polymer in the reaction mixture so as to avoid inter-polymer particle (i.e., inter-bead) crosslinking reactions and resulting aggregation. In one such embodiment, for example, the ratio of solvent embodiment the ratio of solvent comprised by the dispersing solvent system to preformed poly(allylamine) polymer in the reaction mixture is at least 10:1 (milliliters of solvent:grams of preformed poly(allylamine) polymer). By way of further example, in one such embodiment the ratio of solvent comprised by the dispersing solvent system to preformed poly(allylamine) polymer in the reaction mixture is at least 20:1 (milliliters of solvent:grams of preformed poly(allylamine) polymer). In each of the foregoing embodiments, the dispersing solvent system may comprise a combination of (i) an inert solvent (relative to the preformed poly (allylamine) polymer) such as one of the non-polar solvents previously identified in connection with the organic solvent system in which the preformed poly(allylamine) polymer is formed in the first crosslinking step and (ii) a crosslinking solvent (e.g., DCE or DCP). Alternatively, in each of the foregoing embodiments, the dispersing solvent system may exclusively comprise as solvents one or more crosslinking agents (e.g., DCE and/or DCP, but no inert solvent), thus performing a dual-purpose role, as both solvent (dispersant) and crosslinker. In a further alternative, in each of the foregoing embodiments, the dispersing solvent system may exclusively comprise as solvents neat crosslinking agent (e.g., DCE or DCP, but not both and no inert solvent), thus performing a dual-purpose role, as both solvent (dispersant) and crosslinker.

As noted above, in certain embodiments a swelling agent for the preformed poly(allylamine) polymer is included in the second crosslinking step reaction mixture, i.e., along with the crosslinking agent. In general, the swelling agent and the crosslinking agent may be miscible or immiscible and the swelling agent may be any composition or combination of compositions that have the capacity to swell the preformed poly(allylamine) polymer. Exemplary swelling agents include polar solvents such as water, methanol, ethanol, n-propanol, isopropanol, n-butanol, formic acid, acetic acid, acetonitrile, dimethylformamide, dimethylsulfoxide, nitromethane, propylene carbonate, or a combination thereof. Additionally, the amount of swelling agent included in the second crosslinking step reaction mixture will typically be less than absorption capacity of the preformed poly(allylamine) polymer for the swelling agent. For example, it is generally preferred that the weight ratio of swelling agent to preformed polymer in the second crosslinking step reaction mixture be less than 4:1. By way of further example, in some embodiments the weight ratio of swelling agent to preformed polymer in the second crosslinking step reaction mixture will be less than 3:1. By way of further example, in some embodiments the weight ratio of swelling agent to preformed polymer in the second crosslinking step reaction mixture will be less than 2:1. By way of further example, in some embodiments the weight ratio of swelling agent to preformed polymer in the second crosslinking step reaction mixture will be less than 1:1. By way of further example, in some embodiments the weight ratio of swelling agent to preformed polymer in the second crosslinking step reaction mixture will be less than 0.5:1. By way of further example, in some embodiments the weight ratio of swelling agent to preformed polymer in the second crosslinking step reaction mixture will be less than 0.4:1. By way of further example, in some embodiments the weight ratio of swelling agent to preformed polymer in the reaction mixture will be less than 0.3:1. In general, however, the weight ratio of swelling agent to preformed polymer in the second crosslinking step reaction mixture will typically be at least 0.05:1, respectively.

The second crosslinking step may be carried out at a temperature in the range of about 25° C. to about 85° C. Typically, the second crosslinking step will be carried out at a temperature in the range of about 35° C. to about 80° C. In some embodiments, the second crosslinking step will be carried out at a temperature in the range of about 45° C. to about 80° C. In some embodiments, the second crosslinking step will be carried out at a temperature in the range of about 55° C. to about 75° C. In some embodiments, the second crosslinking step will be carried out at a temperature in the range of about 60° C. to about 75° C. In some embodiments, the second crosslinking step will be carried out at a temperature in the range of about 65° C. to about 75° C. In general, the temperature may be held relatively constant over the course of the second crosslinking step or it may be ramped in a continuous or step-wise manner.

The second crosslinking step may be carried out for a period of about 2 to 20 hours. Typically, the second crosslinking step will be carried out for a period of about 4 to 20 h. In some embodiments, the second crosslinking step will be carried out for a period of about 5 to 20 h. In some embodiments, the second crosslinking step will be carried out for a period of about 6 to 20 h. In some embodiments, the second crosslinking step will be carried out for a period of about 8 to 20 h. In some embodiments, the second crosslinking step will be carried out for a period of about 10 to 20 h. In some embodiments, the second crosslinking step will be carried out for a period of about 12 to 18 h. In some embodiments, the second crosslinking step will be carried out for a period of about 14 to 18 h. In some embodiments, the second crosslinking step will be carried out for a period of about 15 to 17 h.

In one embodiment, the resulting preformed poly(allylamine) polymer is at least partially deprotonated with a base and combined with a non-protonating swelling agent to swell the free amine polymer without protonating the amine functions prior to the second crosslinking step. Thus, for example, the amount of the non-protonating swelling agent may be selected to tune the subsequent degree of crosslinking effectively forming a template that is then locked into place via the amine consuming crosslinking step.

The benefits of deprotonated preformed polymer beads in the second crosslinking step highlights the advantages of using two steps to achieve the final product. In the first crosslinking step, to form the amine polymer bead, all monomers (e.g., allylamine and DAPDA) are protonated to remain in the aqueous phase and to avoid the radical transfer reactions that severely limit the polymerization of non-protonated allylamine (and derivatives). Once the bead is formed through carbon-carbon crosslinks, the bead can then be deprotonated and further crosslinked with an amine reactive crosslinker in the second crosslinking step.

In one embodiment, selectivity for chloride over other competing ions is achieved with highly crosslinked amine polymers. For example, relatively high chloride binding capacity maybe be attained by reacting a preformed poly (allylamine) polymer bead with neat crosslinker in the presence of a swelling agent (water). While this "non-dispersed" reaction provides access to high selectivity for chloride over competing ions in the SIB assays, it also results in macroscopically (and microscopically) aggregated polymer beads. Accordingly, it is advantageous to include a solvent (e.g., heptane) in the second crosslinking step to disperse the preformed crosslinked polymer beads so as to avoid inter-bead reactions and resulting aggregation. The use of too much solvent (dispersant), however, can dilute the reaction solution to the point where the resulting bead is not sufficiently crosslinked to have the desired selectivity for chloride over other competing anions. By using a crosslinking agent that also functions as a solvent (dispersant), however, sufficient solvent (dispersant) may be included in the reaction mixture to avoid inter-bead reactions and aggregation without diluting the mixture to the point where the degree of amine-consuming crosslinking is insufficient. For example, in an effort to utilize the dispersing properties of a solvent (to avoid aggregation during the reaction) while maintaining reactivity, DCE and DCP were used neat, thus performing a dual purpose role, as both solvent (dispersant) and crosslinker. Interestingly, DCE was discovered to have excellent dispersal properties as a solvent, when compared to similar reactions with DCP and/or heptane. Additionally, less aggregation was observed when the beads were first dispersed in DCE and then in a second operation, the water is added to swell the beads. If water is added to the preformed poly(allylamine) polymer before the bead is dispersed in the DCE, aggregation may occur.

In each of the foregoing embodiments, the reaction mixture for the second crosslinking step may contain a wide range of amounts of crosslinking agents. For example, in one embodiment the crosslinker may be used in large excess relative to the amount of preformed poly(allylamine) polymer in the reaction mixtures. Stated differently, in such embodiments the crosslinking agent is a crosslinking solvent, i.e., it is both a solvent for the reaction mixture and a crosslinking agent for the preformed poly(allylamine) polymer. In such embodiments, other solvents may optionally be included in the dispersing solvent system of the second crosslinking step reaction mixture, but are not required. Alternatively, the preformed poly(allylamine) polymer, swelling agent and crosslinker may be dispersed in a dispersing solvent system that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, N,N-dimethylformamide, dimethylsulfoxide, nitromethane, or a combination thereof. By way of further example, when the swelling agent comprises a polar solvent, the dispersing solvent system for the second crosslinking step will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent comprised by the dispersing solvent system may be the same; i.e., the solvent is a crosslinking solvent such as 1,2-dichloroethane, 1,3-dichloropropane, 1,4-dichlorobutane or a combination thereof.

It is notable that in a crosslinking solvent (e.g., a DCE-dispersed reaction), there is a large excess of crosslinker regardless of the amount of crosslinking solvent (e.g., DCE) used to disperse the bead (e.g., both 1 g:3 mL::bead:DCE and 1 g:10 mL::bead:DCE are a large excess of crosslinker, most of which is not consumed during the reaction). Despite this, the relative degree of crosslinking, and the chloride capacity and performance in the SIB assay is relatively unaffected by changes in the ratio of reactive crosslinker to polymer bead. This is possible because the reaction is limited by the acid-neutralizing capacity of the polymer bead, rather than the amount of crosslinker (e.g., DCE).

To more efficiently react with DCE or other crosslinker, the amines of the preformed polymer bead preferably have a free electron pair (neutral, deprotonated). As the free amines of the preformed polymer bead react with the crosslinker (e.g., DCE), HCl is produced and the amines become protonated, thus limiting the reaction. For this reason, the preformed poly(allylamine) polymer beads preferably start as the free amine in the second crosslinking step. If the preformed poly(allylamine) polymer bead is protonated after the first step of carbon-carbon crosslinking, amine-consuming crosslinking in the second crosslinking step will be limited, thus reducing the desired selectivity for chloride over other competing ions. This has been demonstrated by adding known quantities of HCl to preformed poly(allylamine) polymer beads immediately before crosslinking with DCE in the second crosslinking step. When less than 3 mol % HCl (to amine in preformed polymer amine bead) is added prior to crosslinking in the second crosslinking step, total chloride capacity (SGF) and chloride selectivity in SIB are similar to beads not treated with HCl in the second crosslinking step. When greater than 5 mol % HCl (to amine in preformed polymer amine bead) is added prior to crosslinking in the second crosslinking step, total chloride capacity (SGF) increases and chloride selectivity in SIB decreases, indicating lower incorporation of crosslinker.

The use of 1,2-dichloroethane ("DCE") as the crosslinking solvent also generates HCl molecules during the second crosslinking step. These HCl molecules protonate some of the free amine sites which block the reaction sites for the crosslinking reaction and thereby limit the number of binding sites available for crosslinking. Consequently, the use of DCE creates a self-limiting effect on the secondary crosslinking.

Given the large excess of dual crosslinker/solvent, mono-incorporation of this reagent can occur leading to alkyl chloride functional groups on the crosslinked polymer bead that are hydrophobic in nature and can increase non-specific interactions with undesirable solutes other than HCl that are more hydrophobic in nature. Washing with ammonium hydroxide solution converts the alkyl-chloride to alkyl-amine functions that are hydrophilic and minimize non-specific interactions with undesirable solutes. Other modifications that yield more hydrophilic groups than alkyl chloride such as —OH are suitable to quench mono-incorporated crosslinker/solvent.

As noted above, in certain embodiments a swelling agent for the preformed poly(allylamine) polymer may be included in the second crosslinking step reaction mixture for the second crosslinking step along with the crosslinking agent. In general, the swelling agent and the crosslinking agent may be miscible or immiscible and the swelling agent may be any composition or combination of compositions that have the capacity to swell the preformed poly(allylamine) polymer. Exemplary swelling agents include polar solvents such as water, methanol, ethanol, n-propanol, isopropanol, n-butanol, formic acid, acetic acid, acetonitrile, dimethylformamide, dimethylsulfoxide, nitromethane, propylene carbonate, or a combination thereof. Additionally, the amount of swelling agent included in the second crosslinking step reaction mixture will typically be less than absorption capacity of the preformed poly(allylamine) polymer for the swelling agent. For example, it is generally preferred that the weight ratio of swelling agent to preformed polymer in the second crosslinking step reaction mixture be less than 4:1. By way of further example, in some embodiments the weight ratio of swelling agent to preformed polymer in the second crosslinking step reaction mixture will be less than 3:1. By way of further example, in some embodiments the weight ratio of swelling agent to preformed polymer in the second crosslinking step reaction mixture will be less than 2:1. By way of further example, in some embodiments the weight ratio of swelling agent to preformed polymer in the second crosslinking step reaction mixture will be less than 1:1. By way of further example, in some embodiments the weight ratio of swelling agent to preformed polymer in the second crosslinking step reaction mixture will be less than 0.5:1. By way of further example, in some embodiments the weight ratio of swelling agent to preformed polymer in the second crosslinking step reaction mixture will be less than 0.4:1. By way of further example, in some embodiments the weight ratio of swelling agent to preformed polymer in the second crosslinking step reaction mixture will be less than 0.3:1. In general, however, the weight ratio of swelling agent to preformed polymer in the second crosslinking step reaction mixture will typically be at least 0.05:1, respectively.

When the swelling agent comprises water, the weight ratio of water to preformed poly(allylamine) polymer in the second crosslinking step reaction mixture will typically be less than about 4:1 (water to polymer). For example, in one such embodiment the second crosslinking step reaction mixture comprises water as a swelling agent and the weight ratio of water to preformed poly(allylamine) polymer in the second crosslinking step reaction mixture will typically be less than about 3.5:1. By way of further example, in one such embodiment the second crosslinking step reaction mixture comprises water as a swelling agent and the weight ratio of water to preformed poly(allylamine) polymer in the second crosslinking step reaction mixture will typically be less than about 3:1. By way of further example, in one such embodiment the second crosslinking step reaction mixture comprises water as a swelling agent and the weight ratio of water to preformed poly(allylamine) polymer in the second crosslinking step reaction mixture will typically be less than about 2.5:1. By way of further example, in one such embodiment the second crosslinking step reaction mixture comprises water as a swelling agent and the weight ratio of water to preformed poly(allylamine) polymer in the second crosslinking step reaction mixture will typically be less than about 2:1. By way of further example, in one such embodiment the second crosslinking step reaction mixture comprises water as a swelling agent and the weight ratio of water to preformed poly(allylamine) polymer in the second crosslinking step reaction mixture will typically be less than about 1.5:1. By way of further example, in one such embodiment the second crosslinking step reaction mixture comprises water as a swelling agent and the weight ratio of water to preformed poly(allylamine) polymer in the second crosslinking step reaction mixture will typically be less than about 1:1. By way of further example, in one such embodiment the second crosslinking step reaction mixture comprises water as a swelling agent and the weight ratio of water to preformed poly(allylamine) polymer in the second crosslinking step reaction mixture will typically be less than about 0.75:1. By way of further example, in one such embodiment the second crosslinking step reaction mixture comprises water as a swelling agent and the weight ratio of water to preformed poly(allylamine) polymer in the second crosslinking step reaction mixture will typically be less than about 0.5:1. By way of further example, in one such embodiment the second crosslinking step reaction mixture comprises water as a swelling agent and the weight ratio of water to preformed poly(allylamine) polymer in the second crosslinking step reaction mixture will typically be less than about 0.25:1. In general, however, when water is employed as a swelling agent the weight ratio of water to preformed poly(allylamine) polymer in the second crosslinking step reaction mixture will typically be at least about 0.15:1 (water to polymer) but less than the water absorption capacity of the preformed poly(allylamine) polymer. By way of further example, in one embodiment the weight ratio of water to preformed poly(allylamine) polymer in the second crosslinking step reaction mixture will typically be at least about 0.2:1 but less than the water absorption capacity of the preformed poly(allylamine) polymer. By way of further example, in one embodiment the weight ratio of water to preformed poly(allylamine) polymer in the second crosslinking step reaction mixture will typically be at least about 0.25:1 but less than the water absorption capacity of the preformed poly(allylamine) polymer. By way of further example, in one embodiment the weight ratio of water to preformed poly(allylamine) polymer in the second crosslinking step reaction mixture will typically be at least about 0.5:1 but less than the water absorption capacity of the preformed poly(allylamine) polymer. By way of further example, in one embodiment the weight ratio of water to preformed poly(allylamine) polymer in the second crosslinking step reaction mixture will typically be at least about 0.75:1 but less than the water absorption capacity of the preformed poly(allylamine) polymer. By way of further example, in one embodiment the weight ratio of water to preformed poly(allylamine) polymer in the second crosslinking step reaction mixture will typically be at least about 1:1 but less than the water absorption capacity of the preformed poly(allylamine) polymer. By way of further example, in one embodiment the weight ratio of water to preformed poly(allylamine) polymer in the second crosslinking step reaction mixture will typically be at least about 1.5:1 but less than the water absorption capacity of the preformed poly(allylamine) polymer. By way of further example, in one embodiment the weight ratio of water to preformed poly(allylamine) polymer in the second crosslinking step reaction mixture will typically be at least about 2:1 but less than the water absorption capacity of the preformed poly(allylamine) polymer. By way of further example, in one embodiment the weight ratio of water to preformed poly(allylamine) polymer in the second crosslinking step reaction mixture will typically be at least about 2.5:1 but less than the water absorption capacity of the preformed poly(allylamine) polymer. By way of further example, in one embodiment the weight ratio of water to preformed poly(allylamine) polymer in the second crosslinking step reaction mixture will typically be at least about 3:1 but less than the water absorption capacity of the preformed poly(allylamine) polymer. By way of further example, in one embodiment the weight ratio of water to preformed poly(allylamine) polymer in the second crosslinking step reaction mixture will typically be at least about 3.5:1 but less than the water absorption capacity of the preformed poly(allylamine) polymer. Thus, in certain embodiments the weight ratio of water to preformed poly(allylamine) polymer will be in the range of about 0.15:1 to about 4:1. By way of further example, in certain embodiments the weight ratio of water to preformed poly(allylamine) polymer will be in the range of about 0.2:1 to about 3.5:1. By way of further example, in certain embodiments the weight ratio of water to preformed poly(allylamine) polymer will be in the range of about 0.2:1 to about 3:1.

The second crosslinking step reaction mixture may contain a wide range of amounts of crosslinking agents. For example, in one embodiment the crosslinker may be used in large excess relative to the amount of preformed poly(allylamine) polymer in the second crosslinking step reaction mixtures. Stated differently, in such embodiments the crosslinking agent is a crosslinking solvent, i.e., it is both a solvent for the second crosslinking step reaction mixture and a crosslinking agent for the preformed poly(allylamine) polymer. In such embodiments, other solvents may optionally be included in the second crosslinking step reaction mixture but are not required. Alternatively, the preformed poly(allylamine) polymer, swelling agent and crosslinker may be dispersed in a solvent that is miscible with the crosslinker and immiscible with the swelling agent. For example, in some embodiments the swelling agent may be a polar solvent; in some such embodiments, for example, the swelling agent may comprise water, methanol, ethanol, n-propanol, isopropanol, formic acid, acetic acid, acetonitrile, dimethylformamide, dimethylsulfoxide, nitromethane, or a combination thereof. By way of further example, when the swelling agent comprises a polar solvent, the solvent system for the second crosslinking step reaction mixture will typically comprise a non-polar solvent such as pentane, cyclopentane, hexane, cyclohexane, benzene, toluene, 1,4-dioxane, chloroform, diethyl ether, dichloromethane, dichloroethane, dichloropropane, dichlorobutane, or a combination thereof. In certain embodiments, the crosslinker and the solvent may be the same; i.e., the solvent is a crosslinking solvent such as 1,2-dichloroethane, 1,3-dichloropropane, 1,4-dichlorobutane or a combination thereof.

In those embodiments in which the second crosslinking step reaction mixture comprises a swelling agent, it is sometimes preferred to combine the preformed poly(allylamine) polymer with the solvent (sometimes alternatively referred to as a dispersant) before the preformed poly(allylamine) polymer is combined with the swelling agent in the second crosslinking step reaction mixture. In certain embodiments, the resulting crosslinked polymer tends to be less aggregated when the preformed poly(allylamine) polymer is combined with a solvent (dispersant) that is immiscible with the swelling agent before the preformed poly(allylamine) polymer is combined with the swelling agent. Thus, in certain embodiments less than 25% of the particles in a representative sample of a population of post polymerization crosslinked amine particles are aggregated into agglomerates. For example, in some embodiments less than 20% of the particles in a representative sample of a population of post polymerization crosslinked amine particles are aggregated into agglomerates. By way of further example, in some embodiments less than 15% of the particles in a representative sample of a population of post polymerization crosslinked amine particles are aggregated into agglomerates. By way of further example, in some embodiments less than 10% of the particles in a representative sample of a population of post polymerization crosslinked amine particles are aggregated into agglomerates. By way of further example, in some embodiments less than 5% of the particles in a representative sample of a population of post polymerization crosslinked amine particles are aggregated into agglomerates. By way of further example, in some embodiments less than 1% of the particles in a representative sample of a population of post polymerization crosslinked amine particles are aggregated into agglomerates. Aggregation can be evaluated using microscopy or other means of measuring particle size distribution. Lack of aggregation can be defined as generally separated, free-flowing beads lacking macroscopic and/or microscopic clumps. Particle size distribution (as defined elsewhere) can indicate that aggregation has occurred, for example if the average size (d(50)) and/or d(90) of the crosslinked poly(allylamine) polymer increases after the crosslinking step relative to the preformed poly(allylamine) polymer breads as previously described.

In one embodiment, a preformed poly(allylamine) polymer is formed in a first step and the preformed poly(allylamine) polymer is further crosslinked in a second crosslinking step without isolating the preformed poly(allylamine) polymer between the first and second crosslinking steps (sometimes referred to as a "one-pot synthesis"). For example, in one such embodiment a preformed poly(allylamine) polymer is formed in a first step reaction mixture (as previously described herein) and, without isolating the preformed poly(allylamine) polymer formed in the first step reaction mixture, the preformed poly(allylamine) polymer is then crosslinked using any of the crosslinkers disclosed herein (including, e.g., a crosslinker selected from Table B).

By way of further example, in one such embodiment the preformed polymer may be dispersed in any of the non-polar solvents disclosed herein (including for example, a crosslinking solvent) to form a second crosslinking step reaction mixture and a swelling agent is added to this reaction mixture. In one such exemplary embodiment, the crosslinker is selected from Table B, the solvent is a crosslinking water-immiscible solvent such as 1,2-dichloroethane ("DCE") or 1,3-dichloropropane ("DCP"), and the swelling agent comprises water. In each of the foregoing embodiments, the preformed polymer may be an amine-containing polymer containing a residue of a monomer described in any of Formulae 1, 1a, 1 b, 1c, 2, 2a and 2b or a linear polymer comprised of a repeat unit described by Formula 3; for example, in each of the foregoing embodiments, the preformed polymer may contain the residue of two or more small molecule amines and crosslinkers disclosed in Table C.

In one exemplary embodiment, a preformed polyamine polymer is crosslinked under, for example suspension conditions to generate a particle of targeted particle size and morphology. The crosslinker can be either water miscible or water miscible. When a water immiscible crosslinker (e.g., DCE or DCP) is used as the dispersant, high chloride binding selectivities are achieved, as demonstrated, for example, in SIB.

In one embodiment, an amine polymer can be formed and then further crosslinked in the same reaction flask and in one reaction series. A crosslinked amine polymer can be prepared under, for example, suspension conditions to generate a particle of targeted particle size and morphology. In the same reaction flask, and without isolation, the water content in the beads can be lowered by Dean Stark methods or other similar evaporative techniques. The water is adjusted to the targeted amount such that a second crosslinking reaction can be conducted to produce a final polymer with the desired properties and characteristics.

In one embodiment, the crosslinked poly(allylamine) amine polymer formed in a second crosslinking step (as previously described) is treated to reduce the concentration of any residual amine-reactive groups (e.g., amine-reactive functional groups) introduced to the crosslinked polymer by a crosslinker. For example, in one such embodiment the crosslinked poly(allylamine) polymer is treated with a quenching agent such as a base, washed, heated, or otherwise treated to remove or quench the amine-reactive groups. By way of further example, in one such embodiment the crosslinked poly(allylamine) polymer is treated with ammonium hydroxide. The ammonium hydroxide treatment can occur immediately after the reaction, during the washing steps, or after the polymer has been washed and dried, in which case the polymer can be processed through another series of washing steps. In another such embodiment, the crosslinked poly(allylamine) polymer is heated in a conventional or in a vacuum oven at a temperature above room temperature for a period of time, for example 60° C. for greater than 36 hours. The oven incubation may occur under an inert atmosphere (e.g., nitrogen or argon) to reduce the possibility of oxidation. The reactive group in the crosslinker may include, but is not limited to alkyl halide, epoxide, phosgene, anhydride, carbamate, carbonate, isocyanate, thioisocyanate, esters, activated esters, carboxylic acids and derivatives, sulfonates and derivatives, acyl halides, aziridines, α,β-unsaturated carbonyls, ketones, aldehydes, pentafluoroaryl groups, vinyl, allyl, acrylate, methacrylate, acrylamide, methacrylamide, styrenic, acrylonitriles and combinations thereof. In one such exemplary embodiment, the crosslinker's reactive group will include alkyl halide, epoxide, anhydrides, isocyanates, allyl, vinyl, acrylamide, and combinations thereof. In one such embodiment, the crosslinker's reactive group will be alkyl halide, epoxide, or allyl.

Crosslinked Poly(allylamine) Polymers

As previously noted, the crosslinked poly(allylamine) polymers having the medical uses described herein possess the capacity to remove clinically significant quantities of one or more target species: (i) protons, (ii) the conjugate base(s) of one or more strong acids, and/or (iii) one or more strong acids (e.g., HCl and/or $H_2SO_4$).

In general, the crosslinked poly(allylamine) polymer has a preferred particle size range that is (i) large enough to avoid passive or active absorption through the GI tract and (ii) small enough to not cause grittiness or unpleasant mouth feel when ingested as a powder, sachet and/or chewable tablet/dosage form with a mean particle size of at least 3 microns. For example, in one such embodiment the crosslinked poly(allylamine) polymer comprises a population of particles having a mean particle size (volume distribution) in the range of 5 to 1,000 microns. By way of further example, in one such embodiment the crosslinked poly(allylamine) polymer comprises a population of particles having a mean particle size (volume distribution) in the range of 5 to 500 microns. By way of further example, in one such embodiment the crosslinked poly(allylamine) polymer comprises a population of particles having a mean particle size (volume distribution) in the range of 10 to 400 microns. By way of further example, in one such embodiment the crosslinked poly(allylamine) polymer comprises a population of particles having a mean particle size (volume distribution) in the range of 10 to 300 microns. By way of further example, in one such embodiment the crosslinked poly(allylamine) polymer comprises a population of particles having a mean particle size (volume distribution) in the range of 20 to 250 microns. By way of further example, in one such embodiment the crosslinked poly(allylamine) polymer has a particle size range of 30 to 250 microns. By way of further example, in one such embodiment the crosslinked poly(allylamine) polymer has a particle size range of 40 to 180 microns. In certain embodiments, less than 7% of the particles in the population (on a number basis) have a diameter less than 10 microns. For example, in such embodiments less than 5% of the particles in the particles in the population (on a number basis) have a diameter less than 10 microns. By way of further example, in such embodiments less than 2.5% of the particles in the particles in the population (on a number basis) have a diameter less than 10 microns. By way of further example, in such embodiments less than 1% of the particles in the particles in the population (on a number basis) have a diameter less than 10 microns. In each of the exemplary embodiments recited in this paragraph, the particles are preferably in the form of beads.

To minimize GI side effects in patients that are often related to a large volume polymer gel moving through the GI tract, a low Swelling Ratio of the crosslinked poly(allylamine) polymer is preferred (0.5 to 10 times its own weight in water). For example, in one such embodiment the crosslinked poly(allylamine) polymer has a Swelling Ratio of less than 9. By way of further example, in one such embodiment the crosslinked poly(allylamine) polymer has a Swelling Ratio of less than 8. By way of further example, in one such embodiment the crosslinked poly(allylamine) polymer has a Swelling Ratio of less than 7. By way of further example, in one such embodiment the crosslinked poly(allylamine) polymer has a Swelling Ratio of less than 6. By way of further example, in one such embodiment the crosslinked poly(allylamine) polymer has a Swelling Ratio of less than 5. By way of further example, in one such embodiment the crosslinked poly(allylamine) polymer has a Swelling Ratio of less than 4. By way of further example, in one such embodiment the crosslinked poly(allylamine) polymer has a Swelling Ratio of less than 3. By way of further example, in one such embodiment the crosslinked poly(allylamine) polymer has a Swelling Ratio of less than 2. By way of further example, in one such embodiment the crosslinked poly(allylamine) polymer has a Swelling Ratio of less than 1.9. By way of further example, in one such embodiment the crosslinked poly(allylamine) polymer has a Swelling Ratio of less than 1.8. By way of further example, in one such embodiment the crosslinked poly(allylamine) polymer has a Swelling Ratio of less than 1.7. By way of further example, in one such embodiment the crosslinked poly(allylamine) polymer has a Swelling Ratio of less than 1.6. By way of further example, in one such embodiment the crosslinked poly(allylamine) polymer has a Swelling Ratio of less than 1.5. By way of further example, in one such embodiment the crosslinked poly(allylamine) polymer has a Swelling Ratio of less than 1.4. By way of further example, in one such embodiment the crosslinked poly(allylamine) polymer has a Swelling Ratio of less than 1.3. By way of further example, in one such embodiment the crosslinked poly(allylamine) polymer has a Swelling Ratio of less than 1.2. By way of further example, in one such embodiment the crosslinked poly(allylamine) polymer has a Swelling Ratio of less than 1. By way of further example, in one such embodiment the crosslinked poly(allylamine) polymer has a Swelling Ratio of less than 0.9. By way of further example, in one such embodiment the crosslinked poly(allylamine) polymer has a Swelling Ratio of less than 0.8. By way of further example, in one such embodiment the crosslinked poly(allylamine) polymer has a Swelling Ratio of less than 0.7. By way of further example, in one such embodiment the crosslinked poly(allylamine) polymer has a Swelling Ratio of less than 0.6. By way of further example, in one such embodiment the crosslinked poly(allylamine) polymer has a Swelling Ratio of at least 0.5 and less than 2.

The amount of the target species (e.g., bile acids, phosphate, protons, conjugate base of a strong acid and/or strong acid) that is bound as the crosslinked poly(allylamine) polymer transits the GI tract is largely a function of the binding capacity of the composition for the target species (e.g., bile acids, phosphate, protons, the conjugate base of a strong acid, and/or a strong acid) and the quantity of the crosslinked poly(allylamine) polymer administered per day as a daily dose. In general, when the target species is a proton, a conjugate base of a strong acid and/or a strong acid the theoretical binding capacity for the target species may be determined using a SGF assay and determining the amount of a species that appeared in or disappeared from the SGF buffer during the SGF assay.

In general, the crosslinked poly(allylamine) polymer will have a theoretical binding capacity for the target species (wherein the target species is a proton, a conjugate base of a strong acid and/or a strong acid) of at least about 0.5 mEq/g (as determined in an SGF assay). For example, in some embodiments the crosslinked poly(allylamine) polymer will have a theoretical binding capacity for the target species of at least about 1 mEq/g. By way of further example, in some embodiments the crosslinked poly(allylamine) polymer will have a theoretical binding capacity for the target species of at least about 2 mEq/g. By way of further example, in some embodiments the crosslinked poly(allylamine) polymer will have a theoretical binding capacity for the target species of at least about 3 mEq/g. By way of further example, in some embodiments the crosslinked poly(allylamine) polymer will have a theoretical binding capacity for the target species of at least about 4 mEq/g. By way of further example, in some embodiments the crosslinked poly(allylamine) polymer will have a theoretical binding capacity for the target species of at least about 5 mEq/g. By way of further example, in some embodiments the crosslinked poly(allylamine) polymer will have a theoretical binding capacity for the target species of at least about 7.5 mEq/g. By way of further example, in some embodiments the crosslinked poly(allylamine) polymer will have a theoretical binding capacity for the target species of at least about 10 mEq/g. By way of further example, in some embodiments the crosslinked poly(allylamine) polymer will have a theoretical binding capacity for the target species of at least about 12.5 mEq/g. By way of further example, in some embodiments the crosslinked poly(allylamine) polymer will have a theoretical binding capacity for the target species of at least about 15 mEq/g. By way of further example, in some embodiments the crosslinked poly(allylamine) polymer will have a theoretical binding capacity for the target species of at least about 20 mEq/g. In general, the crosslinked poly(allylamine) polymer will typically have a theoretical binding capacity for the target species that is not in excess of about 35 mEq/g. For example, in some embodiments, the theoretical binding capacity of the crosslinked poly(allylamine) polymers for the target species that is not be excess of 30 mEq/g. Thus, for example, the theoretical binding capacity of the crosslinked poly(allylamine) polymers for the target species may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

In general, the crosslinked poly(allylamine) polymer will have a theoretical binding capacity for protons of at least about 0.5 mEq/g (as determined in an SGF assay). For example, in some embodiments the crosslinked poly(allylamine) polymer will have a theoretical binding capacity for protons of at least about 1 mEq/g. By way of further example, in some embodiments the crosslinked poly(allylamine) polymer will have a theoretical binding capacity for protons of at least about 2 mEq/g. By way of further example, in some embodiments the crosslinked poly(allylamine) polymer will have a theoretical binding capacity for protons of at least about 3 mEq/g. By way of further example, in some embodiments the crosslinked poly(allylamine) polymer will have a theoretical binding capacity for protons of at least about 4 mEq/g. By way of further example, in some embodiments the crosslinked poly(allylamine) polymer will have a theoretical binding capacity for protons of at least about 5 mEq/g. By way of further example, in some embodiments the crosslinked poly(allylamine) polymer will have a theoretical binding capacity for protons of at least about 7.5 mEq/g. By way of further example, in some embodiments the crosslinked poly(allylamine) polymer will have a theoretical binding capacity for protons of at least about 10 mEq/g. By way of further example, in some embodiments the crosslinked poly(allylamine) polymer will have a theoretical binding capacity for protons of at least about 12.5 mEq/g. By way of further example, in some embodiments the crosslinked poly(allylamine) polymer will have a theoretical binding capacity for protons of at least about 15 mEq/g. By way of further example, in some embodiments the crosslinked poly(allylamine) polymer will have a theoretical binding capacity for protons of at least about 20 mEq/g. In general, the crosslinked poly(allylamine) polymer will typically have a theoretical binding capacity for protons that is not in excess of about 35 mEq/g. For example, in some embodiments, the theoretical binding capacity of the crosslinked poly(allylamine) polymers for protons that is not be excess of 30 mEq/g. Thus, for example, the theoretical binding capacity of the crosslinked poly(allylamine) polymers for protons may range from 2 to 25 mEq/g, 3 to 25 mEq/g, 5 to 25 mEq/g, 10 to 25 mEq/g, 5 to 20 mEq/g, 6 to 20 mEq/g, 7.5 to 20 mEq/g, or even 10 to 20 mEq/g. In those embodiments in which the target species comprises protons and at least one conjugate base, the binding capacities recited in this paragraph are the theoretical binding capacities for protons and the theoretical binding capacities for the conjugate base(s), independently and individually, and not the sum thereof.

Phosphate, bicarbonate, bicarbonate equivalents, the conjugate bases of bile and fatty acids are potential interfering anions for chloride or other conjugate bases of strong acids in the stomach and small intestine. Therefore, rapid and preferential binding of chloride over phosphate, bicarbonate equivalents, and the conjugate bases of bile and fatty acids in the small intestine is desirable and the SIB assay may be used to determine kinetics and preferential binding. Since the transit time of the colon is slow (2-3 days) relative to the small intestine, and since conditions in the colon will not be encountered by an orally administered crosslinked poly(allylamine) polymer until after stomach and small intestine conditions have been encountered, kinetics of chloride binding by a crosslinked poly(allylamine) polymer do not need to be as rapid in the colon or under in vitro conditions designed to mimic the late small intestine/colon. It is, however, desirable that chloride binding and selectivity over other interfering anions is high, for example, at 24 and/or 48 hours or longer.

In one embodiment, the crosslinked poly(allylamine) polymer is characterized by a chloride ion binding capacity of at least 1 mEq/g in a Simulated Small Intestine Inorganic ("SIB") assay. For example, in one such embodiment the crosslinked poly(allylamine) polymer is characterized by a chloride ion binding capacity of at least 1.5 mEq/g in a SIB assay. By way of further example, in one such embodiment the crosslinked poly(allylamine) polymer is characterized by a chloride ion binding capacity of at least 2 mEq/g in a SIB assay. By way of further example, in one such embodiment the crosslinked poly(allylamine) polymer is characterized by a chloride ion binding capacity of at least 2.5 mEq/g in a SIB assay. By way of further example, in one such embodiment the crosslinked poly(allylamine) polymer is characterized by a chloride ion binding capacity of at least 3 mEq/g in a SIB assay. By way of further example, in one such embodiment the crosslinked poly(allylamine) polymer is characterized by a chloride ion binding capacity of at least 3.5 mEq/g in a SIB assay. By way of further example, in one such embodiment the crosslinked poly(allylamine) polymer is characterized by a chloride ion binding capacity of at least 4 mEq/g in a SIB assay. By way of further example, in one such embodiment the crosslinked poly(allylamine) polymer is characterized by a chloride ion binding capacity of at least 4.5 mEq/g in a SIB assay. By way of further example, in one such embodiment the crosslinked poly(allylamine) polymer is characterized by a chloride ion binding capacity of at least 5 mEq/g in a SIB assay. By way of further example, in one such embodiment the crosslinked poly(allylamine) polymer is characterized by a chloride ion binding capacity of at least 5.5 mEq/g in a SIB assay. By way of further example, in one such embodiment the crosslinked poly(allylamine) polymer is characterized by a chloride ion binding capacity of at least 6 mEq/g in a SIB assay.

In one embodiment, the crosslinked poly(allylamine) polymer binds a significant amount of chloride relative to phosphate as exhibited, for example, in a SIB assay. For example, in one embodiment the ratio of the amount of bound chloride to bound phosphate in a SIB assay is at least 0.1:1, respectively. By way of further example, in one such embodiment the ratio of the amount of bound chloride to bound phosphate in a SIB assay is at least 0.2:1, respectively. By way of further example, in one such embodiment the ratio of the amount of bound chloride to bound phosphate in a SIB assay is at least 0.25:1, respectively. By way of further example, in one such embodiment the ratio of the amount of bound chloride to bound phosphate in a SIB assay is at least 0.3:1, respectively. By way of further example, in one such embodiment the ratio of the amount of bound chloride to bound phosphate in a SIB assay is at least 0.35:1, respectively. By way of further example, in one such embodiment the ratio of the amount of bound chloride to bound phosphate in a SIB assay is at least 0.4:1, respectively. By way of further example, in one such embodiment the ratio of the amount of bound chloride to bound phosphate in a SIB assay is at least 0.45:1, respectively. By way of further example, in one such embodiment the ratio of the amount of bound chloride to bound phosphate in a SIB assay is at least 0.5:1, respectively. By way of further example, in one such embodiment the ratio of the amount of bound chloride to bound phosphate in a SIB assay is at least 2:3, respectively. By way of further example, in one such embodiment the ratio of the amount of bound chloride to bound phosphate in a SIB assay is at least 0.75:1, respectively. By way of further example, in one such embodiment the ratio of the amount of bound chloride to bound phosphate in a SIB assay is at least 0.9:1, respectively. By way of further example, in one such embodiment the ratio of the amount of bound chloride to bound phosphate in a SIB assay is at least 1:1, respectively. By way of further example, in one such embodiment the ratio of the amount of bound chloride to bound phosphate in a SIB assay is at least 1.25:1, respectively. By way of further example, in one such embodiment the ratio of the amount of bound chloride to bound phosphate in a SIB assay is at least 1.5:1, respectively. By way of further example, in one such embodiment the ratio of the amount of bound chloride to bound phosphate in a SIB assay is at least 1.75:1, respectively. By way of further example, in one such embodiment the ratio of the amount of bound chloride to bound phosphate in a SIB assay is at least 2:1, respectively. By way of further example, in one such embodiment the ratio of the amount of bound chloride to bound phosphate in a SIB assay is at least 2.25:1, respectively. By way of further example, in one such embodiment the ratio of the amount of bound chloride to bound phosphate in a SIB assay is at least 2.5:1, respectively. By way of further example, in one such embodiment the ratio of the amount of bound chloride to bound phosphate in a SIB assay is at least 2.75:1, respectively. By way of further example, in one such embodiment the ratio of the amount of bound chloride to bound phosphate in a SIB assay is at least 3:1, respectively. By way of further example, in one such embodiment the ratio of the amount of bound chloride to bound phosphate in a SIB assay is at least 4:1, respectively. By way of further example, in one such embodiment the ratio of the amount of bound chloride to bound phosphate in a SIB assay is at least 5:1, respectively.

In one embodiment, the crosslinked poly(allylamine) polymer is characterized by a proton-binding capacity and a chloride binding capacity in Simulated Gastric Fluid of at least 1 mEq/g in a SGF assay. For example, in one such embodiment the crosslinked poly(allylamine) polymer is characterized by a proton-binding capacity and a chloride binding capacity in a SGF assay of at least 2 mEq/g. By way of further example, in one such embodiment the crosslinked poly(allylamine) polymer is characterized by a proton-binding capacity and a chloride binding capacity in a SGF assay of at least 3 mEq/g. By way of further example, in one such embodiment the crosslinked poly(allylamine) polymer is characterized by a proton-binding capacity and a chloride binding capacity in a SGF assay of at least 4 mEq/g. By way of further example, in one such embodiment the crosslinked poly(allylamine) polymer is characterized by a proton-binding capacity and a chloride binding capacity in a SGF assay of at least 5 mEq/g. By way of further example, in one such embodiment the crosslinked poly(allylamine) polymer is characterized by a proton-binding capacity and a chloride binding capacity in a SGF assay of at least 6 mEq/g. By way of further example, in one such embodiment the crosslinked poly(allylamine) polymer is characterized by a proton-binding capacity and a chloride binding capacity in a SGF assay of at least 7 mEq/g. By way of further example, in one such embodiment the crosslinked poly(allylamine) polymer is characterized by a proton-binding capacity and a chloride binding capacity in a SGF assay of at least 8 mEq/g. By way of further example, in one such embodiment the crosslinked poly(allylamine) polymer is characterized by a proton-binding capacity and a chloride binding capacity in a SGF assay of at least 9 mEq/g. By way of further example, in one such embodiment the crosslinked poly(allylamine) polymer is characterized by a proton-binding capacity and a chloride binding capacity in a SGF assay of at least 10 mEq/g. By way of further example, in one such embodiment the crosslinked poly(allylamine) polymer is characterized by a proton-binding capacity and a chloride binding capacity in a SGF assay of at least 11 mEq/g. By way of further example, in one such embodiment the crosslinked poly(allylamine) polymer is characterized by a proton-binding capacity and a chloride binding capacity in a SGF assay of at least 12 mEq/g. By way of further example, in one such embodiment the crosslinked poly(allylamine) polymer is characterized by a proton-binding capacity and a chloride binding capacity in a SGF assay of at least 13 mEq/g. By way of further example, in one such embodiment the crosslinked poly(allylamine) polymer is characterized by a proton-binding capacity and a chloride binding capacity in a SGF assay of at least 14 mEq/g. By way of further example, in one such embodiment the crosslinked poly(allylamine) polymer is characterized by a proton-binding capacity and a chloride binding capacity after 1 hour in SGF that is at least 50% of the proton-binding capacity and the chloride binding capacity, respectively, of the crosslinked poly(allylamine) polymer at 24 hours in SGF. By way of further example, in one such embodiment the crosslinked poly(allylamine) polymer is characterized by a proton-binding capacity and a chloride binding capacity after 1 hour in SGF that is at least 60% of the proton-binding capacity and the chloride binding capacity, respectively, of the crosslinked poly(allylamine) polymer at 24 hours in SGF. By way of further example, in one such embodiment the crosslinked poly(allylamine) polymer is characterized by a proton-binding capacity and a chloride binding capacity after 1 hour in SGF that is at least 70% of the proton-binding capacity and the chloride binding capacity, respectively, of the crosslinked poly(allylamine) polymer at 24 hours in SGF. By way of further example, in one such embodiment the crosslinked poly(allylamine) polymer is characterized by a proton-binding capacity and a chloride binding capacity after 1 hour in SGF that is at least 80% of the proton-binding capacity and the chloride binding capacity, respectively, of the crosslinked poly(allylamine) polymer at 24 hours in SGF. By way of further example, in one such embodiment the crosslinked poly(allylamine) polymer is characterized by a proton-binding capacity and a chloride binding capacity after 1 hour in SGF that is at least 90% of the proton-binding capacity and the chloride binding capacity, respectively, of the crosslinked poly(allylamine) polymer at 24 hours in SGF.

In those embodiments in which the crosslinked poly(allylamine) polymer binds chloride ions, it is generally preferred that the crosslinked poly(allylamine) polymer selectively bind chloride ions relative to other counter ions such as bicarbonate equivalent anions, phosphate anions, and the conjugate bases of bile and fatty acids. Stated differently, it is generally preferred in these embodiments that the crosslinked poly(allylamine) polymer (i) remove more chloride ions than bicarbonate equivalent anions (ii) remove more chloride ions than phosphate anions, and (iii) remove more chloride ions than the conjugate bases of bile and fatty acids. Advantageously, therefore, treatment with the crosslinked poly(allylamine) polymer does not induce or exacerbate hypophosphatemia (i.e., a serum phosphorous concentration of less than about 2.4 mg/dL, does not significantly elevate low density lipoproteins ("LDL"), or otherwise negatively impact serum or colon levels of metabolically relevant anions.

In one embodiment, the crosslinked poly(allylamine) polymer is a crosslinked poly(allylamine) polymer comprising a structure corresponding to Formula 4:

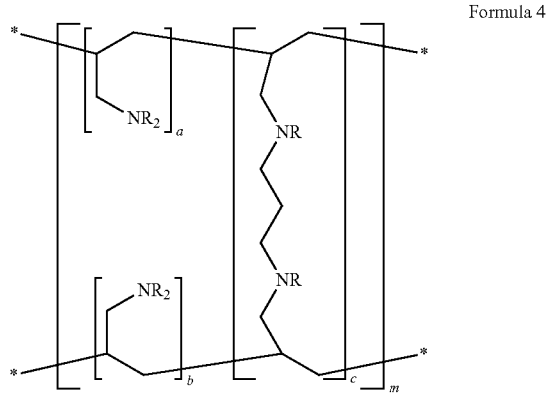

Formula 4 wherein each R is independently hydrogen or an ethylene crosslink between two nitrogen atoms of the crosslinked amine polymer and a, b, c, and m are integers. Typically, m is a large integer indicating an extended polymer network in which each polymer bead is considered a single molecule. Stated differently, when molecular weight is calculated using the volume of a polymer bead and the bulk density of the polymer, m is large enough to indicate a molecular weight in excess of $3.2 \times 10^8$ g/mol. In one such embodiment, a ratio of the sum of a and b to c (i.e., a+b:c) is in the range of about 1:1 to 9:1. For example, in one such embodiment a ratio of the sum of a and b to c (i.e., a+b:c) is in the range of about 1:1 to 8:1. By way of further example, in one such embodiment the sum of a and b to c (i.e., a+b:c) is in the range of about 1:1 to 7:1. By way of further example, in one such embodiment the sum of a and b to c (i.e., a+b:c) is in the range of about 1:1 to 6:1. By way of further example, in one such embodiment a ratio of the sum of a and b to c (i.e., a+b:c) is in the range of about 1:1 to 5:1. By way of further example, in one such embodiment the sum of a and b to c (i.e., a+b:c) is in the range of about 1:1 to 4:1. By way of further example, in one such embodiment the sum of a and b to c (i.e., a+b:c) is in the range of about 1:1 to 3:1. By way of further example, in one such embodiment the sum of a and b to c a+b:c) is in the range of about 1:1 to 2:1. By way of further example, in one such embodiment the sum of a and b to c a+b:c) is about 1:1. By way of further example, in one such embodiment a ratio of the sum of a and b to c (i.e., a+b:c) is in the range of about 1.5:1 to 4:1. By way of further example, in one such embodiment a ratio of the sum of a and b to c (i.e., a+b:c) is in the range of about 1.75:1 to 3:1. For example, in one such embodiment a ratio of the sum of a and b is 57, c is 24 and m is large integer indicating an extended polymer network. In each of the foregoing embodiments a ratio of the sum of a and b to c a+b:c) may be in the range of about 2:1 to 2.5:1. For example, in such embodiments the ratio of the sum of a and b to c a+b:c) may be in the range of about 2.1:1 to 2.2:1. By way of further example, in such embodiments the ratio of the sum of a and b to c (i.e., a+b:c) may be in the range of about 2.2:1 to 2.3:1. By way of further example, in such embodiments the ratio of the sum of a and b to c (i.e., a+b:c) may be in the range of about 2.3:1 to 2.4:1. By way of further example, in such embodiments the ratio of the sum of a and b to c (i.e., a+b:c) may be in the range of about 2.4:1 to 2.5:1. In each of the foregoing embodiments, each R may independently be hydrogen or an ethylene crosslink between two nitrogen atoms. Typically, however, 35-95% of the R substituents will be hydrogen and 5-65% will be an ethylene crosslink

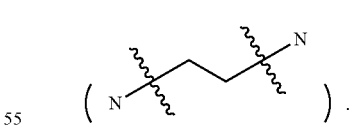

For example, in one such embodiment, 50-95% of the R substituents will be hydrogen and 5-50% will be an ethylene crosslink

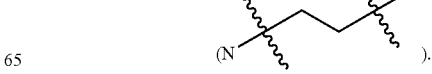

For example, in one such embodiment, 55-90% of the R substituents are hydrogen and 10-45% are an ethylene crosslink

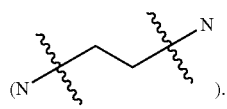

By way of further example, in one such embodiment, 60-90% of the R substituents are hydrogen and 10-40% are an ethylene crosslink. By way of further example, in one such embodiment, 65-90% of the R substituents are hydrogen and 10-35% are an ethylene crosslink.

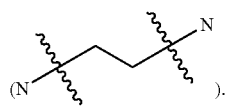

By way of further example, in one such embodiment, 70-90% of the R substituents are hydrogen and 10-30% are an ethylene crosslink. By way of further example, in one such embodiment, 75-85% of the R substituents are hydrogen and 15-25% are an ethylene crosslink. By way of further example, in one such embodiment, 65-75% of the R substituents are hydrogen and 25-35% are an ethylene crosslink. By way of further example, in one such embodiment, 55-65% of the R substituents are hydrogen and 35-45% are an ethylene crosslink. In some embodiments, a, b, c and R are such that the carbon to nitrogen ratio of the polymer of Formula 4 may range from about 2:1 to about 6:1, respectively. For example, in one such embodiment, the carbon to nitrogen ratio of the polymer of Formula 4 may range from about 2.5:1 to about 5:1, respectively. By way of further example, in one such embodiment, the carbon to nitrogen ratio of the polymer of Formula 4 may range from about 3:1 to about 4.5:1, respectively. By way of further example, in one such embodiment, the carbon to nitrogen ratio of the polymer of Formula 4 may range from about 3.25:1 to about 4.25:1, respectively. By way of further example, in one such embodiment, the carbon to nitrogen ratio of the polymer of Formula 4 may range from about 3.4:1 to about 4:1, respectively. By way of further example, in one such embodiment, the carbon to nitrogen ratio of the polymer of Formula 4 may range from about 3.5:1 to about 3.9:1, respectively. By way of further example, in one such embodiment, the carbon to nitrogen ratio of the polymer of Formula 4 may range from about 3.55:1 to about 3.85:1, respectively. In each of the foregoing embodiments recited in this paragraph, the polymer of Formula 4 is derived from monomers and crosslinkers, each of which comprise less than 5 wt % oxygen.

In one embodiment, the crosslinked poly(allylamine) polymer is a crosslinked poly(allylamine) polymer comprising the residue of (i) a monoallylamine corresponding to Formula 1 or a salt thereof, (ii) a multiallylamine corresponding to Formula 3 or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. In one exemplary embodiment, the crosslinked poly(allylamine) polymer is a crosslinked poly(allylamine) polymer comprising the residue of (i) a monoallylamine corresponding to Formula 1 or a salt thereof, (ii) a multiallylamine corresponding to Formula 3A or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. In another exemplary embodiment, the crosslinked poly(allylamine) polymer is a crosslinked poly(allylamine) polymer comprising the residue of (i) 2-Propen-1-ylamine or a salt thereof, (ii) a multiallylamine corresponding to Formula 3 or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. In another exemplary embodiment, the crosslinked poly(allylamine) polymer is a crosslinked poly(allylamine) polymer comprising the residue of (i) corresponding to Formula 1 or a salt thereof, (ii) a multiallylamine appearing in Table C or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. In another exemplary embodiment, the crosslinked poly(allylamine) polymer is a crosslinked poly(allylamine) polymer comprising the residue of (i) corresponding to Formula 1 or a salt thereof, (ii) 1,3-Bis(allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups In another exemplary embodiment, the crosslinked poly(allylamine) polymer is a crosslinked poly(allylamine) polymer comprising the residue of (i) 2-Propen-1-ylamine or a salt thereof, (ii) 1,3-Bis(allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. In another exemplary embodiment, the crosslinked poly(allylamine) polymer is a crosslinked poly(allylamine) polymer comprising the residue of (i) 2-Propen-1-ylamine or a salt thereof, (ii) 1,3-Bis(allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups In another exemplary embodiment, the crosslinked poly(allylamine) polymer is a crosslinked poly(allylamine) polymer comprising the residue of (i) 2-Propen-1-ylamine or a salt thereof, (ii) 1,3-Bis (allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups, wherein the molar ratio of 2-Propen-1-ylamine (or salt(s) thereof) to 1,3-Bis (allylamino)propane (or salt(s) thereof) is in the range of 60:40 to 95:5, respectively. In another exemplary embodiment, the crosslinked poly(allylamine) polymer is a crosslinked poly(allylamine) polymer comprising the residue of (i) 2-Propen-1-ylamine or a salt thereof, (ii) 1,3-Bis(allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups, wherein the mole ratio of 2-Propen-1-ylamine (or salt(s) thereof to 1,3-Bis (allylamino)propane (or salt(s) thereof) is in the range of 65:35 to 90:10, respectively. In another exemplary embodiment, the crosslinked poly(allylamine) polymer is a crosslinked poly(allylamine) polymer comprising the residue of (i) 2-Propen-1-ylamine or a salt thereof, (ii) 1,3-Bis(allylamino)propane or a salt thereof, and (iii) the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups, wherein the mole ratio of 2-Propen-1-ylamine (or salt(s) thereof) to 1,3-Bis (allylamino)propane (or salt(s) thereof) is in the range of 65:35 to 75:25, respectively. For example, in each of the foregoing embodiments recited in this paragraph the crosslinker residue may be a residue of a dihaloalkane. By way of further example, in each of the foregoing embodiments recited in this paragraph, the crosslinker residue may be a residue of 1,2-dibromoethane, 1,2-dichloroethane, 1-bromo-2-chloroethane, 1,3-dibromopropane, 1,3-dichloropropane, or 1-bromo-3-chloropropane. By way of further example, in each of the foregoing embodiments exemplary embodiments recited in this paragraph, the residue of the monoallylamine and/or the residue of the multiallylamine may be residue of a hydrochloric acid salt, sulfuric acid salt, phosphoric acid salt, hydrobromic acid salt or a combination thereof.

Pharmaceutical Compositions & Administration

In general, the dosage levels of the crosslinked poly (allylamine) polymers for therapeutic and/or prophylactic uses may range from about 0.5 g/day to about 100 g/day. To facilitate patient compliance, it is generally preferred that the dose be in the range of about 1 g/day to about 50 g/day. For example, in one such embodiment, the dose will be about 2 g/day to about 25 g/day. By way of further example, in one such embodiment, the dose will be about 3 g/day to about 25 g/day. By way of further example, in one such embodiment, the dose will be about 4 g/day to about 25 g/day. By way of further example, in one such embodiment, the dose will be about 5 g/day to about 25 g/day. By way of further example, in one such embodiment, the dose will be about 2.5 g/day to about 20 g/day. By way of further example, in one such embodiment, the dose will be about 2.5 g/day to about 15 g/day. By way of further example, in one such embodiment, the dose will be about 1 g/day to about 10 g/day. Optionally, the daily dose may be administered as a single dose (i.e., one time a day), or divided into multiple doses (e.g., two, three or more doses) over the course of a day. In general, the crosslinked poly(allylamine) polymers may be administered as a fixed daily dose or titrated based on the serum bicarbonate values of the patient in need of treatment or other indicators of acidosis. The titration may occur at the onset of treatment or throughout, as required, and starting and maintenance dosage levels may differ from patient to patient based on severity of the underlying disease.

The effectiveness of the crosslinked poly(allylamine) polymer may be established in animal models, or in human volunteers and patients. In addition, in vitro, ex vivo and in vivo approaches are useful to establish HCl or other target species binding. In vitro binding solutions can be used to measure the binding capacity for proton, chloride and other ions at different pHs. Ex vivo extracts, such as the gastro-intestinal lumen contents from human volunteers or from model animals can be used for similar purposes. The selectivity of binding and/or retaining certain ions preferentially over others can also be demonstrated in such in vitro and ex vivo solutions. In vivo models of metabolic acidosis can be used to test the effectiveness of the crosslinked poly(allylamine) polymer in normalizing acid/base balance—for example 5/6 nephrectomized rats fed casein-containing chow (as described in Phisitkul S, Hacker C, Simoni J, Tran R M, Wesson D E. Dietary protein causes a decline in the glomerular filtration rate of the remnant kidney mediated by metabolic acidosis and endothelin receptors. Kidney international. 2008; 73(2):192-9), or adenine-fed rats (Terai K, K Mizukami and M Okada. 2008. Comparison of chronic renal failure rats and modification of the preparation protocol as a hyperphosphatemia model. Nephrol. 13: 139-146).

Metabolic acidosis, regardless of etiology, lowers extracellular fluid bicarbonate and, thus, decreases extracellular pH. The relationship between serum pH and serum bicarbonate is described by the Henderson-Hasselbalch equation $$pH = pK' + \log [HCO_3^-]/[(0.03 \times PaCO_2)]$$

where 0.03 is the physical solubility coefficient for $CO_2$, $[HCO_3^-]$ and $PaCO_2$ are the concentrations of bicarbonate and the partial pressure of carbon dioxide, respectively.

There are several laboratory tests that can be used to define metabolic acidosis. The tests fundamentally measure either bicarbonate ($HCO_3^-$) or proton ($H^+$) concentration in various biological samples, including venous or arterial blood. These tests can measure either bicarbonate ($HCO_3^-$) or proton ($H^+$) concentration by enzymatic methodology, by ion selective electrodes or by blood gas analysis. In both the enzymatic and ion selective electrode methods, bicarbonate is "measured." Using blood gas analysis, bicarbonate level can be calculated using the Henderson-Hasselbalch equation.

Arterial blood gas (ABG) analysis is commonly performed for clinical evaluation, but the procedure has certain limitations in the form of reduced patient acceptability because of painful procedure and the potential to cause complications such as arterial injury, thrombosis with distal ischaemia, haemorrhage, aneurysm formation, median nerve damage and reflex sympathetic dystrophy. Venous blood gas (VBG) analysis is a relatively safer procedure as fewer punctures are required thus reducing the risk of needle stick injury to the health care workers. Therefore, as set out below, when the invention requires assessment of metabolic acidosis, it is preferred to complete this assessment using VBG analysis. Any measurements specified herein are preferably achieved by VBG analysis where possible, for example measurements of blood or serum bicarbonate levels.

The most useful measurements for the determination of acidosis rely on a measurement of the venous plasma bicarbonate (or total carbon dioxide [$tCO_2$]), or arterial plasma bicarbonate (or total carbon dioxide [$tCO_2$]), serum electrolytes $Cl^-$, $K^+$, and $Na^+$, and a determination of the anion gap. In the clinical laboratory, measurement of venous plasma or serum electrolytes includes an estimation of the $tCO_2$. This measurement reflects the sum of circulating $CO_2$ [i.e., the total $CO_2$ represented by bicarbonate ($HCO_3^-$), carbonic acid, ($H_2CO_3$) and dissolved $CO_2$ ($0.03 \times PCO_2$)]. $tCO_2$ can also be related to $HCO_3^-$ by using a simplified and standardized form of the Henderson-Hasselbalch equation: $tCO_2=HCO_3^-+0.03\ PCO_2$, where $PCO_2$ is the measured partial pressure of $CO_2$. Since $HCO_3^-$ concentration is greater than 90% of the $tCO_2$, and there are small amounts of $H_2CO_3$, then venous $tCO_2$ is often used as a reasonable approximation of the venous $HCO_3^-$ concentration in the blood. Especially during chronic kidney disease, an abnormal plasma $HCO_3^-$ value <22 mEq/L generally indicates metabolic acidosis.

In one embodiment, the crosslinked poly(allylamine) polymers are provided (by oral administration) to an animal, including a human, in a dosing regimen of one, two or even multiple (i.e., at least three) doses per day to treat an acid-base disorder (e.g., metabolic acidosis) and achieve a clinically significant and sustained increase of serum bicarbonate or other target species as previously described. For example, in one embodiment a daily dose of the crosslinked poly(allylamine) polymer (whether orally administered in a single dose or multiple doses over the course of the day) has sufficient capacity to remove at least 5 mmol of protons, chloride ions or each per day. By way of further example, in one such embodiment a daily dose of the crosslinked poly (allylamine) polymer has sufficient capacity to remove at least 10 mmol of protons, chloride ions or each per day. By way of further example, in one such embodiment a daily dose of the crosslinked poly(allylamine) polymer has sufficient capacity to remove at least 20 mmol of protons, the conjugate base of a strong acid, and/or a strong acid each per day. By way of further example, in one such embodiment a daily dose of the crosslinked poly(allylamine) polymer has sufficient capacity to remove at least 30 mmol of protons, the conjugate base of a strong acid, and/or a strong acid each per day. By way of further example, in one such embodiment a daily dose of the crosslinked poly(allylamine) polymer has sufficient capacity to remove at least 40 mmol of protons, the conjugate base of a strong acid, and/or a strong acid each per day. By way of further example, in one such embodiment a daily dose of the crosslinked poly(allylamine) polymer has sufficient capacity to remove at least 50 mmol of protons, the conjugate base of a strong acid, and/or a strong acid each per day.

The dosage unit form of the pharmaceutical comprising the crosslinked poly(allylamine) polymer may be any form appropriate for oral administration. Such dosage unit forms include powders, tablets, pills, lozenges, sachets, cachets, elixirs, suspensions, syrups, soft or hard gelatin capsules, and the like. In one embodiment, the pharmaceutical composition comprises only the crosslinked poly(allylamine) polymer. Alternatively, the pharmaceutical composition may comprise a carrier, a diluent, or excipient in addition to the crosslinked poly(allylamine) polymer. Examples of carriers, excipients, and diluents that may be used in these formulations as well as others, include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc. Pharmaceutical excipients useful in the pharmaceutical compositions further include a binder, such as microcrystalline cellulose, colloidal silica and combinations thereof (Prosolv 90), carbopol, providone and xanthan gum; a flavoring agent, such as sucrose, mannitol, xylitol, maltodextrin, fructose, or sorbitol; a lubricant, such as magnesium stearate, stearic acid, sodium stearyl fumurate and vegetable based fatty acids; and, optionally, a disintegrant, such as croscarmellose sodium, gellan gum, low-substituted hydroxypropyl ether of cellulose, sodium starch glycolate. Other additives may include plasticizers, pigments, talc, and the like. Such additives and other suitable ingredients are well-known in the art; see, e.g., Gennaro A R (ed), Remington's Pharmaceutical Sciences, 20th Edition.

In one embodiment, the crosslinked poly(allylamine) polymer may be co-administered with other active pharmaceutical agents depending on the condition being treated. This co-administration may include simultaneous administration of the two agents in the same dosage form, simultaneous administration in separate dosage forms, and separate administration. For example, for the treatment of metabolic acidosis, the crosslinked poly(allylamine) polymer may be co-administered with common treatments that are required to treat underlying co-morbidities including but not limited to hypertension, diabetes, obesity, heart failure and complications of Chronic Kidney Disease. These medications and the crosslinked poly(allylamine) polymer can be formulated together in the same dosage form and administered simultaneously as long as they do not display any clinically significant drug-drug-interactions. Alternatively, these treatments and the crosslinked poly(allylamine) polymer may be separately and sequentially administered with the administration of one being followed by the administration of the other.

In one embodiment, the daily dose of the chronic metabolic acidosis treatment is compliance enhancing (approximately 15 g or less per day) and achieves a clinically significant and sustained increase of serum bicarbonate of approximately 3 mEq/L at these daily doses. The non-absorbed nature of the polymer and the lack of sodium load and/or introduction of other deleterious ions for such an oral drug enable for the first time a safe, chronic treatment of metabolic acidosis without worsening blood pressure/hypertension and/or without causing increased fluid retention and fluid overload. Another benefit is further slowing of the progression of kidney disease and time to onset of lifelong renal replacement therapy (End Stage Renal Disease "ESRD" including 3 times a week dialysis) or need for kidney transplants. Both are associated with significant mortality, low quality of life and significant burden to healthcare systems around the world. In the United States alone, approximately 20% of the 400,000 ESRD patients die and 100,000 new patients start dialysis every year.

A further aspect of the present disclosure is a pharmaceutical product comprising a sealed package and the crosslinked poly(allylamine) polymer of the present disclosure within the sealed package. The sealed package is preferably substantially impermeable to moisture and oxygen to increase the stability of the pharmaceutical composition. For example, the dosage unit form may comprise a sealed container (e.g., a sealed sachet) that prevents or reduces ingress of moisture and oxygen upon packaging the poly (allylamine) polymer in the container. The container size can be optimized to reduce head space in the container after packing and any head space may be filled with an inert gas such as nitrogen. Furthermore, container material of construction can be chosen to minimize the moisture and oxygen ingress inside the container after packaging. For example, poly(allylamine) polymer may be packaged in a multilayer sachet containing at least one or more layer that serves as a barrier layer to moisture and oxygen ingress. In another example, the poly(allylamine) polymer may be packaged in a single layer or multilayer plastic, metal or glass container that has at least one or more barrier layers incorporated in the structure that limits oxygen and/or moisture ingress after packaging. For example, in one such embodiment the sachet (or other container or package) may comprise a multi-layer laminate of an inner contact layer, an outer layer; and a barrier layer disposed between the contact layer and outer layer. In one exemplary embodiment, the container includes one or more oxygen-scavenging layers.

Treatment of Acid-Base Disorders

In accordance with the present disclosure, acid-base disorders may be treated using pharmaceutical compositions comprising a nonabsorbable composition having the capacity to remove clinically significant quantities of protons, the conjugate base of one or more strong acids, and/or one or more strong acids. An individual afflicted with a an acute or chronic acid/base disorder characterized by a baseline serum bicarbonate value of less than 22 mEq/l may thus be treated by oral administration of a pharmaceutical composition comprising the nonabsorbable composition which then transits the individual's digestive system, binds a target species (protons, one or more conjugate base(s) of a strong acid and/or one or more strong acid(s)) as it transits the digestive system, and removes the bound target species by normal biological function (defecation).

The baseline serum bicarbonate value may be the serum bicarbonate concentration determined at a single time point or may be the mean or median value of two or more serum bicarbonate concentrations determined at two or more timepoints. For example, in one embodiment the baseline serum bicarbonate value may be the value of the serum bicarbonate concentration determined at a single time point and the baseline serum bicarbonate value is used as a basis to determine an acute acidic condition requiring immediate treatment. In another embodiment, the baseline serum bicarbonate treatment value is the mean value of the serum bicarbonate concentration for serum samples drawn at different time points (e.g., different days). By way of further example, in one such embodiment the baseline serum bicarbonate treatment value is the mean value of the serum bicarbonate concentration for serum samples drawn on different days (e.g., at least 2, 3, 4, 5 or more days, that may be consecutive or separated by one or more days or even weeks). By way of further example, in one such embodiment the baseline serum bicarbonate treatment value is the mean value of the serum bicarbonate concentration for serum samples drawn on two consecutive days preceding the initiation of treatment.

In one embodiment, the acid-base disorder being treated is characterized by a baseline serum bicarbonate value of less than 21 mEq/l. For example, in one such embodiment the acid-base disorder being treated is characterized by a baseline serum bicarbonate value of less than 20 mEq/l. By way of further example, in one such embodiment the acid-base disorder being treated is characterized by a baseline serum bicarbonate value of less than 19 mEq/l. By way of further example, in one such embodiment the acid-base disorder being treated is characterized by a baseline serum bicarbonate value of less than 18 mEq/l. By way of further example, in one such embodiment the acid-base disorder being treated is characterized by a baseline serum bicarbonate value of less than 17 mEq/l. By way of further example, in one such embodiment the acid-base disorder being treated is characterized by a baseline serum bicarbonate value of less than 16 mEq/l. By way of further example, in one such embodiment the acid-base disorder being treated is characterized by a baseline serum bicarbonate value of less than 15 mEq/l. By way of further example, in one such embodiment the acid-base disorder being treated is characterized by a baseline serum bicarbonate value of less than 14 mEq/l. By way of further example, in one such embodiment the acid-base disorder being treated is characterized by a baseline serum bicarbonate value of less than 13 mEq/l. By way of further example, in one such embodiment the acid-base disorder being treated is characterized by a baseline serum bicarbonate value of less than 12 mEq/l. By way of further example, in one such embodiment the acid-base disorder being treated is characterized by a baseline serum bicarbonate value of less than 11 mEq/l. By way of further example, in one such embodiment the acid-base disorder being treated is characterized by a baseline serum bicarbonate value of less than 10 mEq/l. By way of further example, in one such embodiment the acid-base disorder being treated is characterized by a baseline serum bicarbonate value of less than 9 mEq/l.

In general, however, the acid-base disorder being treated is characterized by a baseline serum bicarbonate value of at least 9 mEq/l. For example, in one such embodiment, the acid-base disorder is characterized by a baseline serum bicarbonate value of at least 10 mEq/l. By way of further example, in one such embodiment, the acid-base disorder is characterized by a baseline serum bicarbonate value of at least 11 mEq/l. By way of further example, in one such embodiment, the acid-base disorder is characterized by a baseline serum bicarbonate value of at least 12 mEq/l. By way of further example, in one such embodiment, the acid-base disorder is characterized by a baseline serum bicarbonate value of at least 13 mEq/l. By way of further example, in one such embodiment, the acid-base disorder is characterized by a baseline serum bicarbonate value of at least 14 mEq/l. By way of further example, in one such embodiment, the acid-base disorder is characterized by a baseline serum bicarbonate value of at least 15 mEq/l. By way of further example, in one such embodiment, the acid-base disorder is characterized by a baseline serum bicarbonate value of at least 16 mEq/l. By way of further example, in one such embodiment, the acid-base disorder is characterized by a baseline serum bicarbonate value of at least 17 mEq/l. By way of further example, in one such embodiment, the acid-base disorder is characterized by a baseline serum bicarbonate value of at least 18 mEq/l. By way of further example, in one such embodiment, the acid-base disorder is characterized by a baseline serum bicarbonate value of at least 19 mEq/l. By way of further example, in one such embodiment, the acid-base disorder is characterized by a baseline serum bicarbonate value of at least 20 mEq/l. By way of further example, in one such embodiment, the acid-base disorder is characterized by a baseline serum bicarbonate value of at least 21 mEq/l.

In certain embodiments, the acid-base disorder being treated is characterized by a baseline serum bicarbonate value in the range of 9 to 21 mEq/l. For example, in one such embodiment the acid-base disorder is characterized by a baseline serum bicarbonate value in the range of 12 to 20 mEq/l. By way of further example, in one such embodiment the acid-base disorder is characterized by a baseline serum bicarbonate value in the range of 12 to 19 mEq/l. By way of further example, in one such embodiment the acid-base disorder is characterized by a baseline serum bicarbonate value in the range of 12 to 18 mEq/l. By way of further example, in one such embodiment the acid-base disorder is characterized by a baseline serum bicarbonate value in the range of 12 to 17 mEq/l. By way of further example, in one such embodiment the acid-base disorder is characterized by a baseline serum bicarbonate value in the range of 12 to 16 mEq/l. By way of further example, in one such embodiment the acid-base disorder is characterized by a baseline serum bicarbonate value in the range of 9 to 11 mEq/l. By way of further example, in one such embodiment the acid-base disorder is characterized by a baseline serum bicarbonate value in the range of 12-14. By way of further example, in one such embodiment the acid-base disorder is characterized by a baseline serum bicarbonate value in the range of 15-17. By way of further example, in one such embodiment the acid-base disorder is characterized by a baseline serum bicarbonate value in the range of 18-21.

In certain embodiments, oral administration of a pharmaceutical composition containing a nonabsorbable composition increases the individual's serum bicarbonate value from baseline to an increased serum bicarbonate value that exceeds the baseline serum bicarbonate value by at least 1 mEq/l. For example, in one such embodiment the treatment increases the individual's serum bicarbonate value to an increased serum bicarbonate value that exceeds the baseline serum bicarbonate value by at least 1.5 mEq/l. By way of further example in one such embodiment the treatment increases the individual's serum bicarbonate value to an increased serum bicarbonate value that exceeds the baseline serum bicarbonate value by at least 2 mEq/l. By way of further example in one such embodiment the treatment the individual's serum bicarbonate value to an increased serum bicarbonate value that exceeds the baseline serum bicarbonate value by at least 2.5 mEq/l. By way of further example in one such embodiment the treatment increases the individual's serum bicarbonate value to an increased serum bicarbonate value that exceeds the baseline serum bicarbonate value by at least at least 3 mEq/l. By way of further example in one such embodiment the treatment increases the baseline serum bicarbonate value to an increased serum bicarbonate value that exceeds the baseline serum bicarbonate value by at least 3.5 mEq/l. By way of further example in one such embodiment the treatment increases the individual's serum bicarbonate value to an increased serum bicarbonate value that exceeds the baseline serum bicarbonate value by at least 4 mEq/l. By way of further example in one such embodiment the treatment increases the individual's serum bicarbonate value to an increased serum bicarbonate value that exceeds the baseline serum bicarbonate value by at least 5 mEq/l but does not exceed 29 mEq/l. By way of further example in one such embodiment the treatment increases the individual's serum bicarbonate value to an increased serum bicarbonate value that exceeds the baseline serum bicarbonate value by at least 5 mEq/l but does not exceed 28 mEq/l. By way of further example in one such embodiment the treatment increases the individual's serum bicarbonate value to an increased serum bicarbonate value that exceeds the baseline serum bicarbonate value by at least 5 mEq/l but does not exceed 27 mEq/l. By way of further example in one such embodiment the treatment increases the individual's serum bicarbonate value to an increased serum bicarbonate value that exceeds the baseline serum bicarbonate value by at least 5 mEq/l but does not exceed 26 mEq/l. By way of further example in one such embodiment the treatment increases the individual's serum bicarbonate value to an increased serum bicarbonate value that exceeds the baseline serum bicarbonate value by at least 6 mEq/l but does not exceed 29 mEq/l. By way of further example in one such embodiment the treatment increases the individual's serum bicarbonate value to an increased serum bicarbonate value that exceeds the baseline serum bicarbonate value by at least 6 mEq/l but does not exceed 28 mEq/l. By way of further example in one such embodiment the treatment increases the individual's serum bicarbonate value to an increased serum bicarbonate value that exceeds the baseline serum bicarbonate value by at least 6 mEq/l but does not exceed 27 mEq/l. By way of further example in one such embodiment the treatment increases the individual's serum bicarbonate value to an increased serum bicarbonate value that exceeds the baseline serum bicarbonate value by at least 6 mEq/l but does not exceed 26 mEq/l. By way of further example in one such embodiment the treatment increases the individual's serum bicarbonate value to an increased serum bicarbonate value that exceeds the baseline serum bicarbonate value by at least 7 mEq/l but does not exceed 29 mEq/l. By way of further example in one such embodiment the treatment increases the individual's serum bicarbonate value to an increased serum bicarbonate value that exceeds the baseline serum bicarbonate value by at least 7 mEq/l but does not exceed 28 mEq/l. By way of further example in one such embodiment the treatment increases the individual's serum bicarbonate value to an increased serum bicarbonate value that exceeds the baseline serum bicarbonate value by at least 7 mEq/l but does not exceed 27 mEq/l. By way of further example in one such embodiment the treatment increases the individual's serum bicarbonate value to an increased serum bicarbonate value that exceeds the baseline serum bicarbonate value by at least 7 mEq/l but does not exceed 26 mEq/l. By way of further example in one such embodiment the treatment increases the individual's serum bicarbonate value to an increased serum bicarbonate value that exceeds the baseline serum bicarbonate value by at least 8 mEq/l but does not exceed 29 mEq/l. By way of further example in one such embodiment the treatment increases the individual's serum bicarbonate value to an increased serum bicarbonate value that exceeds the baseline serum bicarbonate value by at least 8 mEq/l but does not exceed 28 mEq/l. By way of further example in one such embodiment the treatment increases the individual's serum bicarbonate value to an increased serum bicarbonate value that exceeds the baseline serum bicarbonate value by at least 8 mEq/l but does not exceed 27 mEq/l. By way of further example in one such embodiment the treatment increases the individual's serum bicarbonate value to an increased serum bicarbonate value that exceeds the baseline serum bicarbonate value by at least 8 mEq/l but does not exceed 26 mEq/l. By way of further example in one such embodiment the treatment increases the individual's serum bicarbonate value to an increased serum bicarbonate value that exceeds the baseline serum bicarbonate value by at least 9 mEq/l but does not exceed 29 mEq/l. By way of further example in one such embodiment the treatment increases the individual's serum bicarbonate value to an increased serum bicarbonate value that exceeds the baseline serum bicarbonate value by at least 9 mEq/l but does not exceed 28 mEq/l. By way of further example in one such embodiment the treatment increases the individual's serum bicarbonate value to an increased serum bicarbonate value that exceeds the baseline serum bicarbonate value by at least 9 mEq/l but does not exceed 27 mEq/l. By way of further example in one such embodiment the treatment increases the individual's serum bicarbonate value to an increased serum bicarbonate value that exceeds the baseline serum bicarbonate value by at least 9 mEq/l but does not exceed 26 mEq/l. In each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 12 to 20 mEq/l by at least 1 mEq/l. For example, in one such embodiment the treatment increases the individual's serum bicarbonate value from a baseline serum bicarbonate value in the range of 12 to 20 mEq/l by at least 1.5 mEq/l. By way of further example, in one such embodiment the treatment increases the individual's serum bicarbonate value from a baseline serum bicarbonate value in the range of 12 to 20 mEq/l by at least 2 mEq/l. By way of further example, in one such embodiment the treatment increases the individual's serum bicarbonate value from a baseline serum bicarbonate value in the range of 12 to 20 mEq/l by at least 2.5 mEq/l. By way of further example, in one such embodiment the treatment increases the individual's serum bicarbonate value from a baseline serum bicarbonate value in the range of 12 to 20 mEq/l by at least 3 mEq/l. By way of further example, in one such embodiment the treatment increases the individual's serum bicarbonate value from a baseline serum bicarbonate value in the range of 12 to 20 mEq/l by at least 3.5 mEq/l. By way of further example, in one such embodiment the treatment increases the individual's serum bicarbonate value from a baseline serum bicarbonate value in the range of 12 to 20 mEq/l by at least 4 mEq/l. By way of further example, in one such embodiment the treatment increases the individual's serum bicarbonate value from a baseline serum bicarbonate value in the range of 12 to 20 mEq/l by at least 4.5 mEq/l. By way of further example, in one such embodiment the treatment increases the individual's serum bicarbonate value from a baseline serum bicarbonate value in the range of 12 to 20 mEq/l by at least 5 mEq/l. By way of further example, in one such embodiment the treatment increases the individual's serum bicarbonate value from a baseline serum bicarbonate value in the range of 12 to 20 mEq/l by at least 5.5 mEq/l. By way of further example, in one such embodiment the treatment increases the individual's serum bicarbonate value from a baseline serum bicarbonate value in the range of 12 to 20 mEq/l by at least 6 mEq/l. In each of the foregoing exemplary embodiments recited in this paragraph, the increased serum bicarbonate value preferably does not exceed 29 mEq/l. For example, in each of the foregoing exemplary embodiments, the increased serum bicarbonate value may not exceed 28 mEq/l. By way of further example, in each of the foregoing exemplary embodiments, the increased serum bicarbonate value may not exceed 27 mEq/l. By way of further example, in each of the foregoing exemplary embodiments, the increased serum bicarbonate value may not exceed 26 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, treatment with the nonabsorbable composition increases the individual's serum bicarbonate value from a baseline serum bicarbonate value in the range of 9 to 21 mEq/l by at least 1 mEq/l. For example, in one such embodiment the treatment increases the individual's serum bicarbonate value from a baseline serum bicarbonate value in the range of 9 to 21 mEq/l by at least 1.5 mEq/l. By way of further example, in one such embodiment the treatment increases the individual's serum bicarbonate value from a baseline serum bicarbonate value in the range of 9 to 21 mEq/l by at least 2 mEq/l. By way of further example, in one such embodiment the treatment increases the individual's serum bicarbonate value from a baseline serum bicarbonate value in the range of 9 to 21 mEq/l by at least 2.5 mEq/l. By way of further example, in one such embodiment the treatment increases the individual's serum bicarbonate value from a baseline serum bicarbonate value in the range of 9 to 21 mEq/l by at least 3 mEq/l. By way of further example, in one such embodiment the treatment increases the individual's serum bicarbonate value from a baseline serum bicarbonate value in the range of 9 to 21 mEq/l by at least 3.5 mEq/l. By way of further example, in one such embodiment the treatment increases the individual's serum bicarbonate value from a baseline serum bicarbonate value in the range of 9 to 21 mEq/l by at least 4 mEq/l. By way of further example, in one such embodiment the treatment increases the individual's serum bicarbonate value from a baseline serum bicarbonate value in the range of 9 to 21 mEq/l by at least 4.5 mEq/l. By way of further example, in one such embodiment the treatment increases the individual's serum bicarbonate value from a baseline serum bicarbonate value in the range of 9 to 21 mEq/l by at least 5 mEq/l. By way of further example, in one such embodiment the treatment increases the individual's serum bicarbonate value from a baseline serum bicarbonate value in the range of 9 to 21 mEq/l by at least 5.5 mEq/l. By way of further example, in one such embodiment the treatment increases the individual's serum bicarbonate value from a baseline serum bicarbonate value in the range of 9 to 21 mEq/l by at least 6 mEq/l. In each of the foregoing exemplary embodiments recited in this paragraph, the increased serum bicarbonate value preferably does not exceed 29 mEq/l. For example, in each of the foregoing exemplary embodiments, the increased serum bicarbonate value may not exceed 28 mEq/l. By way of further example, in each of the foregoing exemplary embodiments, the increased serum bicarbonate value may not exceed 27 mEq/l. By way of further example, in each of the foregoing exemplary embodiments, the increased serum bicarbonate value may not exceed 26 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the acid-base disorder is treated with a pharmaceutical composition comprising the nonabsorbable composition and the treatment increases the individual's serum bicarbonate value from a baseline serum bicarbonate value in the range of 12 to 14 mEq/l by at least 1 mEq/l. For example, in one such embodiment the treatment increases the individual's serum bicarbonate value from a baseline serum bicarbonate value in the range of 12 to 14 mEq/l by at least 1.5 mEq/l. By way of further example, in one such embodiment the treatment increases the individual's serum bicarbonate value from a baseline serum bicarbonate value in the range of 12 to 14 mEq/l by at least 2 mEq/l. By way of further example, in one such embodiment the treatment increases the individual's serum bicarbonate value from a baseline serum bicarbonate value in the range of 12 to 14 mEq/l by at least 2.5 mEq/l. By way of further example, in one such embodiment the treatment increases the individual's serum bicarbonate value from a baseline serum bicarbonate value in the range of 12 to 14 mEq/l by at least 3 mEq/l. By way of further example, in one such embodiment the treatment increases the individual's serum bicarbonate value from a baseline serum bicarbonate value in the range of 12 to 14 mEq/l by at least 3.5 mEq/l. By way of further example, in one such embodiment the treatment increases the individual's serum bicarbonate value from a baseline serum bicarbonate value in the range of 12 to 14 mEq/l by at least 4 mEq/l. By way of further example, in one such embodiment the treatment increases the individual's serum bicarbonate value from a baseline serum bicarbonate value in the range of 12 to 14 mEq/l by at least 4.5 mEq/l. By way of further example, in one such embodiment the treatment increases the individual's serum bicarbonate value from a baseline serum bicarbonate value in the range of 12 to 14 mEq/l by at least 5 mEq/l. By way of further example, in one such embodiment the treatment increases the individual's serum bicarbonate value from a baseline serum bicarbonate value in the range of 12 to 14 mEq/l by at least 6 mEq/l. By way of further example, in one such embodiment the treatment increases the individual's serum bicarbonate value from a baseline serum bicarbonate value in the range of 12 to 14 mEq/l by at least 7 mEq/l. By way of further example, in one such embodiment the treatment increases the individual's serum bicarbonate value from a baseline serum bicarbonate value in the range of 12 to 14 mEq/l by at least 8 mEq/l. By way of further example, in one such embodiment the treatment increases the individual's serum bicarbonate value from a baseline serum bicarbonate value in the range of 12 to 14 mEq/l by at least 9 mEq/l. In each of the foregoing exemplary embodiments recited in this paragraph, the increased serum bicarbonate value preferably does not exceed 29 mEq/l. For example, in each of the foregoing exemplary embodiments, the increased serum bicarbonate value may not exceed 28 mEq/l. By way of further example, in each of the foregoing exemplary embodiments, the increased serum bicarbonate value may not exceed 27 mEq/l. By way of further example, in each of the foregoing exemplary embodiments, the increased serum bicarbonate value may not exceed 26 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the treatment increases the individual's serum bicarbonate value from a baseline serum bicarbonate value in the range of 15 to 17 mEq/l by at least 1 mEq/l. For example, in one such embodiment the treatment increases the individual's serum bicarbonate value from a baseline serum bicarbonate value in the range of 15 to 17 mEq/l by at least 1.5 mEq/l. By way of further example, in one such embodiment the treatment increases the individual's serum bicarbonate value from a baseline serum bicarbonate value in the range of 15 to 17 mEq/l by at least 2 mEq/l. By way of further example, in one such embodiment the treatment increases the individual's serum bicarbonate value from a baseline serum bicarbonate value in the range of 15 to 17 mEq/l by at least 2.5 mEq/l. By way of further example, in one such embodiment the treatment increases the individual's serum bicarbonate value from a baseline serum bicarbonate value in the range of 15 to 17 mEq/l by at least 3 mEq/l. By way of further example, in one such embodiment the treatment increases the individual's serum bicarbonate value from a baseline serum bicarbonate value in the range of 15 to 17 mEq/l by at least 3.5 mEq/l. By way of further example, in one such embodiment the treatment increases the individual's serum bicarbonate value from a baseline serum bicarbonate value in the range of 15 to 17 mEq/l by at least 4 mEq/l. By way of further example, in one such embodiment the treatment increases the individual's serum bicarbonate value from a baseline serum bicarbonate value in the range of 15 to 17 mEq/l by at least 4.5 mEq/l. By way of further example, in one such embodiment the treatment increases the individual's serum bicarbonate value from a baseline serum bicarbonate value in the range of 15 to 17 mEq/l by at least 5 mEq/l. By way of further example, in one such embodiment the treatment increases the individual's serum bicarbonate value from a baseline serum bicarbonate value in the range of 15 to 17 mEq/l by at least 6 mEq/l. By way of further example, in one such embodiment the treatment increases the individual's serum bicarbonate value from a baseline serum bicarbonate value in the range of 15 to 17 mEq/l by at least 7 mEq/l. By way of further example, in one such embodiment the treatment increases the individual's serum bicarbonate value from a baseline serum bicarbonate value in the range of 15 to 17 mEq/l by at least 8 mEq/l. By way of further example, in one such embodiment the treatment increases the individual's serum bicarbonate value from a baseline serum bicarbonate value in the range of 15 to 17 mEq/l by at least 9 mEq/l. In each of the foregoing exemplary embodiments recited in this paragraph, the increased serum bicarbonate value preferably does not exceed 29 mEq/l. For example, in each of the foregoing exemplary embodiments, the increased serum bicarbonate value may not exceed 28 mEq/l. By way of further example, in each of the foregoing exemplary embodiments, the increased serum bicarbonate value may not exceed 27 mEq/l. By way of further example, in each of the foregoing exemplary embodiments, the increased serum bicarbonate value may not exceed 26 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the treatment increases the individual's serum bicarbonate value from a baseline serum bicarbonate value in the range of 18 to 21 mEq/l by at least 1 mEq/l. For example, in one such embodiment the treatment increases the individual's serum bicarbonate value from a baseline serum bicarbonate value in the range of 18 to 21 mEq/l by at least 1.5 mEq/l. By way of further example, in one such embodiment the treatment increases the individual's serum bicarbonate value from a baseline serum bicarbonate value in the range of 18 to 21 mEq/l by at least 2 mEq/l. By way of further example, in one such embodiment the treatment increases the individual's serum bicarbonate value from a baseline serum bicarbonate value in the range of 18 to 21 mEq/l by at least 2.5 mEq/l. By way of further example, in one such embodiment the treatment increases the individual's serum bicarbonate value from a baseline serum bicarbonate value in the range of 18 to 21 mEq/l by at least 3 mEq/l. By way of further example, in one such embodiment the treatment increases the individual's serum bicarbonate value from a baseline serum bicarbonate value in the range of 18 to 21 mEq/l by at least 3.5 mEq/l. By way of further example, in one such embodiment the treatment increases the individual's serum bicarbonate value from a baseline serum bicarbonate value in the range of 18 to 21 mEq/l by at least 4 mEq/l. By way of further example, in one such embodiment the treatment increases the individual's serum bicarbonate value from a baseline serum bicarbonate value in the range of 18 to 21 mEq/l by at least 4.5 mEq/l. By way of further example, in one such embodiment the treatment increases the individual's serum bicarbonate value from a baseline serum bicarbonate value in the range of 18 to 21 mEq/l by at least 5 mEq/l. By way of further example, in one such embodiment the treatment increases the individual's serum bicarbonate value from a baseline serum bicarbonate value in the range of 18 to 21 mEq/l by at least 5.5 mEq/l. By way of further example, in one such embodiment the treatment increases the individual's serum bicarbonate value from a baseline serum bicarbonate value in the range of 18 to 21 mEq/l by at least 6 mEq/l. In each of the foregoing exemplary embodiments recited in this paragraph, the increased serum bicarbonate value preferably does not exceed 29 mEq/l. For example, in each of the foregoing exemplary embodiments, the increased serum bicarbonate value may not exceed 28 mEq/l. By way of further example, in each of the foregoing exemplary embodiments, the increased serum bicarbonate value may not exceed 27 mEq/l. By way of further example, in each of the foregoing exemplary embodiments, the increased serum bicarbonate value may not exceed 26 mEq/l. Further, in each of the foregoing exemplary embodiments recited in this paragraph, the treatment enables the increased serum bicarbonate value to be sustained over a prolonged period of at least one week, at least one month, at least two months, at least three months, at least six months, or even at least one year.

In certain embodiments, the treatment increases the individual's serum bicarbonate value from a baseline serum bicarbonate value in the range of 12 to 21 mEq/l to an increased value in the range of 22 mEq/l to 26 mEq/l. For example, in one such embodiment the treatment increases the individual's serum bicarbonate value from a baseline serum bicarbonate value in the range of 12 to 17 mEq/l to an increased value in the range of 22 mEq/l to 26 mEq/l. By way of further example, in one such embodiment the treatment increases the individual's serum bicarbonate value from a baseline serum bicarbonate value in the range of 12 to 14 mEq/l to an increased value in the range of 22 mEq/l to 26 mEq/l. By way of further example, in one such embodiment the treatment increases the individual's serum bicarbonate value from a baseline serum bicarbonate value in the range of 15 to 17 mEq/l to an increased value in the range of 22 mEq/l to 26 mEq/l. By way of further example, in one such embodiment the treatment increases the individual's serum bicarbonate value from a baseline serum bicarbonate value in the range of 18 to 21 mEq/l to an increased value in the range of 22 mEq/l to 26 mEq/l. In each of the foregoing embodiments recited in this paragraph, the treatment enables the increased serum bicarbonate value to be sustained over a prolonged period of at least one week, at least one month, at least two months, at least three months, at least six months, or even at least one year.

In certain embodiments, the treatment achieves a clinically significant increase is achieved within a treatment period of less than one month. For example, in one such embodiment, the treatment achieves a clinically significant increase within a treatment period of 25 days. By way of further example, in one such embodiment the treatment achieves the clinically significant increase is achieved within a treatment period of 3 weeks. By way of further example, in one such embodiment the treatment achieves the clinically significant increase is achieved within a treatment period of 15 days. By way of further example, in one such embodiment the treatment achieves the clinically significant increase is achieved within a treatment period of 2 weeks. By way of further example, in one such embodiment the treatment achieves the clinically significant increase is achieved within a treatment period of 10 days. By way of further example, in one such embodiment the treatment achieves the clinically significant increase is achieved within a treatment period of 1 week. By way of further example, in one such embodiment the treatment achieves the clinically significant increase is achieved within a treatment period of 6 days. By way of further example, in one such embodiment the treatment achieves the clinically significant increase is achieved within a treatment period of 5 days. By way of further example, in one such embodiment the treatment achieves the clinically significant increase is achieved within a treatment period of 4 days. By way of further example, in one such embodiment the treatment achieves the clinically significant increase is achieved within a treatment period of 3 days. By way of further example, in one such embodiment the treatment achieves the clinically significant increase is achieved within a treatment period of 2 days. By way of further example, in one such embodiment the treatment achieves the clinically significant increase is achieved within a treatment period of 1 day. By way of further example, in one such embodiment the treatment achieves the clinically significant increase is achieved within a treatment period of 12 hours.

In certain embodiments, the treatment achieves a clinically significant increase is achieved without any change in the individual's diet or dietary habits relative to the period immediately preceding the initiation of treatment. For example, in one such embodiment the clinically significant increase is achieved independent of the individual's diet or dietary habits.

In certain embodiments, the individual's serum bicarbonate value returns to the baseline value ±2.5 mEq/l within 1 month of the cessation of treatment. For example, in one such embodiment the individual's serum bicarbonate value returns to the baseline value ±2.5 mEq/l within 3 weeks of the cessation of treatment. By way of further example, in one such embodiment the individual's serum bicarbonate value returns to the baseline value ±2.5 mEq/l within 2 weeks of the cessation of treatment. By way of further example, in one such embodiment the individual's serum bicarbonate value returns to the baseline value ±2.5 mEq/l within 10 days of the cessation of treatment. By way of further example, in one such embodiment the individual's serum bicarbonate value returns to the baseline value ±2.5 mEq/l within 9 days of the cessation of treatment. By way of further example, in one such embodiment the individual's serum bicarbonate value returns to the baseline value ±2.5 mEq/l within 8 days of the cessation of treatment. By way of further example, in one such embodiment the individual's serum bicarbonate value returns to the baseline value ±2.5 mEq/l within 7 days of the cessation of treatment. By way of further example, in one such embodiment the individual's serum bicarbonate value returns to the baseline value ±2.5 mEq/l within 6 days of the cessation of treatment. By way of further example, in one such embodiment the individual's serum bicarbonate value returns to the baseline value ±2.5 mEq/l within 5 days of the cessation of treatment. By way of further example, in one such embodiment the individual's serum bicarbonate value returns to the baseline value ±2.5 mEq/l within 4 days of the cessation of treatment. By way of further example, in one such embodiment the individual's serum bicarbonate value returns to the baseline value ±2.5 mEq/l within 3 days of the cessation of treatment. By way of further example, in one such embodiment the individual's serum bicarbonate value returns to the baseline value ±2.5 mEq/l within 2 days of the cessation of treatment. By way of further example, in one such embodiment the individual's serum bicarbonate value returns to the baseline value ±2.5 mEq/l within 1 day of the cessation of treatment.

In certain embodiments, the individual's serum bicarbonate value returns to the baseline value ±2 mEq/l within 1 month of the cessation of treatment. For example, in one such embodiment the individual's serum bicarbonate value returns to the baseline value ±2 mEq/l within 3 weeks of the cessation of treatment. By way of further example, in one such embodiment the individual's serum bicarbonate value returns to the baseline value ±2 mEq/l within 2 weeks of the cessation of treatment. By way of further example, in one such embodiment the individual's serum bicarbonate value returns to the baseline value ±2 mEq/l within 10 days of the cessation of treatment. By way of further example, in one such embodiment the individual's serum bicarbonate value returns to the baseline value ±2 mEq/l within 9 days of the cessation of treatment. By way of further example, in one such embodiment the individual's serum bicarbonate value returns to the baseline value ±2 mEq/l within 8 days of the cessation of treatment. By way of further example, in one such embodiment the individual's serum bicarbonate value returns to the baseline value ±2 mEq/l within 7 days of the cessation of treatment. By way of further example, in one such embodiment the individual's serum bicarbonate value returns to the baseline value ±2 mEq/l within 6 days of the cessation of treatment. By way of further example, in one such embodiment the individual's serum bicarbonate value returns to the baseline value ±2 mEq/l within 5 days of the cessation of treatment. By way of further example, in one such embodiment the individual's serum bicarbonate value returns to the baseline value ±2 mEq/l within 4 days of the cessation of treatment. By way of further example, in one such embodiment the individual's serum bicarbonate value returns to the baseline value ±2 mEq/l within 3 days of the cessation of treatment. By way of further example, in one such embodiment the individual's serum bicarbonate value returns to the baseline value ±2 mEq/l within 2 days of the cessation of treatment. By way of further example, in one such embodiment the individual's serum bicarbonate value returns to the baseline value ±2 mEq/l within 1 day of the cessation of treatment.

In certain embodiments, the individual's serum bicarbonate value returns to the baseline value ±1.5 mEq/l within 1 month of the cessation of treatment. For example, in one such embodiment the individual's serum bicarbonate value returns to the baseline value ±1.5 mEq/l within 3 weeks of the cessation of treatment. By way of further example, in one such embodiment the individual's serum bicarbonate value returns to the baseline value ±1.5 mEq/l within 2 weeks of the cessation of treatment. By way of further example, in one such embodiment the individual's serum bicarbonate value returns to the baseline value ±1.5 mEq/l within 10 days of the cessation of treatment. By way of further example, in one such embodiment the individual's serum bicarbonate value returns to the baseline value ±1.5 mEq/l within 9 days of the cessation of treatment. By way of further example, in one such embodiment the individual's serum bicarbonate value returns to the baseline value ±1.5 mEq/l within 8 days of the cessation of treatment. By way of further example, in one such embodiment the individual's serum bicarbonate value returns to the baseline value ±1.5 mEq/l within 7 days of the cessation of treatment. By way of further example, in one such embodiment the individual's serum bicarbonate value returns to the baseline value ±1.5 mEq/l within 6 days of the cessation of treatment. By way of further example, in one such embodiment the individual's serum bicarbonate value returns to the baseline value ±1.5 mEq/l within 5 days of the cessation of treatment. By way of further example, in one such embodiment the individual's serum bicarbonate value returns to the baseline value ±1.5 mEq/l within 4 days of the cessation of treatment. By way of further example, in one such embodiment the individual's serum bicarbonate value returns to the baseline value ±1.5 mEq/l within 3 days of the cessation of treatment. By way of further example, in one such embodiment the individual's serum bicarbonate value returns to the baseline value ±1.5 mEq/l within 2 days of the cessation of treatment. By way of further example, in one such embodiment the individual's serum bicarbonate value returns to the baseline value ±1.5 mEq/l within 1 day of the cessation of treatment.

In certain embodiments, the individual's serum bicarbonate value returns to the baseline value ±1 mEq/l within 1 month of the cessation of treatment. For example, in one such embodiment the individual's serum bicarbonate value returns to the baseline value ±1 mEq/l within 3 weeks of the cessation of treatment. By way of further example, in one such embodiment the individual's serum bicarbonate value returns to the baseline value ±1 mEq/l within 2 weeks of the cessation of treatment. By way of further example, in one such embodiment the individual's serum bicarbonate value returns to the baseline value ±1 mEq/l within 10 days of the cessation of treatment. By way of further example, in one such embodiment the individual's serum bicarbonate value returns to the baseline value ±1 mEq/l within 9 days of the cessation of treatment. By way of further example, in one such embodiment the individual's serum bicarbonate value returns to the baseline value ±1 mEq/l within 8 days of the cessation of treatment. By way of further example, in one such embodiment the individual's serum bicarbonate value returns to the baseline value ±1 mEq/l within 7 days of the cessation of treatment. By way of further example, in one such embodiment the individual's serum bicarbonate value returns to the baseline value ±1 mEq/l within 6 days of the cessation of treatment. By way of further example, in one such embodiment the individual's serum bicarbonate value returns to the baseline value ±1 mEq/l within 5 days of the cessation of treatment. By way of further example, in one such embodiment the individual's serum bicarbonate value returns to the baseline value ±1 mEq/l within 4 days of the cessation of treatment. By way of further example, in one such embodiment the individual's serum bicarbonate value returns to the baseline value ±1 mEq/l within 3 days of the cessation of treatment. By way of further example, in one such embodiment the individual's serum bicarbonate value returns to the baseline value ±1 mEq/l within 2 days of the cessation of treatment. By way of further example, in one such embodiment the individual's serum bicarbonate value returns to the baseline value ±1 mEq/l within 1 day of the cessation of treatment.

In certain embodiments, upon the cessation of treatment the individual's serum bicarbonate value decreases by at least 1 mEq/l within 1 month of the cessation of treatment.

For example, in one such embodiment. For example, in one such embodiment the individual's serum bicarbonate value decreases by at least 1 mEq/l within 3 weeks of the cessation of treatment. By way of further example, in one such embodiment the individual's serum bicarbonate value decreases by at least 1 mEq/l within 2 weeks of the cessation of treatment. By way of further example, in one such embodiment the individual's serum bicarbonate value decreases by at least 1 mEq/l within 10 days of the cessation of treatment. By way of further example, in one such embodiment the individual's serum bicarbonate value decreases by at least 1 mEq/l within 9 days of the cessation of treatment. By way of further example, in one such embodiment the individual's serum bicarbonate value decreases by at least 1 mEq/l within 8 days of the cessation of treatment. By way of further example, in one such embodiment the individual's serum bicarbonate value decreases by at least 1 mEq/l within 7 days of the cessation of treatment. By way of further example, in one such embodiment the individual's serum bicarbonate value decreases by at least 1 mEq/l within 6 days of the cessation of treatment. By way of further example, in one such embodiment the individual's serum bicarbonate value decreases by at least 1 mEq/l within 5 days of the cessation of treatment. By way of further example, in one such embodiment the individual's serum bicarbonate value decreases by at least 1 mEq/l within 4 days of the cessation of treatment. By way of further example, in one such embodiment the individual's serum bicarbonate value decreases by at least 1 mEq/l within 3 days of the cessation of treatment. By way of further example, in one such embodiment the individual's serum bicarbonate value decreases by at least 1 mEq/l within 2 days of the cessation of treatment. By way of further example, in one such embodiment the individual's serum bicarbonate value decreases by at least 1 mEq/l within 1 day of the cessation of treatment. By way of further example, in one such embodiment the individual's serum bicarbonate value decreases by at least 1 mEq/l within 12 hours of the cessation of treatment.

In certain embodiments, upon the cessation of treatment the individual's serum bicarbonate value decreases by at least 1.5 mEq/l within 1 month of the cessation of treatment. For example, in one such embodiment. For example, in one such embodiment the individual's serum bicarbonate value decreases by at least 1.5 mEq/l within 3 weeks of the cessation of treatment. By way of further example, in one such embodiment the individual's serum bicarbonate value decreases by at least 1.5 mEq/l within 2 weeks of the cessation of treatment. By way of further example, in one such embodiment the individual's serum bicarbonate value decreases by at least 1.5 mEq/l within 10 days of the cessation of treatment. By way of further example, in one such embodiment the individual's serum bicarbonate value decreases by at least 1.5 mEq/l within 9 days of the cessation of treatment. By way of further example, in one such embodiment the individual's serum bicarbonate value decreases by at least 1.5 mEq/l within 8 days of the cessation of treatment. By way of further example, in one such embodiment the individual's serum bicarbonate value decreases by at least 1.5 mEq/l within 7 days of the cessation of treatment. By way of further example, in one such embodiment the individual's serum bicarbonate value decreases by at least 1.5 mEq/l within 6 days of the cessation of treatment. By way of further example, in one such embodiment the individual's serum bicarbonate value decreases by at least 1.5 mEq/l within 5 days of the cessation of treatment. By way of further example, in one such embodiment the individual's serum bicarbonate value decreases by at least 1.5 mEq/l within 4 days of the cessation of treatment. By way of further example, in one such embodiment the individual's serum bicarbonate value decreases by at least 1.5 mEq/l within 3 days of the cessation of treatment. By way of further example, in one such embodiment the individual's serum bicarbonate value decreases by at least 1.5 mEq/l within 2 days of the cessation of treatment. By way of further example, in one such embodiment the individual's serum bicarbonate value decreases by at least 1.5 mEq/l within 1 day of the cessation of treatment. By way of further example, in one such embodiment the individual's serum bicarbonate value decreases by at least 1.5 mEq/l within 12 hours of the cessation of treatment.

In certain embodiments, upon the cessation of treatment the individual's serum bicarbonate value decreases by at least 2 mEq/l within 1 month of the cessation of treatment. For example, in one such embodiment. For example, in one such embodiment the individual's serum bicarbonate value decreases by at least 2 mEq/l within 3 weeks of the cessation of treatment. By way of further example, in one such embodiment the individual's serum bicarbonate value decreases by at least 2 mEq/l within 2 weeks of the cessation of treatment. By way of further example, in one such embodiment the individual's serum bicarbonate value decreases by at least 2 mEq/l within 10 days of the cessation of treatment. By way of further example, in one such embodiment the individual's serum bicarbonate value decreases by at least 2 mEq/l within 9 days of the cessation of treatment. By way of further example, in one such embodiment the individual's serum bicarbonate value decreases by at least 2 mEq/l within 8 days of the cessation of treatment. By way of further example, in one such embodiment the individual's serum bicarbonate value decreases by at least 2 mEq/l within 7 days of the cessation of treatment. By way of further example, in one such embodiment the individual's serum bicarbonate value decreases by at least 2 mEq/l within 6 days of the cessation of treatment. By way of further example, in one such embodiment the individual's serum bicarbonate value decreases by at least 2 mEq/l within 5 days of the cessation of treatment. By way of further example, in one such embodiment the individual's serum bicarbonate value decreases by at least 2 mEq/l within 4 days of the cessation of treatment. By way of further example, in one such embodiment the individual's serum bicarbonate value decreases by at least 2 mEq/l within 3 days of the cessation of treatment. By way of further example, in one such embodiment the individual's serum bicarbonate value decreases by at least 2 mEq/l within 2 days of the cessation of treatment. By way of further example, in one such embodiment the individual's serum bicarbonate value decreases by at least 2 mEq/l within 1 day of the cessation of treatment. By way of further example, in one such embodiment the individual's serum bicarbonate value decreases by at least 2 mEq/l within 12 hours of the cessation of treatment.

In certain embodiments, upon the cessation of treatment the individual's serum bicarbonate value decreases by at least 2.5 mEq/l within 1 month of the cessation of treatment. For example, in one such embodiment. For example, in one such embodiment the individual's serum bicarbonate value decreases by at least 2.5 mEq/l within 3 weeks of the cessation of treatment. By way of further example, in one such embodiment the individual's serum bicarbonate value decreases by at least 2.5 mEq/l within 2 weeks of the cessation of treatment. By way of further example, in one such embodiment the individual's serum bicarbonate value decreases by at least 2.5 mEq/l within 10 days of the cessation of treatment. By way of further example, in one such embodiment the individual's serum bicarbonate value decreases by at least 2.5 mEq/l within 9 days of the cessation of treatment. By way of further example, in one such embodiment the individual's serum bicarbonate value decreases by at least 2.5 mEq/l within 8 days of the cessation of treatment. By way of further example, in one such embodiment the individual's serum bicarbonate value decreases by at least 2.5 mEq/l within 7 days of the cessation of treatment. By way of further example, in one such embodiment the individual's serum bicarbonate value decreases by at least 2.5 mEq/l within 6 days of the cessation of treatment. By way of further example, in one such embodiment the individual's serum bicarbonate value decreases by at least 2.5 mEq/l within 5 days of the cessation of treatment. By way of further example, in one such embodiment the individual's serum bicarbonate value decreases by at least 2.5 mEq/l within 4 days of the cessation of treatment. By way of further example, in one such embodiment the individual's serum bicarbonate value decreases by at least 2.5 mEq/l within 3 days of the cessation of treatment. By way of further example, in one such embodiment the individual's serum bicarbonate value decreases by at least 2.5 mEq/l within 2 days of the cessation of treatment. By way of further example, in one such embodiment the individual's serum bicarbonate value decreases by at least 2.5 mEq/l within 1 day of the cessation of treatment. By way of further example, in one such embodiment the individual's serum bicarbonate value decreases by at least 2.5 mEq/l within 12 hours of the cessation of treatment.

In certain embodiments, upon the cessation of treatment the individual's serum bicarbonate value decreases by at least 3 mEq/l within 1 month of the cessation of treatment. For example, in one such embodiment. For example, in one such embodiment the individual's serum bicarbonate value decreases by at least 3 mEq/l within 3 weeks of the cessation of treatment. By way of further example, in one such embodiment the individual's serum bicarbonate value decreases by at least 3 mEq/l within 2 weeks of the cessation of treatment. By way of further example, in one such embodiment the individual's serum bicarbonate value decreases by at least 3 mEq/l within 10 days of the cessation of treatment. By way of further example, in one such embodiment the individual's serum bicarbonate value decreases by at least 3 mEq/l within 9 days of the cessation of treatment. By way of further example, in one such embodiment the individual's serum bicarbonate value decreases by at least 3 mEq/l within 8 days of the cessation of treatment. By way of further example, in one such embodiment the individual's serum bicarbonate value decreases by at least 3 mEq/l within 7 days of the cessation of treatment. By way of further example, in one such embodiment the individual's serum bicarbonate value decreases by at least 3 mEq/l within 6 days of the cessation of treatment. By way of further example, in one such embodiment the individual's serum bicarbonate value decreases by at least 3 mEq/l within 5 days of the cessation of treatment. By way of further example, in one such embodiment the individual's serum bicarbonate value decreases by at least 3 mEq/l within 4 days of the cessation of treatment. By way of further example, in one such embodiment the individual's serum bicarbonate value decreases by at least 3 mEq/l within 3 days of the cessation of treatment. By way of further example, in one such embodiment the individual's serum bicarbonate value decreases by at least 3 mEq/l within 2 days of the cessation of treatment. By way of further example, in one such embodiment the individual's serum bicarbonate value decreases by at least 3 mEq/l within 1 day of the cessation of treatment. By way of further example, in one such embodiment the individual's serum bicarbonate value decreases by at least 3 mEq/l within 12 hours of the cessation of treatment.

In certain embodiments, upon the cessation of treatment the individual's serum bicarbonate value decreases by at least 3.5 mEq/l within 1 month of the cessation of treatment. For example, in one such embodiment. For example, in one such embodiment the individual's serum bicarbonate value decreases by at least 3.5 mEq/l within 3 weeks of the cessation of treatment. By way of further example, in one such embodiment the individual's serum bicarbonate value decreases by at least 3.5 mEq/l within 2 weeks of the cessation of treatment. By way of further example, in one such embodiment the individual's serum bicarbonate value decreases by at least 3.5 mEq/l within 10 days of the cessation of treatment. By way of further example, in one such embodiment the individual's serum bicarbonate value decreases by at least 3.5 mEq/l within 9 days of the cessation of treatment. By way of further example, in one such embodiment the individual's serum bicarbonate value decreases by at least 3.5 mEq/l within 8 days of the cessation of treatment. By way of further example, in one such embodiment the individual's serum bicarbonate value decreases by at least 3.5 mEq/l within 7 days of the cessation of treatment. By way of further example, in one such embodiment the individual's serum bicarbonate value decreases by at least 3.5 mEq/l within 6 days of the cessation of treatment. By way of further example, in one such embodiment the individual's serum bicarbonate value decreases by at least 3.5 mEq/l within 5 days of the cessation of treatment. By way of further example, in one such embodiment the individual's serum bicarbonate value decreases by at least 3.5 mEq/l within 4 days of the cessation of treatment. By way of further example, in one such embodiment the individual's serum bicarbonate value decreases by at least 3.5 mEq/l within 3 days of the cessation of treatment. By way of further example, in one such embodiment the individual's serum bicarbonate value decreases by at least 3.5 mEq/l within 2 days of the cessation of treatment. By way of further example, in one such embodiment the individual's serum bicarbonate value decreases by at least 3.5 mEq/l within 1 day of the cessation of treatment. By way of further example, in one such embodiment the individual's serum bicarbonate value decreases by at least 3.5 mEq/l within 12 hours of the cessation of treatment.

In certain embodiments, upon the cessation of treatment the individual's serum bicarbonate value decreases by at least 4 mEq/l within 1 month of the cessation of treatment. For example, in one such embodiment. For example, in one such embodiment the individual's serum bicarbonate value decreases by at least 4 mEq/l within 3 weeks of the cessation of treatment. By way of further example, in one such embodiment the individual's serum bicarbonate value decreases by at least 4 mEq/l within 2 weeks of the cessation of treatment. By way of further example, in one such embodiment the individual's serum bicarbonate value decreases by at least 4 mEq/l within 10 days of the cessation of treatment. By way of further example, in one such embodiment the individual's serum bicarbonate value decreases by at least 4 mEq/l within 9 days of the cessation of treatment. By way of further example, in one such embodiment the individual's serum bicarbonate value decreases by at least 4 mEq/l within 8 days of the cessation of treatment. By way of further example, in one such embodiment the individual's serum bicarbonate value decreases by at least 4 mEq/l within 7 days of the cessation of treatment. By way of further example, in one such embodiment the individual's serum bicarbonate value decreases by at least 4 mEq/l within 6 days of the cessation of treatment. By way of further example, in one such embodiment the individual's serum bicarbonate value decreases by at least 4 mEq/l within 5 days of the cessation of treatment. By way of further example, in one such embodiment the individual's serum bicarbonate value decreases by at least 4 mEq/l within 4 days of the cessation of treatment. By way of further example, in one such embodiment the individual's serum bicarbonate value decreases by at least 4 mEq/l within 3 days of the cessation of treatment. By way of further example, in one such embodiment the individual's serum bicarbonate value decreases by at least 4 mEq/l within 2 days of the cessation of treatment. By way of further example, in one such embodiment the individual's serum bicarbonate value decreases by at least 4 mEq/l within 1 day of the cessation of treatment. By way of further example, in one such embodiment the individual's serum bicarbonate value decreases by at least 4 mEq/l within 12 hours of the cessation of treatment.

In certain embodiments, upon the cessation of treatment the individual's serum bicarbonate value decreases by at least 4.5 mEq/l within 1 month of the cessation of treatment. For example, in one such embodiment. For example, in one such embodiment the individual's serum bicarbonate value decreases by at least 4.5 mEq/l within 3 weeks of the cessation of treatment. By way of further example, in one such embodiment the individual's serum bicarbonate value decreases by at least 4.5 mEq/l within 2 weeks of the cessation of treatment. By way of further example, in one such embodiment the individual's serum bicarbonate value decreases by at least 4.5 mEq/l within 10 days of the cessation of treatment. By way of further example, in one such embodiment the individual's serum bicarbonate value decreases by at least 4.5 mEq/l within 9 days of the cessation of treatment. By way of further example, in one such embodiment the individual's serum bicarbonate value decreases by at least 4.5 mEq/l within 8 days of the cessation of treatment. By way of further example, in one such embodiment the individual's serum bicarbonate value decreases by at least 4.5 mEq/l within 7 days of the cessation of treatment. By way of further example, in one such embodiment the individual's serum bicarbonate value decreases by at least 4.5 mEq/l within 6 days of the cessation of treatment. By way of further example, in one such embodiment the individual's serum bicarbonate value decreases by at least 4.5 mEq/l within 5 days of the cessation of treatment. By way of further example, in one such embodiment the individual's serum bicarbonate value decreases by at least 4.5 mEq/l within 4 days of the cessation of treatment. By way of further example, in one such embodiment the individual's serum bicarbonate value decreases by at least 4.5 mEq/l within 3 days of the cessation of treatment. By way of further example, in one such embodiment the individual's serum bicarbonate value decreases by at least 4.5 mEq/l within 2 days of the cessation of treatment. By way of further example, in one such embodiment the individual's serum bicarbonate value decreases by at least 4.5 mEq/l within 1 day of the cessation of treatment. By way of further example, in one such embodiment the individual's serum bicarbonate value decreases by at least 4.5 mEq/l within 12 hours of the cessation of treatment.

In certain embodiments, upon the cessation of treatment the individual's serum bicarbonate value decreases by at least 5 mEq/l within 1 month of the cessation of treatment. For example, in one such embodiment. For example, in one such embodiment the individual's serum bicarbonate value decreases by at least 5 mEq/l within 3 weeks of the cessation of treatment. By way of further example, in one such embodiment the individual's serum bicarbonate value decreases by at least 5 mEq/l within 2 weeks of the cessation of treatment. By way of further example, in one such embodiment the individual's serum bicarbonate value decreases by at least 5 mEq/l within 10 days of the cessation of treatment. By way of further example, in one such embodiment the individual's serum bicarbonate value decreases by at least 5 mEq/l within 9 days of the cessation of treatment. By way of further example, in one such embodiment the individual's serum bicarbonate value decreases by at least 5 mEq/l within 8 days of the cessation of treatment. By way of further example, in one such embodiment the individual's serum bicarbonate value decreases by at least 5 mEq/l within 7 days of the cessation of treatment. By way of further example, in one such embodiment the individual's serum bicarbonate value decreases by at least 5 mEq/l within 6 days of the cessation of treatment. By way of further example, in one such embodiment the individual's serum bicarbonate value decreases by at least 5 mEq/l within 5 days of the cessation of treatment. By way of further example, in one such embodiment the individual's serum bicarbonate value decreases by at least 5 mEq/l within 4 days of the cessation of treatment. By way of further example, in one such embodiment the individual's serum bicarbonate value decreases by at least 5 mEq/l within 3 days of the cessation of treatment. By way of further example, in one such embodiment the individual's serum bicarbonate value decreases by at least 5 mEq/l within 2 days of the cessation of treatment. By way of further example, in one such embodiment the individual's serum bicarbonate value decreases by at least 5 mEq/l within 1 day of the cessation of treatment. By way of further example, in one such embodiment the individual's serum bicarbonate value decreases by at least 5 mEq/l within 12 hours of the cessation of treatment.

In one embodiment, the baseline serum bicarbonate value is the value of the serum bicarbonate concentration determined at a single time point. In another embodiment, the baseline serum bicarbonate value is the mean value of at least two serum bicarbonate concentrations determined at different time-points. For example, in one such embodiment the baseline serum bicarbonate value is the mean value of at least two serum bicarbonate concentrations for serum samples drawn on different days. By way of further example, the baseline serum bicarbonate value is the mean or median value of at least two serum bicarbonate concentrations for serum samples drawn on non-consecutive days. By way of further example, in one such method the non-consecutive days are separated by at least two days. By way of further example, in one such method the non-consecutive days are separated by at least one week. By way of further example, in one such method the non-consecutive days are separated by at least two weeks. By way of further example, in one such method the non-consecutive days are separated by at least three weeks.

In certain embodiments, the daily dose is no more than 100 g/day of the nonabsorbable composition. For example, in one such embodiment the daily dose is no more than 90 g/day of the nonabsorbable composition. By way of further example, in one such embodiment the daily dose is no more than 75 g/day of the nonabsorbable composition. By way of further example, in one such embodiment the daily dose is no more than 65 g/day of the nonabsorbable composition. By way of further example, in one such embodiment the daily dose is no more than 50 g/day of the nonabsorbable composition. By way of further example, in one such embodiment the daily dose is no more than 40 g/day of the nonabsorbable composition. By way of further example, in one such embodiment the daily dose is no more than 30 g/day of the nonabsorbable composition. By way of further example, in one such embodiment the daily dose is no more than 25 g/day of the nonabsorbable composition. By way of further example, in one such embodiment the daily dose is no more than 20 g/day of the nonabsorbable composition. By way of further example, in one such embodiment the daily dose is no more than 15 g/day of the nonabsorbable composition. By way of further example, in one such embodiment the daily dose is no more than 10 g/day of the nonabsorbable composition. By way of further example, in one such embodiment the daily dose is no more than 5 g/day of the nonabsorbable composition.

In certain embodiments, the individual is treated with the daily dose for a period of at least one day. For example, in one such embodiment the individual is treated with the daily dose for a period of at least one week. By way of further example, in one such embodiment the individual is treated with the daily dose for a period of at least one month. By way of further example, in one such embodiment the individual is treated with the daily dose for a period of at least two months. By way of further example, in one such embodiment the individual is treated with the daily dose for a period of at least three months. By way of further example, in one such embodiment the individual is treated with the daily dose for a period of at least several months. By way of further example, in one such embodiment the individual is treated with the daily dose for a period of at least six months. By way of further example, in one such embodiment the individual is treated with the daily dose for a period of at least one year.

In certain embodiments of the method of the present disclosure, the daily dose of the nonabsorbable composition has the capacity to remove at least about 5 mEq/day of the target species. For example, in one such embodiment the daily dose of the nonabsorbable composition has the capacity to remove at least about 6 mEq/day of the target species. By way of further example, in one such embodiment the daily dose of the nonabsorbable composition has the capacity to remove at least about 7 mEq/day of the target species. By way of further example, in one such embodiment the daily dose of the nonabsorbable composition has the capacity to remove at least about 8 mEq/day of the target species. By way of further example, in one such embodiment the daily dose of the nonabsorbable composition has the capacity to remove at least about 9 mEq/day of the target species. By way of further example, in one such embodiment the daily dose of the nonabsorbable composition has the capacity to remove at least about 10 mEq/day of the target species. By way of further example, in one such embodiment the daily dose of the nonabsorbable composition has the capacity to remove at least about 11 mEq/day of the target species. By way of further example, in one such embodiment the daily dose of the nonabsorbable composition has the capacity to remove at least about 12 mEq/day of the target species. By way of further example, in one such embodiment the daily dose of the nonabsorbable composition has the capacity to remove at least about 13 mEq/day of the target species. By way of further example, in one such embodiment the daily dose of the nonabsorbable composition has the capacity to remove at least about 14 mEq/day of the target species. By way of further example, in one such embodiment the daily dose of the nonabsorbable composition has the capacity to remove at least about 15 mEq/day of the target species. By way of further example, in one such embodiment the daily dose of the nonabsorbable composition has the capacity to remove at least about 16 mEq/day of the target species. By way of further example, in one such embodiment the daily dose of the nonabsorbable composition has the capacity to remove at least about 17 mEq/day of the target species. By way of further example, in one such embodiment the daily dose of the nonabsorbable composition has the capacity to remove at least about 18 mEq/day of the target species. By way of further example, in one such embodiment the daily dose of the nonabsorbable composition has the capacity to remove at least about 19 mEq/day of the target species. By way of further example, in one such embodiment the daily dose of the nonabsorbable composition has the capacity to remove at least about 20 mEq/day of the target species. By way of further example, in one such embodiment the daily dose of the nonabsorbable composition has the capacity to remove at least about 21 mEq/day of the target species. By way of further example, in one such embodiment the daily dose of the nonabsorbable composition has the capacity to remove at least about 22 mEq/day of the target species. By way of further example, in one such embodiment the daily dose of the nonabsorbable composition has the capacity to remove at least about 23 mEq/day of the target species. By way of further example, in one such embodiment the daily dose of the nonabsorbable composition has the capacity to remove at least about 24 mEq/day of the target species. By way of further example, in one such embodiment the daily dose of the nonabsorbable composition has the capacity to remove at least about 25 mEq/day of the target species. By way of further example, in one such embodiment the daily dose of the nonabsorbable composition has the capacity to remove at least about 26 mEq/day of the target species. By way of further example, in one such embodiment the daily dose of the nonabsorbable composition has the capacity to remove at least about 27 mEq/day of the target species. By way of further example, in one such embodiment the daily dose of the nonabsorbable composition has the capacity to remove at least about 28 mEq/day of the target species. By way of further example, in one such embodiment the daily dose of the nonabsorbable composition has the capacity to remove at least about 29 mEq/day of the target species. By way of further example, in one such embodiment the daily dose of the nonabsorbable composition has the capacity to remove at least about 30 mEq/day of the target species. By way of further example, in one such embodiment the daily dose of the nonabsorbable composition has the capacity to remove at least about 31 mEq/day of the target species. By way of further example, in one such embodiment the daily dose of the nonabsorbable composition has the capacity to remove at least about 32 mEq/day of the target species. By way of further example, in one such embodiment the daily dose of the nonabsorbable composition has the capacity to remove at least about 33 mEq/day of the target species.

By way of further example, in one such embodiment the daily dose of the nonabsorbable composition has the capacity to remove at least about 34 mEq/day of the target species. By way of further example, in one such embodiment the daily dose of the nonabsorbable composition has the capacity to remove at least about 35 mEq/day of the target species. By way of further example, in one such embodiment the daily dose of the nonabsorbable composition has the capacity to remove at least about 36 mEq/day of the target species. By way of further example, in one such embodiment the daily dose of the nonabsorbable composition has the capacity to remove at least about 37 mEq/day of the target species. By way of further example, in one such embodiment the daily dose of the nonabsorbable composition has the capacity to remove at least about 38 mEq/day of the target species. By way of further example, in one such embodiment the daily dose of the nonabsorbable composition has the capacity to remove at least about 39 mEq/day of the target species. By way of further example, in one such embodiment the daily dose of the nonabsorbable composition has the capacity to remove at least about 40 mEq/day of the target species. By way of further example, in one such embodiment the daily dose of the nonabsorbable composition has the capacity to remove at least about 41 mEq/day of the target species. By way of further example, in one such embodiment the daily dose of the nonabsorbable composition has the capacity to remove at least about 42 mEq/day of the target species. By way of further example, in one such embodiment the daily dose of the nonabsorbable composition has the capacity to remove at least about 43 mEq/day of the target species. By way of further example, in one such embodiment the daily dose of the nonabsorbable composition has the capacity to remove at least about 44 mEq/day of the target species. By way of further example, in one such embodiment the daily dose of the nonabsorbable composition has the capacity to remove at least about 45 mEq/day of the target species. By way of further example, in one such embodiment the daily dose of the nonabsorbable composition has the capacity to remove at least about 46 mEq/day of the target species. By way of further example, in one such embodiment the daily dose of the nonabsorbable composition has the capacity to remove at least about 47 mEq/day of the target species. By way of further example, in one such embodiment the daily dose of the nonabsorbable composition has the capacity to remove at least about 48 mEq/day of the target species. By way of further example, in one such embodiment the daily dose of the nonabsorbable composition has the capacity to remove at least about 49 mEq/day of the target species. By way of further example, in one such embodiment the daily dose of the nonabsorbable composition has the capacity to remove at least about 50 mEq/day of the target species.

In certain embodiments of the method of the present disclosure, the daily dose of the nonabsorbable composition removes at least about 5 mEq/day of the target species. For example, in one such embodiment the daily dose of the nonabsorbable composition removes at least about 6 mEq/day of the target species. By way of further example, in one such embodiment the daily dose of the nonabsorbable composition removes at least about 7 mEq/day of the target species. By way of further example, in one such embodiment the daily dose of the nonabsorbable composition removes at least about 8 mEq/day of the target species. By way of further example, in one such embodiment the daily dose of the nonabsorbable composition removes at least about 9 mEq/day of the target species. By way of further example, in one such embodiment the daily dose of the nonabsorbable composition removes at least about 10 mEq/day of the target species. By way of further example, in one such embodiment the daily dose of the nonabsorbable composition removes at least about 11 mEq/day of the target species. By way of further example, in one such embodiment the daily dose of the nonabsorbable composition removes at least about 12 mEq/day of the target species. By way of further example, in one such embodiment the daily dose of the nonabsorbable composition removes at least about 13 mEq/day of the target species. By way of further example, in one such embodiment the daily dose of the nonabsorbable composition removes at least about 14 mEq/day of the target species. By way of further example, in one such embodiment the daily dose of the nonabsorbable composition removes at least about 15 mEq/day of the target species. By way of further example, in one such embodiment the daily dose of the nonabsorbable composition removes at least about 16 mEq/day of the target species. By way of further example, in one such embodiment the daily dose of the nonabsorbable composition removes at least about 17 mEq/day of the target species. By way of further example, in one such embodiment the daily dose of the nonabsorbable composition removes at least about 18 mEq/day of the target species. By way of further example, in one such embodiment the daily dose of the nonabsorbable composition removes at least about 19 mEq/day of the target species. By way of further example, in one such embodiment the daily dose of the nonabsorbable composition removes at least about 20 mEq/day of the target species. By way of further example, in one such embodiment the daily dose of the nonabsorbable composition removes at least about 21 mEq/day of the target species. By way of further example, in one such embodiment the daily dose of the nonabsorbable composition removes at least about 22 mEq/day of the target species. By way of further example, in one such embodiment the daily dose of the nonabsorbable composition removes at least about 23 mEq/day of the target species. By way of further example, in one such embodiment the daily dose of the nonabsorbable composition removes at least about 24 mEq/day of the target species. By way of further example, in one such embodiment the daily dose of the nonabsorbable composition removes at least about 25 mEq/day of the target species. By way of further example, in one such embodiment the daily dose of the nonabsorbable composition removes at least about 26 mEq/day of the target species. By way of further example, in one such embodiment the daily dose of the nonabsorbable composition removes at least about 27 mEq/day of the target species. By way of further example, in one such embodiment the daily dose of the nonabsorbable composition removes at least about 28 mEq/day of the target species. By way of further example, in one such embodiment the daily dose of the nonabsorbable composition removes at least about 29 mEq/day of the target species. By way of further example, in one such embodiment the daily dose of the nonabsorbable composition removes at least about 30 mEq/day of the target species. By way of further example, in one such embodiment the daily dose of the nonabsorbable composition removes at least about 31 mEq/day of the target species. By way of further example, in one such embodiment the daily dose of the nonabsorbable composition removes at least about 32 mEq/day of the target species. By way of further example, in one such embodiment the daily dose of the nonabsorbable composition removes at least about 33 mEq/day of the target species. By way of further example, in one such embodiment the daily dose of the nonabsorbable composition removes at least about 34 mEq/day of the target species. By way of further example, in one such embodiment the daily dose of the nonabsorbable composition removes at least about 35 mEq/day of the target species. By way of further example, in one such embodiment the daily dose of the nonabsorbable composition removes at least about 36 mEq/day of the target species. By way of further example, in one such embodiment the daily dose of the nonabsorbable composition removes at least about 37 mEq/day of the target species. By way of further example, in one such embodiment the daily dose of the nonabsorbable composition removes at least about 38 mEq/day of the target species. By way of further example, in one such embodiment the daily dose of the nonabsorbable composition removes at least about 39 mEq/day of the target species. By way of further example, in one such embodiment the daily dose of the nonabsorbable composition removes at least about 40 mEq/day of the target species. By way of further example, in one such embodiment the daily dose of the nonabsorbable composition removes at least about 41 mEq/day of the target species. By way of further example, in one such embodiment the daily dose of the nonabsorbable composition removes at least about 42 mEq/day of the target species. By way of further example, in one such embodiment the daily dose of the nonabsorbable composition removes at least about 43 mEq/day of the target species. By way of further example, in one such embodiment the daily dose of the nonabsorbable composition removes at least about 44 mEq/day of the target species. By way of further example, in one such embodiment the daily dose of the nonabsorbable composition removes at least about 45 mEq/day of the target species. By way of further example, in one such embodiment the daily dose of the nonabsorbable composition removes at least about 46 mEq/day of the target species. By way of further example, in one such embodiment the daily dose of the nonabsorbable composition removes at least about 47 mEq/day of the target species. By way of further example, in one such embodiment the daily dose of the nonabsorbable composition removes at least about 48 mEq/day of the target species. By way of further example, in one such embodiment the daily dose of the nonabsorbable composition removes at least about 49 mEq/day of the target species. By way of further example, in one such embodiment the daily dose of the nonabsorbable composition removes at least about 50 mEq/day of the target species.

In certain embodiments of the method of the present disclosure, the daily dose of the nonabsorbable composition removes less than 60 mEq/day of the target species. For example, in one such method the daily dose removes less than 55 mEq/day of the target species. By way of further example, in one such embodiment the daily dose removes less than 50 mEq/day of the target species. By way of further example, in one such embodiment the daily dose removes less than 45 mEq/day of the target species. By way of further example, in one such embodiment the daily dose removes less than 40 mEq/day of the target species. By way of further example, in one such embodiment the daily dose removes less than 35 mEq/day of the target species. By way of further example, in one such embodiment the daily dose removes less than 34 mEq/day of the target species. By way of further example, in one such embodiment the daily dose removes less than 33 mEq/day of the target species. By way of further example, in one such embodiment the daily dose removes less than 32 mEq/day of the target species. By way of further example, in one such embodiment the daily dose removes less than 31 mEq/day of the target species. By way of further example, in one such embodiment the daily dose removes less than 30 mEq/day of the target species. By way of further example, in one such embodiment the daily dose removes less than 29 mEq/day of the target species. By way of further example, in one such embodiment the daily dose removes less than 28 mEq/day of the target species. By way of further example, in one such embodiment the daily dose removes less than 27 mEq/day of the target species. By way of further example, in one such embodiment the daily dose removes less than 26 mEq/day of the target species. By way of further example, in one such embodiment the daily dose removes less than 25 mEq/day of the target species. By way of further example, in one such embodiment the daily dose removes less than 24 mEq/day of the target species. By way of further example, in one such embodiment the daily dose removes less than 23 mEq/day of the target species. By way of further example, in one such embodiment the daily dose removes less than 22 mEq/day of the target species. By way of further example, in one such embodiment the daily dose removes less than 21 mEq/day of the target species. By way of further example, in one such embodiment the daily dose removes less than 20 mEq/day of the target species. By way of further example, in one such embodiment the daily dose removes less than 19 mEq/day of the target species. By way of further example, in one such embodiment the daily dose removes less than 18 mEq/day of the target species. By way of further example, in one such embodiment the daily dose removes less than 17 mEq/day of the target species. By way of further example, in one such embodiment the daily dose removes less than 16 mEq/day of the target species. By way of further example, in one such embodiment the daily dose removes less than 15 mEq/day of the target species. By way of further example, in one such embodiment the daily dose removes less than 14 mEq/day of the target species. By way of further example, in one such embodiment the daily dose removes less than 13 mEq/day of the target species. By way of further example, in one such embodiment the daily dose removes less than 12 mEq/day of the target species. By way of further example, in one such embodiment the daily dose removes less than 11 mEq/day of the target species. By way of further example, in one such embodiment the daily dose removes less than 10 mEq/day of the target species. By way of further example, in one such embodiment the daily dose removes less than 9 mEq/day of the target species. By way of further example, in one such embodiment the daily dose removes less than 8 mEq/day of the target species. By way of further example, in one such embodiment the daily dose removes less than 7 mEq/day of the target species. By way of further example, in one such embodiment the daily dose removes less than 6 mEq/day of the target species.

In certain embodiments of the method of the present disclosure, the daily dose of the nonabsorbable composition has insufficient capacity to remove more than 60 mEq/day of the target species. For example, in one such method the daily dose has insufficient capacity to remove more than 55 mEq/day of the target species. By way of further example, in one such embodiment the daily dose has insufficient capacity to remove more than 50 mEq/day of the target species. By way of further example, in one such embodiment the daily dose has insufficient capacity to remove more than 45 mEq/day of the target species. By way of further example, in one such embodiment the daily dose has insufficient capacity to remove more than 40 mEq/day of the target species. By way of further example, in one such embodiment the daily dose has insufficient capacity to remove more than 35 mEq/day of the target species. By way of further example, in one such embodiment the daily dose has insufficient capacity to remove more than 34 mEq/day of the target species. By way of further example, in one such embodiment the daily dose has insufficient capacity to remove more than 33 mEq/day of the target species. By way of further example, in one such embodiment the daily dose has insufficient capacity to remove more than 32 mEq/day of the target species. By way of further example, in one such embodiment the daily dose has insufficient capacity to remove more than 31 mEq/day of the target species. By way of further example, in one such embodiment the daily dose has insufficient capacity to remove more than 30 mEq/day of the target species. By way of further example, in one such embodiment the daily dose has insufficient capacity to remove more than 29 mEq/day of the target species. By way of further example, in one such embodiment the daily dose has insufficient capacity to remove more than 28 mEq/day of the target species. By way of further example, in one such embodiment the daily dose has insufficient capacity to remove more than 27 mEq/day of the target species. By way of further example, in one such embodiment the daily dose has insufficient capacity to remove more than 26 mEq/day of the target species. By way of further example, in one such embodiment the daily dose has insufficient capacity to remove more than 25 mEq/day of the target species. By way of further example, in one such embodiment the daily dose has insufficient capacity to remove more than 24 mEq/day of the target species. By way of further example, in one such embodiment the daily dose has insufficient capacity to remove more than 23 mEq/day of the target species. By way of further example, in one such embodiment the daily dose has insufficient capacity to remove more than 22 mEq/day of the target species. By way of further example, in one such embodiment the daily dose has insufficient capacity to remove more than 21 mEq/day of the target species. By way of further example, in one such embodiment the daily dose has insufficient capacity to remove more than 20 mEq/day of the target species. By way of further example, in one such embodiment the daily dose has insufficient capacity to remove more than 19 mEq/day of the target species. By way of further example, in one such embodiment the daily dose has insufficient capacity to remove more than 18 mEq/day of the target species. By way of further example, in one such embodiment the daily dose has insufficient capacity to remove more than 17 mEq/day of the target species. By way of further example, in one such embodiment the daily dose has insufficient capacity to remove more than 16 mEq/day of the target species. By way of further example, in one such embodiment the daily dose has insufficient capacity to remove more than 15 mEq/day of the target species. By way of further example, in one such embodiment the daily dose has insufficient capacity to remove more than 14 mEq/day of the target species. By way of further example, in one such embodiment the daily dose has insufficient capacity to remove more than 13 mEq/day of the target species. By way of further example, in one such embodiment the daily dose has insufficient capacity to remove more than 12 mEq/day of the target species. By way of further example, in one such embodiment the daily dose has insufficient capacity to remove more than 11 mEq/day of the target species. By way of further example, in one such embodiment the daily dose has insufficient capacity to remove more than 10 mEq/day of the target species. By way of further example, in one such embodiment the daily dose has insufficient capacity to remove more than 9 mEq/day of the target species. By way of further example, in one such embodiment the daily dose has insufficient capacity to remove more than 8 mEq/day of the target species. By way of further example, in one such embodiment the daily dose has insufficient capacity to remove more than 7 mEq/day of the target species. By way of further example, in one such embodiment the daily dose has insufficient capacity to remove more than 6 mEq/day of the target species.

The present disclosure further includes the following enumerated embodiments.

Embodiment 1. A process for the preparation of a crosslinked poly(allylamine) polymer comprising
(a) in a first step, forming a poly(allylamine) polymer in the form of beads in a concurrent polymerization and crosslinking reaction mixture comprising a monoallylamine, a multiallylamine, a radical polymerization initiator, a surfactant, an acid, water and an organic solvent system wherein less than 2.5% of the total number of carbon atoms comprised by the crosslinked poly(allylamine) polymer are $sp^2$ allyl carbons, and
(b) in a second step, further crosslinking the poly(allylamine) polymer in a reaction mixture comprising a crosslinking agent, a swelling agent for the poly(allylamine) polymer, and a dispersing solvent system to form a crosslinked poly(allylamine) polymer having a swelling ratio of less than 2.

Embodiment 2. The process of any previous enumerated embodiment wherein $sp^2$ allyl carbons constitute less than 2.25% of the total number of carbon atoms comprised by the poly(allylamine) polymer formed in the first step.

Embodiment 3. The process of any previous enumerated embodiment wherein $sp^2$ allyl carbons comprised by the poly(allylamine) polymer constitute less than 2% of the total number of carbon atoms comprised by the poly(allylamine) polymer formed in the first step.

Embodiment 4. The process of any previous enumerated embodiment wherein $sp^2$ allyl carbons comprised by the poly(allylamine) polymer constitute less than 1.9% of the total number of carbon atoms comprised by the poly(allylamine) polymer formed in the first step.

Embodiment 5. The process of any previous enumerated embodiment wherein $sp^2$ allyl carbons comprised by the poly(allylamine) polymer constitute less than 1.8% of the total number of carbon atoms comprised by the poly(allylamine) polymer formed in the first step.

Embodiment 6. The process of any previous enumerated embodiment wherein $sp^2$ allyl carbons comprised by the poly(allylamine) polymer constitute less than 1.7% of the total number of carbon atoms comprised by the poly(allylamine) polymer formed in the first step.

Embodiment 7. The process of any previous enumerated embodiment wherein $sp^2$ allyl carbons comprised by the poly(allylamine) polymer constitute less than 1.6% of the total number of carbon atoms comprised by the poly(allylamine) polymer formed in the first step.

Embodiment 8. The process of any previous enumerated embodiment wherein $sp^2$ allyl carbons comprised by the poly(allylamine) polymer constitute less than 1.5% of the total number of carbon atoms comprised by the poly(allylamine) polymer formed in the first step.

Embodiment 9. The process of any previous enumerated embodiment wherein $sp^2$ allyl carbons comprised by the poly(allylamine) polymer constitute less than 1.4% of the total number of carbon atoms comprised by the poly(allylamine) polymer formed in the first step.

Embodiment 10A. The process of any previous enumerated embodiment wherein $sp^2$ allyl carbons comprised by the poly(allylamine) polymer constitute less than 1.3% of the total number of carbon atoms comprised by the poly(allylamine) polymer formed in the first step.

Embodiment 10B. The process of any previous enumerated embodiment wherein $sp^2$ allyl carbons comprised by the poly(allylamine) polymer constitute less than 1.25% of the total number of carbon atoms comprised by the poly(allylamine) polymer formed in the first step.

Embodiment 10C. The process of any previous enumerated embodiment wherein $sp^2$ allyl carbons comprised by the poly(allylamine) polymer constitute less than 1.2% of the total number of carbon atoms comprised by the poly(allylamine) polymer formed in the first step.

Embodiment 10D. The process of any previous enumerated embodiment wherein $sp^2$ allyl carbons comprised by the poly(allylamine) polymer constitute less than 1.1% of the total number of carbon atoms comprised by the poly(allylamine) polymer formed in the first step.

Embodiment 10E. The process of any previous enumerated embodiment wherein $sp^2$ allyl carbons comprised by the poly(allylamine) polymer constitute less than 1.0% of the total number of carbon atoms comprised by the poly(allylamine) polymer formed in the first step.

Embodiment 10F. The process of any previous enumerated embodiment wherein $sp^2$ allyl carbons comprised by the poly(allylamine) polymer constitute less than 0.9% of the total number of carbon atoms comprised by the poly(allylamine) polymer formed in the first step.

Embodiment 10G. The process of any previous enumerated embodiment wherein $sp^2$ allyl carbons comprised by the poly(allylamine) polymer constitute less than 0.8% of the total number of carbon atoms comprised by the poly(allylamine) polymer formed in the first step.

Embodiment 10H. The process of any previous enumerated embodiment wherein $sp^2$ allyl carbons comprised by the poly(allylamine) polymer constitute less than 0.75% of the total number of carbon atoms comprised by the poly(allylamine) polymer formed in the first step.

Embodiment 10I. The process of any previous enumerated embodiment wherein $sp^2$ allyl carbons comprised by the poly(allylamine) polymer constitute less than 0.7% of the total number of carbon atoms comprised by the poly(allylamine) polymer formed in the first step.

Embodiment 10J. The process of any previous enumerated embodiment wherein $sp^2$ allyl carbons comprised by the poly(allylamine) polymer constitute less than 0.6% of the total number of carbon atoms comprised by the poly(allylamine) polymer formed in the first step.

Embodiment 10K. The process of any previous enumerated embodiment wherein $sp^2$ allyl carbons comprised by the poly(allylamine) polymer constitute less than 0.5% of the total number of carbon atoms comprised by the poly(allylamine) polymer formed in the first step.

Embodiment 10L. The process of any previous enumerated embodiment wherein $sp^2$ allyl carbons comprised by the poly(allylamine) polymer constitute less than 0.4% of the total number of carbon atoms comprised by the poly(allylamine) polymer formed in the first step.

Embodiment 10M. The process of any previous enumerated embodiment wherein $sp^2$ allyl carbons comprised by the poly(allylamine) polymer constitute less than 0.3% of the total number of carbon atoms comprised by the poly(allylamine) polymer formed in the first step.

Embodiment 10N. The process of any previous enumerated embodiment wherein $sp^2$ allyl carbons comprised by the poly(allylamine) polymer constitute less than 0.25% of the total number of carbon atoms comprised by the poly(allylamine) polymer formed in the first step.

Embodiment 10O. The process of any previous enumerated embodiment wherein $sp^2$ allyl carbons comprised by the poly(allylamine) polymer constitute less than 0.2% of the total number of carbon atoms comprised by the poly(allylamine) polymer formed in the first step.

Embodiment 11A. The process of any previous enumerated embodiment wherein $sp^2$ allyl carbons comprised by the poly(allylamine) polymer constitute less than 0.1% of the total number of carbon atoms comprised by the poly(allylamine) polymer formed in the first step.

Embodiment 11B. The process of any previous enumerated embodiment wherein $sp^2$ allyl carbons comprised by the poly(allylamine) polymer constitute less than 0.05% of the total number of carbon atoms comprised by the poly(allylamine) polymer formed in the first step.

Embodiment 12A. The process or poly(allylamine) polymer of any previous enumerated embodiment wherein the number of $sp^2$ allyl carbons, if any, comprised by the poly(allylamine) polymer is less than the detection limit as determined by NMR.

Embodiment 12B. The process of any previous enumerated embodiment wherein the percentage of $sp^2$ allyl carbons comprised by the poly(allylamine) polymer is determined by NMR; optionally wherein integration of the $sp^2$ allyl carbon peaks between 110-150 ppm and alkyl carbon peaks between 0-80 ppm is used to quantitate the percent $sp^2$ allyl carbons of the poly(allylamine) polymer using the formula $$\% \, sp2 \text{ allyl carbons} = \frac{\text{peak integration (110-150 ppm)}}{\text{peak integration (0-80 ppm)} + \text{peak integration (110-150 ppm)}} \times 100.$$

Embodiment 13. The process of any previous enumerated embodiment wherein the percentage of $sp^2$ allyl carbons, if any, comprised by the poly(allylamine) polymer formed in the first step is less than the detection limit for $sp^2$ allyl carbons as determined by NMR; optionally wherein integration of the $sp^2$ allyl carbon peaks between 110-150 ppm and alkyl carbon peaks between 0-80 ppm is used to quantitate the percent $sp^2$ allyl carbons of the poly(allylamine) polymer using the formula $$\% \, sp2 \text{ allyl carbons} = \frac{\text{peak integration (110-150 ppm)}}{\text{peak integration (0-80 ppm)} + \text{peak integration (110-150 ppm)}} \times 100.$$

Embodiment 14. The process of any previous enumerated embodiment wherein the poly(allylamine) polymer formed in the first step has a swelling ratio of less than 10.

Embodiment 15. The process of any previous enumerated embodiment wherein the poly(allylamine) polymer formed in the first step has a swelling ratio of less than 9.

Embodiment 16. The process of any previous enumerated embodiment wherein the poly(allylamine) polymer formed in the first step has a swelling ratio of less than 8.

Embodiment 17. The process of any previous enumerated embodiment wherein the poly(allylamine) polymer formed in the first step has a swelling ratio of less than 7.

Embodiment 18. The process of any previous enumerated embodiment wherein the poly(allylamine) polymer formed in the first step has a swelling ratio of less than 6.

Embodiment 19. The process of any previous enumerated embodiment wherein the poly(allylamine) polymer formed in the first step has a swelling ratio of less than 5.

Embodiment 20. The process of any previous enumerated embodiment wherein the poly(allylamine) polymer formed in the first step has a swelling ratio of at least 4.

Embodiment 21. The process of any previous enumerated embodiment wherein the poly(allylamine) polymer formed in the first step has a swelling ratio of at least 3.

Embodiment 22. The process of any previous enumerated embodiment wherein the crosslinked poly(allylamine) polymer contains less than 20 ppm allylamine.

Embodiment 23. The process of any previous enumerated embodiment wherein the concurrent polymerization and crosslinking reaction mixture comprises a radical polymerization selected from the group consisting of cationic and free-radical polymerization initiators.

Embodiment 24. The process of any previous enumerated embodiment wherein the concurrent polymerization and crosslinking reaction mixture comprises a free-radical polymerization initiator selected from free-radical peroxy polymerization initiators and azo polymerization initiators.

Embodiment 25. The process of any previous enumerated embodiment wherein the concurrent polymerization and crosslinking reaction mixture comprises a free-radical polymerization selected from the group consisting of azodiisobutyronitrile, azodiisovaleronitrile, dimethylazodiisobutyrate, 2,2'azo bis(isobutyronitrile), 2,2'-azobis(N,N'-dimethyl-eneisobutyramidine)dihydrochloride, 2,2'-azobis(2-methylpropionamidine)dihydrochloride, 2,2'-azobis(2-amidinopropane)dihydrochloride, 2,2'-azobis(N,N'-dimethyleneisobutyramidine), 1,1'-azo bis(I-cyclohexanecarbo-nitrile), 4,4'-azobis(4-cyanopentanoic acid), 2,2'-azobis(isobutyramide)dihydrate, 2,2'-azobis(2-methylpropane), 2,2'-azobis(2-methylbutyronitrile), VAZO 67, cyanopentanoic acid, the peroxypivalates, dodecylbenzene peroxide, benzoyl peroxide, di-t-butyl hydroperoxide, t-butyl peracetate, acetyl peroxide, dicumyl peroxide, cumylhydroperoxide, and dimethyl bis(butylperoxy)hexane.

Embodiment 26. The process of any previous enumerated embodiment wherein the ratio of number of allyl equivalents possessed by the monoallylamine and multiallylamine, in combination, to the number of initiator equivalents in the concurrent polymerization and crosslinking reaction mixture is in the range of about 6:1 to about 70:1, respectively.

Embodiment 27. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 7:1 to about 60:1, respectively.

Embodiment 28. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 8:1 to about 50:1, respectively.

Embodiment 29. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 10:1 to about 45:1, respectively.

Embodiment 30. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 15:1 to about 40:1, respectively.

Embodiment 31. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 17.5:1 to about 35:1, respectively.

Embodiment 32. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 20:1 to about 30:1, respectively.

Embodiment 33. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 22.5:1 to about 30:1, respectively.

Embodiment 34. The process of any previous enumerated embodiment wherein the number of allyl equivalents possessed by the monoallylamine and multiallylamine, in combination, to the number of initiator equivalents in the concurrent polymerization and crosslinking reaction mixture is in the range of about 25:1 to about 27.5:1, respectively.

Embodiment 35. The process of any previous enumerated embodiment wherein the weight ratio of the combined amount of monoallylamine and multiallylamine relative to the amount of water in the concurrent polymerization and crosslinking reaction mixture is in the range of about 0.01 to about 3, respectively.

Embodiment 36. The process of any previous enumerated embodiment wherein the weight ratio of the combined amount of monoallylamine and multiallylamine relative to the amount of water in the concurrent polymerization and crosslinking reaction mixture is in the range of about 0.05 to about 2.75, respectively.

Embodiment 37. The process of any previous enumerated embodiment wherein the weight ratio of the combined amount of monoallylamine and multiallylamine relative to the amount of water in the concurrent polymerization and crosslinking reaction mixture is in the range of about 0.07 to about 2.5, respectively.

Embodiment 38. The process of any previous enumerated embodiment wherein the weight ratio of the combined amount of monoallylamine and multiallylamine relative to the amount of water in the concurrent polymerization and crosslinking reaction mixture is in the range of about 0.1 to about 2.25, respectively.

Embodiment 39. The process of any previous enumerated embodiment wherein the weight ratio of the combined amount of monoallylamine and multiallylamine relative to the amount of water in the concurrent polymerization and crosslinking reaction mixture is in the range of about 0.15 to about 2, respectively.

Embodiment 40. The process of any previous enumerated embodiment wherein the weight ratio of the combined amount of monoallylamine and multiallylamine relative to the amount of water in the concurrent polymerization and crosslinking reaction mixture is in the range of about 0.2 to about 1.75, respectively.

Embodiment 41. The process of any previous enumerated embodiment wherein the weight ratio of the combined amount of monoallylamine and multiallylamine relative to the amount of water in the concurrent polymerization and crosslinking reaction mixture is in the range of about 0.25 to about 1.5, respectively.

Embodiment 42. The process of any previous enumerated embodiment wherein the weight ratio of the combined amount of monoallylamine and multiallylamine relative to the amount of water in the concurrent polymerization and crosslinking reaction mixture is in the range of about 0.25 to about 1.25, respectively.

Embodiment 43. The process of any previous enumerated embodiment wherein the weight ratio of the combined amount of monoallylamine and multiallylamine relative to the amount of water in the concurrent polymerization and crosslinking reaction mixture is in the range of about 0.3 to about 1, respectively.

Embodiment 44. The process of any previous enumerated embodiment wherein the weight ratio of the combined amount of monoallylamine and multiallylamine relative to the amount of water in the concurrent polymerization and crosslinking reaction mixture is in the range of about 0.35 to about 0.75, respectively.

Embodiment 45. The process of any previous enumerated embodiment wherein the weight ratio of the combined amount of monoallylamine and multiallylamine relative to the amount of water in the concurrent polymerization and crosslinking reaction mixture is in the range of about 0.4 to about 0.5, respectively.

Embodiment 46. The process of any previous enumerated embodiment wherein the ratio of the number of allyl equivalents to the number of water equivalents in the concurrent polymerization and crosslinking reaction mixture is in the range of about 0.01:1 to about 1:1, respectively.

Embodiment 47. The process of any previous enumerated embodiment wherein the ratio of the number of allyl equivalents to the number of water equivalents in the concurrent polymerization and crosslinking reaction mixture is in the range of about 0.015:1 to about 0.75:1, respectively.

Embodiment 48. The process of any previous enumerated embodiment wherein the ratio of the number of allyl equivalents to the number of water equivalents in the concurrent polymerization and crosslinking reaction mixture is in the range of about 0.02:1 to about 0.5:1, respectively.

Embodiment 49. The process of any previous enumerated embodiment wherein the ratio of the number of allyl equivalents to the number of water equivalents in the concurrent polymerization and crosslinking reaction mixture is in the range of about 0.03:1 to about 0.4:1, respectively.

Embodiment 50. The process of any previous enumerated embodiment wherein the ratio of the number of allyl equivalents to the number of water equivalents in the concurrent polymerization and crosslinking reaction mixture is in the range of about 0.04:1 to about 0.3:1, respectively.

Embodiment 51. The process of any previous enumerated embodiment wherein the ratio of the number of allyl equivalents to the number of water equivalents in the concurrent polymerization and crosslinking reaction mixture is in the range of about 0.05:1 to about 0.25:1, respectively.

Embodiment 52. The process of any previous enumerated embodiment wherein the ratio of the number of allyl equivalents to the number of water equivalents in the concurrent polymerization and crosslinking reaction mixture is in the range of about 0.06:1 to about 0.2:1, respectively.

Embodiment 53. The process of any previous enumerated embodiment wherein the ratio of the number of allyl equivalents to the number of water equivalents in the concurrent polymerization and crosslinking reaction mixture is in the range of about 0.07:1 to about 0.175:1, respectively.

Embodiment 54. The process of any previous enumerated embodiment wherein the ratio of the number of allyl equivalents to the number of water equivalents in the concurrent polymerization and crosslinking reaction mixture is in the range of about 0.08:1 to about 0.15:1, respectively.

Embodiment 55. The process of any previous enumerated embodiment wherein the surfactant comprised by the concurrent polymerization and crosslinking reaction mixture comprises an ionic or non-ionic surfactant.

Embodiment 56. The process of any previous enumerated embodiment wherein the surfactant comprised by the concurrent polymerization and crosslinking reaction mixture comprises an ionic surfactant.

Embodiment 57. The process of any previous enumerated embodiment wherein the surfactant comprised by the concurrent polymerization and crosslinking reaction mixture comprises a non-ionic surfactant.

Embodiment 58. The process of any previous enumerated embodiment wherein the surfactant comprised by the concurrent polymerization and crosslinking reaction mixture is an ionic or non-ionic surfactant selected from the group consisting of sorbitan monolaurate, sorbitan monooleate, sorbitan monostearate, sorbitan monopalmitate, ethylene glycol monostearate, glyceryl monostearate, polyethylene glycol monostearate, polyethylene glycol hydrogenated castor oil, polyoxyethylene sorbitan monolaurate, polyoxyethylene sorbitan monooleate, polyethylene glycol and diisooctyl sulfosuccinate, branched dodecylbenzenesulfonic acid, linear dodecylbenzenesulfonic acid, sodium branched alkylbenzenesulfonate, sodium branched dodecylbenzenesulfonate, sodium alpha olefin sulfonate, sodium linear alkylbenzenesulfonate, isopropylamine branched alkylbenzenesulfonate, and sodium lauryl sulfate.

Embodiment 59. The process of any previous enumerated embodiment wherein the organic solvent system comprised by the concurrent polymerization and crosslinking reaction mixture comprises a water-immiscible organic solvent.

Embodiment 60. The process of any previous enumerated embodiment wherein the organic solvent system comprised by the concurrent polymerization and crosslinking reaction mixture comprises hexane, cyclohexane, heptane, octane, decane, petroleum ether, liquid paraffin, chlorobenzene, toluene, xylenes, ethyl acetate, propyl acetate and isopropyl acetate, or a combination of two or more thereof.

Embodiment 61. The process of any previous enumerated embodiment wherein the concurrent polymerization and crosslinking reaction mixture is heated to a temperature in the range of about 25° C. to about 85° C.

Embodiment 62. The process of any previous enumerated embodiment wherein the concurrent polymerization and crosslinking reaction mixture is heated to a temperature in the range of about 30° C. to about 80° C.

Embodiment 63. The process of any previous enumerated embodiment wherein the concurrent polymerization and crosslinking reaction mixture is heated to a temperature in the range of about 35° C. to about 70° C.

Embodiment 64. The process of any previous enumerated embodiment wherein the concurrent polymerization and crosslinking reaction mixture is heated to a temperature in the range of about 40° C. to about 70° C.

Embodiment 65. The process of any previous enumerated embodiment wherein the concurrent polymerization and crosslinking reaction mixture is heated to about 45° C. to about 70° C.

Embodiment 66. The process of any previous enumerated embodiment wherein the temperature of the concurrent polymerization and crosslinking reaction mixture is held relatively constant over the course of the reaction.

Embodiment 67. The process of any previous enumerated embodiment wherein the temperature of the concurrent polymerization and crosslinking reaction mixture is ramped in a continuous or step-wise manner over the course of the reaction.

Embodiment 68. The process of any previous enumerated embodiment wherein the concurrent polymerization and crosslinking reaction step is carried out for a reaction time of at least about 2 hours.

Embodiment 69. The process of any previous enumerated embodiment wherein the concurrent polymerization and crosslinking reaction step is carried out for a reaction time of at least about 5 hours.

Embodiment 70. The process of any previous enumerated embodiment wherein the concurrent polymerization and crosslinking reaction step is carried out for a reaction time of at least about 10 hours.

Embodiment 71. The process of any previous enumerated embodiment wherein the concurrent polymerization and crosslinking reaction step is carried out for a reaction time of at least about 15 hours.

Embodiment 72. The process of any previous enumerated embodiment wherein the concurrent polymerization and crosslinking reaction step is carried out for a reaction time of at least about 20 hours.

Embodiment 73. The process of any previous enumerated embodiment wherein the concurrent polymerization and crosslinking reaction step is carried out for a reaction time of at least about 25 hours.

Embodiment 74. The process of any previous enumerated embodiment wherein the concurrent polymerization and crosslinking reaction step is carried out for a reaction time of at least about 30 hours.

Embodiment 75. The process of any previous enumerated embodiment wherein the concurrent polymerization and crosslinking reaction step is carried out for a reaction time of at least about 35 hours.

Embodiment 76. The process of any previous enumerated embodiment wherein the concurrent polymerization and crosslinking reaction step is carried out for a reaction time of at least about 40 hours.

Embodiment 77. The process of any previous enumerated embodiment wherein the concurrent polymerization and crosslinking reaction step is carried out for a reaction time of at least about 50 hours.

Embodiment 78. The process of any previous enumerated embodiment wherein the concurrent polymerization and crosslinking reaction step is carried out as a batch process.

Embodiment 79. The process of any previous enumerated embodiment wherein the concurrent polymerization and crosslinking reaction step is carried out as a semi-batch process.

Embodiment 80. The process of any previous enumerated embodiment wherein the concurrent polymerization and crosslinking reaction step is carried out as a continuous process.

Embodiment 81. The process of any previous enumerated embodiment wherein the concurrent polymerization and crosslinking reaction step reaction mixture comprises at least 0.4 equivalents of acid per allyl amine equivalent.

Embodiment 82. The process of any previous enumerated embodiment wherein the concurrent polymerization and crosslinking reaction step reaction mixture comprises at least 0.6 equivalents of acid per allyl amine equivalent.

Embodiment 83. The process of any previous enumerated embodiment wherein the concurrent polymerization and crosslinking reaction step reaction mixture comprises at least 0.8 equivalents of acid per allyl amine equivalent.

Embodiment 84. The process of any previous enumerated embodiment wherein the concurrent polymerization and crosslinking reaction step reaction mixture comprises at least 0.9 equivalents of acid per allyl amine equivalent.

Embodiment 85. The process of any previous enumerated embodiment wherein the concurrent polymerization and crosslinking reaction step reaction mixture comprises at least 0.95 equivalents of acid per allyl amine equivalent.

Embodiment 86. The process of any previous enumerated embodiment wherein the concurrent polymerization and crosslinking reaction step reaction mixture comprises at least 1.0 equivalents of acid per allyl amine equivalent.

Embodiment 87. The process of any previous enumerated embodiment wherein the concurrent polymerization and crosslinking reaction step reaction mixture comprises at least 1 equivalent of acid per allyl amine equivalent.

Embodiment 88. The process of any previous enumerated embodiment wherein the concurrent polymerization and crosslinking reaction step reaction mixture comprises an acid selected from the group consisting of hydrochloric acid, phosphoric acid, sulfuric acid, acetic acid, methylphosphoric acid, formic acid, citric acid, and combinations thereof.

Embodiment 89. The process of any previous enumerated embodiment wherein the acid is a mineral acid.

Embodiment 90. The process of any previous enumerated embodiment wherein the acid comprises hydrochloric acid, sulfuric acid, or phosphoric acid.

Embodiment 91. The process of any previous enumerated embodiment wherein the acid is introduced to the first step reaction mixture independent of the addition of the monoallylamine and multiallylamine to the first step reaction mixture.

Embodiment 92. The process of any previous enumerated embodiment wherein the acid is introduced to the first step reaction mixture as a component of the acid salt of the monoallylamine, the multiallylamine or both the monoallylamine and the multiallylamine.

Embodiment 93. The process of any previous enumerated embodiment wherein the poly(allylamine) polymer has an absorption capacity for the swelling agent, and the amount of swelling agent in the second step reaction mixture is less than the absorption capacity of the poly(allylamine) polymer as formed in the first step for the swelling agent.

Embodiment 94. The process of any previous enumerated embodiment wherein the poly(allylamine) polymer has an absorption capacity for the swelling agent, the poly(allylamine) polymer is swollen with the swelling agent, and the poly(allylamine) polymer is deprotonated with a base before it is swollen with the swelling agent.

Embodiment 95. The process of any previous enumerated embodiment wherein the dispersing solvent system comprises a non-polar solvent.

Embodiment 96. The process of any previous enumerated embodiment wherein the dispersing solvent system comprises a solvent that is chemically inert to the preformed poly(allylamine) polymer.

Embodiment 97. The process of any previous enumerated embodiment wherein the dispersing solvent system comprises a crosslinking solvent.

Embodiment 98. The process of any of enumerated embodiment wherein the dispersing solvent system is neat crosslinking agent.

Embodiment 99. The process of any previous enumerated embodiment wherein the swelling agent is immiscible with the dispersing solvent system.

Embodiment 100. The process of any previous enumerated embodiment wherein the weight ratio of the swelling agent to the crosslinked poly(allylamine) polymer in the second step reaction mixture is less than 4:1.

Embodiment 101. The process of any previous enumerated embodiment wherein the weight ratio of the swelling agent to the crosslinked poly(allylamine) polymer in the second step reaction mixture is less than 3:1.

Embodiment 102. The process of any previous enumerated embodiment wherein the weight ratio of the swelling agent to the crosslinked poly(allylamine) polymer in the second step reaction mixture is less than 2:1.

Embodiment 103. The process of any previous enumerated embodiment wherein the weight ratio of the swelling agent to the crosslinked poly(allylamine) polymer in the second step reaction mixture is less than 1:1.

Embodiment 104. The process of any previous enumerated embodiment wherein the swelling agent is a polar solvent.

Embodiment 105. The process of any previous enumerated embodiment wherein the swelling agent is water, methanol, ethanol, n-propanol, isopropanol, n-butanol, formic acid, acetic acid, acetonitrile, dimethylformamide, dimethylsulfoxide, nitromethane, propylene carbonate, or a combination thereof.

Embodiment 106. The process of any previous enumerated embodiment wherein the swelling agent is water.

Embodiment 107. The process of any previous enumerated embodiment wherein the weight ratio of the swelling agent to the crosslinked poly(allylamine) polymer in the second step reaction mixture is less than 0.5:1.

Embodiment 108. The process of any previous enumerated embodiment wherein the weight ratio of the swelling agent to the crosslinked poly(allylamine) polymer in the second step reaction mixture is less than 0.4:1.

Embodiment 109. The process of any previous enumerated embodiment wherein the weight ratio of the swelling agent to the crosslinked poly(allylamine) polymer in the second step reaction mixture is less than 0.3:1.

Embodiment 110. The process of any previous enumerated embodiment wherein the weight ratio of the swelling agent to the crosslinked poly(allylamine) polymer in the second step reaction mixture is at least 0.15:1.

Embodiment 111. The process of any previous enumerated embodiment wherein the crosslinking agent comprises at least two amine-reactive functional groups.

Embodiment 112. The process of any previous enumerated embodiment wherein the crosslinking agent is a composition containing at least two amine-reactive groups selected from the group consisting of alkyl halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, $\alpha,\beta$-unsaturated carbonyls, ketones, aldehydes, and pentafluoroaryl groups.

Embodiment 113. The process of any previous enumerated embodiment wherein the crosslinking agent is a crosslinking agent selected from Table B.

Embodiment 114. The process of any previous enumerated embodiment wherein the crosslinking agent is a dichloroalkane.

Embodiment 115. The process of any previous enumerated embodiment wherein the crosslinking agent is dichloroethane or dichloropropane Embodiment 116. The process of any previous enumerated embodiment wherein the crosslinking agent is dichloroethane.

Embodiment 117. The process of any previous enumerated embodiment wherein the swelling agent and the crosslinking agent are immiscible.

Embodiment 118. The process of any previous enumerated embodiment wherein the crosslinked poly(allylamine) polymer is combined with the crosslinking agent and the dispersing solvent system before the polymer is swollen with the swelling agent.

Embodiment 119. The process of any previous enumerated embodiment wherein the second step reaction mixture is at a temperature in the range of about 25° C. to about 85° C.

Embodiment 120. The process of any previous enumerated embodiment wherein the second step reaction is carried out at a temperature in the range of about 35° C. to about 80° C.

Embodiment 121. The process of any previous enumerated embodiment wherein the second step reaction mixture is carried out at a temperature in the range of about 45° C. to about 80° C.

Embodiment 122. The process of any previous enumerated embodiment wherein the second step reaction is carried out at a temperature in the range of about 55° C. to about 75° C.

Embodiment 123. The process of any previous enumerated embodiment wherein the second step reaction is carried out at a temperature in the range of about 60° C. to about 75° C.

Embodiment 124. The process of any previous enumerated embodiment wherein the second step reaction is carried out at a temperature in the range of about 65° C. to about 75° C.

Embodiment 125. The process of any previous enumerated embodiment wherein the temperature of the second step reaction mixture is held relatively constant over the course of the second step.

Embodiment 126. The process of any previous enumerated embodiment wherein the temperature of the second step reaction mixture is increased in a continuous or step-wise manner over the course of the second step.

Embodiment 127. The process of any previous enumerated embodiment wherein the second step reaction is carried out for a period of about 2 to 20 hours.

Embodiment 128. The process of any previous enumerated embodiment wherein the second step reaction is carried out for a period of about 4 to 20 h.

Embodiment 129. The process of any previous enumerated embodiment wherein the second step reaction is carried out for a period of about 5 to 20 h.

Embodiment 130. The process of any previous enumerated embodiment wherein the second step reaction is carried out for a period of about 6 to 20 h.

Embodiment 131. The process of any previous enumerated embodiment wherein the second step reaction is carried out for a period of about 8 to 20 h.

Embodiment 132. The process of any previous enumerated embodiment wherein the second step reaction is carried out for a period of about 10 to 20 h.

Embodiment 133. The process of any previous enumerated embodiment wherein the second step reaction is carried out for a period of about 12 to 18 h.

Embodiment 134. The process of any previous enumerated embodiment wherein the second step reaction is carried out for a period of about 14 to 18 h.

Embodiment 135. The process of any previous enumerated embodiment wherein the second step reaction is carried out for a period of about 15 to 17 h.

Embodiment 136. A crosslinked poly(allylamine) polymer in bead form prepared according to any of the preceding process claims.

Embodiment 137. A crosslinked poly(allylamine) polymer in bead form comprising the residues of a monoallylamine or a salt thereof and a multiallylamine or a salt thereof wherein (i) the crosslinked poly(allylamine) polymer has a swelling ratio of less than 2 and (ii) $sp^2$ allyl carbons comprised by the crosslinked poly(allylamine) polymer constitute less than 2.5% of the total number of carbon atoms comprised by the crosslinked poly(allylamine) polymer.

Embodiment 138. A crosslinked poly(allylamine) polymer in bead form comprising the residues of a monoallylamine or a salt thereof and a multiallylamine or a salt thereof wherein (i) the crosslinked poly(allylamine) polymer contains less than 20 ppm allylamine and (ii) $sp^2$ allyl carbons comprised by the crosslinked poly(allylamine) polymer constitute less than 2.5% of the total number of carbon atoms comprised by the crosslinked poly(allylamine) polymer.

Embodiment 139. The process or crosslinked poly(allylamine) polymer of any previous enumerated embodiment wherein $sp^2$ allyl carbons comprised by the crosslinked poly(allylamine) polymer constitute less than 2.25% of the total number of carbon atoms comprised by the crosslinked poly(allylamine) polymer.

Embodiment 140. The process or crosslinked poly(allylamine) polymer of any previous enumerated embodiment wherein $sp^2$ allyl carbons comprised by the crosslinked poly(allylamine) polymer constitute less than 2% of the total number of carbon atoms comprised by the crosslinked poly(allylamine) polymer.

Embodiment 141. The process or crosslinked poly(allylamine) polymer of any previous enumerated embodiment wherein $sp^2$ allyl carbons comprised by the crosslinked poly(allylamine) polymer constitute less than 1.9% of the total number of carbon atoms comprised by the crosslinked poly(allylamine) polymer.

Embodiment 142. The process or crosslinked poly(allylamine) polymer of any previous enumerated embodiment wherein $sp^2$ allyl carbons comprised by the crosslinked poly(allylamine) polymer constitute less than 1.8% of the total number of carbon atoms comprised by the crosslinked poly(allylamine) polymer.

Embodiment 143. The process or crosslinked poly(allylamine) polymer of any previous enumerated embodiment wherein $sp^2$ allyl carbons comprised by the crosslinked poly(allylamine) polymer constitute less than 1.7% of the total number of carbon atoms comprised by the crosslinked poly(allylamine) polymer.

Embodiment 144. The process or crosslinked poly(allylamine) polymer of any previous enumerated embodiment wherein $sp^2$ allyl carbons comprised by the crosslinked poly(allylamine) polymer constitute less than 1.6% of the total number of carbon atoms comprised by the crosslinked poly(allylamine) polymer.

Embodiment 145A. The process or crosslinked poly(allylamine) polymer of any previous enumerated embodiment wherein $sp^2$ allyl carbons comprised by the crosslinked poly(allylamine) polymer constitute less than 1.5% of the total number of carbon atoms comprised by the crosslinked poly(allylamine) polymer.

Embodiment 145B. The process of any previous enumerated embodiment wherein $sp^2$ allyl carbons comprised by the crosslinked poly(allylamine) polymer constitute less than 1.4% of the total number of carbon atoms comprised by the crosslinked poly(allylamine).

Embodiment 145C. The process of any previous enumerated embodiment wherein $sp^2$ allyl carbons comprised by the crosslinked poly(allylamine) polymer constitute less than 1.3% of the total number of carbon atoms comprised by the crosslinked poly(allylamine).

Embodiment 145D1. The process of any previous enumerated embodiment wherein $sp^2$ allyl carbons comprised by the crosslinked poly(allylamine) polymer constitute less than 1.25% of the total number of carbon atoms comprised by the crosslinked poly(allylamine).

Embodiment 145D2. The process of any previous enumerated embodiment wherein $sp^2$ allyl carbons comprised by the crosslinked poly(allylamine) polymer constitute less than 1.2% of the total number of carbon atoms comprised by the crosslinked poly(allylamine).

Embodiment 145E. The process of any previous enumerated embodiment wherein $sp^2$ allyl carbons comprised by the crosslinked poly(allylamine) polymer constitute less than 1.1% of the total number of carbon atoms comprised by the crosslinked poly(allylamine).

Embodiment 145F. The process of any previous enumerated embodiment wherein $sp^2$ allyl carbons comprised by the crosslinked poly(allylamine) polymer constitute less than 1.0% of the total number of carbon atoms comprised by the crosslinked poly(allylamine).

Embodiment 145G. The process of any previous enumerated embodiment wherein $sp^2$ allyl carbons comprised by the crosslinked poly(allylamine) polymer constitute less than 0.9% of the total number of carbon atoms comprised by the crosslinked poly(allylamine).

Embodiment 145H. The process of any previous enumerated embodiment wherein $sp^2$ allyl carbons comprised by the crosslinked poly(allylamine) polymer constitute less than 0.8% of the total number of carbon atoms comprised by the crosslinked poly(allylamine).

Embodiment 145I. The process of any previous enumerated embodiment wherein $sp^2$ allyl carbons comprised by the crosslinked poly(allylamine) polymer constitute less than 0.75% of the total number of carbon atoms comprised by the crosslinked poly(allylamine).

Embodiment 145J. The process of any previous enumerated embodiment wherein $sp^2$ allyl carbons comprised by the crosslinked poly(allylamine) polymer constitute less than 0.7% of the total number of carbon atoms comprised by the crosslinked poly(allylamine).

Embodiment 145K. The process of any previous enumerated embodiment wherein $sp^2$ allyl carbons comprised by the crosslinked poly(allylamine) polymer constitute less than 0.6% of the total number of carbon atoms comprised by the crosslinked poly(allylamine).

Embodiment 145L. The process of any previous enumerated embodiment wherein $sp^2$ allyl carbons comprised by the crosslinked poly(allylamine) polymer constitute less than 0.5% of the total number of carbon atoms comprised by the crosslinked poly(allylamine).

Embodiment 145M. The process of any previous enumerated embodiment wherein $sp^2$ allyl carbons comprised by the crosslinked poly(allylamine) polymer constitute less than 0.4% of the total number of carbon atoms comprised by the crosslinked poly(allylamine).

Embodiment 146. The process of any previous enumerated embodiment wherein $sp^2$ allyl carbons comprised by the crosslinked poly(allylamine) polymer constitute less than 0.3% of the total number of carbon atoms comprised by the crosslinked poly(allylamine).

Embodiment 147. The process of any previous enumerated embodiment wherein $sp^2$ allyl carbons comprised by the crosslinked poly(allylamine) polymer constitute less than 0.25% of the total number of carbon atoms comprised by the crosslinked poly(allylamine).

Embodiment 148. The process or crosslinked poly(allylamine) polymer of any previous enumerated embodiment wherein $sp^2$ allyl carbons comprised by the crosslinked poly(allylamine) polymer constitute less than 0.2% of the total number of carbon atoms comprised by the crosslinked poly(allylamine) polymer.

Embodiment 149. The process or crosslinked poly(allylamine) polymer of any previous enumerated embodiment wherein $sp^2$ allyl carbons comprised by the crosslinked poly(allylamine) polymer constitute less than 0.1% of the total number of carbon atoms comprised by the crosslinked poly(allylamine) polymer.

Embodiment 150. The process of any previous enumerated embodiment wherein the percentage of $sp^2$ allyl carbons comprised by the poly(allylamine) polymer is determined by NMR; optionally wherein integration of the $sp^2$ allyl carbon peaks between 110-150 ppm and alkyl carbon peaks between 0-80 ppm is used to quantitate the percent $sp^2$ allyl carbons of the poly(allylamine) polymer using the formula $$\% \ sp2 \ \text{allyl carbons} = \frac{\text{peak integration (110-150 ppm)}}{\text{peak integration (0-80 ppm)} + \text{peak integration (110-150 ppm)}} \times 100.$$

Embodiment 151. The process or crosslinked poly(allylamine) polymer of any previous enumerated embodiment wherein the number of $sp^2$ allyl carbons, if any, comprised by the crosslinked poly(allylamine) polymer is less than the detection limit as determined by NMR.

Embodiment 152. The process or crosslinked poly(allylamine) polymer of any previous enumerated embodiment wherein the crosslinked poly(allylamine) polymer contains less than 15 ppm allylamine.

Embodiment 153. The process or crosslinked poly(allylamine) polymer of any previous enumerated embodiment wherein the crosslinked poly(allylamine) polymer contains less than 12.5 ppm allylamine.

Embodiment 154. The process or crosslinked poly(allylamine) polymer of any previous enumerated embodiment wherein the crosslinked poly(allylamine) polymer contains less than 10 ppm allylamine.

Embodiment 155. The process or crosslinked poly(allylamine) polymer of any previous enumerated embodiment wherein the crosslinked poly(allylamine) polymer contains less than 7.5 ppm allylamine.

Embodiment 156. The process or crosslinked poly(allylamine) polymer of any previous enumerated embodiment wherein the crosslinked poly(allylamine) polymer contains less than 5 ppm allylamine.

Embodiment 157. The process or crosslinked poly(allylamine) polymer of any previous enumerated embodiment wherein the crosslinked poly(allylamine) polymer contains less than 4 ppm allylamine.

Embodiment 158. The process or crosslinked poly(allylamine) polymer of any previous enumerated embodiment wherein the crosslinked poly(allylamine) polymer contains less than 3 ppm allylamine.

Embodiment 159. The process or crosslinked poly(allylamine) polymer of any previous enumerated embodiment wherein the crosslinked poly(allylamine) polymer contains less than 2 ppm allylamine.

Embodiment 160. The process or crosslinked poly(allylamine) polymer of any previous enumerated embodiment wherein the crosslinked poly(allylamine) polymer contains less than 1 ppm allylamine.

Embodiment 161. The process or crosslinked poly(allylamine) polymer of any previous enumerated embodiment wherein the crosslinked poly(allylamine) polymer contains less than 500 ppb allylamine.

Embodiment 162. The process or crosslinked poly(allylamine) polymer of any previous enumerated embodiment wherein the crosslinked poly(allylamine) polymer contains less than 100 ppb allylamine.

Embodiment 163. The process or crosslinked poly(allylamine) polymer of any previous enumerated embodiment wherein the crosslinked poly(allylamine) polymer contains less than 50 ppb allylamine.

Embodiment 164. The process or crosslinked poly(allylamine) polymer of any previous enumerated embodiment wherein the crosslinked poly(allylamine) polymer contains less than 1 ppb allylamine.

Embodiment 165. The process or crosslinked poly(allylamine) polymer of any previous enumerated embodiment wherein the crosslinked poly(allylamine) polymer has a swelling ratio of less than 1.9.

Embodiment 166. The process or crosslinked poly(allylamine) polymer of any previous enumerated embodiment wherein the crosslinked poly(allylamine) polymer has a swelling ratio of less than 1.8.

Embodiment 167. The process or crosslinked poly(allylamine) polymer of any previous enumerated embodiment wherein the crosslinked poly(allylamine) polymer has a swelling ratio of less than 1.7.

Embodiment 168. The process or crosslinked poly(allylamine) polymer of any previous enumerated embodiment wherein the crosslinked poly(allylamine) polymer has a swelling ratio of less than 1.6.

Embodiment 169. The process or crosslinked poly(allylamine) polymer of any previous enumerated embodiment wherein the crosslinked poly(allylamine) polymer has a swelling ratio of less than 1.5.

Embodiment 170. The process or crosslinked poly(allylamine) polymer of any previous enumerated embodiment wherein the crosslinked poly(allylamine) polymer has a swelling ratio of less than 1.4.

Embodiment 171. The process or crosslinked poly(allylamine) polymer of any previous enumerated embodiment wherein the crosslinked poly(allylamine) polymer has a swelling ratio of less than 1.3.

Embodiment 172. The process or crosslinked poly(allylamine) polymer of any previous enumerated embodiment wherein the crosslinked poly(allylamine) polymer has a swelling ratio of less than 1.2.

Embodiment 173. The process or crosslinked poly(allylamine) polymer of any previous enumerated embodiment wherein the crosslinked poly(allylamine) polymer has a swelling ratio of less than 1.1.

Embodiment 174. The process or crosslinked poly(allylamine) polymer of any previous enumerated embodiment wherein the crosslinked poly(allylamine) polymer has a swelling ratio of less than 1.

Embodiment 175. The process or crosslinked poly(allylamine) polymer of any previous enumerated embodiment wherein the crosslinked poly(allylamine) polymer has a swelling ratio of less than 0.9.

Embodiment 176. The process or crosslinked poly(allylamine) polymer of any previous enumerated embodiment wherein the crosslinked poly(allylamine) polymer has a swelling ratio of less than 0.8.

Embodiment 177. The process or crosslinked poly(allylamine) polymer of any previous enumerated embodiment wherein the crosslinked poly(allylamine) polymer has a swelling ratio of less than 0.7.

Embodiment 178. The process or crosslinked poly(allylamine) polymer of any previous enumerated embodiment wherein the poly(allylamine) polymer has a stability profile such that upon storage in a sealed enclosure for 3 months at 25° C. after manufacture the poly(allylamine) polymer contains less than 20 ppm allylamine.

Embodiment 179. The process or crosslinked poly(allylamine) polymer of any previous enumerated embodiment wherein the poly(allylamine) polymer contains less than 15 ppm allylamine upon storage in a sealed enclosure for 3 months at 25° C. after manufacture.

Embodiment 180. The process or crosslinked poly(allylamine) polymer of any previous enumerated embodiment wherein the poly(allylamine) polymer contains less than 12.5 ppm allylamine upon storage in a sealed enclosure for 3 months at 25° C. after manufacture.

Embodiment 181. The process or crosslinked poly(allylamine) polymer of any previous enumerated embodiment wherein the poly(allylamine) polymer contains less than 10 ppm allylamine upon storage in a sealed enclosure for 3 months at 25° C. after manufacture.

Embodiment 182. The process or crosslinked poly(allylamine) polymer of any previous enumerated embodiment wherein the poly(allylamine) polymer contains less than 7.5 ppm allylamine upon storage in a sealed enclosure for 3 months at 25° C. after manufacture.

Embodiment 183. The process or crosslinked poly(allylamine) polymer of any previous enumerated embodiment wherein the poly(allylamine) polymer contains less than 5 ppm allylamine upon storage in a sealed enclosure for 3 months at 25° C. after manufacture.

Embodiment 184. The process or crosslinked poly(allylamine) polymer of any previous enumerated embodiment wherein the poly(allylamine) polymer contains less than 4 ppm allylamine upon storage in a sealed enclosure for 3 months at 25° C. after manufacture.

Embodiment 185. The process or crosslinked poly(allylamine) polymer of any previous enumerated embodiment wherein the poly(allylamine) polymer contains less than 3 ppm allylamine upon storage in a sealed enclosure for 3 months at 25° C. after manufacture.

Embodiment 186. The process or crosslinked poly(allylamine) polymer of any previous enumerated embodiment wherein the poly(allylamine) polymer contains less than 2 ppm allylamine upon storage in a sealed enclosure for 3 months at 25° C. after manufacture.

Embodiment 187. The process or crosslinked poly(allylamine) polymer of any previous enumerated embodiment wherein the poly(allylamine) polymer contains less than 1 ppm allylamine upon storage in a sealed enclosure for 3 months at 25° C. after manufacture.

Embodiment 188. The process or crosslinked poly(allylamine) polymer of any previous enumerated embodiment wherein the poly(allylamine) polymer contains less than 500 ppb allylamine upon storage in a sealed enclosure for 3 months at 25° C. after manufacture.

Embodiment 189. The process or crosslinked poly(allylamine) polymer of any previous enumerated embodiment wherein the poly(allylamine) polymer contains less than 100 ppb allylamine upon storage in a sealed enclosure for 3 months at 25° C. after manufacture.

Embodiment 190. The process or crosslinked poly(allylamine) polymer of any previous enumerated embodiment wherein the poly(allylamine) polymer contains less than 50 ppb allylamine upon storage in a sealed enclosure for 3 months at 25° C. after manufacture.

Embodiment 191. The process or crosslinked poly(allylamine) polymer of any previous enumerated embodiment wherein the poly(allylamine) polymer contains less than 1 ppb allylamine upon storage in a sealed enclosure for 3 months at 25° C. after manufacture.

Embodiment 192. The process or crosslinked poly(allylamine) polymer of any previous enumerated embodiment wherein the amount of allylamine, if any, in the poly(allylamine) polymer is less than the detection limit for allylamine upon storage in a sealed enclosure for 3 months at 25° C. after manufacture.

Embodiment 193. The process or crosslinked poly(allylamine) polymer of any previous enumerated embodiment wherein the poly(allylamine) polymer has a stability profile such that upon storage in a sealed enclosure for 6 months at 25° C. after manufacture the poly(allylamine) polymer contains less than 20 ppm allylamine.

Embodiment 194. The process or crosslinked poly(allylamine) polymer of any previous enumerated embodiment wherein the poly(allylamine) polymer contains less than 15 ppm allylamine upon storage in a sealed enclosure for 6 months at 25° C. after manufacture.

Embodiment 195. The process or crosslinked poly(allylamine) polymer of any previous enumerated embodiment wherein the poly(allylamine) polymer contains less than 12.5 ppm allylamine upon storage in a sealed enclosure for 6 months at 25° C. after manufacture.

Embodiment 196. The process or crosslinked poly(allylamine) polymer of any previous enumerated embodiment wherein the poly(allylamine) polymer contains less than 10 ppm allylamine upon storage in a sealed enclosure for 6 months at 25° C. after manufacture.

Embodiment 197. The process or crosslinked poly(allylamine) polymer of any previous enumerated embodiment wherein the poly(allylamine) polymer contains less than 7.5 ppm allylamine upon storage in a sealed enclosure for 6 months at 25° C. after manufacture.

Embodiment 198. The process or crosslinked poly(allylamine) polymer of any previous enumerated embodiment wherein the poly(allylamine) polymer contains less than 5 ppm allylamine upon storage in a sealed enclosure for 6 months at 25° C. after manufacture.

Embodiment 199. The process or crosslinked poly(allylamine) polymer of any previous enumerated embodiment wherein the poly(allylamine) polymer contains less than 4 ppm allylamine upon storage in a sealed enclosure for 6 months at 25° C. after manufacture.

Embodiment 200. The process or crosslinked poly(allylamine) polymer of any previous enumerated embodiment wherein the poly(allylamine) polymer contains less than 3 ppm allylamine upon storage in a sealed enclosure for 6 months at 25° C. after manufacture.

Embodiment 201. The process or crosslinked poly(allylamine) polymer of any previous enumerated embodiment wherein the poly(allylamine) polymer contains less than 2 ppm allylamine upon storage in a sealed enclosure for 6 months at 25° C. after manufacture.

Embodiment 202. The process or crosslinked poly(allylamine) polymer of any previous enumerated embodiment wherein the poly(allylamine) polymer contains less than 1 ppm allylamine upon storage in a sealed enclosure for 6 months at 25° C. after manufacture.

Embodiment 203. The process or crosslinked poly(allylamine) polymer of any previous enumerated embodiment wherein the poly(allylamine) polymer contains less than 500 ppb allylamine upon storage in a sealed enclosure for 6 months at 25° C. after manufacture.

Embodiment 204. The process or crosslinked poly(allylamine) polymer of any previous enumerated embodiment wherein the poly(allylamine) polymer contains less than 100 ppb allylamine upon storage in a sealed enclosure for 6 months at 25° C. after manufacture.

Embodiment 205. The process or crosslinked poly(allylamine) polymer of any previous enumerated embodiment wherein the poly(allylamine) polymer contains less than 50 ppb allylamine upon storage in a sealed enclosure for 6 months at 25° C. after manufacture.

Embodiment 206. The process or crosslinked poly(allylamine) polymer of any previous enumerated embodiment wherein the poly(allylamine) polymer contains less than 1 ppb allylamine upon storage in a sealed enclosure for 6 months at 25° C. after manufacture.

Embodiment 207. The process or crosslinked poly(allylamine) polymer of any previous enumerated embodiment wherein the amount of allylamine, if any, in the poly(allylamine) polymer is less than the detection limit for allylamine upon storage in a sealed enclosure for 6 months at 25° C. after manufacture.

Embodiment 208. The process or crosslinked poly(allylamine) polymer of any previous enumerated embodiment wherein the poly(allylamine) polymer has a stability profile such that upon storage in a sealed enclosure for 9 months at 25° C. after manufacture the poly(allylamine) polymer contains less than 20 ppm allylamine.

Embodiment 209. The process or crosslinked poly(allylamine) polymer of any previous enumerated embodiment wherein the poly(allylamine) polymer contains less than 12.5 ppm allylamine upon storage in a sealed enclosure for 9 months at 25° C. after manufacture.

Embodiment 210. The process or crosslinked poly(allylamine) polymer of any previous enumerated embodiment wherein the poly(allylamine) polymer contains less than 10 ppm allylamine upon storage in a sealed enclosure for 9 months at 25° C. after manufacture.

Embodiment 211. The process or crosslinked poly(allylamine) polymer of any previous enumerated embodiment wherein the poly(allylamine) polymer contains less than 7.5 ppm allylamine upon storage in a sealed enclosure for 9 months at 25° C. after manufacture.

Embodiment 212. The process or crosslinked poly(allylamine) polymer of any previous enumerated embodiment wherein the poly(allylamine) polymer contains less than 5 ppm allylamine upon storage in a sealed enclosure for 9 months at 25° C. after manufacture.

Embodiment 213. The process or crosslinked poly(allylamine) polymer of any previous enumerated embodiment wherein the poly(allylamine) polymer contains less than 4 ppm allylamine upon storage in a sealed enclosure for 9 months at 25° C. after manufacture.

Embodiment 214. The process or crosslinked poly(allylamine) polymer of any previous enumerated embodiment wherein the poly(allylamine) polymer contains less than 3 ppm allylamine upon storage in a sealed enclosure for 9 months at 25° C. after manufacture.

Embodiment 215. The process or crosslinked poly(allylamine) polymer of any previous enumerated embodiment wherein the poly(allylamine) polymer contains less than 2 ppm allylamine upon storage in a sealed enclosure for 9 months at 25° C. after manufacture.

Embodiment 216. The process or crosslinked poly(allylamine) polymer of any previous enumerated embodiment wherein the poly(allylamine) polymer contains less than 1 ppm allylamine upon storage in a sealed enclosure for 9 months at 25° C. after manufacture.

Embodiment 217. The process or crosslinked poly(allylamine) polymer of any previous enumerated embodiment wherein the poly(allylamine) polymer contains less than 500 ppb allylamine upon storage in a sealed enclosure for 9 months at 25° C. after manufacture.

Embodiment 218. The process or crosslinked poly(allylamine) polymer of any previous enumerated embodiment wherein the poly(allylamine) polymer contains less than 100 ppb allylamine upon storage in a sealed enclosure for 9 months at 25° C. after manufacture.

Embodiment 219. The process or crosslinked poly(allylamine) polymer of any previous enumerated embodiment wherein the poly(allylamine) polymer contains less than 50 ppb allylamine upon storage in a sealed enclosure for 9 months at 25° C. after manufacture.

Embodiment 220. The process or crosslinked poly(allylamine) polymer of any previous enumerated embodiment wherein the poly(allylamine) polymer contains less than 1 ppb allylamine upon storage in a sealed enclosure for 9 months at 25° C. after manufacture.

Embodiment 221. The process or crosslinked poly(allylamine) polymer of any previous enumerated embodiment wherein the amount of allylamine, if any, in the poly(allylamine) polymer is less than the detection limit for allylamine upon storage in a sealed enclosure for 9 months at 25° C. after manufacture.

Embodiment 222. The process or crosslinked poly(allylamine) polymer of any previous enumerated embodiment wherein the poly(allylamine) polymer has a stability profile such that upon storage in a sealed enclosure for 12 months at 25° C. after manufacture the poly(allylamine) polymer contains less than 20 ppm allylamine.

Embodiment 223. The process or crosslinked poly(allylamine) polymer of any previous enumerated embodiment wherein the poly(allylamine) polymer contains less than 15 ppm allylamine upon storage in a sealed enclosure for 12 months at 25° C. after manufacture.

Embodiment 224. The process or crosslinked poly(allylamine) polymer of any previous enumerated embodiment wherein the poly(allylamine) polymer contains less than 12.5 ppm allylamine upon storage in a sealed enclosure for 12 months at 25° C. after manufacture.

Embodiment 225. The process or crosslinked poly(allylamine) polymer of any previous enumerated embodiment wherein the poly(allylamine) polymer contains less than 10 ppm allylamine upon storage in a sealed enclosure for 12 months at 25° C. after manufacture.

Embodiment 226. The process or crosslinked poly(allylamine) polymer of any previous enumerated embodiment wherein the poly(allylamine) polymer contains less than 7.5 ppm allylamine upon storage in a sealed enclosure for 12 months at 25° C. after manufacture.

Embodiment 227. The process or crosslinked poly(allylamine) polymer of any previous enumerated embodiment wherein the poly(allylamine) polymer contains less than 5 ppm allylamine upon storage in a sealed enclosure for 12 months at 25° C. after manufacture.

Embodiment 228. The process or crosslinked poly(allylamine) polymer of any previous enumerated embodiment wherein the poly(allylamine) polymer contains less than 4 ppm allylamine upon storage in a sealed enclosure for 12 months at 25° C. after manufacture.

Embodiment 229. The process or crosslinked poly(allylamine) polymer of any previous enumerated embodiment wherein the poly(allylamine) polymer contains less than 3 ppm allylamine upon storage in a sealed enclosure for 12 months at 25° C. after manufacture.

Embodiment 230. The process or crosslinked poly(allylamine) polymer of any previous enumerated embodiment wherein the poly(allylamine) polymer contains less than 2 ppm allylamine upon storage in a sealed enclosure for 12 months at 25° C. after manufacture.

Embodiment 231. The process or crosslinked poly(allylamine) polymer of any previous enumerated embodiment wherein the poly(allylamine) polymer contains less than 1 ppm allylamine upon storage in a sealed enclosure for 12 months at 25° C. after manufacture.

Embodiment 232. The process or crosslinked poly(allylamine) polymer of any previous enumerated embodiment wherein the poly(allylamine) polymer contains less than 500 ppb allylamine upon storage in a sealed enclosure for 12 months at 25° C. after manufacture.

Embodiment 233. The process or crosslinked poly(allylamine) polymer of any previous enumerated embodiment wherein the poly(allylamine) polymer contains less than 100 ppb allylamine upon storage in a sealed enclosure for 12 months at 25° C. after manufacture.

Embodiment 234. The process or crosslinked poly(allylamine) polymer of any previous enumerated embodiment wherein the poly(allylamine) polymer contains less than 50 ppb allylamine upon storage in a sealed enclosure for 12 months at 25° C. after manufacture.

Embodiment 235. The process or crosslinked poly(allylamine) polymer of any previous enumerated embodiment wherein the poly(allylamine) polymer contains less than 1 ppb allylamine upon storage in a sealed enclosure for 12 months at 25° C. after manufacture.

Embodiment 236. The process or crosslinked poly(allylamine) polymer of any previous enumerated embodiment wherein the amount of allylamine, if any, in the poly(allylamine) polymer is less than the detection limit for allylamine upon storage in a sealed enclosure for 12 months at 25° C. after manufacture.

Embodiment 237. The process or crosslinked poly(allylamine) polymer of any previous enumerated embodiment wherein the crosslinked poly(allylamine) polymer contains less than the detection limit for allylamine.

Embodiment 238. The process or crosslinked poly(allylamine) polymer of any previous enumerated embodiment wherein the poly(allylamine) polymer has a stability profile such that upon storage in a sealed enclosure for 3 months at 25° C. the allylamine content of the poly(allylamine) polymer increases less than 20 ppm allylamine.

Embodiment 239. The process or crosslinked poly(allylamine) polymer of any previous enumerated embodiment wherein the allylamine content of the poly(allylamine) polymer increases less than 15 ppm upon storage in a sealed enclosure for 3 months at 25° C.

Embodiment 240. The process or crosslinked poly(allylamine) polymer of any previous enumerated embodiment wherein the allylamine content of the poly(allylamine) polymer increases less than 12.5 ppm allylamine upon storage in a sealed enclosure for 3 months at 25° C.

Embodiment 241. The process or crosslinked poly(allylamine) polymer of any previous enumerated embodiment wherein the allylamine content of the poly(allylamine) polymer increases less than 10 ppm allylamine upon storage in a sealed enclosure for 3 months at 25° C.

Embodiment 242. The process or crosslinked poly(allylamine) polymer of any previous enumerated embodiment wherein the allylamine content of the poly(allylamine) polymer increases less than 7.5 ppm allylamine upon storage in a sealed enclosure for 3 months at 25° C.

Embodiment 243. The process or crosslinked poly(allylamine) polymer of any previous enumerated embodiment wherein the allylamine content of the poly(allylamine) polymer increases less than 5 ppm allylamine upon storage in a sealed enclosure for 3 months at 25° C.

Embodiment 244. The process or crosslinked poly(allylamine) polymer of any previous enumerated embodiment wherein the allylamine content of the poly(allylamine) polymer increases less than 4 ppm allylamine upon storage in a sealed enclosure for 3 months at 25° C.

Embodiment 245. The process or crosslinked poly(allylamine) polymer of any previous enumerated embodiment wherein the allylamine content of the poly(allylamine) polymer increases less than 3 ppm allylamine upon storage in a sealed enclosure for 3 months at 25° C.

Embodiment 246. The process or crosslinked poly(allylamine) polymer of any previous enumerated embodiment wherein the allylamine content of the poly(allylamine) polymer increases less than 2 ppm allylamine upon storage in a sealed enclosure for 3 months at 25° C.

Embodiment 247. The process or crosslinked poly(allylamine) polymer of any previous enumerated embodiment wherein the allylamine content of the poly(allylamine) polymer increases less than 1 ppm allylamine upon storage in a sealed enclosure for 3 months at 25° C.

Embodiment 248. The process or crosslinked poly(allylamine) polymer of any previous enumerated embodiment wherein the allylamine content of the poly(allylamine) polymer increases less than 500 ppb allylamine upon storage in a sealed enclosure for 3 months at 25° C.

Embodiment 249. The process or crosslinked poly(allylamine) polymer of any previous enumerated embodiment wherein the allylamine content of the poly(allylamine) polymer increases less than 100 ppb allylamine upon storage in a sealed enclosure for 3 months at 25° C.

Embodiment 250. The process or crosslinked poly(allylamine) polymer of any previous enumerated embodiment wherein the allylamine content of the poly(allylamine) polymer increases less than 50 ppb allylamine upon storage in a sealed enclosure for 3 months at 25° C.

Embodiment 251. The process or crosslinked poly(allylamine) polymer of any previous enumerated embodiment wherein the allylamine content of the poly(allylamine) polymer increases less than 1 ppb allylamine upon storage in a sealed enclosure for 3 months at 25° C.

Embodiment 252. The process or crosslinked poly(allylamine) polymer of any previous enumerated embodiment wherein the amount of allylamine, if any, in the poly(allylamine) polymer is less than the detection limit for allylamine upon storage in a sealed enclosure for 3 months at 25° C.

Embodiment 253. The process or crosslinked poly(allylamine) polymer of any previous enumerated embodiment wherein the poly(allylamine) polymer has a stability profile such that upon storage in a sealed enclosure for 6 months at 25° C. after manufacture the allylamine content of the poly(allylamine) polymer increases less than 20 ppm allylamine.

Embodiment 254. The process or crosslinked poly(allylamine) polymer of any previous enumerated embodiment wherein the allylamine content of the poly(allylamine) polymer increases less than 15 ppm allylamine upon storage in a sealed enclosure for 6 months at 25° C.

Embodiment 255. The process or crosslinked poly(allylamine) polymer of any previous enumerated embodiment wherein the allylamine content of the poly(allylamine) polymer increases less than 12.5 ppm allylamine upon storage in a sealed enclosure for 6 months at 25° C.

Embodiment 256. The process or crosslinked poly(allylamine) polymer of any previous enumerated embodiment wherein the allylamine content of the poly(allylamine) polymer increases less than 10 ppm allylamine upon storage in a sealed enclosure for 6 months at 25° C.

Embodiment 257. The process or crosslinked poly(allylamine) polymer of any previous enumerated embodiment wherein the allylamine content of the poly(allylamine) polymer increases less than 7.5 ppm allylamine upon storage in a sealed enclosure for 6 months at 25° C.

Embodiment 258. The process or crosslinked poly(allylamine) polymer of any previous enumerated embodiment wherein the allylamine content of the poly(allylamine) polymer increases less than 5 ppm allylamine upon storage in a sealed enclosure for 6 months at 25° C.

Embodiment 259. The process or crosslinked poly(allylamine) polymer of any previous enumerated embodiment wherein the allylamine content of the poly(allylamine) polymer increases less than 4 ppm allylamine upon storage in a sealed enclosure for 6 months at 25° C.

Embodiment 260. The process or crosslinked poly(allylamine) polymer of any previous enumerated embodiment wherein the allylamine content of the poly(allylamine) polymer increases less than 3 ppm allylamine upon storage in a sealed enclosure for 6 months at 25° C.

Embodiment 261. The process or crosslinked poly(allylamine) polymer of any previous enumerated embodiment wherein the allylamine content of the poly(allylamine) polymer increases less than 2 ppm allylamine upon storage in a sealed enclosure for 6 months at 25° C.

Embodiment 262. The process or crosslinked poly(allylamine) polymer of any previous enumerated embodiment wherein the allylamine content of the poly(allylamine) polymer increases less than 1 ppm allylamine upon storage in a sealed enclosure for 6 months at 25° C.

Embodiment 263. The process or crosslinked poly(allylamine) polymer of any previous enumerated embodiment wherein the allylamine content of the poly(allylamine) polymer increases less than 500 ppb allylamine upon storage in a sealed enclosure for 6 months at 25° C.

Embodiment 264. The process or crosslinked poly(allylamine) polymer of any previous enumerated embodiment wherein the allylamine content of the poly(allylamine) polymer increases less than 100 ppb allylamine upon storage in a sealed enclosure for 6 months at 25° C.

Embodiment 265. The process or crosslinked poly(allylamine) polymer of any previous enumerated embodiment wherein the allylamine content of the poly(allylamine) polymer increases less than 50 ppb allylamine upon storage in a sealed enclosure for 6 months at 25° C.

Embodiment 266. The process or crosslinked poly(allylamine) polymer of any previous enumerated embodiment wherein the allylamine content of the poly(allylamine) polymer increases less than 1 ppb allylamine upon storage in a sealed enclosure for 6 months at 25° C.

Embodiment 267. The process or crosslinked poly(allylamine) polymer of any previous enumerated embodiment wherein the amount of allylamine, if any, in the poly (allylamine) polymer is less than the detection limit for allylamine upon storage in a sealed enclosure for 6 months at 25° C.

Embodiment 268. The process or crosslinked poly(allylamine) polymer of any previous enumerated embodiment wherein the poly(allylamine) polymer has a stability profile such that upon storage in a sealed enclosure for 9 months at 25° C. after manufacture the allylamine content of the poly(allylamine) polymer increases less than 20 ppm allylamine.

Embodiment 269. The process or crosslinked poly(allylamine) polymer of any previous enumerated embodiment wherein the allylamine content of the poly(allylamine) polymer increases less than 12.5 ppm allylamine upon storage in a sealed enclosure for 9 months at 25° C.

Embodiment 270. The process or crosslinked poly(allylamine) polymer of any previous enumerated embodiment wherein the allylamine content of the poly(allylamine) polymer increases less than 10 ppm allylamine upon storage in a sealed enclosure for 9 months at 25° C.

Embodiment 271. The process or crosslinked poly(allylamine) polymer of any previous enumerated embodiment wherein the allylamine content of the poly(allylamine) polymer increases less than 7.5 ppm allylamine upon storage in a sealed enclosure for 9 months at 25° C.

Embodiment 272. The process or crosslinked poly(allylamine) polymer of any previous enumerated embodiment wherein the allylamine content of the poly(allylamine) polymer increases less than 5 ppm allylamine upon storage in a sealed enclosure for 9 months at 25° C.

Embodiment 273. The process or crosslinked poly(allylamine) polymer of any previous enumerated embodiment wherein the allylamine content of the poly(allylamine) polymer increases less than 4 ppm allylamine upon storage in a sealed enclosure for 9 months at 25° C.

Embodiment 274. The process or crosslinked poly(allylamine) polymer of any previous enumerated embodiment wherein the allylamine content of the poly(allylamine) polymer increases less than 3 ppm allylamine upon storage in a sealed enclosure for 9 months at 25° C.

Embodiment 275. The process or crosslinked poly(allylamine) polymer of any previous enumerated embodiment wherein the allylamine content of the poly(allylamine) polymer increases less than 2 ppm allylamine upon storage in a sealed enclosure for 9 months at 25° C.

Embodiment 276. The process or crosslinked poly(allylamine) polymer of any previous enumerated embodiment wherein the allylamine content of the poly(allylamine) polymer increases less than 1 ppm allylamine upon storage in a sealed enclosure for 9 months at 25° C.

Embodiment 277. The process or crosslinked poly(allylamine) polymer of any previous enumerated embodiment wherein the allylamine content of the poly(allylamine) polymer increases less than 500 ppb allylamine upon storage in a sealed enclosure for 9 months at 25° C.

Embodiment 278. The process or crosslinked poly(allylamine) polymer of any previous enumerated embodiment wherein the allylamine content of the poly(allylamine) polymer increases less than 100 ppb allylamine upon storage in a sealed enclosure for 9 months at 25° C.

Embodiment 279. The process or crosslinked poly(allylamine) polymer of any previous enumerated embodiment wherein the allylamine content of the poly(allylamine) polymer increases less than 50 ppb allylamine upon storage in a sealed enclosure for 9 months at 25° C.

Embodiment 280. The process or crosslinked poly(allylamine) polymer of any previous enumerated embodiment wherein the allylamine content of the poly(allylamine) polymer increases less than 1 ppb allylamine upon storage in a sealed enclosure for 9 months at 25° C.

Embodiment 281. The process or crosslinked poly(allylamine) polymer of any previous enumerated embodiment wherein the amount of allylamine, if any, in the poly(allylamine) polymer is less than the detection limit for allylamine upon storage in a sealed enclosure for 9 months at 25° C.

Embodiment 282. The process or crosslinked poly(allylamine) polymer of any previous enumerated embodiment wherein the poly(allylamine) polymer has a stability profile such that upon storage in a sealed enclosure for 12 months at 25° C. after manufacture the allylamine content of the poly(allylamine) polymer increases less than 20 ppm allylamine.

Embodiment 283. The process or crosslinked poly(allylamine) polymer of any previous enumerated embodiment wherein the allylamine content of the poly(allylamine) polymer increases less than 15 ppm allylamine upon storage in a sealed enclosure for 12 months at 25° C.

Embodiment 284. The process or crosslinked poly(allylamine) polymer of any previous enumerated embodiment wherein the allylamine content of the poly(allylamine) polymer increases less than 12.5 ppm allylamine upon storage in a sealed enclosure for 12 months at 25° C.

Embodiment 285. The process or crosslinked poly(allylamine) polymer of any previous enumerated embodiment wherein the allylamine content of the poly(allylamine) polymer increases less than 10 ppm allylamine upon storage in a sealed enclosure for 12 months at 25° C.

Embodiment 286. The process or crosslinked poly(allylamine) polymer of any previous enumerated embodiment wherein the allylamine content of the poly(allylamine) polymer increases less than 7.5 ppm allylamine upon storage in a sealed enclosure for 12 months at 25° C.

Embodiment 287. The process or crosslinked poly(allylamine) polymer of any previous enumerated embodiment wherein the allylamine content of the poly(allylamine) polymer increases less than 5 ppm allylamine upon storage in a sealed enclosure for 12 months at 25° C.

Embodiment 288. The process or crosslinked poly(allylamine) polymer of any previous enumerated embodiment wherein the allylamine content of the poly(allylamine) polymer increases less than 4 ppm allylamine upon storage in a sealed enclosure for 12 months at 25° C.

Embodiment 289. The process or crosslinked poly(allylamine) polymer of any previous enumerated embodiment wherein the allylamine content of the poly(allylamine) polymer increases less than 3 ppm allylamine upon storage in a sealed enclosure for 12 months at 25° C.

Embodiment 290. The process or crosslinked poly(allylamine) polymer of any previous enumerated embodiment wherein the allylamine content of the poly(allylamine) polymer increases less than 2 ppm allylamine upon storage in a sealed enclosure for 12 months at 25° C.

Embodiment 291. The process or crosslinked poly(allylamine) polymer of any previous enumerated embodiment wherein the allylamine content of the poly(allylamine) polymer increases less than 1 ppm allylamine upon storage in a sealed enclosure for 12 months at 25° C.

Embodiment 292. The process or crosslinked poly(allylamine) polymer of any previous enumerated embodiment wherein the allylamine content of the poly(allylamine) polymer increases less than 500 ppb allylamine upon storage in a sealed enclosure for 12 months at 25° C.

Embodiment 293. The process or crosslinked poly(allylamine) polymer of any previous enumerated embodiment wherein the allylamine content of the poly(allylamine) polymer increases less than 100 ppb allylamine upon storage in a sealed enclosure for 12 months at 25° C.

Embodiment 294. The process or crosslinked poly(allylamine) polymer of any previous enumerated embodiment wherein the allylamine content of the poly(allylamine) polymer increases less than 50 ppb allylamine upon storage in a sealed enclosure for 12 months at 25° C.

Embodiment 295. The process or crosslinked poly(allylamine) polymer of any previous enumerated embodiment wherein the allylamine content of the poly(allylamine) polymer increases less than 1 ppb allylamine upon storage in a sealed enclosure for 12 months at 25° C.

Embodiment 296. The process or crosslinked poly(allylamine) polymer of any previous enumerated embodiment wherein the amount of allylamine, if any, in the poly(allylamine) polymer is less than the detection limit for allylamine upon storage in a sealed enclosure for 12 months at 25° C.

Embodiment 297. The process or crosslinked poly(allylamine) polymer of any previous enumerated embodiment wherein the allylamine content may be determined by the Cation IC Extraction Procedure.

Embodiment 298. The process or crosslinked poly(allylamine) polymer of any previous enumerated embodiment wherein the allylamine content is determined using the In-Air Stability Assay (Stability Assay 1).

Embodiment 299. The process or crosslinked poly(allylamine) polymer of any previous enumerated embodiment wherein the allylamine content is determined using the Heated Stability Assay (Stability Assay 2).

Embodiment 300. The process or crosslinked poly(allylamine) polymer of any previous enumerated embodiment wherein the allylamine content is determined using the Stability assessment when packaged in a MylarFoil sachet assay (Stability Assay 3).

Embodiment 301. The process or crosslinked poly(allylamine) polymer of any previous enumerated embodiment wherein the crosslinked poly(allylamine) polymer comprises the residue of a monoallylamine corresponding to Formula 1 or a salt thereof:

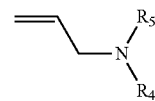

Formula 1 wherein
i) $R_4$ and $R_5$ are independently hydrogen, hydrocarbyl, or substituted hydrocarbyl;
ii) $R_4$ and $R_5$ are independently hydrogen, saturated hydrocarbon, unsaturated aliphatic, aryl, heteroaryl, unsaturated heteroaliphatic, heterocyclic, or heteroalkyl;
iii) $R_4$ and $R_5$ are independently hydrogen, aliphatic, heteroaliphatic, aryl, or heteroaryl;
iv) $R_4$ and $R_5$ are independently hydrogen, alkyl, alkenyl, vinyl, aryl, aminoalkyl, alkanol, haloalkyl, hydroxyalkyl, ethereal, heteroaryl or heterocyclic;
v) $R_4$ and $R_5$ are independently hydrogen, alkyl, aminoalkyl, alkanol, aryl, haloalkyl, hydroxyalkyl, ethereal, or heterocyclic;

vi) $R_4$ and $R_5$ (in combination with the nitrogen atom to which they are attached) together constitute part of a ring structure;

vii) $R_4$ and $R_5$ are independently hydrogen, aliphatic or heteroaliphatic;

viii) $R_4$ and $R_5$ are independently hydrogen, or aminoalkyl; or ix) $R_4$ and $R_5$ are hydrogen.

Embodiment 302. The process or crosslinked poly(allylamine) polymer of any previous enumerated embodiment wherein the crosslinked poly(allylamine) polymer comprises the residue of a multiallylamine corresponding to Formula 3 or a salt thereof:

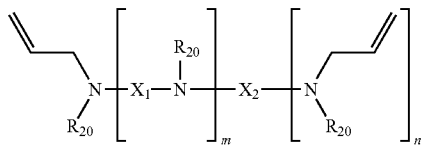

Formula 3 wherein each $R_{20}$ is hydrogen, hydrocarbyl or substituted hydrocarbyl, each $X_1$ is independently hydrocarbyl or substituted hydrocarbyl, $X_2$ is hydrocarbyl or substituted hydrocarbyl, m is a non-negative integer and n is at least 1.

Embodiment 303. The process or crosslinked poly(allylamine) polymer of any previous enumerated embodiment wherein the crosslinked poly(allylamine) polymer comprises the residue of a multiallylamine corresponding to Formula 3 or a salt thereof and each $R_{20}$ is independently hydrogen, aliphatic, aryl, heteroaliphatic, or heteroaryl.

Embodiment 304. The process or crosslinked poly(allylamine) polymer of any previous enumerated embodiment wherein the crosslinked poly(allylamine) polymer comprises the residue of a multiallylamine corresponding to Formula 3 or a salt thereof and each $R_{20}$ is independently hydrogen, aliphatic, or heteroaliphatic.

Embodiment 305. The process or crosslinked poly(allylamine) polymer of any previous enumerated embodiment wherein the crosslinked poly(allylamine) polymer comprises the residue of a multiallylamine corresponding to Formula 3 or a salt thereof and each $R_{20}$ is independently hydrogen, alkyl, allyl, vinyl, or aminoalkyl.

Embodiment 306. The process or crosslinked poly(allylamine) polymer of any previous enumerated embodiment wherein the crosslinked poly(allylamine) polymer comprises the residue of a multiallylamine corresponding to Formula 3 or a salt thereof and each $R_{20}$ is independently hydrogen, alkyl, allyl, vinyl, $-(CH_2)_d NH_2$, or $-(CH_2)_d N[(CH_2)_e NH_2)]_2$ where d and e are independently 2-4.

Embodiment 307. The process or crosslinked poly(allylamine) polymer of any previous enumerated embodiment wherein the crosslinked poly(allylamine) polymer comprises the residue of a multiallylamine corresponding to Formula 3 or a salt thereof and n has a value selected from the group consisting of 1-20, 1-15, 1-10, 1-5, 1-2, and 1.

Embodiment 308. The process or crosslinked poly(allylamine) polymer of any previous enumerated embodiment wherein the crosslinked poly(allylamine) polymer comprises the residue of a multiallylamine corresponding to Formula 3 or a salt thereof and m has a value selected from the group consisting of 0-5, 0-4, 0-3, 0-2, and 0-1.

Embodiment 309. The process or crosslinked poly(allylamine) polymer of any previous enumerated embodiment wherein the crosslinked poly(allylamine) polymer comprises the residue of a multiallylamine corresponding to Formula 3 or a salt thereof and n is 2-4.

Embodiment 310. The process or crosslinked poly(allylamine) polymer of any previous enumerated embodiment wherein the crosslinked poly(allylamine) polymer comprises the residue of a multiallylamine corresponding to Formula 3A or a salt thereof

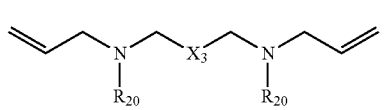

Formula 3A wherein each $R_{20}$ is hydrogen, hydrocarbyl or substituted hydrocarbyl, $X_3$ is $-CH(R_{70})-$ or $-CH_2N(R_{70})CH_2-$, and $R_{70}$ is hydrogen, hydroxyl, or aminoalkyl.

Embodiment 311. The process or crosslinked poly(allylamine) polymer of any previous enumerated embodiment wherein the crosslinked poly(allylamine) polymer comprises the residue of a multiallylamine corresponding to Formula 3A or a salt thereof and each $R_{20}$ is hydrogen, hydrocarbyl or substituted hydrocarbyl, $X_3$ is $-CH(R_{70})-$ or $-CH_2N(R_{70})CH_2-$, and $R_{70}$ is hydrogen, hydroxyl, or aminoalkyl.

Embodiment 312. The process or crosslinked poly(allylamine) polymer of any previous enumerated embodiment wherein the crosslinked poly(allylamine) polymer comprises the residue of a multiallylamine corresponding to Formula 3A or a salt thereof and each $R_{20}$ is independently hydrogen, aliphatic, aryl, heteroaliphatic, or heteroaryl.

Embodiment 313. The process or crosslinked poly(allylamine) polymer of any previous enumerated embodiment wherein the crosslinked poly(allylamine) polymer comprises the residue of a multiallylamine corresponding to Formula 3A or a salt thereof and each $R_{20}$ is independently hydrogen, aliphatic, or heteroaliphatic.

Embodiment 314. The process or crosslinked poly(allylamine) polymer of any previous enumerated embodiment wherein the crosslinked poly(allylamine) polymer comprises the residue of a multiallylamine corresponding to Formula 3A or a salt thereof and each $R_{20}$ is independently hydrogen, alkyl, allyl, vinyl, or aminoalkyl.

Embodiment 315. The process or crosslinked poly(allylamine) polymer of any previous enumerated embodiment wherein the crosslinked poly(allylamine) polymer comprises the residue of a multiallylamine corresponding to Formula 3A or a salt thereof and each $R_{20}$ is independently hydrogen, alkyl, allyl, vinyl, $-(CH_2)_d NH_2$, or $-(CH_2)_d N[(CH_2)_e NH_2)]_2$ where d and e are independently 2-4.

Embodiment 316. The process or crosslinked poly(allylamine) polymer of any previous enumerated embodiment wherein the crosslinked poly(allylamine) polymer comprises the residue of a multiallylamine corresponding to Formula 3A or a salt thereof and $X_3$ is $-CH(R_{70})-$.

Embodiment 317. The process or crosslinked poly(allylamine) polymer of any previous enumerated embodiment wherein the crosslinked poly(allylamine) polymer comprises the residue of a multiallylamine corresponding to Formula 3A or a salt thereof wherein $X_3$ is $-CH(R_{70})-$ and $R_{70}$ is hydrogen or hydroxy.

Embodiment 318. The process or crosslinked poly(allylamine) polymer of any previous enumerated embodiment wherein the crosslinked poly(allylamine) polymer comprises the residue of a multiallylamine corresponding to Formula 3A or a salt thereof wherein $X_3$ is —CH($R_{70}$)— and $R_{70}$ is hydrogen.

Embodiment 319. The process or crosslinked poly(allylamine) polymer of any previous enumerated embodiment wherein the crosslinked poly(allylamine) polymer comprises the residue of a multiallylamine corresponding to Formula 3A or a salt thereof wherein $X_3$ is —CH$_2$N($R_{70}$)CH$_2$—.

Embodiment 320. The process or crosslinked poly(allylamine) polymer of any previous enumerated embodiment wherein the crosslinked poly(allylamine) polymer comprises the residue of a multiallylamine corresponding to Formula 3A or a salt thereof wherein $X_3$ is —CH$_2$N($R_{70}$)CH$_2$— and $R_{70}$ is hydrogen or am inoalkyl.

Embodiment 321A. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof wherein the molar ratio of the residues of the monoallylamine or salt thereof to the residues of the multiallylamine or salt thereof is in the range of 60:40 to 95:5, respectively.

Embodiment 321B. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof wherein the molar ratio of the residues of the monoallylamine or salt thereof to the residues of the multiallylamine or salt thereof is in the range of 60:40 to 90:10, respectively.

Embodiment 321C. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof wherein the molar ratio of the residues of the monoallylamine or salt thereof to the residues of the multiallylamine or salt thereof is in the range of 60:40 to 85:15, respectively.

Embodiment 321D. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof wherein the molar ratio of the residues of the monoallylamine or salt thereof to the residues of the multiallylamine or salt thereof is in the range of 65:35 to 90:10, respectively.

Embodiment 321E. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof and the molar ratio of the monoallylamine or salt thereof to the multiallylamine or salt thereof is in the range of 65:35 to 85:15, respectively.

Embodiment 321F. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof wherein the molar ratio of the residues of the monoallylamine or salt thereof to the residues of the multiallylamine or salt thereof is in the range of 65:35 to 80:20, respectively.

Embodiment 321G. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof and the molar ratio of the monoallylamine or salt thereof to the multiallylamine or salt thereof is in the range of 65:35 to 75:25, respectively.

Embodiment 321H. The process or crosslinked poly(allylamine) polymer of any previous enumerated embodiment wherein the crosslinked poly(allylamine) polymer comprises the residue of (i) a monoallylamine or a salt thereof and (ii) a multiallylamine or a salt thereof and the molar ratio of the monoallylamine or salt thereof to the multiallylamine or salt thereof is 70:30, respectively.

Embodiment 321I. The process or crosslinked poly(allylamine) polymer of any previous enumerated embodiment wherein the residue of the monoallylamine or salt thereof is a residue of a monoallylamine or salt thereof selected from the group consisting of 2-Propen-1-ylamine, 1-(Allylamino)-2-aminoethane, and 1-[N-Allyl(2-aminoethyl)amino]-2-aminoethane, and the salts thereof.

Embodiment 321J. The process or crosslinked poly(allylamine) polymer of any previous enumerated embodiment wherein the residue of the multiallylamine or salt thereof is a residue of a multiallylamine or salt thereof selected from the group consisting of 1,4-Bis(allylamino)butane, 1,2-Bis(allylamino)ethane, 2-(Allylamino)-1-[2-(allylamino)ethylamino]ethane, 1,3-Bis(allylamino)propane, 1,3-Bis(allylamino)-2-propanol, and N,N,N-triallylamine diallylbutyldiamine, and the salts thereof.

Embodiment 321K. The process or crosslinked poly(allylamine) polymer of any previous enumerated embodiment wherein the residue of the monoallylamine is a residue of a monoallylamine salt selected from the group consisting of hydrochloric acid salts, sulfuric acid salts, phosphoric acid salts, hydrobromic acid salts and combinations thereof of the monoallylamine.

Embodiment 321L. The process or crosslinked poly(allylamine) polymer of any previous enumerated embodiment wherein the residue of the multiallylamine is a residue of a multiallylamine salt selected from the group consisting of hydrochloric acid salts, sulfuric acid salts, phosphoric acid salts, hydrobromic acid salts and combinations thereof of the multiallylamine.

Embodiment 321M. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof.

Embodiment 321N. The process or crosslinked poly(allylamine) polymer of any previous enumerated embodiment wherein the crosslinked poly(allylamine) polymer comprises (i) the residue of a monoallylamine selected from the group consisting of 2-Propen-1-ylamine, 1-(Allylamino)-2-aminoethane, and 1-[N-Allyl(2-aminoethyl)amino]-2-aminoethane, and the salts thereof, and (ii) the residue of a multiallylamine selected from the group consisting of 1,4-Bis(allylamino)butane, 1,2-Bis(allylamino)ethane, 2-(Allylamino)-1-[2-(allylamino)ethyl-amino]ethane, 1,3-Bis(allylamino)propane, 1,3-Bis(allylamino)-2-propanol, and N,N,N-triallylamine diallylbutyldiamine, and the salts thereof.

Embodiment 321O. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof.

Embodiment 321P. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof.

Embodiment 321Q. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 60:40 to 90:10, respectively.

Embodiment 321R. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 60:40 to 85:15, respectively.

Embodiment 321S. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 65:35 to 90:10, respectively.

Embodiment 321T. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 65:35 to 85:15, respectively.

Embodiment 321U. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 65:35 to 80:20, respectively.

Embodiment 321V. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio in the range of 65:35 to 75:25, respectively.

Embodiment 321W. The process or crosslinked poly(allylamine) polymer of any previous enumerated embodiment wherein the crosslinked poly(allylamine) polymer comprises the residue of N,N'-diallyl-1,3-diaminopropane or a salt thereof and the residue of 2-Propen-1-ylamine or a salt thereof in a molar ratio of 70:30, respectively.

Embodiment 322A. The process or crosslinked poly(allylamine) polymer of any previous enumerated embodiment wherein the crosslinked poly(allylamine) polymer comprises the residue of styrene, allylamine hydrochloride, substituted allylamine hydrochloride, substituted styrene, alkyl acrylate, substituted alkyl acrylate, alkyl methacrylate, substituted alkyl methacrylate, acrylonitrile, methacrylonitrile, acrylamide, methacrylamide, N-alkylacrylamide, N-alkylmethacrylamide, N,N-dialkylacrylamide, N,N-dialkylmethacrylamide, isoprene, butadiene, ethylene, vinyl acetate, N-vinyl amide, maleic acid derivatives, vinyl ether, allyle, methallyl monomers and combinations thereof.

Embodiment 322B. The process or crosslinked poly(allylamine) polymer of any previous enumerated embodiment wherein the crosslinked poly(allylamine) polymer comprises the residue of 2-propen-1-ylamine, 1-(allylamino)-2-aminoethane, 1-[N-allyl(2-aminoethyl)amino]-2-aminoethane, methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, amethylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N—N-butylmethacrylamide, N-methylolmethacrylamide, N-ethylolmethacrylamide, N-tert-butylacrylamide, N—N-butylacrylamide, N-methylolacrylamide, N-ethylolacrylamide, 4-acryloylmorpholine, vinyl benzoic acid (all isomers), diethylaminostyrene (all isomers), a-methylvinyl benzoic acid (all isomers), diethylamino a-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, N-vinylformamide, N-vinyl acetamide, allylamine, methallylamine, allylalcohol, methyl-vinylether, ethylvinylether, butylvinyltether, butadiene, isoprene, chloroprene, ethylene, vinyl acetate, or a combination thereof.

Embodiment 323. The process or crosslinked poly(allylamine) polymer of any previous enumerated embodiment wherein the crosslinked poly(allylamine) polymer has a structure corresponding to Formula 4:

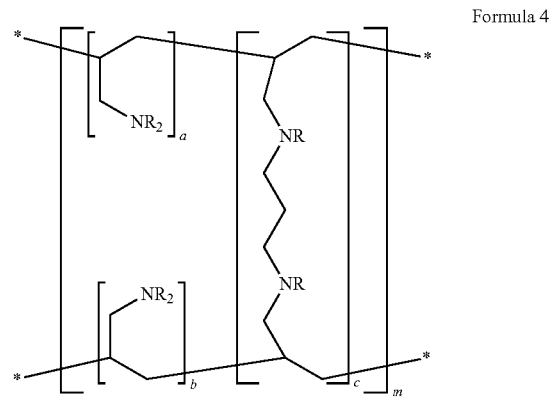

Formula 4 wherein each R is independently hydrogen or an ethylene crosslink between two nitrogen atoms of the crosslinked amine polymer

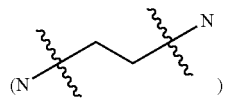

and a, b, c, and m are integers.

Embodiment 324. The process or crosslinked poly(allylamine) polymer of any previous enumerated embodiment wherein the crosslinked poly(allylamine) polymer has a structure corresponding to Formula 4 and m is a large number indicating an extended polymer network.

Embodiment 325. The process or crosslinked poly(allylamine) polymer of any previous enumerated embodiment wherein the crosslinked poly(allylamine) polymer has a structure corresponding to Formula 4 and m is a large number indicating an extended polymer network in which each polymer bead is considered a single molecule.

Embodiment 326A. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 9:1.

Embodiment 326B. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 8:1.

Embodiment 326C. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 7:1.

Embodiment 326D. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 6:1.

Embodiment 326E. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 5:1.

Embodiment 326F. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 4:1.

Embodiment 326G. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 3:1.

Embodiment 326H. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1 to 2:1.

Embodiment 326I. The process or crosslinked poly(allylamine) polymer of any previous enumerated embodiment wherein the crosslinked poly(allylamine) polymer has a structure corresponding to Formula 4 and the sum of a and b to c (i.e., a+b:c) is in the range of about 1:1.

Embodiment 327. The process or crosslinked poly(allylamine) polymer of any previous enumerated embodiment wherein the crosslinked poly(allylamine) polymer has a structure corresponding to Formula 4 and the sum of a and b to c a+b:c) is in the range of about 1.5:1 to 4:1.

Embodiment 328. The process or crosslinked poly(allylamine) polymer of any previous enumerated embodiment wherein the crosslinked poly(allylamine) polymer has a structure corresponding to Formula 4 and the sum of a and b to c a+b:c) is in the range of about 1.75:1 to 3:1.

Embodiment 329. The process or crosslinked poly(allylamine) polymer of any previous enumerated embodiment wherein the crosslinked poly(allylamine) polymer has a structure corresponding to Formula 4 and the sum of a and b to c a+b:c) is in the range of about 2:1 to 2.5:1.

Embodiment 330. The process or crosslinked poly(allylamine) polymer of any previous enumerated embodiment wherein the crosslinked poly(allylamine) polymer has a structure corresponding to Formula 4 and the sum of a and b is 57 and c is 24.

Embodiment 331. The process or crosslinked poly(allylamine) polymer of any previous enumerated embodiment wherein the crosslinked poly(allylamine) polymer has a structure corresponding to Formula 4 wherein 50-95% of the R substituents are hydrogen and 5-50% are an ethylene crosslink between two nitrogens of the crosslinked amine polymer.

Embodiment 332. The process or crosslinked poly(allylamine) polymer of any previous enumerated embodiment wherein the crosslinked poly(allylamine) polymer has a structure corresponding to Formula 4 wherein 55-90% of the R substituents are hydrogen and 10-45% are an ethylene crosslink between two nitrogens of the crosslinked amine polymer.

Embodiment 333. The process or crosslinked poly(allylamine) polymer of any previous enumerated embodiment wherein the crosslinked poly(allylamine) polymer has a structure corresponding to Formula 4 wherein 60-90% of the R substituents are hydrogen and 10-40% are an ethylene crosslink between two nitrogens of the crosslinked amine polymer.

Embodiment 334. The process or crosslinked poly(allylamine) polymer of any previous enumerated embodiment wherein the crosslinked poly(allylamine) polymer has a structure corresponding to Formula 4 wherein 65-90% of the R substituents are hydrogen and 10-35% are an ethylene crosslink between two nitrogens of the crosslinked amine polymer.

Embodiment 335. The process or crosslinked poly(allylamine) polymer of any previous enumerated embodiment wherein the crosslinked poly(allylamine) polymer has a structure corresponding to Formula 4 wherein 70-90% of the R substituents are hydrogen and 10-30% are an ethylene crosslink between two nitrogens of the crosslinked amine polymer.

Embodiment 336. The process or crosslinked poly(allylamine) polymer of any previous enumerated embodiment wherein the crosslinked poly(allylamine) polymer has a structure corresponding to Formula 4 wherein 75-85% of the R substituents are hydrogen and 15-25% are an ethylene crosslink between two nitrogens of the crosslinked amine polymer.

Embodiment 337. The process or crosslinked poly(allylamine) polymer of any previous enumerated embodiment wherein the crosslinked poly(allylamine) polymer has a structure corresponding to Formula 4 wherein 80-85% of the R substituents are hydrogen and 15-20% are an ethylene crosslink between two nitrogens of the crosslinked amine polymer.

Embodiment 338A. The process or crosslinked poly(allylamine) polymer of any previous enumerated embodiment wherein the crosslinked poly(allylamine) polymer has a structure corresponding to Formula 4 wherein about 81% of the R substituents are hydrogen and about 19% are an ethylene crosslink.

Embodiment 338B. The process or crosslinked poly(allylamine) polymer of any previous enumerated embodiment wherein the crosslinked poly(allylamine) polymer comprises the residue of a crosslinker containing at least two amine-reactive groups selected from the group consisting of halides, epoxides, phosgene, anhydrides, carbamates, carbonates, isocyanates, thioisocyanates, esters, activated esters, carboxylic acids and derivatives thereof, sulfonates and derivatives thereof, acyl halides, aziridines, α,β-unsaturated carbonyls, ketones, aldehydes, and pentafluoroaryl groups. Exemplary crosslinking agents that may be used in such post-polymerization crosslinking reactions further include, but are not limited to, one or more multifunctional crosslinking agents such as: dihaloalkanes, haloalkyloxiranes, alkyloxirane sulfonates, di(haloalkyl)amines, tri(haloalkyl)amines, diepoxides, triepoxides, tetraepoxides, bis(halomethyl)benzenes, tri(halomethyl)benzenes, tetra(halomethyl)benzenes, epihalohydrins such as epichlorohydrin and epibromohydrin poly(epichlorohydrin), (iodomethyl)oxirane, glycidyl tosylate, glycidyl 3-nitrobenzenesulfonate, 4-tosyloxy-1,2-epoxybutane, bromo-1,2-epoxybutane, 1,2-dibromoethane, 1,3-dichloropropane, 1,2-dichloroethane, 1-bromo-2-chloroethane, 1,3-dibromopropane, bis(2-chloroethyl)amine, tris(2-chloroethyl)amine, and bis(2-chloroethyl)methylamine, 1,3-butadiene diepoxide, 1,5-hexadiene diepoxide, diglycidyl ether, 1,2,7,8-diepoxyoctane, 1,2,9,10-diepoxydecane, ethylene glycol diglycidyl ether, propylene glycol diglycidyl ether, 1,4-butanediol diglycidyl ether, 1,2 ethanedioldiglycidyl ether, glycerol diglycidyl ether, 1,3-diglycidyl glyceryl ether, N,N-diglycidylaniline, neopentyl glycol diglycidyl ether, diethylene glycol diglycidyl ether, 1,4-bis(glycidyloxy)benzene, resorcinol digylcidyl ether, 1,6-hexanediol diglycidyl ether, trimethylolpropane diglycidyl ether, 1,4-cyclohexanedimethanol diglycidyl ether, 1,3-bis-(2,3-epoxypropyloxy)-2-(2,3-dihydroxypropyloxy)propane, 1,2-cyclohexanedicarboxylic acid diglycidyl ester, 2,2'-bis(glycidyloxy)diphenylmethane, bisphenol F diglycidyl ether, 1,4-bis(2',3'epoxypropyl)perfluoro-n-butane, 2,6-di(oxiran-2-ylmethyl)-1,2,3,5,6,7-hexahydropyrrolo[3,4-f]isoindol-1,3,5,7-tetraone, bisphenol A diglycidyl ether, ethyl 5-hydroxy-6,8-di(oxiran-2-ylmethyl)-4-oxo-4-h-chromene-2-carboxylate, bis[4-(2,3-epoxy-propylthio)phenyl]-sulfide, 1,3-bis(3-glycidoxypropyl)tetramethyldisiloxane, 9,9-bis[4-(glycidyloxy)phenyl]fluorine, triepoxyisocyanurate, glycerol triglycidyl ether, N,N-diglycidyl-4-glycidyloxyaniline, isocyanuric acid (S,S,S)-triglycidyl ester, isocyanuric acid (R,R,R)-triglycidyl ester, triglycidyl isocyanurate, trimethylolpropane triglycidyl ether, glycerol propoxylate triglycidyl ether, triphenylolmethane triglycidyl ether, 3,7,14-tris[[3-(epoxypropoxy)propyl]dimethylsilyloxy]-1,3,5,7,9,11,14-heptacyclopentyltricyclo[7,3,3,15,11]heptasiloxane, 4,4'methylenebis(N, N-diglycidylaniline), bis(halomethyl)benzene, bis(halomethyl)biphenyl and bis(halomethyl)naphthalene, toluene diisocyanate, acrylol chloride, methyl acrylate, ethylene bisacrylamide, pyrometallic dianhydride, succinyl dichloride, dimethylsuccinate, 3-chloro-1-(3-chloropropylamino-2-propanol, 1,2-bis(3-chloropropylamino)ethane, Bis(3-chloropropyl)amine, 1,3-Dichloro-2-propanol, 1,3-Dichloropropane, 1-chloro-2,3-epoxypropane, and tris[(2-oxiranyl)methyl]amine.

Embodiment 338C. The process or crosslinked poly(allylamine) polymer of any previous enumerated embodiment wherein the crosslinked poly(allylamine) polymer comprises the residue of a crosslinker containing at least two amine-reactive groups selected from the group consisting of halides.

Embodiment 338D. The process or crosslinked poly(allylamine) polymer of any previous enumerated embodiment wherein the crosslinked poly(allylamine) polymer comprises the residue of a dihaloalkane.

Embodiment 338E. The process or crosslinked poly(allylamine) polymer of any previous enumerated embodiment wherein the crosslinked poly(allylamine) polymer comprises the residue of 1,2-dibromoethane, 1,2-dichloroethane, 1-bromo-2-chloroethane, 1,3-dichloropropane, 1,3-dibromopropane, and 1-bromo-3-chloropropane.

Embodiment 338F. The process or crosslinked poly(allylamine) polymer of any previous enumerated embodiment wherein the crosslinked poly(allylamine) polymer comprises 10-35 mol % of the residue of a crosslinker selected from the group consisting of 1,2-dibromoethane, 1,2-dichloroethane, 1-bromo-2-chloroethane, 1,3-dichloropropane, 1,3-dibromopropane, 1-bromo-3-chloropropane and combinations thereof.

Embodiment 338G. The process or crosslinked poly(allylamine) polymer of any previous enumerated embodiment wherein the crosslinked poly(allylamine) polymer comprises 15-35 mol % of the residue of a crosslinker selected from the group consisting of 1,2-dibromoethane, 1,2-dichloroethane, 1-bromo-2-chloroethane, 1,3-dichloropropane, 1,3-dibromopropane, 1-bromo-3-chloropropane and combinations thereof.

Embodiment 338H. The process or crosslinked poly(allylamine) polymer of any previous enumerated embodiment wherein the crosslinked poly(allylamine) polymer comprises 10-30 mol % of the residue of a crosslinker selected from the group consisting of 1,2-dibromoethane, 1,2-dichloroethane, 1-bromo-2-chloroethane, 1,3-dichloropropane, 1,3-dibromopropane, 1-bromo-3-chloropropane and combinations thereof.

Embodiment 338I. The process or crosslinked poly(allylamine) polymer of any previous enumerated embodiment wherein the crosslinked poly(allylamine) polymer comprises 15-30 mol % of the residue of a crosslinker selected from the group consisting of 1,2-dibromoethane, 1,2-dichloroethane, 1-bromo-2-chloroethane, 1,3-dichloropropane, 1,3-dibromopropane, 1-bromo-3-chloropropane and combinations thereof.

Embodiment 338J. The process or crosslinked poly(allylamine) polymer of any previous enumerated embodiment wherein the crosslinked poly(allylamine) polymer comprises 20-25 mol % of the residue of a crosslinker selected from the group consisting of 1,2-dibromoethane, 1,2-dichloroethane, 1-bromo-2-chloroethane, 1,3-dichloropropane, 1,3-dibromopropane, 1-bromo-3-chloropropane and combinations thereof.

Embodiment 339A. The process or crosslinked poly(allylamine) polymer of any previous enumerated embodiment wherein the crosslinked poly(allylamine) polymer comprises (i) the residue of a monoallylamine or a salt thereof and (ii) the residue of a multiallylamine or a salt thereof in a mole ratio of about 1:1 to about 9:1, respectively.

Embodiment 339B. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 9:1, respectively.

Embodiment 339C. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 8:1, respectively.

Embodiment 339D. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 7:1, respectively.

Embodiment 339E. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 6:1, respectively.

Embodiment 339F. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 5:1, respectively.

Embodiment 339G. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 4:1, respectively.

Embodiment 339H. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 3:1, respectively.

Embodiment 339I. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is less than 2:1, respectively.

Embodiment 339J. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 1:1, respectively.

Embodiment 339K. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 2:1, respectively.

Embodiment 339L. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 3:1, respectively.

Embodiment 339M. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 4:1, respectively.

Embodiment 339N. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 5:1, respectively.

Embodiment 339O. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 6:1, respectively.

Embodiment 339P. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 7:1, respectively.

Embodiment 339Q. The process or crosslinked poly(allylamine) polymer of any previous enumerated embodiment wherein the mole ratio of (i) the residue of a monoallylamine or a salt thereof to (ii) the residue of a multiallylamine or a salt thereof in the crosslinked poly(allylamine) polymer is at least 8:1, respectively.

Embodiment 339R. The process or crosslinked poly(allylamine) polymer of any previous enumerated embodiment wherein (i) the multiallylamine or salt thereof is N,N'-diallyl-1,3-diaminopropane or a salt thereof, (ii) the monoallylamine or salt thereof is 2-Propen-1-ylamine or a salt thereof and (iii) the crosslinked poly(allylamine) polymer contains the residue of N,N'-diallyl-1,3-diaminopropane or a salt thereof and the residue of monoallylamine is 2-Propen-1-ylamine or a salt thereof.

Embodiment 339S. The process or crosslinked poly(allylamine) polymer of any previous enumerated embodiment wherein (i) the multiallylamine or salt thereof is N,N'-diallyl-1,3-diaminopropane or a salt thereof, (ii) the monoallylamine or salt thereof is 2-Propen-1-ylamine or a salt thereof, (iii) the crosslinking agent is 1,2-dichloroethane and (iv) the crosslinked poly(allylamine) polymer contains the residue of N,N'-diallyl-1,3-diaminopropane or a salt thereof, the residue of 2-Propen-1-ylamine or a salt thereof, and the residue of 1,2-dichloroethane.

Embodiment 339T. The process or crosslinked poly(allylamine) polymer of any previous enumerated embodiment wherein (a) the multiallylamine or salt thereof is N,N'-diallyl-1,3-diaminopropane or a salt thereof, (b) the monoallylamine or salt thereof is 2-Propen-1-ylamine or a salt thereof, (c) the crosslinking agent is 1,2-dichloroethane and (d) the crosslinked poly(allylamine) polymer comprises (i) 10-35 mol % residue of N,N'-diallyl-1,3-diaminopropane or a salt thereof, (ii) 30-80 mol % residue of 2-Propen-1-ylamine or a salt thereof, and (iii) 10-35 mol % residue of 1,2-dichloroethane.

Embodiment 339U. The process or crosslinked poly(allylamine) polymer of any previous enumerated embodiment wherein (a) the multiallylamine or salt thereof is N,N'-diallyl-1,3-diaminopropane or a salt thereof, (b) the monoallylamine or salt thereof is 2-Propen-1-ylamine or a salt thereof, (c) the crosslinking agent is 1,2-dichloroethane and (d) the crosslinked poly(allylamine) polymer comprises (i)

15-30 mol % residue of N,N'-diallyl-1,3-diaminopropane or a salt thereof, (ii) 40-70 mol % residue of 2-Propen-1-ylamine or a salt thereof, and (iii) 15-30 mol % residue of 1,2-dichloroethane.

Embodiment 339V. The process or crosslinked poly(allylamine) polymer of any previous enumerated embodiment wherein (a) the multiallylamine or salt thereof is N,N'-diallyl-1,3-diaminopropane or a salt thereof, (b) the monoallylamine or salt thereof is 2-Propen-1-ylamine or a salt thereof, (c) the crosslinking agent is 1,2-dichloroethane and (d) the crosslinked poly(allylamine) polymer comprises (i) 20-25 mol % residue of N,N'-diallyl-1,3-diaminopropane or a salt thereof, (ii) 50-60 mol % residue of 2-Propen-1-ylamine or a salt thereof, and (iii) 20-25 mol % residue of 1,2-dichloroethane.

Embodiment 339W. The process or crosslinked poly(allylamine) polymer of any previous enumerated embodiment wherein the crosslinked poly(allylamine) polymer comprises the residue of N,N'-diallyl-1,3-diaminopropane or a salt thereof, the residue of 2-Propen-1-ylamine or a salt thereof, and the residue of 1,2-dichloroethane.

Embodiment 340. The process or crosslinked poly(allylamine) polymer of any previous enumerated embodiment wherein the crosslinked poly(allylamine) polymer is 1,3-Propanediamine, $N^1,N^3$-di-2-propen-1-yl-, polymer with 1,2-dichloroethane and 2-propen-1-amine.

Embodiment 341. The process or crosslinked poly(allylamine) polymer of any previous enumerated embodiment wherein the crosslinked poly(allylamine) polymer is characterized by a chloride ion binding capacity of at least 1 mEq/g in a Simulated Small Intestine Inorganic ("SIB") assay.

Embodiment 342. The process or crosslinked poly(allylamine) polymer of any previous enumerated embodiment wherein the crosslinked poly(allylamine) polymer is characterized by a chloride ion binding capacity of at least of at least 1.5 mEq/g in a SIB assay.

Embodiment 343. The process or crosslinked poly(allylamine) polymer of any previous enumerated embodiment wherein the crosslinked poly(allylamine) polymer is characterized by a chloride ion binding capacity of at least at least 2 mEq/g in a SIB assay.

Embodiment 344. The process or crosslinked poly(allylamine) polymer of any previous enumerated embodiment wherein the crosslinked poly(allylamine) polymer is characterized by a chloride ion binding capacity of at least 2.5 mEq/g in a SIB assay.

Embodiment 345. The process or crosslinked poly(allylamine) polymer of any previous enumerated embodiment wherein the crosslinked poly(allylamine) polymer is characterized by a chloride ion binding capacity of at least 3 mEq/g in a SIB assay.

Embodiment 346. The process or crosslinked poly(allylamine) polymer of any previous enumerated embodiment wherein the crosslinked poly(allylamine) polymer is characterized by a chloride ion binding capacity of at least 3.5 mEq/g in a SIB assay.

Embodiment 347. The process or crosslinked poly(allylamine) polymer of any previous enumerated embodiment wherein the crosslinked poly(allylamine) polymer is characterized by a chloride ion binding capacity of at least 4 mEq/g in a SIB assay.

Embodiment 348. The process or crosslinked poly(allylamine) polymer of any previous enumerated embodiment wherein the crosslinked poly(allylamine) polymer is characterized by a chloride ion binding capacity of at least 4.5 mEq/g in a SIB assay.

Embodiment 349. The process or crosslinked poly(allylamine) polymer of any previous enumerated embodiment wherein the crosslinked poly(allylamine) polymer is characterized by a chloride ion binding capacity of at least 5 mEq/g in a SIB assay.

Embodiment 350. The process or crosslinked poly(allylamine) polymer of any previous enumerated embodiment wherein the crosslinked poly(allylamine) polymer is characterized by a chloride ion binding capacity of at least 5.5 mEq/g in a SIB assay.

Embodiment 351. The process or crosslinked poly(allylamine) polymer of any previous enumerated embodiment wherein the crosslinked poly(allylamine) polymer is characterized by a chloride ion binding capacity of at least 6 mEq/g in a SIB assay.

Embodiment 352. The process or crosslinked poly(allylamine) polymer of any previous enumerated embodiment wherein the crosslinked poly(allylamine) polymer is characterized by a chloride ion to phosphate ion binding ratio in a SIB assay of at least 0.1:1, respectively.

Embodiment 353. The process or crosslinked poly(allylamine) polymer of any previous enumerated embodiment wherein the crosslinked poly(allylamine) polymer is characterized by a chloride ion to phosphate ion binding ratio in a SIB assay of at least 0.2:1, respectively.

Embodiment 354. The process or crosslinked poly(allylamine) polymer of any previous enumerated embodiment wherein the crosslinked poly(allylamine) polymer is characterized by a chloride ion to phosphate ion binding ratio in a SIB assay of at least 0.25:1, respectively.

Embodiment 355. The process or crosslinked poly(allylamine) polymer of any previous enumerated embodiment wherein the crosslinked poly(allylamine) polymer is characterized by a chloride ion to phosphate ion binding ratio in a SIB assay of at least 0.3:1, respectively.

Embodiment 356. The process or crosslinked poly(allylamine) polymer of any previous enumerated embodiment wherein the crosslinked poly(allylamine) polymer is characterized by a chloride ion to phosphate ion binding ratio in a SIB assay of at least 0.35:1, respectively.

Embodiment 357. The process or crosslinked poly(allylamine) polymer of any previous enumerated embodiment wherein the crosslinked poly(allylamine) polymer is characterized by a chloride ion to phosphate ion binding ratio in a SIB assay of at least 0.4:1, respectively.

Embodiment 358. The process or crosslinked poly(allylamine) polymer of any previous enumerated embodiment wherein the crosslinked poly(allylamine) polymer is characterized by a chloride ion to phosphate ion binding ratio in a SIB assay of at least 0.45:1, respectively.

Embodiment 359. The process or crosslinked poly(allylamine) polymer of any previous enumerated embodiment wherein the crosslinked poly(allylamine) polymer is characterized by a chloride ion to phosphate ion binding ratio in a SIB assay of at least 0.5:1, respectively.

Embodiment 360. The process or crosslinked poly(allylamine) polymer of any previous enumerated embodiment wherein the crosslinked poly(allylamine) polymer is characterized by a chloride ion to phosphate ion binding ratio in a SIB assay of at least 2:3, respectively.

Embodiment 361. The process or crosslinked poly(allylamine) polymer of any previous enumerated embodiment wherein the crosslinked poly(allylamine) polymer is characterized by a chloride ion to phosphate ion binding ratio in a SIB assay of at least 0.75:1, respectively.

Embodiment 362. The process or crosslinked poly(allylamine) polymer of any previous enumerated embodiment wherein the crosslinked poly(allylamine) polymer is characterized by a chloride ion to phosphate ion binding ratio in a SIB assay of at least 0.9:1, respectively.

Embodiment 363. The process or crosslinked poly(allylamine) polymer of any previous enumerated embodiment wherein the crosslinked poly(allylamine) polymer is characterized by a chloride ion to phosphate ion binding ratio in a SIB assay of at least 1:1, respectively.

Embodiment 364. The process or crosslinked poly(allylamine) polymer of any previous enumerated embodiment wherein the crosslinked poly(allylamine) polymer is characterized by a chloride ion to phosphate ion binding ratio in a SIB assay of at least 1.25:1, respectively.

Embodiment 365. The process or crosslinked poly(allylamine) polymer of any previous enumerated embodiment wherein the crosslinked poly(allylamine) polymer is characterized by a chloride ion to phosphate ion binding ratio in a SIB assay of at least 1.5:1, respectively.

Embodiment 366. The process or crosslinked poly(allylamine) polymer of any previous enumerated embodiment wherein the crosslinked poly(allylamine) polymer is characterized by a chloride ion to phosphate ion binding ratio in a SIB assay of at least 1.75:1, respectively.

Embodiment 367. The process or crosslinked poly(allylamine) polymer of any previous enumerated embodiment wherein the crosslinked poly(allylamine) polymer is characterized by a chloride ion to phosphate ion binding ratio in a SIB assay of at least 2:1, respectively.

Embodiment 368. The process or crosslinked poly(allylamine) polymer of any previous enumerated embodiment wherein the crosslinked poly(allylamine) polymer is characterized by a chloride ion to phosphate ion binding ratio in a SIB assay of at least 2.25:1, respectively.

Embodiment 369. The process or crosslinked poly(allylamine) polymer of any previous enumerated embodiment wherein the crosslinked poly(allylamine) polymer is characterized by a chloride ion to phosphate ion binding ratio in a SIB assay of at least 2.5:1, respectively.

Embodiment 370. The process or crosslinked poly(allylamine) polymer of any previous enumerated embodiment wherein the crosslinked poly(allylamine) polymer is characterized by a chloride ion to phosphate ion binding ratio in a SIB assay of at least 2.75:1, respectively.

Embodiment 371. The process or crosslinked poly(allylamine) polymer of any previous enumerated embodiment wherein the crosslinked poly(allylamine) polymer is characterized by a chloride ion to phosphate ion binding ratio in a SIB assay of at least 3:1, respectively.

Embodiment 372. The process or crosslinked poly(allylamine) polymer of any previous enumerated embodiment wherein the ratio of the amount of bound chloride to bound phosphate in a SIB assay is at least 4:1, respectively.

Embodiment 373. The process or crosslinked poly(allylamine) polymer of any previous enumerated embodiment wherein the crosslinked poly(allylamine) polymer is characterized by a chloride ion to phosphate ion binding ratio in a SIB assay of at least 5:1, respectively.

Embodiment 374. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 1 mEq/g in a SGF assay.

Embodiment 375. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 2 mEq/g in a SGF assay.

Embodiment 376. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 3 mEq/g in a SGF assay.

Embodiment 377. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 4 mEq/g in a SGF assay.

Embodiment 378. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 5 mEq/g in a SGF assay.

Embodiment 379. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 6 mEq/g in a SGF assay.

Embodiment 380. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 7 mEq/g in a SGF assay.

Embodiment 381. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 8 mEq/g in a SGF assay.

Embodiment 382. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 9 mEq/g in a SGF assay.

Embodiment 383. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 10 mEq/g in a SGF assay.

Embodiment 384. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 11 mEq/g in a SGF assay.

Embodiment 385. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 12 mEq/g in a SGF assay.

Embodiment 386. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 13 mEq/g in a SGF assay.

Embodiment 387. The process or crosslinked poly(allylamine) polymer of any previous enumerated embodiment wherein the crosslinked poly(allylamine) polymer is characterized by a proton-binding capacity and a chloride binding capacity in Simulated Gastric Fluid of at least 14 mEq/g in a SGF assay.

Embodiment 388. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 50% of the proton-binding capacity and the chloride binding capacity, respectively, of the crosslinked poly(allylamine) polymer at 24 hours in SGF.

Embodiment 389. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 60% of the proton-binding capacity and the chloride binding capacity, respectively, of the crosslinked poly(allylamine) polymer at 24 hours in SGF.

Embodiment 390. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 70% of the proton-binding capacity and the chloride binding capacity, respectively, of the crosslinked poly(allylamine) polymer at 24 hours in SGF.

Embodiment 391. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 60% of the proton-binding capacity and the chloride binding capacity, respectively, of the crosslinked poly(allylamine) polymer at 24 hours in SGF.

Embodiment 392. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 70% of the proton-binding capacity and the chloride binding capacity, respectively, of the crosslinked poly(allylamine) polymer at 24 hours in SGF.

Embodiment 393. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 80% of the proton-binding capacity and the chloride binding capacity, respectively, of the crosslinked poly(allylamine) polymer at 24 hours in SGF.

Embodiment 394. The process or crosslinked poly(allylamine) polymer of any previous enumerated embodiment wherein the crosslinked poly(allylamine) polymer is characterized by a proton-binding capacity and a chloride binding capacity after 1 hour in SGF that is at least 90% of the proton-binding capacity and the chloride binding capacity, respectively, of the crosslinked poly(allylamine) polymer at 24 hours in SGF.

Embodiment 395. A process or crosslinked poly(allylamine) polymer of any previous enumerated embodiment wherein the crosslinked poly(allylamine) polymer comprises the residues of 1,3-Bis(allylamino)propane, 2-Propen-1-ylamine and 1,2-dichloroethane.

Embodiment 396. A process or crosslinked poly(allylamine) polymer of any previous enumerated embodiment wherein the crosslinked poly(allylamine) polymer is a 1,3-Propanediamine,N1,N3-di-2-propen-1-yl-, polymer with 1,2-dichloroethane and 2-propen-1-amine.

Embodiment 397. A process or crosslinked poly(allylamine) polymer of any previous enumerated embodiment wherein the crosslinked poly(allylamine) polymer is an extended polymer network having the molecular formula $(C_9H_{18}N_2 \cdot C_3H_7N\ C_2H_4Cl_2)_x$.

Embodiment 398. A pharmaceutical composition comprising a crosslinked poly(allylamine) polymer of any of the enumerated embodiments.

Embodiment 399. A pharmaceutical product comprising a crosslinked poly(allylamine) polymer of any of the enumerated embodiments in a sealed container.

Embodiment 400. A pharmaceutical product comprising a crosslinked poly(allylamine) polymer of any of the enumerated embodiments in a sealed container comprising a moisture barrier.

Embodiment 401. A pharmaceutical product comprising a crosslinked poly(allylamine) polymer of any of the enumerated embodiments in a sealed container comprising an oxygen barrier.

Embodiment 402. A pharmaceutical product comprising a crosslinked poly(allylamine) polymer of any of the enumerated embodiments in a sealed container comprising a moisture barrier and an oxygen barrier.

Embodiment 403. A pharmaceutical product comprising a crosslinked poly(allylamine) polymer of any of the enumerated embodiments in a sealed sachet.

Embodiment 404. A pharmaceutical product comprising a crosslinked poly(allylamine) polymer of any of the enumerated embodiments in a sealed container comprising a polymer, metal, glass or ceramic material.

Embodiment 405. A pharmaceutical product comprising a sealed container containing a crosslinked poly(allylamine) polymer of any of the enumerated embodiments and an inert atmosphere.

Embodiment 406. A pharmaceutical product comprising a sealed container and a crosslinked poly(allylamine) polymer of any of the enumerated embodiments within the sealed container, the sealed container comprising a multi-layer laminate of an inner contact layer, an outer layer; and a barrier layer disposed between the contact layer and outer layer.

Embodiment 407. A pharmaceutical product comprising a sealed container and a crosslinked poly(allylamine) polymer of any of the enumerated embodiments within the sealed container, the sealed container comprising a multi-layer laminate of an inner contact layer, an outer layer; and an oxygen-barrier layer disposed between the contact layer and outer layer.

Embodiment 408. A pharmaceutical product comprising a sealed container and a crosslinked poly(allylamine) polymer of any of the enumerated embodiments within the sealed container, the sealed container comprising a multi-layer laminate of an inner contact layer, an outer layer; and a moisture-barrier layer disposed between the contact layer and outer layer.

Embodiment 409. A pharmaceutical product comprising a sealed container and a crosslinked poly(allylamine) polymer of any of the enumerated embodiments within the sealed container, the sealed container comprising a multi-layer laminate of an inner contact layer, an outer layer; and an oxygen-barrier layer and a moisture-barrier layer disposed between the contact layer and outer layer.

Embodiment 410. A pharmaceutical product comprising a sealed container and a crosslinked poly(allylamine) polymer of any of the enumerated embodiments within the sealed container, the sealed container comprising a multi-layer laminate of an inner contact layer, an outer layer; and an oxygen-scavenging layer disposed between the contact layer and the outer layer.

Embodiment 411. A composition for use in a method of treating an acid base disorder in a human patient, the composition comprising a crosslinked poly(allylamine) polymer of any of the enumerated embodiments.

Embodiment 412. A composition for use in a method of treating an acid base disorder in a human patient by increasing that patient's serum bicarbonate value by at least 1 mEq/L over 15 days of treatment, said composition comprising a crosslinked poly(allylamine) polymer of any of the enumerated embodiments.

Embodiment 413. The composition for use in a method of treating an acid base disorder of any previous enumerated embodiment wherein the acid base disorder is metabolic acidosis.

Embodiment 414. A method of treating an acid/base disorder in an animal by oral administration of a pharmaceutical composition comprising a crosslinked poly(allylamine) polymer of any of the enumerated embodiments.

Embodiment 415. A method of treating an individual afflicted with an acid-base disorder characterized by a baseline serum bicarbonate value of less than 22 mEq/l, the method comprising oral administration of a daily dose of a pharmaceutical composition comprising a crosslinked poly(allylamine) polymer of any of the enumerated embodiments and having the capacity to bind at least 5 mEq of a target species as it transits the digestive system to achieve a clinically significant increase in the serum bicarbonate value of at least 1 mEq/l from baseline within a treatment period not greater than 1 month, the target species being selected from the group consisting of protons, strong acids, and conjugate bases of strong acids.

Embodiment 416. The composition for use in a method of treating an acid base disorder or method of treatment of any previous enumerated embodiment wherein the acid-base disorder is characterized by a baseline serum bicarbonate value of less than 21 mEq/l.

Embodiment 417. The composition for use in a method of treating an acid base disorder or method of treatment of any previous enumerated embodiment wherein the acid-base disorder is characterized by a baseline serum bicarbonate value of less than 20 mEq/l.

Embodiment 418. The composition for use in a method of treating an acid base disorder or method of treatment of any previous enumerated embodiment wherein the acid-base disorder is characterized by a baseline serum bicarbonate value of less than 19 mEq/l.

Embodiment 419. The composition for use in a method of treating an acid base disorder or method of treatment of any previous enumerated embodiment wherein the acid-base disorder is characterized by a baseline serum bicarbonate value of less than 18 mEq/l.

Embodiment 420. The composition for use in a method of treating an acid base disorder or method of treatment of any previous enumerated embodiment wherein the acid-base disorder is characterized by a baseline serum bicarbonate value of less than 17 mEq/l.

Embodiment 421. The composition for use in a method of treating an acid base disorder or method of treatment of any previous enumerated embodiment wherein the acid-base disorder is characterized by a baseline serum bicarbonate value of less than 16 mEq/l.

Embodiment 422. The composition for use in a method of treating an acid base disorder or method of treatment of any previous enumerated embodiment wherein the acid-base disorder is characterized by a baseline serum bicarbonate value of less than 15 mEq/l.

Embodiment 423. The composition for use in a method of treating an acid base disorder or method of treatment of any previous enumerated embodiment wherein the acid-base disorder is characterized by a baseline serum bicarbonate value of less than 14 mEq/l.

Embodiment 424. The composition for use in a method of treating an acid base disorder or method of treatment of any previous enumerated embodiment wherein the acid-base disorder is characterized by a baseline serum bicarbonate value of less than 13 mEq/l.

Embodiment 425. The composition for use in a method of treating an acid base disorder or method of treatment of any previous enumerated embodiment wherein the acid-base disorder is characterized by a baseline serum bicarbonate value of less than 12 mEq/l.

Embodiment 426. The method of treatment of any previous enumerated embodiment wherein the acid-base disorder is characterized by a baseline serum bicarbonate value of less than 11 mEq/l.

Embodiment 427. The method of treatment of any previous enumerated embodiment wherein the acid-base disorder is characterized by a baseline serum bicarbonate value of less than 10 mEq/l.

Embodiment 428. The composition for use in a method of treating an acid base disorder or method of treatment of any previous enumerated embodiment wherein the acid-base disorder is characterized by a baseline serum bicarbonate value of at least 9 mEq/l.

Embodiment 429. The composition for use in a method of treating an acid base disorder or method of treatment of any previous enumerated embodiment wherein the acid-base disorder is characterized by a baseline serum bicarbonate value of at least 10 mEq/l.

Embodiment 430. The composition for use in a method of treating an acid base disorder or method of treatment of any previous enumerated embodiment wherein the acid-base disorder is characterized by a baseline serum bicarbonate value of at least 11 mEq/l.

Embodiment 431. The composition for use in a method of treating an acid base disorder or method of treatment of any previous enumerated embodiment wherein the acid-base disorder is characterized by a baseline serum bicarbonate value of at least 12 mEq/l.

Embodiment 432. The composition for use in a method of treating an acid base disorder or method of treatment of any previous enumerated embodiment wherein the acid-base disorder is characterized by a baseline serum bicarbonate value of at least 13 mEq/l.

Embodiment 433. The composition for use in a method of treating an acid base disorder or method of treatment of any previous enumerated embodiment wherein the acid-base disorder is characterized by a baseline serum bicarbonate value of at least 14 mEq/l.

Embodiment 434. The composition for use in a method of treating an acid base disorder or method of treatment of any previous enumerated embodiment wherein the acid-base disorder is characterized by a baseline serum bicarbonate value of at least 15 mEq/l.

Embodiment 435. The composition for use in a method of treating an acid base disorder or method of treatment of any previous enumerated embodiment wherein the acid-base disorder is characterized by a baseline serum bicarbonate value of at least 16 mEq/l.

Embodiment 436. The composition for use in a method of treating an acid base disorder or method of treatment of any previous enumerated embodiment wherein the acid-base disorder is characterized by a baseline serum bicarbonate value of at least 17 mEq/l.

Embodiment 437. The composition for use in a method of treating an acid base disorder or method of treatment of any previous enumerated embodiment wherein the acid-base disorder is characterized by a baseline serum bicarbonate value of at least 18 mEq/l.

Embodiment 438. The composition for use in a method of treating an acid base disorder or method of treatment of any previous enumerated embodiment wherein the acid-base disorder is characterized by a baseline serum bicarbonate value of at least 19 mEq/l.

Embodiment 439. The composition for use in a method of treating an acid base disorder or method of treatment of any previous enumerated embodiment wherein the acid-base disorder is characterized by a baseline serum bicarbonate value of at least 20 mEq/l.

Embodiment 440. The composition for use in a method of treating an acid base disorder or method of treatment of any previous enumerated embodiment wherein the acid-base disorder is characterized by a baseline serum bicarbonate value of at least 21 mEq/l.

Embodiment 441. The composition for use in a method of treating an acid base disorder or method of treatment of any previous enumerated embodiment wherein the clinically significant increase is at least 1 mEq/l.

Embodiment 442. The composition for use in a method of treating an acid base disorder or method of treatment of any previous enumerated embodiment wherein the clinically significant increase is at least 1.5 mEq/l.

Embodiment 443. The composition for use in a method of treating an acid base disorder or method of treatment of any previous enumerated embodiment wherein the clinically significant increase is at least 2 mEq/l.

Embodiment 444. The composition for use in a method of treating an acid base disorder or method of treatment of any previous enumerated embodiment wherein the clinically significant increase is at least 2.5 mEq/l.

Embodiment 445. The composition for use in a method of treating an acid base disorder or method of treatment of any previous enumerated embodiment wherein the clinically significant increase is at least 3 mEq/l.

Embodiment 446. The composition for use in a method of treating an acid base disorder or method of treatment of any previous enumerated embodiment wherein the clinically significant increase is at least 3.5 mEq/l.

Embodiment 447. The composition for use in a method of treating an acid base disorder or method of treatment of any previous enumerated embodiment wherein the clinically significant increase is at least 4 mEq/l.

Embodiment 448. The composition for use in a method of treating an acid base disorder or method of treatment of any previous enumerated embodiment wherein the clinically significant increase is at least 4.5 mEq/l.

Embodiment 449. The composition for use in a method of treating an acid base disorder or method of treatment of any previous enumerated embodiment wherein the clinically significant increase is at least 5 mEq/l.

Embodiment 450. The composition for use in a method of treating an acid base disorder or method of treatment of any previous enumerated embodiment wherein the clinically significant increase is at least 5.5 mEq/l.

Embodiment 451. The composition for use in a method of treating an acid base disorder or method of treatment of any previous enumerated embodiment wherein the clinically significant increase is at least 6 mEq/l.

Embodiment 452. The composition for use in a method of treating an acid base disorder or method of treatment of any previous enumerated embodiment wherein the clinically significant increase is at least 6.5 mEq/l.

Embodiment 453. The composition for use in a method of treating an acid base disorder or method of treatment of any previous enumerated embodiment wherein the clinically significant increase is at least 7 mEq/l.

Embodiment 454. The composition for use in a method of treating an acid base disorder or method of treatment of any previous enumerated embodiment wherein the clinically significant increase is at least 7.5 mEq/l.

Embodiment 455. The composition for use in a method of treating an acid base disorder or method of treatment of any previous enumerated embodiment wherein the clinically significant increase is at least 8 mEq/l.

Embodiment 456. The composition for use in a method of treating an acid base disorder or method of treatment of any previous enumerated embodiment wherein the clinically significant increase is at least 8.5 mEq/l.

Embodiment 457. The composition for use in a method of treating an acid base disorder or method of treatment of any previous enumerated embodiment wherein the clinically significant increase is at least 9 mEq/l.

Embodiment 458. The composition for use in a method of treating an acid base disorder or method of treatment of any previous enumerated embodiment wherein the clinically significant increase is achieved within a treatment period of less than one month.

Embodiment 459. The composition for use in a method of treating an acid base disorder or method of treatment of any previous enumerated embodiment wherein the clinically significant increase is achieved within a treatment period of 25 days.

Embodiment 460. The composition for use in a method of treating an acid base disorder or method of treatment of any previous enumerated embodiment wherein the clinically significant increase is achieved within a treatment period of 3 weeks.

Embodiment 461. The composition for use in a method of treating an acid base disorder or method of treatment of any previous enumerated embodiment wherein the clinically significant increase is achieved within a treatment period of 15 days.

Embodiment 462. The composition for use in a method of treating an acid base disorder or method of treatment of any previous enumerated embodiment wherein the clinically significant increase is achieved within a treatment period of 2 weeks.

Embodiment 463. The composition for use in a method of treating an acid base disorder or method of treatment of any previous enumerated embodiment wherein the clinically significant increase is achieved within a treatment period of 10 days.

Embodiment 464. The composition for use in a method of treating an acid base disorder or method of treatment of any previous enumerated embodiment wherein the clinically significant increase is achieved within a treatment period of 1 week.

Embodiment 465. The composition for use in a method of treating an acid base disorder or method of treatment of any previous enumerated embodiment wherein the clinically significant increase is achieved within a treatment period of 6 days.

Embodiment 466. The composition for use in a method of treating an acid base disorder or method of treatment of any previous enumerated embodiment wherein the clinically significant increase is achieved within a treatment period of 5 days.

Embodiment 467. The composition for use in a method of treating an acid base disorder or method of treatment of any previous enumerated embodiment wherein the clinically significant increase is achieved within a treatment period of 4 days.

Embodiment 468. The composition for use in a method of treating an acid base disorder or method of treatment of any previous enumerated embodiment wherein the clinically significant increase is achieved within a treatment period of 3 days.

Embodiment 469. The composition for use in a method of treating an acid base disorder or method of treatment of any previous enumerated embodiment wherein the clinically significant increase is achieved within a treatment period of 2 days.

Embodiment 470. The composition for use in a method of treating an acid base disorder or method of treatment of any previous enumerated embodiment wherein the clinically significant increase is achieved within a treatment period of 1 day.

Embodiment 471. The composition for use in a method of treating an acid base disorder or method of treatment of any previous enumerated embodiment wherein the clinically significant increase is achieved within a treatment period of 12 hours.

Embodiment 472. A composition for use in a method of treating metabolic acidosis in an adult human patient, the composition comprising a crosslinked poly(allylamine) polymer of any of the previous enumerated embodiments.

Embodiment 473. The process or crosslinked poly(allylamine) polymer of any previous enumerated embodiment wherein the crosslinked poly(allylamine) polymer comprises the residue of a crosslinking agent, and the crosslinking agent is selected from Table B.

Having described the invention in detail, it will be apparent that modifications and variations are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

The following chemistry examples are presented in six categories based on the process parameter manipulated:
(a) water content (Table 10_1 polymers 1-6, 12-16, 56-57; Table 10_2 polymers 35-39)
(b) reaction time (Table 10_1 polymers 7; Table 10_2 polymers 29-34, 40-43)
(c) reaction temperature (Table 10_1 polymers 8-11 Table 10_2 polymers 24-28)
(d) initiator content in the radical polymerization (Table 10_1 polymers 17-23, 58)
(e) ratio of DCE to poly(allylamine) polymer (Table 10_2 polymers 44-51)
(f) Ratio of AAH to DAPDA (Table 10_1 polymers 53-55)
(g) container closure (Table 10_2 polymer 52).

A general polymerization procedure is described and in each case specific examples are called out with reference to tables of synthesis parameters that were varied within the general procedure. Tables of the physicochemical performance characteristics of the resulting polymers are also provided.

General Polymerization Procedure for Beads Formed by Radical Polymerization (Addition/Chain Growth) and Post-Polymerization Crosslinking of Poly(Allylamine) Beads An aqueous stock solution was prepared by dissolving a monoallylamine and a multiallylamine crosslinker in water. A reactor equipped with a stirrer was charged with aqueous stock solution and surfactant dissolved in a hydrophobic organic suspending solvent. A solution of radical initiator was prepared. The two mixtures were independently sparged with nitrogen. The initiator solution was added to the reaction mixture while stirring, and subsequently heated for up to 48 hours. A second portion of initiator may be added to the reaction mixture if necessary depending on the polymerization kinetics. After cooling the vessel to room temperature, the organic phase was removed and the beads were purified. The beads were dried. Examples of conditions that are suitable for the synthesis of polymers described in this example include, but are not limited to, the combinations shown in Table 10 part 1. These polymers were then subjected to post-polymerization crosslinking procedures as described below and in Table 10 part 2.

The resulting dried polyamine described in the procedure above was placed into a reactor and a crosslinker, which could optionally act as the solvent, was added. A swelling agent was added to the resulting slurry. The mixture was heated with stirring for a required amount of time to reach completion. The reaction mixture was cooled and the beads were purified by washing and filtration and dried until no further water was removed and the weight remained constant. Examples of post-polymerization crosslinking described in this example include, but are not limited to, the polymers shown in Table 10, Part 2. Table 11 describes key physicochemical properties of the polymer examples shown in Table 10.

a-1) Specific Procedure for Polymer Prepared with Variable Water Contents

An aqueous stock solution was prepared by dissolving allylamine hydrochloride (2-Propen-1-ylamine, "AAH") (371.1 g) and 1,2-Bis(allylamino)propane dihydrochloride ("DAPDA") (386.0 g) in water (757.1 g). A reactor equipped with an overhead stirrer and nitrogen inlet, was charged with aqueous stock solution and surfactant (branched dodecylbenzene sulfonate, 36.0 g) dissolved in heptane (3264 g, "Solvent System 1"). In a separate vessel, a solution of V-50 (76.8 g) in water (435.3 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration with 1 M NaOH (1:1 water:MeOH, v/v), water until filtrate approached neutral pH, IPA, and finally heptane, and then dried for 48 hours. This polymer is shown in Table 10_1 and Table 11_1 as polymer 12.

1,2-Dichlorethane ("DCE") (750 g) was added to a reactor charged with the above resulting polyamine beads (100 g) and equipped with overhead stirring. The beads were dispersed before adding water (25 g) and heated to 65° C. for 16 hours. The cooled beads were purified by washing and filtration with 1 M NaOH (1:1 water:MeOH, v/v), water until filtrate approached neutral pH, and finally methanol, and then dried for 24 hours. This polymer is shown in Table 10_Part 2 and Table 11 as polymer number 14.

a-2) Specific Procedure for Post-Crosslinked Polymer Prepared with Variable Water Contents An aqueous stock solution of AAH was prepared by dissolving allylamine hydrochloride (2-Propen-1-ylamine, "AAH") (402.8 g) in water (207.5 g). An aqueous stock solution of DAPDA was prepared by dissolving 1,2-Bis(allylamino)propane dihydrochloride ("DAPDA", 419.0 g) in water (419.0 g). Into a 6 L, glass jacketed reactor equipped with an overhead stirrer, glass anchor stir paddle, nitrogen inlet and addition funnel, was charged surfactant (branched dodecylbenzene sulfonate, 60.0 g) dissolved in heptane (3284 g) and both aqueous stock solutions. In a separate vessel, a solution of V-50 (83.4 g) in water (472.6 g) was prepared. The two mixtures were independently sparged with nitrogen. Under inert atmosphere, the initiator solution was added to the reaction mixture while stirring, and subsequently heated to 67° C. for 16 hours. Six hours after the first addition of V-50, an additional solution of V-50 (41.7 g in 236.3 g $H_2O$) is prepared, sparged with nitrogen, and added to the reaction mixture. After cooling the vessel to room temperature, the organic phase was removed by decanting, and the beads were purified by washing and filtration once with methanol, 4 times with 1 M NaOH (1:1 water:MeOH, v/v), water until the pH of the solution after washing was 9, and twice with methanol. The beads were dried in a vacuum oven at 60° C. for 48 hours. This polymer is shown in Table 10_1 and Table 11_1 as polymer 37.

The following procedure was performed using different amounts of water (i.e. 6, 8, 10, 12, or 14 g, respectively).

1,2-Dichlorethane ("DCE") (200 g) was added to a jacketed reactor charged with the above resulting polyamine beads (40 g) and equipped with overhead stirring. The beads were dispersed before adding water (10 g) and heated to 65° C. for 16 hours. The slurry was drained, and the crude product was isolated by filtration. The beads were purified by washing and filtration (4 times with 1N NaOH (1:1 water:MeOH, v/v), water until the pH of solution after washing was 9, and once with methanol). The purified beads were dried in a vacuum oven at 60° C. for 24 hours. The dried polymer is packaged in a hermetically sealed container which provides a barrier to oxygen and moisture. This polymer is shown in Table 10_2 and Table 11_2 as polymer 37.

b-1) Specific Procedure for Post-Crosslinked Polymer Prepared with Variable Reaction Time An aqueous stock solution was prepared by dissolving allylamine hydrochloride (2-Propen-1-ylamine, "AAH") (402.8 g) and 1,2-Bis(allylamino)propane dihydrochloride ("DAPDA") (419.0 g) in water (727.4 g). A reactor equipped with an overhead stirrer and nitrogen inlet, was charged with aqueous stock solution and surfactant (branched dodecylbenzene sulfonate, 60.0 g) dissolved in heptane (3261.6 g, "Solvent System 1"). In a separate vessel, a solution of V-50 (83.4 g) in water (472.6 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration with 1 M NaOH (1:1 water:MeOH, v/v), water until filtrate approached neutral pH, IPA, finally heptane, and dried for 48 hours. This polymer is shown in Table 10_1 and Table 11_1 as polymer 28.

1,2-Dichlorethane ("DCE") (799.8 g) was added to a reactor charged with the above resulting polyamine beads (133.3 g) and equipped with overhead stirring. The beads were dispersed before adding water (33.3 g) and heated to 65° C. for 10 hours. The cooled beads were purified by washing and filtration with 1 M NaOH (1:1 water:MeOH, v/v), water until filtrate approached neutral pH, and finally methanol, and dried for 24 hours. This polymer is shown in Table 10_Part 2 and Table 11 as polymer number 28.

b-2) Specific Procedure for Polymer Prepared with Variable Reaction Time

To prepare a 56 wt % aqueous allylamine hydrochloride (AAH) solution, allylamine (AA, 614 kg) was slowly added to a cooled 34 wt % hydrochloric acid solution (1002 L) so that the temperature was between −10° C. and 30° C. The solution was stirred for a minimum of 30 minutes. An aqueous stock solution of DAPDA was prepared by dissolving 1,2-Bis(allylamino)propane dihydrochloride ("DAPDA", 925 kg) in water (925 kg). Into a glass jacketed reactor equipped with an overhead stirrer, glass anchor stir paddle, and nitrogen inlet, was charged surfactant (branched dodecylbenzene sulfonate, 43 kg) dissolved in heptane (2346 kg), 596 kg DAPDA solution, and 514 kg of AAH solution. In a separate vessel, a solution of V-50 (60 kg) in water (291 kg) was prepared. The two mixtures were independently sparged with nitrogen. Under inert atmosphere, the initiator solution was added to the reaction mixture while stirring, and subsequently heated to 67° C. for 16 hours. Six hours after the first addition of V-50, an additional solution of V-50 (30 kg in 145 kg $H_2O$) is prepared, sparged with nitrogen, and added to the reaction mixture. After cooling the vessel to room temperature, the organic phase was removed by decanting, and the beads were purified by washing with 1 M NaOH (1:1 water:MeOH, v/v), water until the pH of the solution after washing was 11, and with methanol. The beads were dried in a vacuum oven at 60° C. for 48 hours. This polymer is shown in Table 10_1 and Table 11_1 as polymer 41.

The following procedure was performed using different reaction times. Reactions were heated to 65° C. for either 12, 16, or 20 hours.

1,2-Dichlorethane ("DCE") (175 g) was added to a jacketed reactor charged with the resulting polyamine beads (35 g) and equipped with overhead stirring. The beads were dispersed before adding water (8.75 g) and heated to 65° C. for 16 hours (see note above regarding reaction time). The slurry was drained, and the crude product was isolated by filtration. The beads were purified by washing with 1 M NaOH (1:1 water:MeOH, v/v), water until the pH of the solution after washing was 11, and with methanol. The purified beads were dried in a vacuum oven at 60° C. for 24 hours. The dried polymer is packaged in a hermetically sealed container which provides a barrier to oxygen and moisture. This polymer is shown in Table 10_2 and Table 11_2 as polymer 41.

c-1) Specific Procedure for Polymer Prepared with Variable Reaction Temperature in the Radical Polymerization Step An aqueous stock solution was prepared by dissolving allylamine hydrochloride (2-Propen-1-ylamine, "AAH") (67.1 g) and 1,2-Bis(allylamino)propane dihydrochloride ("DAPDA") (69.8 g) in water (121.2 g). A reactor equipped with an overhead stirrer and nitrogen inlet, was charged with aqueous stock solution and surfactant (branched dodecylbenzene sulfonate, 10.0 g) dissolved in heptane (543.6 g, "Solvent System 1"). In a separate vessel, a solution of V-50 (13.9 g) in water (78.8 g) was prepared. The two mixtures were independently sparged with nitrogen. Under inert atmosphere, the initiator solution was added to the reaction mixture while stirring, and subsequently heated to 75° C. for 16 hours. After cooling the vessel to room temperature, the organic phase was removed by decanting, and the beads were purified by washing and filtration with 1 M NaOH solution (1:1 water:MeOH, v/v), water until filtrate approached neutral pH, IPA, and finally heptane, and dried for 48 hours. This polymer is shown in Table 10_1 and Table 11_1 as polymer 11.

1,2-Dichlorethane ("DCE") (500.3 g) was added to a reactor charged with the above resulting polyamine beads (66.7 g) and equipped with overhead stirring. The beads were dispersed before adding water (16.7 g) and heated to 65° C. for 16 hours. The cooled beads were purified by washing and filtration with 1 M NaOH (1:1 water:MeOH, v/v), water until filtrate approached neutral pH, and finally methanol, and dried for 24 hours. This polymer is shown in Table 10_Part 2 and Table 11 as polymer number 11.

c-2) Specific Procedure for Post-Crosslinked Polymer Prepared with Variable Reaction Temperature An aqueous stock solution was prepared by dissolving allylamine hydrochloride (2-Propen-1-ylamine, "AAH") (402.8 g) and 1,2-Bis(allylamino)propane dihydrochloride ("DAPDA") (419.0 g) in water (727.4 g). A reactor equipped with an overhead stirrer and nitrogen inlet, was charged with aqueous stock solution and surfactant (branched dodecylbenzene sulfonate, 60.0 g) dissolved in heptane (3261.6 g, "Solvent System 1"). In a separate vessel, a solution of V-50 (83.4 g) in water (472.6 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration with 1 M NaOH solution (1:1 water:MeOH, v/v), water until filtrate approached neutral pH, IPA, and finally heptane, and dried for 48 hours. This polymer is shown in Table 10_1 and Table 11_1 as polymer 28.

1,2-Dichlorethane ("DCE") (750 g) was added to a reactor charged the above resulting polyamine beads (100 g) and equipped with overhead stirring. The beads were dispersed before adding water (25 g) and heated to 75° C. for 16 hours. The cooled beads were purified by washing and filtration with 1 M NaOH (1:1 water:MeOH, v/v), water until filtrate approached neutral pH, and finally methanol, and dried for 24 hours. This polymer is shown in Table 10_Part 2 and Table 11 as polymer number 28.

d-1) Specific Procedure for Polymer Prepared with Variable Initiator Content

An aqueous stock solution was prepared by dissolving allylamine hydrochloride (2-Propen-1-ylamine, "AAH") (64.3 g) and 1,2-Bis(allylamino)propane dihydrochloride ("DAPDA") (66.9 g) in water (242.3). A 3-neck round bottom flask with four side baffles equipped with an overhead stirrer, Dean Stark apparatus and condenser, and nitrogen inlet, was charged with aqueous stock solution and surfactant (branched dodecylbenzene sulfonate, 19.6 g) dissolved in a 74:26 chlorobenzene/heptane solution (1120 g, "Solvent System 2"). In a separate vessel, a solution of V-50 (6.7 g) in water (37.7 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration twice with methanol, water, twice with 1 M HCl, water, 4 times with 1 M NaOH (1:1 water:MeOH, v/v), and water until the pH of the solution after washing was 7. The beads were dried in a lyophilizer for 48 hours. This polymer is shown in Table 10_1 and Table 11_1 as polymer 21.

1,2-Dichlorethane ("DCE") (75.0 g) was added to a reactor charged with the above resulting polyamine beads (10.0 g) and equipped with overhead stirring. The beads were dispersed before adding water (2.5 g) and heated to 65° C. for 16 hours. The cooled beads were purified by washing and filtration twice with methanol, water, twice with 1 M HCl, water, 4 times with 1 M NaOH (1:1 water:MeOH, v/v), and water until the pH of solution after washing was 7. The polymer was dried in a lyophilizer for 48 hours. This polymer is shown in Table 10_Part 2 and Table 11 as polymer 21.

d-2) Specific Procedure for Polymer Prepared with Variable Initiator Content

An aqueous stock solution was prepared by dissolving allylamine hydrochloride (2-Propen-1-ylamine, "AAH") (11.0 g) and 1,2-Bis(allylamino)propane dihydrochloride ("DAPDA") (11.4 g) in water (37.1 g). A 3-neck round bottom flask with four side baffles equipped with an overhead stirrer, Dean Stark apparatus and condenser, and nitrogen inlet, was charged with aqueous stock solution and surfactant (branched dodecylbenzene sulfonate, 3.0 g) dissolved in a 74:26 chlorobenzene/heptane solution (300 g, "Solvent System 2"). In a separate vessel, a solution of V-50 (2.4 g) in water (13.6 g) was prepared. The two mixtures were independently sparged with nitrogen. Under inert atmosphere, the initiator solution was added to the reaction mixture while stirring, and subsequently heated to 67° C. for 16 hours. A second portion of initiator solution (16.0 g) and the reaction mixture were degassed and combined before increasing the temperature to 115° C. for a final dehydration step. After cooling the vessel to room temperature, the organic phase was removed by decanting, and the beads were purified by washing and filtration twice with methanol, water, twice with 1 M HCl, water, 4 times with 1 M NaOH (1:1 water:MeOH, v/v), and water until the pH of the solution after washing was 7. The beads were dried in a lyophilizer for 48 hours. This polymer is shown in Table 10_1 and Table 11_1 as polymer 23.

1,2-Dichlorethane ("DCE") (75.0 g) is added to a reactor charged with the above resulting polyamine beads (10.0 g) and equipped with overhead stirring. The beads are dispersed before adding water (2.5 g) and heated to 65° C. for 16 hours. The cooled beads are purified by washing and filtration twice with methanol, water, twice with 1 M HCl, water, 4 times with 1 M NaOH (1:1 water:MeOH, v/v), and water until the pH of solution after washing was 7. The polymer is dried in a lyophilizer for 48 hours.

d-3) Specific Procedure for Polymer Prepared with Variable Initiator Content

The following procedure was performed using different amounts of V-50 in the first addition (i.e. 4.6, 7.4, and 9.1 g, respectively). A 15 weight % solution of V-50 is always used, and water addition is adjusted accordingly to maintain same total amount of water.

An aqueous stock solution of AAH was prepared by dissolving allylamine hydrochloride (2-Propen-1-ylamine, "AAH") (46.2 g) in water (23.8 g). An aqueous stock solution of DAPDA was prepared by dissolving 1,2-Bis(allylamino)propane dihydrochloride ("DAPDA", 48.0 g) in water (48.0 g). Into a 1 L, glass jacketed reactor equipped with an overhead stirrer, glass anchor stir paddle, nitrogen inlet and addition funnel, was charged surfactant (branched dodecylbenzene sulfonate, 6.6 g) dissolved in heptane (359 g), both aqueous stock solutions, and water (19.3 g). In a separate vessel, a solution of V-50 (9.1 g) in water (51.6 g) was prepared. The two mixtures were independently sparged with nitrogen. Under inert atmosphere, the initiator solution was added to the reaction mixture while stirring, and subsequently heated to 67° C. for 16 hours. Six hours after the first addition of V-50, an additional solution of V-50 (4.6 g in 26.3 g $H_2O$) is prepared, sparged with nitrogen, and added to the reaction mixture. After cooling the vessel to room temperature, the organic phase was removed by decanting, and the beads were purified by washing and filtration once with methanol, 4 times with 1 M NaOH (1:1 water:MeOH, v/v), water until the pH of the solution after washing was 9, and twice with methanol. The beads were dried in a vacuum oven at 60° C. for 48 hours. This polymer is shown in Table 10_1 and Table 11_1 as polymer 19.

1,2-Dichlorethane ("DCE") (200 g) was added to a jacketed reactor charged with the resulting polyamine beads (40 g) and equipped with overhead stirring. The beads were dispersed before adding water (10 g) and heated to 65° C. for 16 hours. The slurry was drained, and the crude product was isolated by filtration. The beads were purified by washing and filtration (4 times with 1N NaOH (1:1 water:MeOH, v/v), water until the pH of solution after washing was 11, and once with methanol). The purified beads were dried in a vacuum oven at 60° C. for 24 hours. The dried polymer is packaged in a hermetically sealed container which provides a barrier to oxygen and moisture. This polymer is shown in Table 10_2 and Table 11_2 as polymer 19.

e-1) Specific Procedure for Polymer Prepared with Variable DCE to Poly(Allylamine) Polymer Ratios An aqueous stock solution of AAH was prepared by dissolving allylamine hydrochloride (2-Propen-1-ylamine, "AAH") (263.0 g) in water (263.0 g). An aqueous stock solution of DAPDA was prepared by dissolving 1,2-Bis(allylamino)propane dihydrochloride ("DAPDA", 273.6 g) in water (273.6 g). Into a 6 L, glass jacketed reactor equipped with an overhead stirrer, glass anchor stir paddle, nitrogen inlet and addition funnel, was charged surfactant (branched dodecylbenzene sulfonate, 84.0 g) dissolved in heptane (3284 g) and both aqueous stock solutions. In a separate vessel, a solution of V-50 (54.5 g) in water (308.6 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration twice with methanol, water, twice with 1 M HCl, water, 3 times with 1 M NaOH (1:1 water:MeOH, v/v), water until the pH of the solution after washing was 9, twice with isopropanol, and twice with heptane. The purified beads were dried in a vacuum oven at 60° C. for 48 hours. This polymer is shown in Table 10_1 and Table 11_1 as polymer 49.

The following procedure was performed using different amounts of polyamine and water, to adjust the DCE:polymer ratio without affecting the overall volume of the reaction or the water:polymer ratio. Reactions were performed with the following amounts of polyamine and water (90 g polyamine, 22.5 g water; 60 g, 15 g; 36 g, 9 g; 18 g, 4.5 g).

1,2-Dichlorethane ("DCE") (450 g) was added to a jacketed reactor charged with the resulting polyamine beads (60 g) and equipped with overhead stirring. The beads were dispersed before adding water (15 g) and heated to 65° C. for 16 hours. The slurry was drained, and the crude product was isolated by filtration. The beads were purified by washing and filtration (twice with methanol, water, twice with 1 M HCl, water, 4 times with 1 M NaOH (aq), water until the pH of the solution after washing was 9, and once with methanol). The purified beads were dried in a vacuum oven at 40° C. for 48 hours. The dried polymer is packaged in a hermetically sealed container which provides a barrier to oxygen and moisture. This polymer is shown in Table 10_2 and Table 11_2 as polymer 49.

e-2) Specific Procedure for Polymer Prepared with Variable DCE to Poly(Allylamine) Polymer Ratios An aqueous stock solution of AAH was prepared by dissolving allylamine hydrochloride (2-Propen-1-ylamine, "AAH") (402.8 g) in water (207.5 g). An aqueous stock solution of DAPDA was prepared by dissolving 1,2-Bis(allylamino)propane dihydrochloride ("DAPDA", 419.0 g) in water (419.0 g). Into a 6 L, glass jacketed reactor equipped with an overhead stirrer, glass anchor stir paddle, nitrogen inlet and addition funnel, was charged surfactant (branched dodecylbenzene sulfonate, 60.0 g) dissolved in heptane (3284 g) and both aqueous stock solutions. In a separate vessel, a solution of V-50 (83.4 g) in water (472.6 g) was prepared. The two mixtures were independently sparged with nitrogen. Under inert atmosphere, the initiator solution was added to the reaction mixture while stirring, and subsequently heated to 67° C. for 16 hours. After cooling the vessel to room temperature, the organic phase was removed by decanting, and the beads were purified by washing and filtration (3 times with 1 M NaOH (1:1 water:MeOH, v/v), water until the pH of the solution after washing was 7, twice with isopropanol and twice with heptane. The beads were dried in a vacuum oven at 60° C. for 48 hours. This polymer is shown in Table 10_1 and Table 11_1 as polymer 45.

The following procedure was performed using different amounts of polyamine and water, to adjust the DCE:polymer ratio without affecting the overall volume of the reaction or the water:polymer ratio. Reactions were performed with the following amounts of polyamine and water (90 g polyamine, 22.5 g water; 60 g, 15 g; 36 g, 9 g; 18 g, 4.5 g).

1,2-Dichlorethane ("DCE") (450 g) was added to a jacketed reactor charged with the above resulting polyamine beads (60 g) and equipped with overhead stirring. The beads were dispersed before adding water (15 g) and heated to 65° C. for 16 hours. The slurry was drained, and the crude product was isolated by filtration. The beads were purified by washing and filtration (4 times with 1N NaOH (1:1 water:MeOH, v/v), water until the pH of solution after washing was 9, and once with methanol). The purified beads were dried in a vacuum oven at 40° C. for 48 hours. The dried polymer is packaged in a hermetically sealed container which provides a barrier to oxygen and moisture. This polymer is shown in Table 10_2 and Table 11_2 as polymer 45.

f-1) Specific Procedure for Polymer Stored with Variable Container Closure

To prepare a 56 wt % aqueous allylamine hydrochloride (AAH) solution, allylamine (AA, 305 kg) was slowly added to a cooled 34 wt % hydrochloric acid solution (585 kg) so that the temperature was between −10° C. and 30° C. The solution was stirred for a minimum of 30 minutes. An aqueous stock solution of DAPDA was prepared by dissolving 1,2-Bis(allylamino)propane dihydrochloride ("DAPDA", 56.2 kg) in water (56.2 kg). Into a glass jacketed reactor equipped with an overhead stirrer, glass anchor stir paddle, and nitrogen inlet, was charged surfactant (branched dodecylbenzene sulfonate, 8.0 kg) dissolved in heptane (437 kg), the DAPDA solution, and 96 kg of AAH solution. In a separate vessel, a solution of V-50 (11.2 kg) in water (63.5 kg) was prepared. The two mixtures were independently sparged with nitrogen. Under inert atmosphere, the initiator solution was added to the reaction mixture while stirring, and subsequently heated to 67° C. for 16 hours. Six hours after the first addition of V-50, an additional solution of V-50 (5.6 kg in 31.7 kg $H_2O$) is prepared, sparged with nitrogen, and added to the reaction mixture. After cooling the vessel to room temperature, the organic phase was removed by decanting, and the beads were purified by washing with 1 M NaOH (1:1 water: MeOH, v/v), water until the pH of the solution after washing was 11, and with methanol. The beads were dried in a vacuum oven at 60° C. for 48 hours. This polymer is shown in Table 10_1 and Table 11_1 as polymer 52.

1,2-Dichlorethane ("DCE") (322 kg) was added to a jacketed reactor charged with the resulting polyamine beads (65.7 kg) and equipped with overhead stirring. The beads were dispersed before adding water (15.6 kg) and heated to 65° C. for 16 hours (see note above regarding reaction time). The slurry was drained, and the crude product was isolated by filtration. The beads were purified by washing with 1 M NaOH (1:1 water:MeOH, v/v), water until the pH of the solution after washing was 11, and with methanol. The purified beads were dried in a vacuum oven at 60° C. for 72 hours. The dried polymer is packaged in a hermetically sealed container which provides a barrier to oxygen and moisture. This polymer is shown in Table 10_2 and Table 11_2 as polymer 52.

More frequently, the sp2 carbon content of poly(allylamine) polymers comprised of allylamine hydrochloride and 1,2-Bis(allylamino)propane hydrochloride was measured prior to crosslinking with 1,2-dichloroethane. As discussed elsewhere, it is advantageous to determine the sp2 carbon content of such preformed poly(allylamine) polymers because a higher signal to noise may be obtained for sp2 carbon by 13C ssNMR at this stage. All values of percent sp2 allyl carbon given in Table 11 part 1 are directly measured. In some cases the percent sp2 allyl carbon in crosslinked poly(allylamine) polymers given in the examples was measured directly by NMR, and these are indicated in Table 11 part 2. Alternatively, the percent sp2 allyl carbon present in the crosslinked poly(allylamine) polymers given in the example was calculated by multiplying the percent sp2 allyl carbon in the corresponding preformed poly(allylamine) polymer by a factor of 0.9. The factor is derived from the addition of sp3 carbon during crosslinking of the preformed poly(allylamine) polymer with 1,2-dichloroethane.

g-1) Specific Procedure for Variable Ratio of DAPDA to AAH

The following procedure was performed using different relative amounts of the AAH and DAPDA. Reactions were performed with the following amounts of AAH and DAPDA (38.9 g AAH, 50.9 g DAPDA; 44.0 g AAH, 45.8 g DAPDA; 49.7 g AAH, 40.2 g DAPDA).

To prepare a 56 wt % aqueous allylamine hydrochloride (AAH) solution, allylamine (AA, 614 kg) was slowly added to a cooled 34 wt % hydrochloric acid solution (1002 L) so that the temperature was between −10° C. and 30° C. The solution was stirred for a minimum of 30 minutes. An aqueous stock solution of DAPDA was prepared by dissolving 1,2-Bis(allylamino)propane dihydrochloride ("DAPDA", 925 kg) in water (925 kg). Into a 1 L, glass jacketed reactor equipped with an overhead stirrer, glass anchor stir paddle, nitrogen inlet and addition funnel, was charged surfactant (branched dodecylbenzene sulfonate, 6.6 g) dissolved in heptane (357 g), AAH stock solution (38.9 g), and DAPDA stock solution (50.9 g). In a separate vessel, a solution of V-50 (9.1 g) in water (51.6 g) was prepared. The two mixtures were independently sparged with nitrogen. Under inert atmosphere, the initiator solution was added to the reaction mixture while stirring, and subsequently heated to 67° C. for 16 hours. Six hours after the first addition of V-50, an additional solution of V-50 (4.5 g in 25.8 g $H_2O$) is prepared, sparged with nitrogen, and added to the reaction mixture. After cooling the vessel to room temperature, the organic phase was removed by decanting, and the beads were purified by washing with 1 M NaOH (1:1 water:MeOH, v/v), water until the pH of the solution after washing was 11, and with methanol. The beads were dried in a vacuum oven at 60° C. for 48 hours. This polymer is shown in Table 10_1 and Table 11_1 as polymer 53.

1,2-Dichlorethane ("DCE") (200 g) was added to a jacketed reactor charged with the resulting polyamine beads (40 g) and equipped with overhead stirring. The beads were dispersed before adding water (10 g) and heated to 65° C. for 16 hours. The slurry was drained, and the crude product was isolated by filtration. The beads were purified by washing with 1 M NaOH (1:1 water:MeOH, v/v), water until the pH of the solution after washing was 11, and with methanol. The purified beads were dried in a vacuum oven at 60° C. for 24 hours. The dried polymer is packaged in a hermetically sealed container which provides a barrier to oxygen and moisture. This polymer is shown in Table 10_2 and Table 11_2 as polymer 53.

TABLE 10

Part 1: Synthesis of radical polymerization beads

| Polymer number | Solvent (g) | Amine (g) | Water (g) | Crosslinker (g) | Surfactant (g) | V-50 (g) | Solvent System | Temp (° C.) | Time (h) |
|---|---|---|---|---|---|---|---|---|---|
| 1 | 3261.6 | 402.8 | 1200 | 419 | 60 | 83.4 | 1 | 67 | 16 |
| 2 | 761 | 61.4 | 280 | 63.8 | 14 | 12.7 | 1 | 67 | 16 |

TABLE 10-continued

Part 1: Synthesis of radical polymerization beads

| Polymer number | Solvent (g) | Amine (g) | Water (g) | Crosslinker (g) | Surfactant (g) | V-50 (g) | Solvent System | Temp (° C.) | Time (h) |
|---|---|---|---|---|---|---|---|---|---|
| 3 | 544 | 47.9 | 200 | 49.9 | 14 | 9.9 | 1 | 67 | 16 |
| 4 | 544 | 52.3 | 200 | 54.4 | 14 | 10.8 | 1 | 67 | 16 |
| 5 | 544 | 61.8 | 200 | 64.3 | 6 | 12.8 | 1 | 67 | 16 |
| 6 | 3261.6 | 402.8 | 1200 | 419 | 60 | 83.4 | 1 | 67 | 16 |
| 7 | 356.6 | 44 | 131.2 | 45.8 | 6.6 | 9.1 | 1 | 67 | 6 |
| 8 | 356.6 | 44 | 131.2 | 45.8 | 6.6 | 9.1 | 1 | 47 | 48 |
| 9 | 356.6 | 44 | 131.2 | 45.8 | 6.6 | 9.1 | 1 | 57 | 28 |
| 10 | 356.6 | 28.8 | 131.2 | 29.9 | 6.6 | 6 | 1 | 57 | 16 |
| 11 | 543.6 | 67.1 | 200 | 69.8 | 10 | 13.9 | 1 | 75 | 16 |
| 12 | 1120 | 61.4 | 280 | 63.8 | 19.6 | 12.7 | 2 | 67 | 16 |
| 13 | 3261.6 | 263 | 1200 | 273.6 | 84 | 54.5 | 1 | 67 | 16 |
| 14 | 3264 | 371.1 | 1200 | 386 | 36 | 76.8 | 1 | 67 | 16 |
| 15 | 544 | 61.8 | 200 | 64.3 | 4 | 12.8 | 1 | 67 | 16 |
| 16 | 544 | 72.8 | 200 | 75.7 | 10 | 15.1 | 1 | 67 | 16 |
| 17 | 356.6 | 46.2 | 159.6 | 48 | 6.6 | 9.1 | 1 | 67 | 16 |
| 18 | 356.6 | 46.2 | 159.6 | 48 | 6.6 | 12 | 1 | 67 | 16 |
| 19 | 356.6 | 46.2 | 159.6 | 48 | 6.6 | 13.7 | 1 | 67 | 16 |
| 20 | 356.6 | 44 | 131.2 | 45.8 | 6.6 | 9.1 | 1 | 67 | 16 |
| 21 | 1120 | 64.3 | 280 | 66.9 | 19.6 | 6.7 | 2 | 67 | 20 |
| 22 | 2400 | 131.5 | 600 | 136.8 | 36 | 27.2 | 2 | 67 | 16 |
| 23 | 300 | 11 | 75.5 | 11.4 | 3 | 4.8 | 2 | 67 | 20 |
| 24 | 3261.6 | 402.8 | 1200 | 419 | 60 | 83.4 | 1 | 67 | 16 |
| 25 | 3261.6 | 402.8 | 1200 | 419 | 60 | 83.4 | 1 | 67 | 16 |
| 26 | 3261.6 | 402.8 | 1200 | 419 | 60 | 83.4 | 1 | 67 | 16 |
| 27 | 3261.6 | 402.8 | 1200 | 419 | 60 | 83.4 | 1 | 67 | 16 |
| 28 | 3261.6 | 402.8 | 1200 | 419 | 60 | 83.4 | 1 | 67 | 16 |
| 29 | 3261.6 | 402.8 | 1200 | 419 | 60 | 83.4 | 1 | 67 | 16 |
| 30 | 3261.6 | 402.8 | 1200 | 419 | 60 | 83.4 | 1 | 67 | 16 |
| 31 | 3261.6 | 402.8 | 1200 | 419 | 60 | 83.4 | 1 | 67 | 16 |
| 32 | 3261.6 | 402.8 | 1200 | 419 | 60 | 83.4 | 1 | 67 | 16 |
| 33 | 3261.6 | 402.8 | 1200 | 419 | 60 | 83.4 | 1 | 67 | 16 |
| 34 | 3261.6 | 402.8 | 1200 | 419 | 60 | 83.4 | 1 | 67 | 16 |
| 35 | 3284 | 402.8 | 1436.3 | 419 | 60 | 125.1 | 1 | 67 | 16 |
| 36 | 3284 | 402.8 | 1436.3 | 419 | 60 | 125.1 | 1 | 67 | 16 |
| 37 | 3284 | 402.8 | 1436.3 | 419 | 60 | 125.1 | 1 | 67 | 16 |
| 38 | 3284 | 402.8 | 1436.3 | 419 | 60 | 125.1 | 1 | 67 | 16 |
| 39 | 3284 | 402.8 | 1436.3 | 419 | 60 | 125.1 | 1 | 67 | 16 |
| 40 | 2346000 | 287800 | 870200 | 298000 | 43000 | 90000 | 1 | 67 | 16 |
| 41 | 2346000 | 287800 | 870200 | 298000 | 43000 | 90000 | 1 | 67 | 16 |
| 42 | 2346000 | 287800 | 870200 | 298000 | 43000 | 90000 | 1 | 67 | 16 |
| 43 | 2346000 | 287800 | 870200 | 298000 | 43000 | 90000 | 1 | 67 | 16 |
| 44 | 3284 | 402.8 | 1394.4 | 419 | 60 | 83.4 | 1 | 67 | 16 |
| 45 | 3284 | 402.8 | 1394.4 | 419 | 60 | 83.4 | 1 | 67 | 16 |
| 46 | 3284 | 402.8 | 1394.4 | 419 | 60 | 83.4 | 1 | 67 | 16 |
| 47 | 3284 | 402.8 | 1394.4 | 419 | 60 | 83.4 | 1 | 67 | 16 |
| 48 | 3284 | 263 | 1200 | 273.6 | 84 | 54.5 | 1 | 67 | 16 |
| 49 | 3284 | 263 | 1200 | 273.6 | 84 | 54.5 | 1 | 67 | 16 |
| 50 | 3284 | 263 | 1200 | 273.6 | 84 | 54.5 | 1 | 67 | 16 |
| 51 | 3284 | 263 | 1200 | 273.6 | 84 | 54.5 | 1 | 67 | 16 |
| 52 | 437000 | 54000 | 188700 | 56400 | 8000 | 16800 | 1 | 67 | 16 |
| 53 | 356.6 | 38.9 | 131.2 | 50.9 | 6.6 | 13.65 | 1 | 67 | 16 |
| 54 | 356.6 | 44 | 131.2 | 45.8 | 6.6 | 13.65 | 1 | 67 | 16 |
| 55 | 356.6 | 49.7 | 131.2 | 40.2 | 6.6 | 13.65 | 1 | 67 | 16 |
| 56 | 61600 | 3400 | 15490 | 3520 | 1110 | 710 | 2 | 67 | 16 |
| 57 | 437000 | 53760 | 163060 | 56000 | 8000 | 11100 | 1 | 67 | 16 |
| 58 | 2346000 | 288400 | 872600 | 300000 | 44000 | 90000 | 1 | 67 | 16 |

NP = not performed

TABLE 10_Part 2

Synthesis of post-crosslinked radical polymerization beads (Contd.)

| Post-crosslinked polymer number | Polymer (g) | DCE (g) | Water (g) | Temp (° C.) | Time (h) |
|---|---|---|---|---|---|
| 1 | 133.3 | 1000 | 33.3 | 65 | 16 |
| 2 | 45 | 337.5 | 11.3 | 65 | 16 |
| 3 | 45 | 337.5 | 11.3 | 65 | 16 |
| 4 | 45 | 337.5 | 11.3 | 65 | 16 |
| 5 | 45 | 337.5 | 11.3 | 65 | 16 |
| 6 | NP | NP | NP | NP | NP |
| 7 | 45 | 337.5 | 11.3 | 65 | 16 |
| 8 | 40 | 300 | 10 | 65 | 16 |

TABLE 10_Part 2-continued

Synthesis of post-crosslinked radical polymerization beads (Contd.)

| Post-crosslinked polymer number | Polymer (g) | DCE (g) | Water (g) | Temp (° C.) | Time (h) |
|---|---|---|---|---|---|
| 9 | 40 | 300 | 10 | 65 | 16 |
| 10 | 20 | 150 | 5 | 65 | 16 |
| 11 | 66.7 | 500.3 | 16.7 | 65 | 16 |
| 12 | 50 | 375 | 12.5 | 65 | 16 |
| 13 | 60 | 450 | 15 | 65 | 16 |
| 14 | 100 | 750 | 25 | 65 | 16 |
| 15 | 45 | 337.5 | 11.3 | 65 | 16 |
| 16 | 45 | 337.5 | 11.3 | 65 | 16 |
| 17 | NP | NP | NP | NP | NP |
| 18 | NP | NP | NP | NP | NP |
| 19 | 40 | 200 | 10 | 65 | 16 |
| 20 | 40 | 300 | 10 | 65 | 16 |
| 21 | 10 | 75 | 2.5 | 65 | 16 |
| 22 | 133 | 997.5 | 33.3 | 65 | 16 |
| 23 | NP | NP | NP | NP | NP |
| 24 | 133.3 | 1000 | 33.3 | 65 | 16 |
| 25 | 66.7 | 500 | 16.7 | 55 | 16 |
| 26 | 66.7 | 500 | 16.7 | 60 | 16 |
| 27 | 45 | 337.5 | 11.3 | 70 | 16 |
| 28 | 66.7 | 500 | 16.7 | 75 | 16 |
| 29 | 133.3 | 799.8 | 33.3 | 65 | 10 |
| 30 | 66.7 | 500 | 16.7 | 65 | 20 |
| 31 | 100 | 750 | 25 | 65 | 10 |
| 32 | 66 | 495 | 16.5 | 65 | 10 |
| 33 | 266.7 | 2000 | 66.7 | 65 | 16 |
| 34 | 266.7 | 2000 | 66.7 | 65 | 16 |
| 35 | 40 | 200 | 6 | 65 | 16 |
| 36 | 40 | 200 | 8 | 65 | 16 |
| 37 | 40 | 200 | 10 | 65 | 16 |
| 38 | 40 | 200 | 12 | 65 | 16 |
| 39 | 40 | 200 | 14 | 65 | 16 |
| 40 | 35 | 175 | 8.75 | 65 | 12 |
| 41 | 35 | 175 | 8.75 | 65 | 16 |
| 42 | 35 | 175 | 8.75 | 65 | 16 |
| 43 | 35 | 175 | 8.75 | 65 | 20 |
| 44 | 90 | 450 | 22.5 | 65 | 16 |
| 45 | 60 | 450 | 15 | 65 | 16 |
| 46 | 36 | 450 | 9 | 65 | 16 |
| 47 | 18 | 450 | 4.5 | 65 | 16 |
| 48 | 90 | 450 | 22.5 | 65 | 16 |
| 49 | 60 | 450 | 15 | 65 | 16 |
| 50 | 36 | 450 | 9 | 65 | 16 |
| 51 | 18 | 450 | 4.5 | 65 | 16 |
| 52 | 65700 | 322000 | 15600 | 65 | 16 |
| 53 | 40 | 200 | 10 | 65 | 16 |
| 54 | 40 | 200 | 10 | 65 | 16 |
| 55 | 40 | 200 | 10 | 65 | 16 |
| 56 | 3800 | 28600 | 950 | 65 | 16 |
| 57 | 63200 | 450000 | 15800 | 65 | 16 |
| 58 | 64600 | 300000 | 16200 | 65 | 16 |

NP = not performed

TABLE 11_Part 1

Properties of radical polymerization beads

| Polymer number | swelling (g/g) | SGF (mmol/g) | % sp2 carbons |
|---|---|---|---|
| 1 | 3.4 | 14.4 | NP |
| 2 | 4.2 | 13.8 | 1.6% |
| 3 | 4.9 | 13.8 | 1.4% |
| 4 | 4.2 | 13.8 | 1.2% |
| 5 | 4.3 | 14.1 | 1.2% |
| 6 | 3.5 | 14 | 1.2% |
| 7 | 3.5 | 14.2 | NP |
| 8 | 3.3 | 14.6 | NP |
| 9 | 3.2 | 14.1 | NP |
| 10 | 3.3 | 14.6 | 2.3% |
| 11 | 3.6 | 14.8 | 2.7% |
| 12 | NP | 14.1 | NP |
| 13 | 4.9 | 13.4 | NP |
| 14 | 3.8 | 14.1 | NP |
| 15 | 3.1 | 14.2 | NP |
| 16 | 2.7 | 14 | 0.7% |
| 17 | 3.7 | 14.4 | 1.4% |
| 18 | 3.8 | 14.1 | 0.8% |
| 19 | 4.1 | 13.5 | 0.6% |
| 20 | 4.4 | 14.4 | 3.2% |
| 21 | NP | 14.1 | 3.4% |
| 22 | NP | 14.1 | 1.8% |
| 23 | NP | 13.5 | 1.2% |
| 24 | 3.5 | 14.1 | NP |
| 25 | 3.5 | 14.1 | NP |
| 26 | 3.5 | 14.1 | NP |
| 27 | 3.5 | 14.1 | NP |
| 28 | 3.5 | 14.1 | NP |
| 29 | 3.9 | 13.6 | NP |
| 30 | 3.6 | 13.4 | NP |
| 31 | 3.9 | 13.6 | NP |
| 32 | 3.9 | 13.6 | NP |
| 33 | 3.5 | 14 | 1.2% |
| 34 | 3.5 | 14 | 1.2% |
| 35 | 3.7 | 14.0 | 0.8% |
| 36 | 3.7 | 14.0 | 0.8% |
| 37 | 3.7 | 14.0 | 0.8% |
| 38 | 3.7 | 14.0 | 0.8% |
| 39 | 3.7 | 14.0 | 0.8% |
| 40 | 3.6 | 14.0 | 0.7% |
| 41 | 3.6 | 14.0 | 0.7% |
| 42 | 3.6 | 14.0 | 0.7% |
| 43 | 3.6 | 14.0 | 0.7% |
| 44 | 3.9 | 13.6 | NP |
| 45 | 3.9 | 13.6 | NP |
| 46 | 3.9 | 13.6 | NP |
| 47 | 3.9 | 13.6 | NP |
| 48 | NP | 13.7 | NP |
| 49 | NP | 13.7 | NP |
| 50 | NP | 13.7 | NP |
| 51 | NP | 13.7 | NP |
| 52 | 3.8 | 13.4 | 0.9% |
| 53 | 4.1 | 13.7 | 0.8% |
| 54 | 4.2 | 13.7 | 0.8% |
| 55 | 4.2 | 14.2 | 0.6% |
| 56 | 4.6 | 13.5 | 1.5% |
| 57 | 4.1 | 13.7 | 1.9% |
| 58 | 3.7 | 13.6 | 0.9% |

NP = not performed

TABLE 11

Part 2: Properties of post-crosslinked radical polymerization beads

| Post-crosslinked polymer number | swelling (g/g) | SGF (mmol/g) | SIB Cl (mmol/g) | SIB P (mmol/g) | % sp2 Carbons | Calculated or Measured[a] | AA at release (ppm) | AME at release (ppm) | AOH at release (ppm) | AA stability assay number | AA stability (ppm/d) |
|---|---|---|---|---|---|---|---|---|---|---|---|
| 1 | NP | 11.1 | 5.2 | 1.3 | NP | NP | 0.9 | <25 | <5 | 1 | 0.4 |
| 2 | 1.1 | 11.4 | 4.8 | 1.3 | 1.4% | C | 3.1 | 494 | <5 | 2 | 11.3 |
| 3 | 1.2 | 11.4 | 4.9 | 1.5 | 1.3% | C | 2.4 | 513 | <5 | 2 | 9.3 |

TABLE 11-continued

| | Part 2: Properties of post-crosslinked radical polymerization beads | | | | | | | | | | |
|---|---|---|---|---|---|---|---|---|---|---|---|
| Post-crosslinked polymer number | swelling (g/g) | SGF (mmol/g) | SIB Cl (mmol/g) | SIB P (mmol/g) | % sp2 Carbons | Calculated or Measured[a] | AA at release (ppm) | AME at release (ppm) | AOH at release (ppm) | AA stability assay number | AA stability (ppm/d) |
|---|---|---|---|---|---|---|---|---|---|---|---|
| 4 | 1.0 | 11.1 | 5.3 | 1 | 1.1% | C | 1.6 | 475 | <5 | 2 | 6.3 |
| 5 | NP | 11.4 | 5.3 | 1 | 1.1% | C | 0.8 | 493 | <5 | 1 | 0.8 |
| 6 | NP | NP | NP | NP | 1.1% | C | NP | NP | NP | NP | NP |
| 7 | NP | 10.8 | 4.3 | 0.8 | NP | NP | 0.7 | <25 | <5 | 1 | 0.3 |
| 8 | NP | 11.3 | 4.0 | 2.3 | NP | NP | 0.6 | <25 | <5 | 1 | 0.6 |
| 9 | NP | 10.6 | 4.4 | 1.3 | NP | NP | 0.5 | <25 | <5 | 1 | 0.4 |
| 10 | NP | 10.8 | 4.1 | 1.1 | 2.1% | C | 0.5 | <25 | <5 | 1 | 1.2 |
| 11 | NP | 11.5 | 4.9 | 1.2 | 2.4% | C | 0.6 | <25 | <5 | 1 | 0.9 |
| 12 | NP | 11.3 | 4.8 | 1.6 | NP | NP | 2.6 | 593 | <5 | 1 | 1.2 |
| 13 | NP | 11.3 | 5 | 1.7 | NP | NP | 3.0 | 522 | <5 | 1 | 1.0 |
| 14 | 1.3 | 11.7 | 5 | 1.5 | NP | NP | 1.4 | 534 | <5 | 1 | 0.6 |
| 15 | 1.1 | 10.8 | 4.9 | 0.9 | NP | NP | 0.7 | 131 | <5 | 1 | 0.6 |
| 16 | 1.3 | 11.4 | 5.5 | 0.9 | 0.6% | C | 1.0 | 398 | <5 | 1 | 0.1 |
| 17 | NP | NP | NP | NP | 1.3% | C | NP | NP | NP | NP | NP |
| 18 | NP | NP | NP | NP | 0.7% | C | NP | NP | NP | NP | NP |
| 19 | NP | 11.1 | 5.0 | 0.8 | 0.5% | C | <0.3 | 70 | 1.6 | 1 | 0.2 |
| 20 | 1.3 | 12.8 | 2.4 | 4.4 | 2.9% | C | 3.6 | <25 | <5 | 1 | 2.5 |
| 21 | NP | 10.9 | 2.7 | 3.5 | 3.1% | C | NP | NP | NP | NP | NP |
| 22 | NP | 11.3 | 4.5 | 2 | 1.6% | C | NP | NP | NP | NP | NP |
| 23 | NP | NP | NP | NP | 1.1% | C | NP | NP | NP | NP | NP |
| 24 | NP | 11.2 | 4.9 | 1.4 | NP | NP | 0.5 | <25 | <5.5 | 1 | 0.6 |
| 25 | NP | 10.2 | 4.5 | 2.2 | NP | NP | 0.5 | <25 | <5.5 | 1 | 0.6 |
| 26 | NP | 11.5 | 4.8 | 1.6 | NP | NP | 0.9 | 149 | <5.5 | 1 | 0.6 |
| 27 | NP | 11.1 | 4.8 | 0.9 | NP | NP | <0.8 | <25 | <5.5 | 1 | 0.3 |
| 28 | NP | 9.9 | 4.5 | 0.8 | NP | NP | <0.8 | <25 | <5.5 | 1 | 0.2 |
| 29 | NP | 11.8 | 5.2 | 1.3 | NP | NP | 0.9 | NP | NP | NP | NP |
| 30 | NP | 10.8 | 4.4 | 1.3 | NP | NP | 0.6 | <25 | <5.5 | 1 | 0.9 |
| 31 | NP | 11.2 | 5.3 | 1.1 | NP | NP | 0.7 | <25 | <5.5 | 1 | 0.6 |
| 32 | NP | 11.0 | 5.5 | 1.1 | NP | NP | 0.9 | <25 | <5.5 | 1 | 0.6 |
| 33 | NP | 11.4 | 5.4 | 1.5 | 0.9% | M | 1.5 | 120 | <5.5 | 2 | 1.8 |
| 34 | NP | 11.4 | 5.4 | 1.5 | 0.9% | M | 1.5 | 120 | <5.5 | 1 | 0.5 |
| 35 | NP | 11.1 | 5.0 | 1.2 | 0.7% | C | 0.3 | 246 | 1.1 | 1 | 0.2 |
| 36 | NP | 11.0 | 5.4 | 0.9 | 0.7% | C | <0.3 | 185 | 1.1 | 1 | 0.1 |
| 37 | NP | 11.2 | 5.3 | 0.8 | 0.7% | C | 0.3 | 213 | <1.0 | 1 | 0.2 |
| 38 | NP | 11.5 | 5.2 | 1.0 | 0.7% | C | 0.6 | 216 | 1.1 | 1 | 0.3 |
| 39 | NP | 11.4 | 5.0 | 1.4 | 0.7% | C | 1.2 | 199 | 1.0 | 1 | 0.3 |
| 40 | 1.3 | 10.8 | 4.9 | 1.3 | 0.6% | C | 1.8 | 202 | <1 | NP | NP |
| 41 | 1.2 | 10.3 | 4.9 | 1.0 | 0.6% | C | <1.25 | 78 | 1.4 | NP | NP |
| 42 | 1.3 | 10.7 | 4.8 | 1.2 | 0.6% | C | 1.7 | 235 | <1 | NP | NP |
| 43 | 1.2 | 10.4 | 4.9 | 0.9 | 0.6% | C | <1.25 | <50 | <1 | NP | NP |
| 44 | 1.2 | 11.2 | 5.3 | 1.0 | NP | NP | <0.8 | <25 | <5.5 | NP | NP |
| 45 | 1.3 | 11.8 | 5.3 | 1.0 | NP | NP | <0.8 | <25 | <5.5 | NP | NP |
| 46 | 1.3 | 11.6 | 5.7 | 0.9 | NP | NP | <0.8 | <25 | <5.5 | NP | NP |
| 47 | 1.3 | 11.4 | 5.5 | 0.9 | NP | NP | <0.8 | <25 | <5.5 | NP | NP |
| 48 | 1.2 | 11.4 | 5.1 | 1.6 | NP | NP | 4.0 | 461 | <5.5 | NP | NP |
| 49 | 1.2 | 11.3 | 5.0 | 1.6 | NP | NP | 3.6 | 477 | <5.5 | NP | NP |
| 50 | 1.2 | 11.3 | 5.2 | 1.3 | NP | NP | 3.0 | 430 | <5.5 | NP | NP |
| 51 | 1.2 | 11.0 | 5.2 | 1.1 | NP | NP | 3.1 | 463 | <5.5 | NP | NP |
| 52 | 1.1 | 10.3 | 4.7 | 1.0 | 0.8% | C | 1.5 | 321 | 4.0 | 3 | NA |
| 53 | 1.5 | 11.1 | 4.4 | 1.7 | 0.7% | C | 1.5 | 324 | 1.2 | NP | NP |
| 54 | 1.5 | 10.8 | 5.3 | 1.1 | 0.7% | C | <1.25 | 179 | 1.4 | NP | NP |
| 55 | 1.5 | 11.3 | 5.9 | 0.8 | 0.5% | C | <1.25 | 154 | 1.5 | NP | NP |
| 56 | 1.1 | 11.0 | 4.7 | 1.5 | 1.3% | M | 4.3 | 503 | 2.8 | NP | NP |
| 57 | 1.2 | 11.1 | 4.5 | 1.3 | 2.0% | M | 3.2 | 454 | 12.8 | NP | NP |
| 58 | 1.2 | 11.2 | 4.4 | 0.9 | <0.7% | M | <1.25 | 107 | 2.0 | NP | NP |

NA = not applicable;
NP = not performed
[a]M indicates that % sp2 carbons was measured directly by NMR spectroscopy.
C indicates that the % sp2 carbons was calculated from the corresponding example from Table 11 part 1 as described above.

TABLE 12

Properties of post-crosslinked radical polymerization beads from Stability Assay 3

| Time (Months) | AA (ppm) | |
|---|---|---|
| | 25° C./60%RH | 40° C./75%RH |
| 0 | 4 | 4 |
| 1 | 4 | 4 |
| 3 | 3 | 3 |
| 6 | 5 | 4 |

RH = relative humidity

What is claimed is:

1. A crosslinked poly(allylamine) polymer in bead form consisting essentially of (i) 20-25 mol % residue of N,N'-diallyl-1,3-diaminopropane or a salt thereof, (ii) 50-60 mol % residue of 2-Propen-1-ylamine or a salt thereof, and (iii) 20-25 mol % residue of 1,2-dichloroethane wherein (i) the crosslinked poly(allylamine) polymer comprises $sp^2$ allyl carbon atoms and has a swelling ratio of less than 2 and (ii) the $sp^2$ allyl carbons comprised by the poly(allylamine) polymer constitute less than 1.0% of the total number of carbon atoms comprised by the crosslinked poly(allylamine) polymer.

2. The crosslinked poly(allylamine) polymer of claim 1 wherein $sp^2$ allyl carbons comprised by the crosslinked poly(allylamine) polymer constitute less than 0.9% of the total number of carbon atoms comprised by the crosslinked poly(allylamine) polymer.

3. The crosslinked poly(allylamine) polymer of claim 1 wherein $sp^2$ allyl carbons comprised by the crosslinked poly(allylamine) polymer constitute less than 0.8% of the total number of carbon atoms comprised by the crosslinked poly(allylamine) polymer.

4. The crosslinked poly(allylamine) polymer of claim 1 wherein the crosslinked poly(allylamine) polymer has a stability profile such that upon storage in a sealed enclosure at 25° C. for 12 months the crosslinked poly(allylamine) polymer contains less than 20 ppm $H_2C=CHCH_2NH_2$ as an impurity.

5. The crosslinked poly(allylamine) polymer of claim 1 wherein the crosslinked poly(allylamine) polymer contains less than 5 ppm $H_2C=CHCH_2NH_2$ as an impurity.

6. The crosslinked poly(allylamine) polymer of any of claims 1 and 2-5 wherein the crosslinked poly(allylamine) polymer is characterized by a chloride ion binding capacity of at least 3 mEq/g in a SIB assay wherein, in the SIB assay, the crosslinked poly(allylamine) polymer is combined with a SIB buffer consisting of 36 mM NaCl, 20 mM $NaH_2PO_4$ and 50 mM 2-(N-morpholino)ethanesulfonic acid (MES) buffered to pH 5.5 at a concentration of 2.5 mg/ml (25 mg dry mass of the crosslinked poly(allylamine) polymer) in 10 mL of the buffer, and the combination is incubated at 37° C. for 1 hour with agitation on an orbital shaker at 200 to 300 rotations per minute.

7. The crosslinked poly(allylamine) polymer of any of claims 1 and 2-5 wherein the crosslinked poly(allylamine) polymer is characterized by a chloride to phosphate ion binding ratio of at least 2:1, respectively, in a SIB assay wherein, in the SIB assay, the crosslinked poly(allylamine) polymer is combined with a SIB buffer consisting of 36 mM NaCl, 20 mM $NaH_2PO_4$ and 50 mM 2-(N-morpholino)ethanesulfonic acid (MES) buffered to pH 5.5 at a concentration of 2.5 mg/ml (25 mg dry mass of the crosslinked poly(allylamine) polymer) in 10 mL of the buffer, and the combination is incubated at 37° C. for 1 hour with agitation on an orbital shaker at 200 to 300 rotations per minute.

8. The crosslinked poly(allylamine) polymer of claim 6 wherein the crosslinked poly(allylamine) polymer is characterized by a proton-binding capacity and a chloride binding capacity of at least 10 mEq/g in a SGF assay wherein, in the SGF assay, the crosslinked poly(allylamine) polymer is combined with a SGF buffer consisting of 35 mM NaCl and 63 mM HCl at pH 1.2 at a concentration of 2.5 mg/ml (25 mg dry mass of the crosslinked poly(allylamine) polymer) in 10 mL of the SGF buffer, and the combination is incubated at 37° C. for 12-16 hours with agitation on a rotisserie mixer.

9. The crosslinked poly(allylamine) polymer of claim 7 wherein the crosslinked poly(allylamine) polymer is characterized by a proton-binding capacity and a chloride binding capacity of at least 10 mEq/g in a SGF assay wherein, in the SGF assay, the crosslinked poly(allylamine) polymer is combined with a SGF buffer consisting of 35 mM NaCl and 63 mM HCl at pH 1.2 at a concentration of 2.5 mg/ml (25 mg dry mass of the crosslinked poly(allylamine) polymer) in 10 mL of the SGF buffer, and the combination is incubated at 37° C. for 12-16 hours with agitation on a rotisserie mixer.

10. The crosslinked poly(allylamine) polymer of any of claims 1 and 2-5 wherein the crosslinked poly(allylamine) polymer is characterized by (i) a chloride ion binding capacity of at least 4 mEq/g in a SIB assay wherein, in the SIB assay, the crosslinked poly(allylamine) polymer is combined with a SIB buffer consisting of 36 mM NaCl, 20 mM $NaH_2PO_4$ and 50 mM 2-(N-morpholino)ethanesulfonic acid (MES) buffered to pH 5.5 at a concentration of 2.5 mg/ml (25 mg dry mass of the crosslinked poly(allylamine) polymer) in 10 mL of the buffer, and the combination is incubated at 37° C. for 1 hour with agitation on an orbital shaker at 200 to 300 rotations per minute, and (ii) a proton-binding capacity and a chloride binding capacity of at least 10 mEq/g in a SGF assay wherein, in the SGF assay, the crosslinked poly(allylamine) polymer is combined with a SGF buffer consisting of 35 mM NaCl and 63 mM HCl at pH 1.2 at a concentration of 2.5 mg/ml (25 mg dry mass of the crosslinked poly(allylamine) polymer) in 10 mL of the SGF buffer, and the combination is incubated at 37° C. for 12-16 hours with agitation on a rotisserie mixer.

* * * * *